US012760065B2

(12) United States Patent
Hayashi et al.

(10) Patent No.: US 12,760,065 B2
(45) Date of Patent: Oct. 13, 2026

(54) BETA-STRAND BRIDGE PEPTIDE

(71) Applicants: Xeno-Interface Inc., Kyoto City (JP); Kyoto University, Kyoto (JP)

(72) Inventors: Kazuhiro Hayashi, Kyoto City (JP); Michiyuki Matsuda, Kyoto (JP)

(73) Assignees: Xeno-Interface Inc., Kyoto City (JP); Kyoto University, Kyoto (JP)

( * ) Notice: Subject to any disclaimer, the term of this patent is extended or adjusted under 35 U.S.C. 154(b) by 1350 days.

(21) Appl. No.: 17/616,146

(22) PCT Filed: Oct. 29, 2021

(86) PCT No.: PCT/JP2021/040138
§ 371 (c)(1),
(2) Date: Dec. 2, 2021

(87) PCT Pub. No.: WO2022/092295
PCT Pub. Date: May 5, 2022

(65) Prior Publication Data
US 2023/0174576 A1 Jun. 8, 2023

(30) Foreign Application Priority Data
Oct. 30, 2020 (JP) ................................ 2020-183344

(51) Int. Cl.
*C07K 4/00* (2006.01)

(52) U.S. Cl.
CPC .................................... *C07K 4/00* (2013.01)

(58) Field of Classification Search
CPC .. C07K 4/00; C07K 7/06; Y02P 20/55; A61K 38/02
See application file for complete search history.

(56) References Cited

U.S. PATENT DOCUMENTS

| | | | |
|---|---|---|---|
| 7,723,469 | B2 | 5/2010 | Walensky et al. |
| 10,081,654 | B2 | 9/2018 | Verdine et al. |
| 2016/0215036 | A1 | 7/2016 | Verdine et al. |
| 2016/0244494 | A1 | 8/2016 | Verdine et al. |
| 2021/0024605 | A1 | 1/2021 | Perrin et al. |

FOREIGN PATENT DOCUMENTS

| | | | |
|---|---|---|---|
| JP | 2016523241 | A | 8/2016 |
| JP | 2017503749 | A | 2/2017 |
| WO | 2008/104000 | A2 | 8/2008 |
| WO | WO 2011051071 | A1 | 5/2011 |
| WO | 2014/052647 | A2 | 4/2014 |
| WO | WO 2014201370 | A1 | 12/2014 |
| WO | WO 2015051030 | A2 | 4/2015 |

OTHER PUBLICATIONS

Sawyer et al. (ACS Chemical Biology. vol. 13. Issue 8, 2018).*

Mooibroek, T.,Intermolecular Non-Covalent Carbon-Bonding Interactions with Methyl Groups: A CSD, PDB and DFT Study Molecules 2019, 24, 3370.*

Zhai et al. (Peptide-based short single ß-strand mimics without hydrogen bonding or aggregation, Chem. Commun., 2020, 56, 1573; published Dec. 19, 2019).*

Galande et al. (ChemBioChem 2005, 6, 1991-1998).*

Almeida et al. (Parallel ß-sheet secondary structure is stabilized and terminated by interstrand disulfide cross-linking. J Am Chem Soc. Jan. 11, 2012;134(1):75-8).*

Li et al., "Stapled Helical Peptides Bearing Different Anchoring Residues," *Chemical Reviews* 120:10079-10144, Aug. 14, 2020. (66 pages).

Loughlin et al., "Update 1 of: Beta-Strand Mimetics," *Chemical Reviews* 110(6):PR32-PR69, Apr. 12, 2010. (38 pages).

Sawyer et al., "Hydrogen Bond Surrogate Stabilization of ß-Hairpins," *ACS Chemical Biology* 13(8):2027-2032, Aug. 17, 2018 (HHS Public Access Author Manuscript, available in PMC Apr. 28, 2020). (12 pages).

Speltz et al., "Branching Out: γ-Methylated Hydrocarbon Stapled Peptides for the Estrogen Receptor/Coactivator Interaction," *Angewandte Chemie International Edition* 55(13):4252-4255, Mar. 18, 2016 (HHS Public Access Author Manuscript, available in PMC Mar. 18, 2017). (11 pages).

Tanaka et al., "Design and synthesis of ß-strand-fixed peptides inhibiting aggregation of amyloid ß-protein," *Bioorganic & Medicinal Chemistry* 28:115676, Jul. 28, 2020. (10 pages).

Bockus et al., "Form and Function in Cyclic Peptide Natural Products: A Pharmacokinetic Perspective," *Current Topics in Medicinal Chemistry* 13:821-836, Feb. 2013.

Cho et al., "Structure of the extracellular region of HER2 alone and in complex with the Herceptin Fab," *Nature* 421:756-760, Feb. 2003, 9 pages.

Grossmann et al., "Inhibition of oncogenic Wnt signaling through direct targeting of ß-catenin," *PNAS* 109(44):17942-17947, Oct. 2012, 15 pages.

Hopkins et al., "The druggable genome," *Nature Reviews* 1:727-730, Sep. 2002.

Moellering et al., "Direct inhibition of the NOTCH transcription factor complex," *Nature 462*, doi:10.1038/nature08543, Nov. 2009, 9 pages.

Pacold et al., "Crystal Structure and Functional Analysis of Ras Binding to Its Effector Phosphoinositide 3-Kinase γ," *Cell* 103:931-943, Dec. 2000.

Verdine et al., "The Challenge of Drugging Undruggable Targets in Cancer: Lessons Learned from Targeting BCL-2 Family Members," *Clin Cancer Res* 13(24):7264-7270, Dec. 2007.

(Continued)

*Primary Examiner* — Jeanette M Lieb
(74) *Attorney, Agent, or Firm* — Seed IP Law Group LLP

(57) ABSTRACT

The present disclosure provides a novel bridge peptide. The present disclosure provides a bridge peptide comprising a bridge moiety and a peptide moiety, wherein position β is tertiary or quaternary when the carbon at which the bridge moiety attaches to the peptide moiety is in position α. The present disclosure provides a novel bridge peptide, particularly a bridge peptide resulting from stably bridging a peptide that does not possess a hydrogen bond to induce or maintain a secondary structure, e.g., a peptide having a β-strand structure.

15 Claims, 15 Drawing Sheets

(56) References Cited

OTHER PUBLICATIONS

Walensky et al., "Activation of Apoptosis in Vivo by a Hydrocarbon-Stapled BH3 Helix," *Science* 305:1466-1470, Sep. 2004.
White et al., "On-resin N-Methylation of cyclic peptides for discovery of orally bioavailable scaffolds," *Nature Chemical Biology 7*, doi: 10.1038/NCHEMBIO.664, Sep. 2011, 74 pages.
Yun et al., "Structures of Lung Cancer-Derived EGFR Mutants and Inhibitor Complexes: Mechanism of Activation and Insights into Differential Inhibitor Sensitivity," *Cancer Cell* 11:217-227, Mar. 2007, 17 pages.

* cited by examiner

Ring-closing olefin metathesis reaction (Michael addition)

(Carbamate formation)

| Peptide sequence | $[M + H]^+$ found | $[M + 2H]^{2+}$ found | $[M + H]^+$ calculated | $[M + 2H]^{2+}$ calculated |
|---|---|---|---|---|
| FITC ~ W I F I K I H R ~ $NH_2$ (WT) | 1572.7790 | 786.4248 | 1571.7568 | 786.3823 |
| FITC ~ W I F **(S)-βDM4** K **(S)-βDM6** H R ~ $NH_2$ (BP 4-6 1st) | 1624.8021 | 812.4327 | 1623.7879 | 812.3979 |
| FITC ~ W I F **(S)-βDM4** K **(S)-βDM6** H R ~ $NH_2$ (BP 4-6 2nd) | 1624.8065 | 812.4223 | 1623.7879 | 812.3979 |

WT

BP 4-6

(a) Comparison of cell membrane permeability

| Peptide (μM) | Mean: FITC-A |
|---|---|
| WT (0.1 μM) | 3192 |
| BP 4-6 1st (0.1 μM) | 5910 |
| BP 4-6 2nd (0.1 μM) | 4454 |

(b) Evaluation of concentration dependence of cell membrane permeability

| Peptide (μM) | Mean: FITC-A |
|---|---|
| BP 4-6 1st (0.1 μM) | 5910 |
| BP 4-6 1st (1 μM) | 19846 |

Figure 16

BETA-STRAND BRIDGE PEPTIDE

TECHNICAL FIELD

The present disclosure relates to chemical biology, more specifically to peptide chemistry.

BACKGROUND ART

Secondary structures represented by α helix, β sheet, β strand, turn, loop, etc. serve an important feature in the bioactive structure of peptides. Various technologies have been proposed for the stabilization of the secondary structure of peptides.

SUMMARY OF INVENTION

Solution to Problem

The present disclosure provides a novel bridge peptide, particularly a peptide that does not have a hydrogen bond for eliciting or maintaining a secondary structure such as a bridge peptide, in which a peptide having a β-strand structure is stably crosslinked.

For example, the present disclosure includes the following.

(Item 1)

A bridge peptide comprising a bridge moiety and a peptide moiety, wherein position, when carbon at which the bridge moiety attaches to the peptide moiety is position α, is tertiary or quaternary.

(Item 2)

The bridge peptide of item 1, wherein the peptide does not have a hydrogen bond to induce or maintain a secondary structure.

(Item 3)

The bridge peptide of any one of the preceding items, wherein the peptide comprises a β-strand structure.

(Item 3A)

The bridge peptide of any one of the preceding items, wherein the β-strand structure is a single unit or is comprised in all structures produced by combining with another secondary structure such as a β hairpin, a β sheet, an α helix, a $3_{10}$ helix, a β-α-β structure, or an α-β-β structure or the line with a β structure and derivatives thereof.

(Item 4)

The bridge peptide of any one of the preceding items, wherein the position β is quaternary.

(Item 5)

The bridge peptide of any one of the preceding items, wherein at least one substituent at the position β comprises a functional group with a size equal to or greater than a methyl group.

(Item 6)

The bridge peptide of any one of the preceding items, wherein two substituents at the position β comprise an independently selected functional group with a size equal to or greater than a methyl group.

(Item 7)

The bridge peptide of any one of the preceding items, wherein a functional group attached to the position β has:

a) a van der Waals volume of 7.24 $Å^3$; or b) a van der Waals radius of 1.2 Å.

(Item 8)

The bridge peptide of any one of the preceding items, wherein at least one of the functional groups attached to the position β has:

a) a van der Waals volume of 21.6 $Å^3$ or greater;

b) a van der Waals radius of 2.00 Å or greater; or c) an A-value of 1.74 (kcal/mol) or greater.

(Item 9)

The bridge peptide of any one of the preceding items, wherein substituents at the position β are each independently hydrogen, optionally substituted alkyl, alkene, alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or two substituents, together with the carbon atom to which they are attached, may form an optionally substituted nonaromatic carbocycle, an optionally substituted nonaromatic heterocycle, optionally substituted aryl, or optionally substituted heteroaryl, provided that two substituents are not both hydrogen.

(Item 10)

The bridge peptide of any one of the preceding items, wherein substituents at the position β are each independently substituted alkyl, substituted alkene, substituted alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or two substituents, together with the carbon atom to which they are attached, may form an optionally substituted nonaromatic carbocycle, an optionally substituted nonaromatic heterocycle, optionally substituted aryl, or optionally substituted heteroaryl, provided that two substituents are not both hydrogen.

(Item 11)

The bridge peptide of any one of the preceding items, wherein substituents at the position β are each independently hydrogen, methyl, methoxy, methoxymethyl, secondary amine substituted with methyl or Boc, tertiary amine (substituted with methyl), quaternary ammonium substituted with methyl, or methyl substituted with halogen, or two substituents, together with the carbon atom to which they are attached, may form an unsubstituted saturated $C_{3-12}$ nonaromatic carbocycle or an optionally substituted saturated 3- to 12-membered nonaromatic heterocycle, provided that two substituents are not both hydrogen.

(Item 12)

The bridge peptide of any one of the preceding items, wherein substituents at the position β are each independently methoxy, methoxymethyl, secondary amine substituted with methyl or Boc, tertiary amine (substituted with methyl), quaternary ammonium substituted with methyl, or methyl substituted with halogen, or two substituents, together with the carbon atom to which they are attached, may form an unsubstituted saturated $C_{3-12}$ nonaromatic carbocycle or an optionally substituted saturated 3- to 12-membered nonaromatic heterocycle, provided that two substituents are not both hydrogen.

(Item 13)

The bridge peptide of any one of the preceding items, wherein the bridge peptide has a crosslink formed by a crosslinking method selected from the group consisting of olefin metathesis, alkyne metathesis, click chemistry, reductive amination, Michael addition, and carbamate formation.

(Item 14)

The bridge peptide of any one of the preceding items, wherein the bridge peptide has a crosslink formed by a crosslinking method selected from the group consisting of olefin metathesis, alkyne metathesis, reductive amination, Michael addition, and carbamate formation.

(Item 15)

The bridge peptide of any one of the preceding items, wherein the position α is hydrogen or halogen.

(Item 15A)

The bridge peptide of any one of items 1 to 15, further comprising one or more features of any one or more of the preceding or following items.

(Item 16)

A method comprising:

providing a bridge peptide having a β-strand structure or a raw material thereof;

processing, or introducing a substituent into, the bridge peptide or raw material thereof so that position β, when carbon at which the bridge moiety of the bridge peptide attaches to the peptide is position α, is tertiary and/or quaternary; and optionally generating the bridge peptide using the raw material.

(Item 16A)

The method of item 16, further comprising one or more features of any one or more of the preceding or following items.

(Item 17)

A compound moiety for crosslinking a peptide moiety comprising a β-strand structure, wherein the compound moiety has an amino acid structure, and position β in the amino acid structure has a tertiary or quaternary structure.

(Item 17A)

The compound moiety of item 17, further comprising one or more features of any one or more of the preceding or following items.

(Item 18)

A bridge peptide comprising a compound moiety for crosslinking a peptide moiety comprising a β-strand structure, wherein the compound moiety has an amino acid structure, and position β in the amino acid structure has a tertiary or quaternary structure.

(Item 18A)

The bridge peptide of item 18, further comprising one or more features of any one or more of the preceding or following items.

(Item 19)

A composition comprising a bridge peptide material for crosslinking a peptide moiety comprising a β-strand structure, wherein the bridge peptide material is a material that comprises an amino acid structure or forms an amino acid structure after synthesis, and position β in the amino acid structure has a tertiary or quaternary structure.

(Item 19A)

The composition of item 19, further comprising one or more features of any one or more of the preceding or following items.

(Item 20)

A compound represented by formula I:

[Chemical Formula 1]

formula I

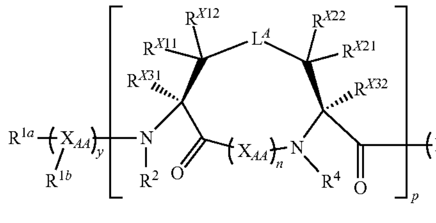

or a stereoisomer thereof or a salt thereof or solvate thereof, wherein $R^{1a}$ and $R^{1b}$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or $R^{1a}$ and $R^{1b}$ together form an optionally substituted non-aromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently hydrogen, optionally substituted alkyl, optionally substituted alkene, optionally substituted alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or $R^{X11}$ and $R^{X12}$, together with the carbon atom to which they are attached, may form an optionally substituted nonaromatic carbocycle, an optionally substituted nonaromatic heterocycle, optionally substituted aryl, or optionally substituted heteroaryl, $R^{X21}$ and $R^{X22}$, together with the carbon atom to which they are attached, may form an optionally substituted nonaromatic substituted nonaromatic carbocycle, an optionally heterocycle, optionally substituted aryl, or optionally substituted heteroaryl, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic carbocycle, an optionally substituted nonaromatic heterocycle, optionally substituted aryl, or an optionally substituted heteroaryl ring, $L^A$ is each independently-(optionally substituted $C_{0-k}$ alkylene)-[optionally substituted alkylene, optionally substituted alkenylene, optionally substituted alkynylene, optionally substituted cycloalkylene, optionally substituted cycloalkenylene, optionally substituted cycloalkynylene, optionally substituted heteroalkylene, optionally substituted heteroalkenylene, optionally substituted heteroalkynylene, optionally substituted heterocycloalkylene, optionally substituted heterocycloalkenylene, optionally substituted heterocycloalkynylene, optionally substituted arylene, or optionally substituted heteroarylene]-(optionally substituted $C_{0-k}$ alkylene)-, wherein k is an integer that is 5 or greater, y and z are each independently an integer from 0 to 100 (preferably 0 to 10), $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is an integer (preferably n is 1), and p is an integer from 1 to 100 (preferably 1 to 10).

(Item 21)

A compound represented by formula I:

[Chemical Formula 2]

formula I

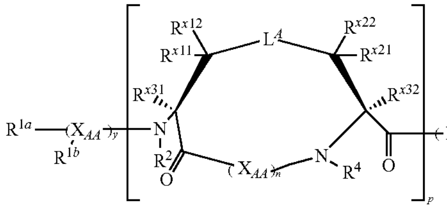

or a stereoisomer thereof or a salt thereof or solvate thereof, wherein $R^{1a}$ and $R^{1b}$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or $R^{1a}$ and $R^{1b}$ together form an optionally substituted nonaromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently hydrogen, methyl, methoxy, methoxymethyl, secondary amine substituted with methyl or Boc, tertiary amine (substituted with methyl), quaternary ammonium substituted with methyl, or methyl substituted with halogen, or $R^{X11}$ and $R^{X12}$, together with the carbon atom to which they are attached, may form an unsubstituted saturated $C_{3-10}$ nonaromatic carbocycle or an optionally substituted saturated 3- to 10-membered nonaromatic heterocycle, $R^{X21}$ and $R^{X22}$, together with the carbon atom to which they are attached, may form an unsubstituted saturated $C_{3-10}$ nonaromatic carbocycle or an optionally substituted saturated 3- to 10-membered nonaromatic heterocycle, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic heterocycle or an optionally substituted heteroaryl ring, $L^A$ is each independently-(optionally substituted $C_{0-k}$ alkylene)-[optionally substituted alkylene, optionally substituted alkenylene, optionally substituted alkynylene, optionally substituted cycloalkylene, optionally substituted cycloalkenylene, optionally substituted cycloalkynylene, heteroalkylene, optionally optionally substituted substituted heteroalkenylene, optionally substituted heteroalkynylene, optionally substituted heterocycloalkylene, optionally substituted heterocycloalkenylene, optionally substituted heterocycloalkynylene, optionally substituted arylene, or optionally substituted heteroarylene]-(optionally substituted $C_{0-k}$ alkylene)-, wherein k is an integer that is 5 or greater, y and z are each independently an integer from 0 to 10, $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is 1, and p is an integer from 1 to 10.

(Item 22)

The compound or a stereoisomer thereof, or a salt or solvate thereof of any one of the preceding items, wherein $R^{X11}$, $R^{X12}$, $R^{X21}$, and $R^{X22}$ are each independently substituted alkyl, substituted alkene, substituted alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or $R^{X11}$ and $R^{X12}$, together with the carbon atom to which they are attached, may form an optionally substituted nonaromatic carbocycle, an optionally substituted nonaromatic heterocycle, optionally substituted aryl, or optionally substituted heteroaryl, and $R^{X21}$ and $R^{X22}$, together with the carbon atom to which they are attached, may form an optionally substituted nonaromatic carbocycle, an substituted nonaromatic optionally heterocycle, optionally substituted aryl, or optionally substituted heteroaryl, provided that $R^{X11}$ and $R^{X12}$ are not both hydrogen, and $R^{X21}$ and $R^{X22}$ are not both hydrogen.

(Item 23)

The compound or a stereoisomer thereof, or a salt or solvate thereof of any one of the preceding items, wherein $R^{X11}$, $R^{X12}$, $R^{X21}$, and $R^{X22}$ are each independently methoxy, methoxymethyl, secondary amine substituted with methyl or Boc, tertiary amine (substituted with methyl), quaternary ammonium substituted with methyl, or methyl substituted with halogen, or $R^{X11}$ and $R^{X12}$, together with the carbon atom to which they are attached, may form an unsubstituted saturated $C_{3-10}$ nonaromatic carbocycle or an optionally substituted saturated 3- to 10-membered nonaromatic heterocycle, $R^{X21}$ and $R^{X22}$, together with the carbon atom to which they are attached, may saturated $C_{3-10}$ nonaromatic carbocycle or an optionally substituted saturated 3- to 10-membered nonaromatic heterocycle, provided that $R^{X11}$ and $R^{X12}$ are not both hydrogen, and $R^{X21}$ and $R^{X22}$ are not both hydrogen.

(Item 24)

The compound or a stereoisomer thereof, or a salt or solvate thereof of any one of the preceding items, wherein the compound comprises a β-strand structure.

(Item 25)

The compound or a stereoisomer thereof, or a salt or solvate thereof of any one of the preceding items, wherein carbon attached to $R^{X11}$, $R^{X12}$, and $L^A$ is quaternary.

(Item 26)

The compound or a stereoisomer thereof, or a salt or solvate thereof of any one of the preceding items, wherein carbon attached to $R^{X21}$, $R^{X22}$, and $L^A$ is quaternary.

(Item 27)

The compound or a stereoisomer thereof, or a salt or solvate thereof of any one of the preceding items, wherein $R^{X11}$, $R^{X12}$, $R^{X21}$, and $R^{X22}$ are each independently methyl, methyl substituted with halogen, —OMe, methoxymethyl, t-butoxy, saturated $C_{3-12}$ carbocyclyl, —N(Me)$_2$, —$CH_2$—N(Me)$_2$, —$N^+$(Me)-(Boc), —$CH_2$—N(Me)-(Boc), —N(t-butyl)$_2$, —$N^+$(Me)$_3$, —$CH_2$—$N^+$(Me)$_3$, —$S^+$(Me)$_2$, —$S^+$(t-butyl)$_2$, —$S^+$(3,5-di-t-butylphenyl)$_2$, —$S^+$(3,5-di-trifluoromethylphenyl)$_2$, —$S^+$(2,6-dimethyl-4-t-butylphenyl)$_2$, —Si(i-butyl)(t-butyl)$_2$, —Si(t-butyl)$_3$, —$P^+$(Me)$_3$, —$P^+$(t-butyl)$_3$, —$P^+$(3,5-di-t-butylphenyl)$_3$, —$P^+$(3,5-di-trifluoromethylphenyl)$_3$, or —$P^+$(2,6-dimethyl-4-t-butylphenyl)$_3$, or $R^{X11}$ and $R^{X12}$, or $R^{X21}$ and $R^{X22}$, together with the carbon atom to which they are attached, form saturated $C_{3-12}$ carbocyclyl, saturated 4- to 6-membered heterocyclyl comprising an oxygen atom, or saturated 4- to 6-membered heterocyclyl comprising a nitrogen atom optionally substituted with 1 or 2 methyl groups or Boc groups.

(Item 28)

The compound or a stereoisomer thereof, or a salt or solvate thereof of any one of the preceding items, wherein $R^{X11}$, $R^{X12}$, $R^{X21}$, and $R^{X22}$ are each independently methyl substituted with halogen, —OMe, methoxymethyl, t-butoxy, saturated $C_{3-12}$ carbocyclyl, —N(Me)$_2$, —$CH_2$—N(Me)$_2$, —N(Me)-(Boc), —$CH_2$—N(Me)-(Boc), —N(t-butyl)$_2$, —$N^+$(Me)$_3$, —$CH_2$—$N^+$(Me)$_3$, —$S^+$(Me)$_2$, —$S^+$(t-butyl)$_2$, —$S^+$(3,5-di-t-butylphenyl)$_2$, —$S^+$(3,5-di-trifluoromethylphenyl)$_2$, —$S^+$(2,6-dimethyl-4-t-butylphenyl)$_2$, —Si(i-butyl)(t-butyl)$_2$, —Si(t-butyl)$_3$, —$P^+$(Me)$_3$, —$P^+$(t-butyl)$_3$, —$P^+$(3,5-di-t-butylphenyl)$_3$, —$P^+$(3,5-di-trifluoromethylphenyl)$_3$, or —$P^+$(2,6-dimethyl-4-t-butylphenyl)$_3$, or $R^{X11}$ and $R^{X12}$, or $R^{X21}$ and $R^{X22}$, together with the carbon atom to which they are attached, form saturated $C_{3-12}$ carbocyclyl, saturated 4- to 6-membered heterocyclyl comprising an oxygen atom, or saturated 4- to 6-membered heterocyclyl comprising a nitrogen atom optionally substituted with 1 or 2 methyl groups or Boc groups.

(Item 29)

The compound or a stereoisomer thereof, or a salt or solvate thereof of any one of the preceding items, wherein $R^{X11}$, $R^{X12}$, $R^{X21}$, and $R^{X22}$ are each independently methyl, monofluoromethyl, difluoromethyl, or trifluoromethyl, or $R^{X11}$ and $R^{X12}$, together with the carbon atom to which they are attached, may form cyclopropane, cyclobutane, cyclopentane, cyclohexane, 1-methyl substituted azetidine, 1-methyl substituted pyrrolidine, 1-methyl substituted piperidine, oxetane, tetrahydrofuran, or tetrahydropyran, and $R^{X21}$ and $R^{X22}$, together with the carbon atom to which they are attached, may form cyclopropane, cyclobutane, cyclopentane, cyclohexane, 1-methyl substituted azetidine, 1-methyl substituted pyrrolidine, 1-methyl substituted piperidine, oxetane, tetrahydrofuran, or tetrahydropyran.

(Item 30)

The compound or a stereoisomer thereof, or a salt or solvate thereof of any one of the preceding items, wherein $R^{X11}$, $R^{X12}$, $R^{X21}$, and $R^{X22}$ are each independently substituted alkyl.

(Item 31)

The compound or a stereoisomer thereof, or a salt or solvate thereof of any one of the preceding items, wherein $R^{X11}$, $R^{X12}$, $R^{X21}$, and $R^{X22}$ are each independentlya substituted with halogen.

(Item 32)

The compound or a stereoisomer thereof, or a salt or solvate thereof of any one of the preceding items, wherein $R^{X11}$, $R^{X12}$, $R^{X21}$, and $R^{X22}$ are each independently alkyl substituted with fluorine.

(Item 33)

The compound or a stereoisomer thereof, or a salt or solvate thereof of any one of the preceding items, wherein $R^{X11}$, $R^{X12}$, $R^{X21}$, and $R^{X22}$ are trifluoromethyl.

(Item 34)

The compound or a stereoisomer thereof, or a salt or solvate thereof of any one of the preceding items, wherein $L^A$ is each independently-(optionally substituted $C_{0-k}$ alkylene)-[optionally substituted alkenylene, optionally substituted alkynylene, optionally substituted heteroarylene, —N(alkyl)-, —$N^+$(H)(alkyl)-, or —$N^+$(alkyl)(alkyl)-]-(optionally substituted $C_{0-k}$ alkylene)-.

(Item 35)

The compound or a stereoisomer thereof, or a salt or solvate thereof of any one of items 23 to 37, wherein $L^A$ is each independently-optionally substituted $C_{0-k}$ alkylene-$C_{0-k}$ alkylene-optionally substituted $C_{0-k}$ substituted alkylene-, -optionally substituted $C_{0-k}$ alkylene-HC═CH-optionally substituted $C_{0-k}$ alkylene-, -optionally substituted $C_{0-k}$ alkylene-C≡C-optionally substituted $C_{0-k}$ alkylene-, -optionally substituted $C_{0-k}$ alkylene-(optionally substituted 5-membered heteroarylene)-optionally substituted $C_{0-k}$ alkylene-, -optionally substituted $C_{0-k}$ alkylene-N(alkyl)-optionally substituted $C_{0-k}$ alkylene-, -optionally substituted $C_{0-k}$ alkylene-$N^+$(H)(alkyl)-optionally substituted $C_{0-k}$ alkylene-, or -optionally substituted $C_{0-k}$ alkylene-$N^+$(alkyl)(alkyl)-optionally substituted $C_{0-k}$ alkylene-, wherein k is each independently an integer that is 5 or greater.

(Item 36)

The compound or a stereoisomer thereof, or a salt or solvate thereof of any one of the preceding items, wherein $L^A$ is each independently-optionally substituted $C_{0-5}$ alkylene-HC═CH-optionally substituted $C_{0-5}$ alkylene-, -optionally substituted $C_{0-5}$ alkylene-C≡C-optionally substituted $C_{0-6}$ alkylene-, -optionally substituted $C_{0-5}$ alkylene-(unsubstituted 5-membered heteroarylene)-optionally substituted $C_{0-5}$ alkylene-, -optionally substituted $C_{0-5}$ alkylene-N($C_{1-6}$ alkyl)- or substituted unsubstituted $C_{0-5}$ alkylene-, -optionally substituted $C_{0-5}$ alkylene-$N^+(H)(C_{1-6}$ alkyl)- or substituted unsubstituted $C_{0-5}$ alkylene-, or -optionally substituted $C_{0-5}$ alkylene-$N^+(C_{1-6}$ alkyl)($C_{1-6}$ alkyl)- or substituted unsubstituted $C_{0-5}$ alkylene-.

(Item 37)

The compound or a stereoisomer thereof, or a salt or solvate thereof of any one of the preceding items, wherein the unsubstituted 5-membered heteroarylene is triazole diyl.

(Item 38)

The compound or a stereoisomer thereof, or a salt or solvate thereof of any one of the preceding items, wherein the unsubstituted 5-membered heteroarylene is 1, 2, 3-triazole-1,4-diyl or 1, 2, 3-triazole-1,5-diyl.

(Item 39)

The compound or a stereoisomer thereof, or a salt or solvate thereof of any one of the preceding items, wherein at least one of $R^{1a}$, $R^{1b}$, $R^2$, $R^4$, $R^6$, $R^{X11}$, $R^{X12}$, $R^{X22}$, $R^{X21}$, $R^{X31}$, $R^{X32}$, and $L^A$ comprises —$P^+$ (optionally substituted alkyl, optionally substituted heteroalkyl, optionally substituted aryl, or optionally substituted heteroaryl)$_3$, —$S^+$ (optionally substituted alkyl, optionally substituted heteroalkyl, optionally substituted aryl, or optionally substituted heteroaryl)$_2$, or —Si (optionally substituted alkyl, optionally substituted heteroalkyl, optionally substituted aryl, or optionally substituted heteroaryl)$_3$.

(Item 40)

The compound or a stereoisomer thereof, or a salt or solvate thereof of any one of the preceding items, wherein the optionally substituted alkyl, optionally substituted aryl, or optionally substituted heteroaryl of the —$P^+$(optionally substituted alkyl, optionally substituted aryl, optionally substituted heteroaryl)$_3$, —$S_+$(optionally or substituted alkyl, optionally substituted aryl, or optionally substituted heteroaryl)$_2$, and —Si(optionally substituted alkyl, optionally substituted aryl, or optionally substituted heteroaryl)$_4$ is substituted with one or more substituents selected from the group consisting of alkyloxy, aryloxy, hydroxy, carboxy, an optionally substituted amino group, optionally substituted-C(═O)$NH_2$, alkylthio, arylthio, optionally substituted —S(═O)$_2$-alkyl, and optionally substituted —S(═O)$_2$-aryl.

(Item 41)

The compound or a stereoisomer thereof, or a salt or solvate thereof of any one of the preceding items, wherein the optionally substituted alkyl, optionally substituted aryl, or optionally substituted heteroaryl of the —$P^+$(optionally substituted alkyl, optionally substituted aryl, or optionally substituted heteroaryl)$_3$, —$S^+$(optionally substituted alkyl, optionally substituted aryl, or optionally substituted heteroaryl)$_2$, and —Si(optionally substituted alkyl, optionally substituted aryl, or optionally substituted heteroaryl)$_4$ is substituted with an amino group disubstituted with alkyl or aryl.

(Item 41A)

The compound or a stereoisomer thereof, or a salt or solvate thereof of any one of the preceding items, which has an amino acid sequence of amino acid positions 0 to 8 or amino acid positions 0 to 9 set forth in the following table:

TABLE A

| PI3K - 4-6 (Ac) | | PI3K - 4-6 (FITC) | |
|---|---|---|---|
| Position | Amino Acid | Position | Amino Acid |
| 0 | R | 0 | R |
| 1 | H | 1 | H |
| 2 | β-DTFM4 | 2 | β-DTFM4 |
| 3 | K | 3 | K |
| 4 | β-DTFM6 | 4 | β-DTFM6 |
| 5 | F | 5 | F |
| 6 | I | 6 | I |
| 7 | W | 7 | W |
| 8 | Ac | 8 | β-Ala |
| | | 9 | FITC |

wherein a double bond moiety of β-DM4 and β-DM6 is crosslinked, wherein the amino acids in Table A are denoted by a one letter code or a three letter code, and DM4, DM6, and FITC are abbreviations for DiMethyl4, DiMethyl6, and FluoresceinIsoThioCyanate, respectively.

(Item 42)

A composition for creating an aggregate of a peptide and a protein, or for use as an aggregation initiator, comprising the bridge peptide of any one of the preceding items, the composition of any one of the preceding items, the compound moiety of any one of the preceding items, or the compound or a stereoisomer thereof, or a salt or solvate thereof of any one of the preceding items.

(Item 43A)

A composition for inhibiting an interaction related to a biopolymer, which is capable of inhibition with a β-strand structure, comprising the bridge peptide of any one of the preceding items, the composition of any one of the preceding items, the compound moiety of any one of the preceding items, or the compound or a stereoisomer thereof, or a salt or solvate thereof of any one of the preceding items.

(Item 43B)

The composition of any one of the preceding items, wherein the interaction between biopolymers comprises Protein-Protein Interaction (PPI).

(Item 44)

A composition for permeation through a cell membrane, comprising the bridge peptide of any one of the preceding items, the composition of any one of the preceding items, the compound moiety of any one of the preceding items, or the compound or a stereoisomer thereof, or a salt or solvate thereof of any one of the preceding items.

(Item 45)

A pharmaceutical composition comprising the bridge peptide of any one of the preceding items, the composition of any one of the preceding items, the compound moiety of any one of the preceding items, or the compound or a stereoisomer thereof, or a salt or solvate thereof of any one of the preceding items.

(Item 46)

A composition for use as a peptidomimetic, comprising the bridge peptide of any one of the preceding items, the composition of any one of the preceding items, the compound moiety of any one of the preceding items, or the compound or a stereoisomer thereof, or a salt or solvate thereof of any one of the preceding items.

(Item 46A)

The composition of any one of items 42 to 46, further comprising one or more features of any one or more of the preceding or following items.

(Item 47)

An amino acid or a stereoisomer thereof, or a salt or solvate thereof, selected from artificial amino acid X described in paragraph (from [Chemical Formula 226] to [Chemical Formula 305]) and other artificial amino acids described herein.

(Item 47A)

An amino acid or a stereoisomer thereof, or a salt or solvate thereof, selected from artificial amino acid X described in paragraph (from [Chemical Formula 226] to [Chemical Formula 305]).

(Item 48)

A composition for use as a raw material for the manufacture of a bridge peptide, comprising an amino acid, or a stereoisomer thereof, or a salt or solvate thereof having a structure selected from the group consisting of artificial amino acid X described in paragraph (from [Chemical Formula 226] to [Chemical Formula 305]) and other artificial amino acids described herein.

(Item 48A)

A composition for use as a raw material for the manufacture of a bridge peptide, comprising an amino acid, or a stereoisomer thereof, or a salt or solvate thereof having a structure selected from artificial amino acid X described in paragraph (from [Chemical Formula 226] to [Chemical Formula 305]).

(Item 49)

The composition of any one of the preceding items, wherein position β of the bridge peptide is tertiary or quaternary.

(Item 50)

The composition of any one of the preceding items, wherein the bridge peptide is the bridge peptide, compound or a stereoisomer thereof, or a salt or solvate thereof of any one of the preceding items.

(Item 51)

An amino acid having a structure selected from the group consisting of compounds of artificial amino acid X described in paragraph [0305] (from [Chemical Formula 226] to [Chemical Formula 305]).

(Item 52)

A composition for use as a raw material for the manufacture of a bridge peptide, comprising an amino acid having a structure selected from the group consisting of artificial amino acid X described in paragraph (from [Chemical Formula 226] to [Chemical Formula 305]).

(Item 53)

The composition of any one of the preceding items, wherein position β of the bridge peptide is tertiary or quaternary.

(Item 54)

The composition of any one of the preceding items, wherein the bridge peptide is the bridge peptide, compound or a stereoisomer thereof, or a salt or solvate thereof of any one of the preceding items.

(Item A1)

A method for crosslinking a peptide moiety comprising a β-strand structure, the method comprising generating a bridge peptide using a bridge peptide material that comprises an amino acid structure or forms an amino acid structure after synthesis, wherein position β in the amino acid structure has a tertiary or quaternary structure.

(Item A2)

A method of creating an aggregate of a peptide and a protein, or for use as an aggregation initiator, comprising creating an aggregate of a peptide and a protein by using the bridge peptide of any one of the preceding items, the composition of any one of the preceding items, the compound moiety of any one of the preceding items, or the compound or a stereoisomer thereof, or a salt or solvate thereof of any one of the preceding items, or preparing an aggregate as an aggregation initiator.

(Item A3A)

A method for inhibiting an interaction related to a biopolymer, which is capable of inhibition with a β-strand structure, comprising contacting a subject of inhibition with a β-strand structure with an effective amount of the bridge peptide of any one of the preceding items, the composition of any one of the preceding items, the compound moiety of any one of the preceding items, or the compound or a stereoisomer thereof, or a salt or solvate thereof of any one of the preceding items.

(Item A3B)

The method of any one of the preceding items, wherein the interaction related to a biopolymer comprises Protein-Protein Interaction (PPI).

(Item A4)

A composition for permeation through a cell membrane, comprising the bridge peptide of any one of the preceding items, the composition of any one of the preceding items, the compound moiety of any one of the preceding items, or the compound or a stereoisomer thereof, or a salt or solvate thereof of any one of the preceding items.

(Item A5)

A method for treating or preventing a disease, disorder, or symptom of a subject, comprising administering to the subject an effective amount of the bridge peptide of any one of the preceding items, the composition of any one of the preceding items, the compound moiety of any one of the preceding items, or the compound or a stereoisomer thereof, or a salt or solvate thereof of any one of the preceding items.

(Item A6)

A method for use as a peptidomimetic, comprising using the bridge peptide of any one of the preceding items, the composition of any one of the preceding items, the compound moiety of any one of the preceding items, or the compound or a stereoisomer thereof, or a salt or solvate thereof of any one of the preceding items as a peptidomimetic.

(Item A7)

The method of any one of items A1 to A6, further comprising one or more features of any one or more of the preceding or following items.

(Item B1)

Use of a bridge peptide material that comprises an amino acid structure or forms an amino acid structure after synthesis, wherein position β in the amino acid structure has a tertiary or quaternary structure, for the manufacture of a medicament for crosslinking a peptide moiety comprising a β-strand structure.

(Item B2)

Use of the bridge peptide of any one of the preceding items, the composition of any one of the preceding items, the compound moiety of any one of the preceding items, or the compound or a stereoisomer thereof, or a salt or solvate thereof of any one of the preceding items, for creating an aggregate of a peptide and a protein, or for the manufacture of a medicament from use as an aggregation initiator.

(Item B3A)

Use of the bridge peptide of any one of the preceding items, the composition of any one of the preceding items, the compound moiety of any one of the preceding items, or the compound or a stereoisomer thereof, or a salt or solvate thereof of any one of the preceding items, for the manufacture of a medicament by inhibiting an interaction related to a biopolymer, which is capable of inhibition with a β-strand structure.

(Item B3B)

The use of any one of the preceding items, wherein the interaction related to a biopolymer comprises Protein-Protein Interaction (PPI).

(Item B4)

Use of the bridge peptide of any one of the preceding items, the composition of any one of the preceding items, the compound moiety of any one of the preceding items, or the compound or a stereoisomer thereof, or a salt or solvate thereof of any one of the preceding items in the manufacture of a medicament for permeation through a cell membrane.

(Item B5)

Use of the bridge peptide of any one of the preceding items, the composition of any one of the preceding items, the compound moiety of any one of the preceding items, or the compound or a stereoisomer thereof, or a salt or solvate thereof of any one of the preceding for treating or preventing a disease, disorder, or symptom of a subject.

(Item B6)

Use of the bridge peptide of any one of the preceding items, the composition of any one of the preceding items, the compound moiety of any one of the preceding items, or the compound or a stereoisomer thereof, or a salt or solvate thereof of any one of the preceding items in the manufacture of a medicament with a peptidomimetic.

(Item B7)

The use of any one of items B1 to B6, further comprising one or more features of any one or more of the preceding or following items.

(Item C1)

A bridge peptide material that comprises an amino acid structure or forms an amino acid structure after synthesis, wherein position β in the amino acid structure has a tertiary or quaternary structure, wherein the material is for cross-linking a peptide comprising moiety a β-strand structure.

(Item C2)

The bridge peptide of any one of the preceding items, the composition of any one of the preceding items, the compound moiety of any one of the preceding items, or the compound or a stereoisomer thereof, or a salt or solvate thereof of any one of the preceding items, for creating an aggregate of a peptide and a protein, or for use as an aggregation initiator.

(Item C3)

The bridge peptide of any one of the preceding items, the composition of any one of the preceding items, the compound moiety of any one of the preceding items, or the compound or a stereoisomer thereof, or a salt or solvate thereof of any one of the preceding items, for inhibiting an interaction related to a biopolymer, which is capable of inhibition with a β-strand structure.

(Item C3A)

The compound or a stereoisomer thereof, or a salt or solvate thereof of any one of the preceding items, wherein the interaction related to a biopolymer comprises Protein-Protein Interaction (PPI).

(Item C4)

The bridge peptide of any one of the preceding items, the composition of any one of the preceding items, the compound moiety of any one of the preceding items, or the compound or a stereoisomer thereof, or a salt or solvate thereof of any one of the preceding items, for permeation through a cell membrane.

(Item C5)

The bridge peptide of any one of the preceding items, the composition of any one of the preceding items, the compound moiety of any one of the preceding items, or the compound or a stereoisomer thereof, or a salt or solvate thereof of any one of the preceding items, for treating or preventing a disease, disorder, or symptom of a subject.

(Item C6)

The bridge peptide of any one of the preceding items, the composition of any one of the preceding items, the compound moiety of any one of the preceding items, or the compound or a stereoisomer thereof, or a salt or solvate thereof of any one of the preceding items, for use as a peptidomimetic.

(Item C7)

The bridge peptide, composition, compound moiety, or compound or a stereoisomer thereof, or a salt or solvate thereof of any one of items C1 to C6, further comprising one or more features of any one or more of the preceding or following items.

The present disclosure is intended so that one or more of the aforementioned features can be provided not only as the explicitly disclosed combinations, but also as other combinations thereof. Further embodiments and advantages of the present disclosure are recognized by those skilled in the art upon reading and understanding the following detailed description as needed.

Advantageous Effects of Invention

The present disclosure can stabilize the β-strand structure of a polypeptide, and provides a peptide in which the β-strand structure can serve a critical role in an important biological function (e.g., interaction with a membrane, formation of an aggregate, or initiation of an aggregation reaction).

BRIEF DESCRIPTION OF DRAWINGS

FIG. 1-2 shows the experimental CD spectra of the bridge peptides of the present disclosure. BP stands for bridge peptide. BP5-6 1st is a bridge peptide composed of β-DM5 (N-terminal side) and β-DM6 (C-terminal side), and was isolated as a first_peak in HPLC purification. BP5-6 2nd is a bridge peptide composed of β-DM5 (N-terminal side) and β-DM6 (C-terminal side), and was isolated as a second_peak in HPLC purification. BP6-4 is a bridge peptide composed of β-DM6 (N-terminal side) and β-DM4 (C-terminal side). BP6-5 is a bridge peptide composed of β-DM6 (N-terminal side) and β-DM5 (C-terminal side). BP6-6 is a bridge peptide composed of β-DM6 (N-terminal side) and β-DM6 (C-terminal side).

FIG. 2 shows the experimental CD spectra of the bridge peptides of the present disclosure. WT stands for wild type. BP4-6 1st is a bridge peptide composed of β-DM4 (N-terminal side) and β-DM6 (C-terminal side), and was isolated as a first_peak in HPLC purification. BP5-6 1st is a bridge peptide composed of β-DM5 (N-terminal side) and β-DM6

(C-terminal side), and was isolated as a first_peak in HPLC purification. BP6-6 is a bridge peptide composed of β-DM6 (N-terminal side) and β-DM6 (C-terminal side).

Figure 3:
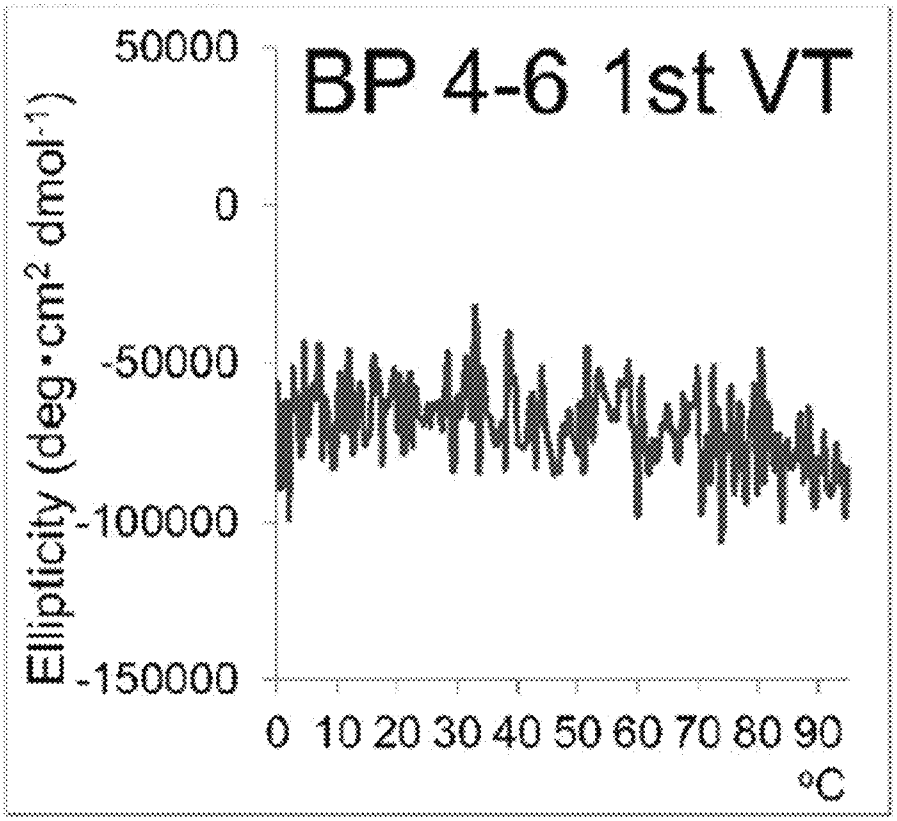

FIG. 3 shows the results of an experiment to evaluate the stability of the bridge peptides of the present disclosure to thermal denaturation.

Figure 4:
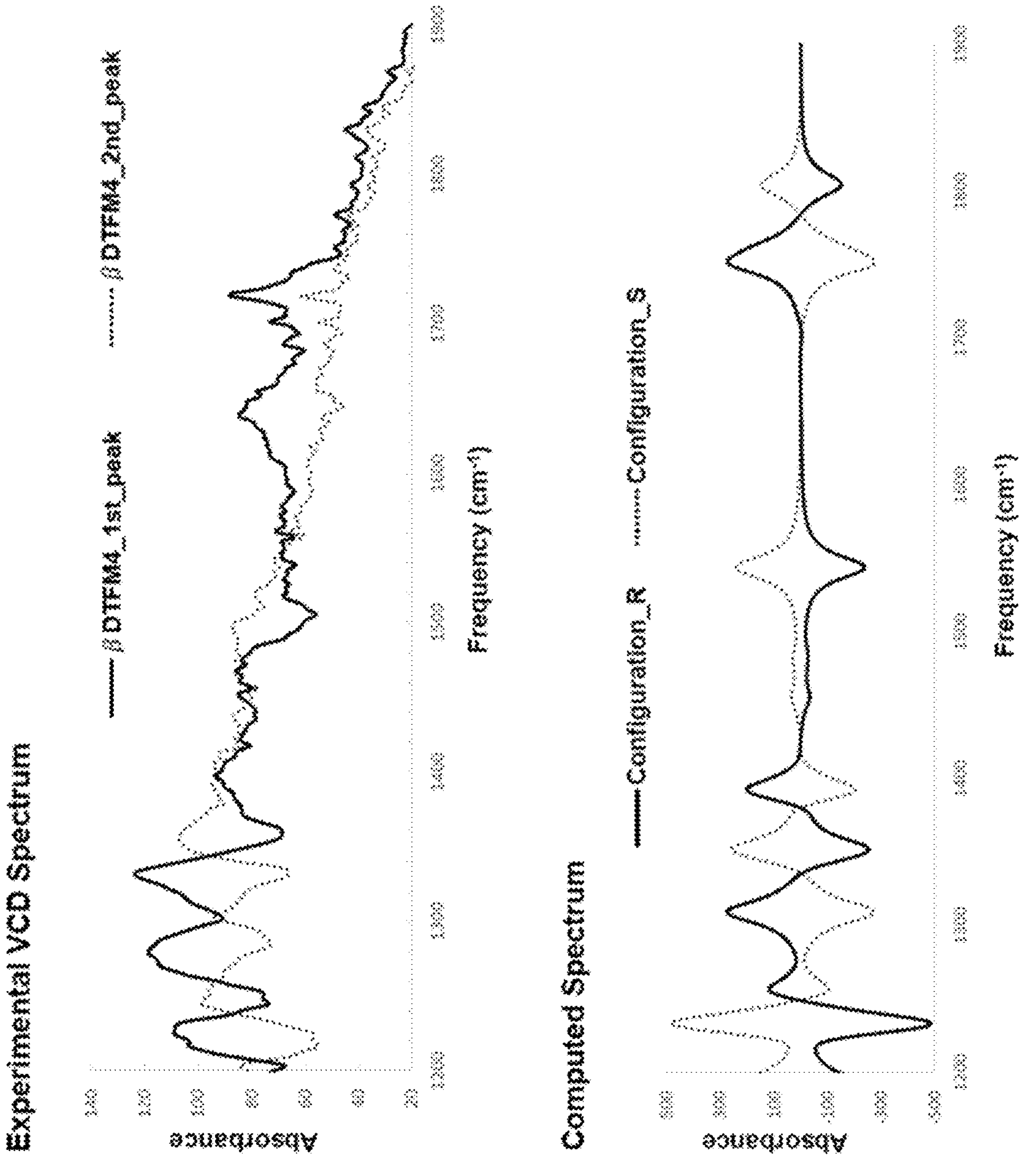

FIG. 4 shows experimental VCD spectra (upper) and theoretical VCD spectra (lower) of βDTFM4_1st_peak and βDTFM4_2nd_peak.

Figure 5:
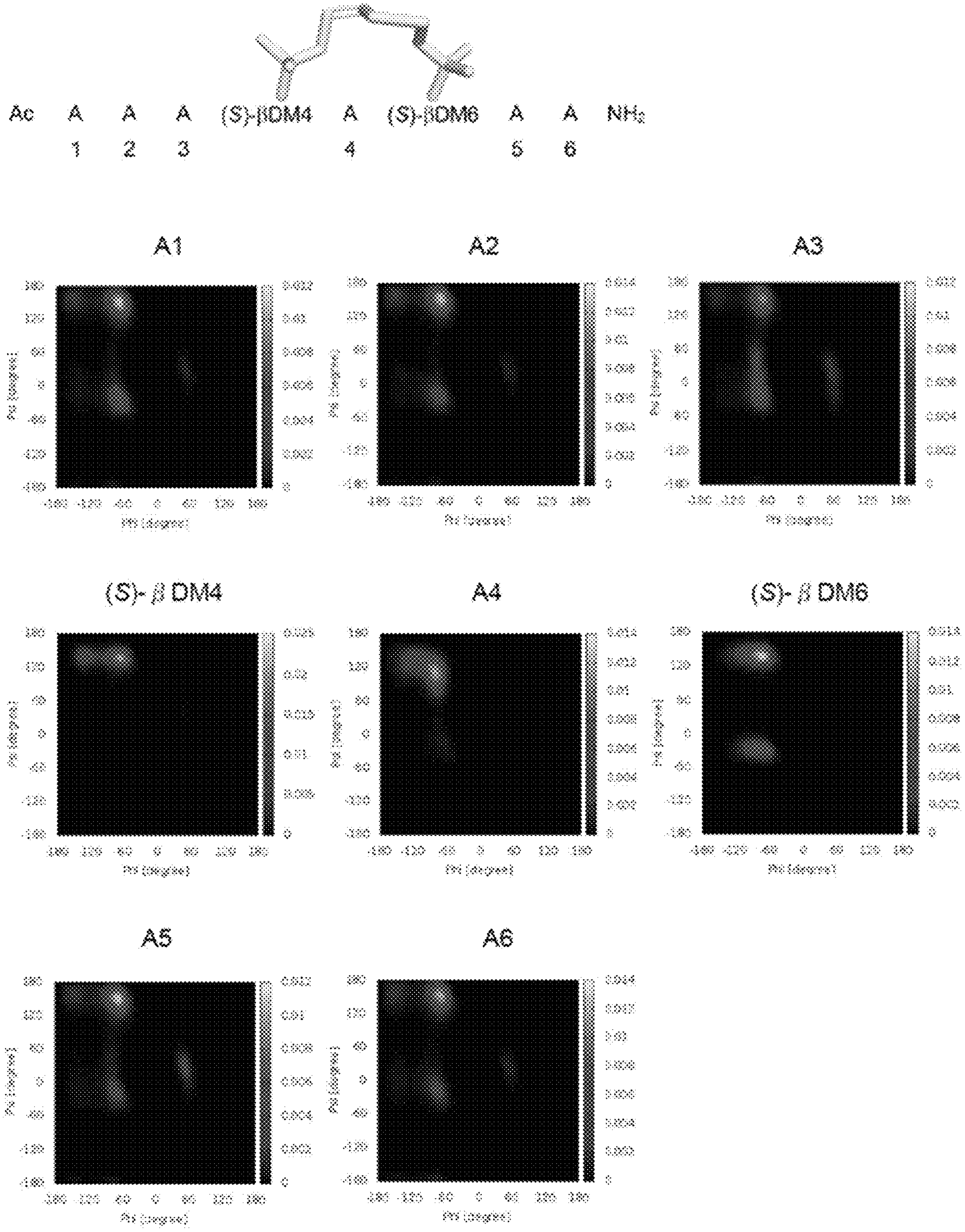

FIG. 5 shows the peptide sequence and the results of Ramachandran plot analysis of BP 4-6Z_Ala.

Figure 6:
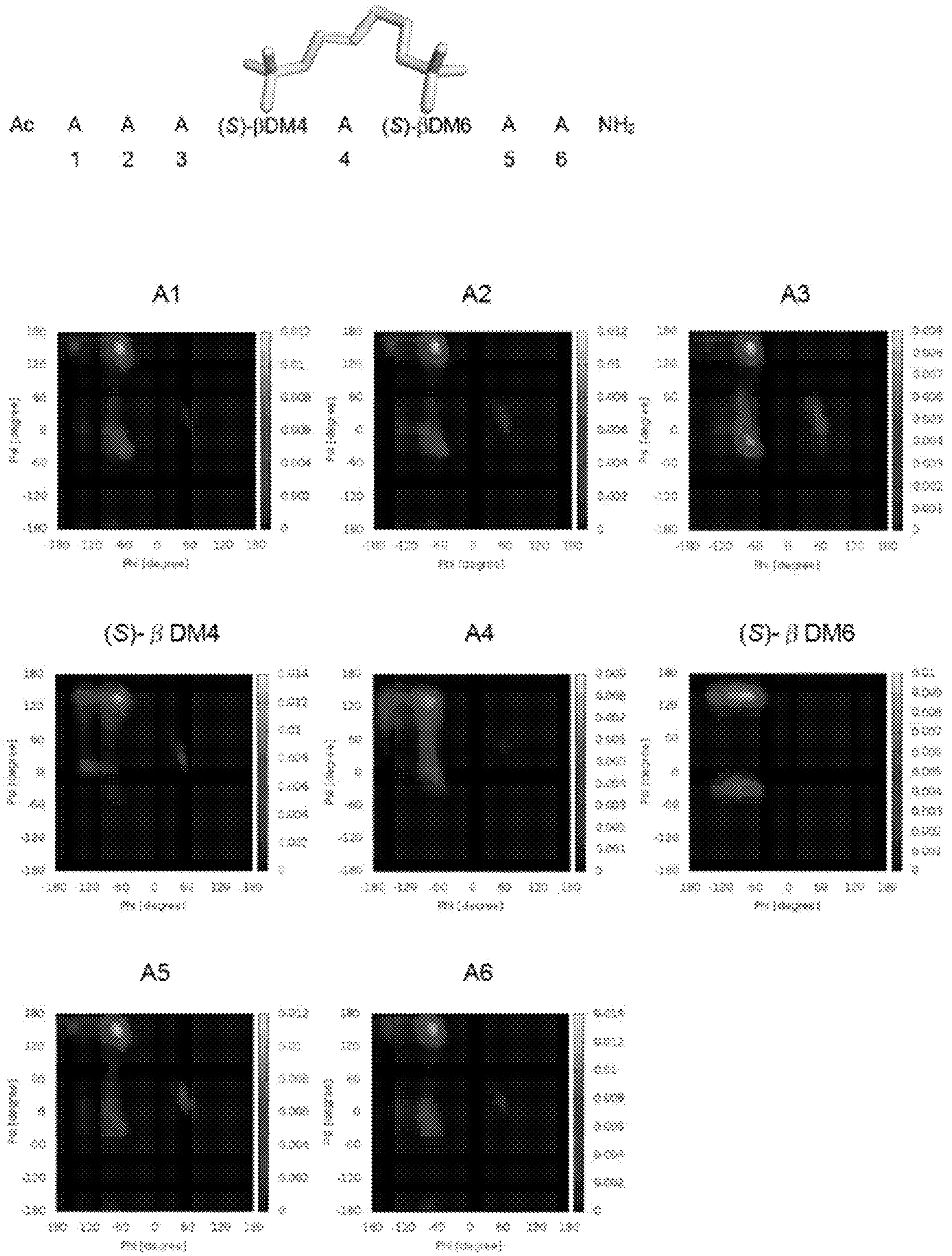

FIG. 6 shows the peptide sequence and the results of Ramachandran plot analysis of BP 4-6E_Ala.

Figure 7:
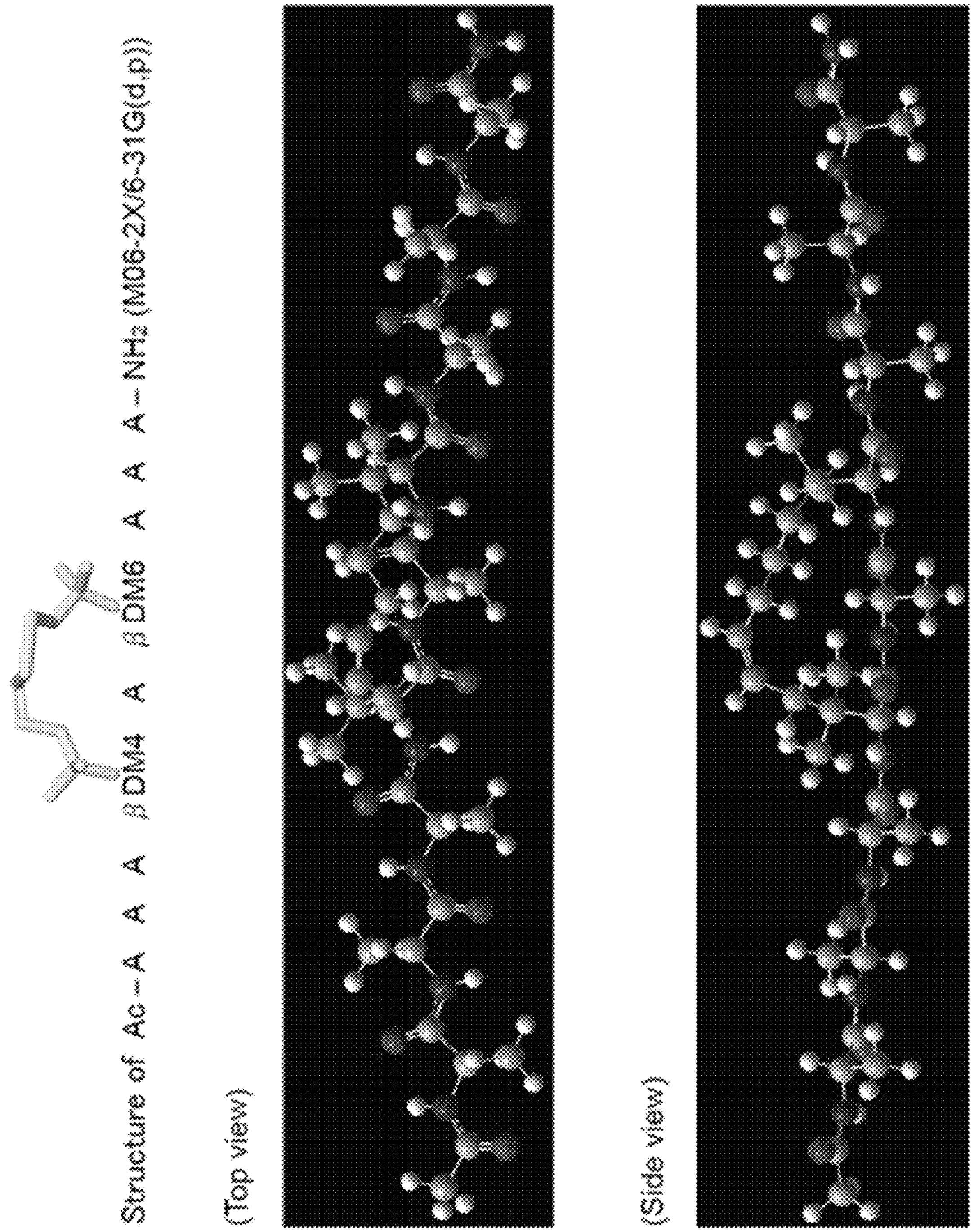

FIG. 7 shows the 3D structure resulted from geometry optimization calculation of one of the bridge peptides containing an olefin in the bridge portion.

Figure 8:
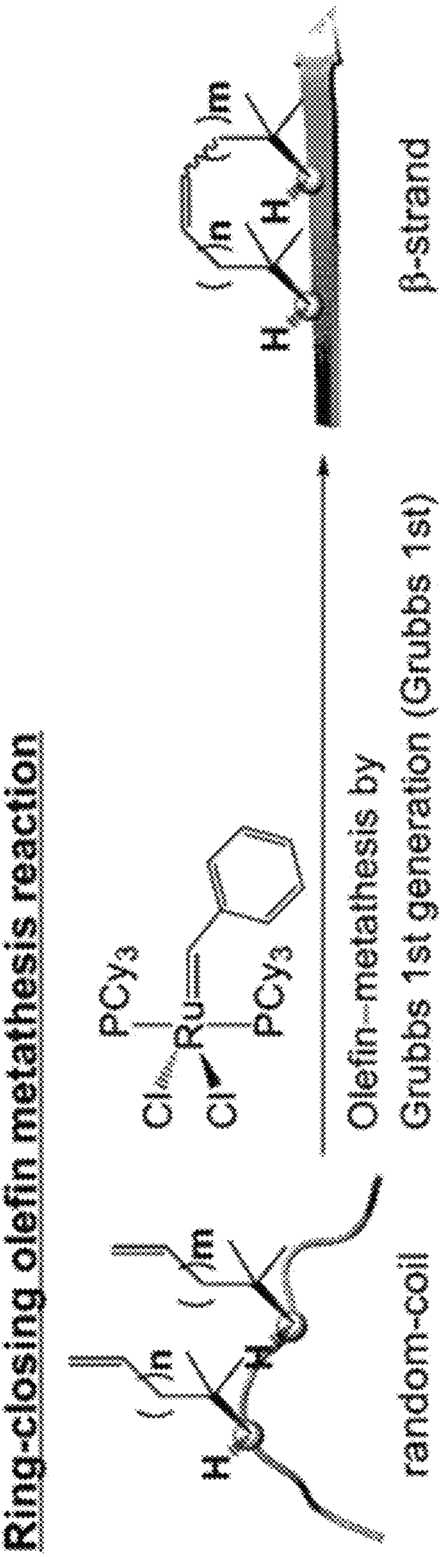

FIG. 8 shows an example of the olefin metathesis reaction.

Figure 9:
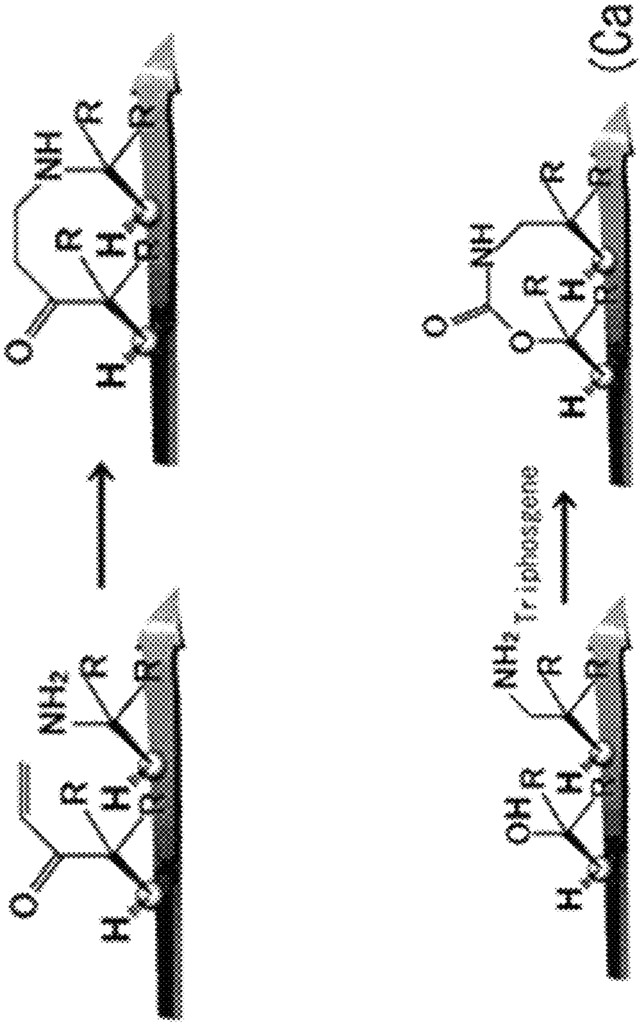

FIG. 9 shows examples of the carbon-carbon bond or carbon-heteroatom bond formations.

Figure 10:
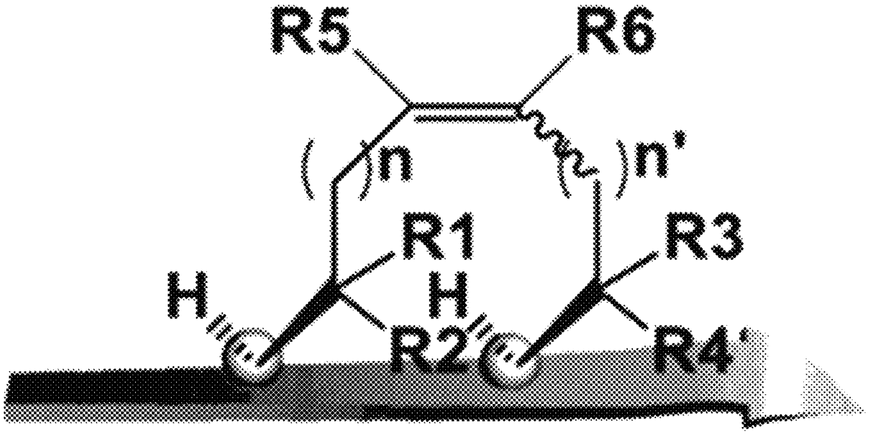

FIG. 10 shows an example of bridge formation by olefin metathesis.

Figure 11:
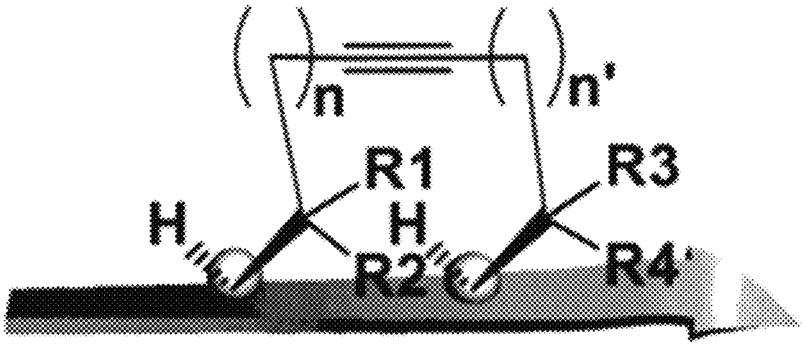

FIG. 11 shows an example of bridge formation by alkyne metathesis.

Figure 12:
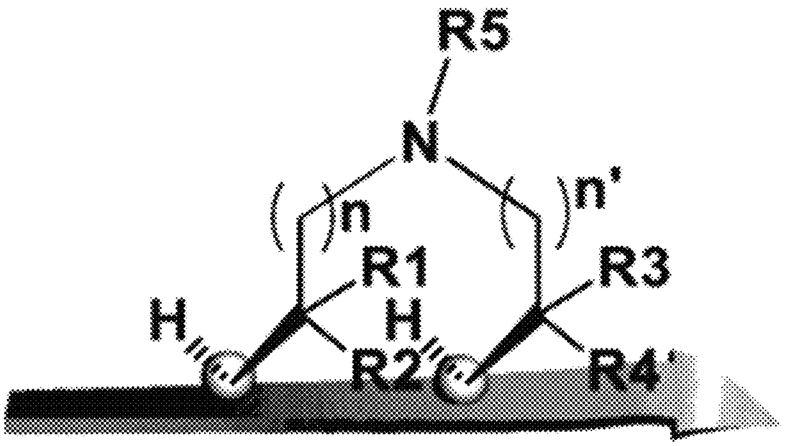

FIG. 12 shows an example of bridge formation by reductive amination.

Figure 13:
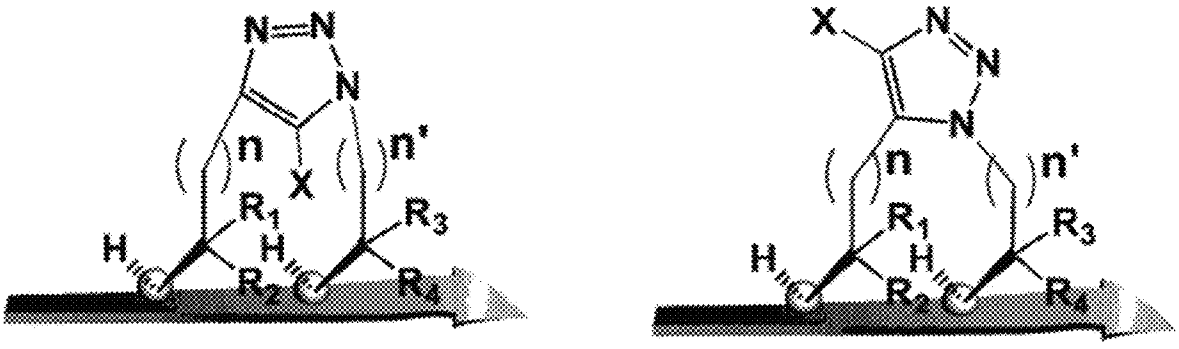

FIG. 13 shows an example of bridge formation by click chemistry.

Figure 14:
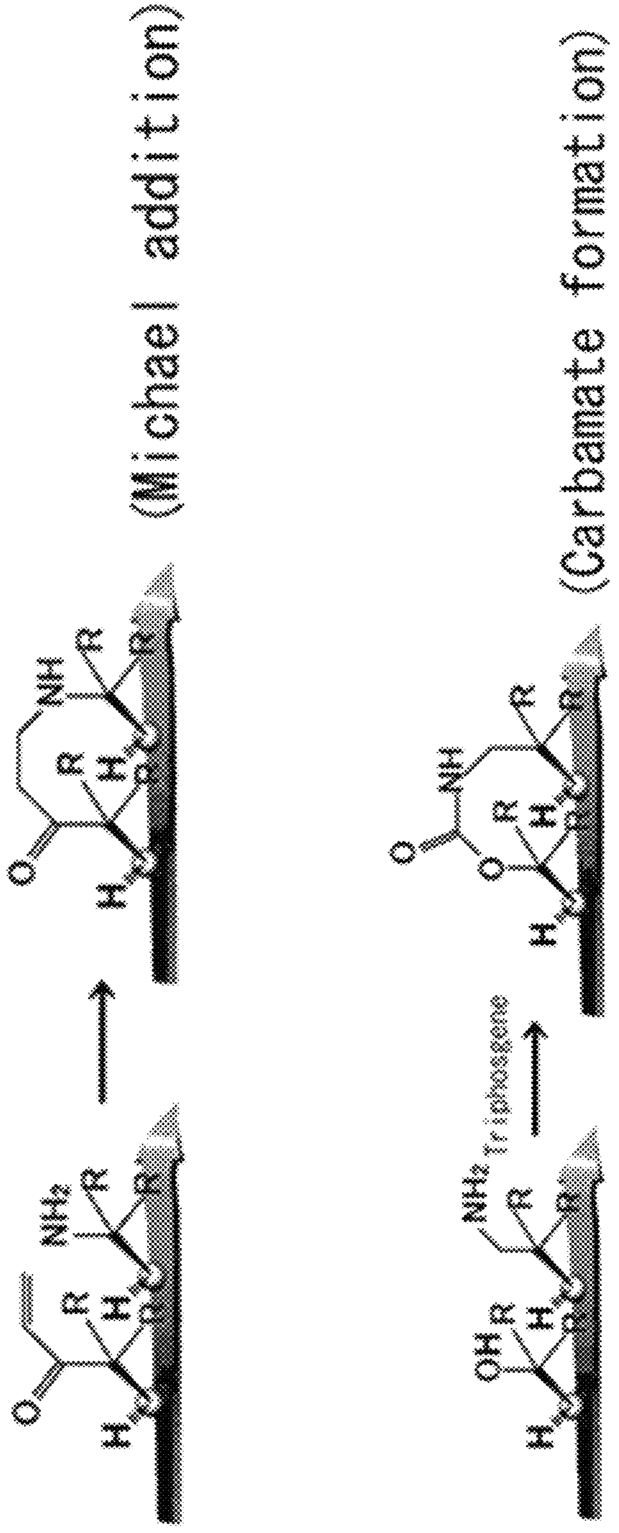

FIG. 14 shows an example of bridge formation by reaction by Ru(II) catalyst.

Figure 15:
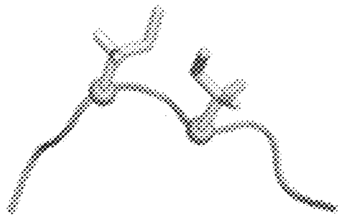
Figure 15:
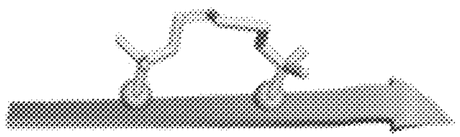

FIG. 15 shows results of the amino acid sequences of the peptides and the identification by mass spectrometry.

FIG. 16 shows results of evaluation of cell membrane permeability by FACS.

DESCRIPTION OF EMBODIMENTS

The present disclosure is explained in more detail hereinafter.

Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present disclosure pertains. In case of a contradiction, the present specification (including the definitions) takes precedence.

The terms and common technologies used in the present disclosure are first described.

Definitions

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

The term "group" refers to a monovalent group, unless specifically noted otherwise. Examples of non-monovalent groups include alkylene group (divalent) and the like. In the following descriptions of substituents or the like, the term "group" may be omitted.

Unless specifically noted otherwise, the number of substituents in a group defined as "optionally substituted" or "substituted" is not particularly limited herein, as long as a substitution is possible. The number of substituents is one or multiple substituents. Moreover, unless noted otherwise, the description for each substituent is also applicable when the substituent is a part of or a substituent of another substituent. "Optionally substituted" is interchangeably used with "unsubstituted or substituted".

If a certain group is optionally substituted, the group is optionally substituted with a monovalent substituent or a divalent substituent. Examples of monovalent substituents include, but are not limited to, alkyl, alkenyl, alkynyl and other aliphatic groups, heteroaliphatic groups, cycloalkyl, cycloalkenyl, cycloalkynyl, and other carbocyclyl, heterocyclyl, aryl, heteroaryl, hydroxy, amino, cyano, thiocyano, nitro, halogen (F, Cl, Br, I, and the like), carboxy, sulfonyl, alkylsulfonyl, arylsulfonyl, heteroarylsulfonyl, carbamoyl, tri-substituted Si (e.g., substituted with three substituents selected from the group consisting of alkyl, aryl, and heteroaryl), hydroxyl protecting groups, amino protecting groups, carbon atom substituents, monovalent groups described herein, and the like. Examples of divalent substituents include, but are not limited to, oxo(=O), imino (=NH), substituted imino(=N—$R^{bb}$), =S, =NN($R^{bb}$)$_2$, =NN$R^{bb}$(=O)$R^{aa}$, =NN$R^{bb}$C(=O)O$R^{aa}$, =NN$R^{bb}$S(=O)2$R^{aa}$, =NO$R^{cc}$, divalent substituents described herein (wherein $R^{aa}$, $R^{bb}$, and $R^{cc}$ are as defined herein), and the like.

Compounds, amino acids, and polypeptides described herein can comprise one or more asymmetric centers, and thus can exist in various isomeric forms, e.g., enantiomers and/or diastereomers. For example, the compounds, amino acids, and polypeptides described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., *Tetrahedron* 33:2725 (1977); Eliel, E. L. Stereochemistry of Carbon Compounds (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The present disclosure additionally encompasses compounds, amino acids, and polypeptides described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, substituent names which end in the suffix "-ene" refer to a biradical derived from the removal of an additional hydrogen atom from monoradical group as defined herein. Thus, for example, the monoradical alkyl, as defined herein, is the biradical alkylene upon removal of an additional hydrogen atom. Likewise, alkenyl is alkenylene; alkynyl is alkynylene; heteroalkyl is heteroalkylene; heteroalkenyl is heteroalkenylene; heteroalkynyl is heteroalkynylene; carbocyclyl is carbocyclylene; heterocyclyl is heterocyclylene; aryl is arylene; and heteroaryl is heteroarylene.

As used herein, the term "$C_{0-k}$ alkylene" refers to alkylene with 0 to k carbon. $C_0$ alkylene refers to a single bond. k is an integer that is 1 or greater, 2 or greater, 3 or greater, 4 or greater, 5 or greater, or 6 or greater. In a certain embodiment, k is 1, 2, 3, 4, 5, 6, 7, 8, 9, 10, 11, 12, 13, 14, 15, 16, 17, 18, 19, 20, or an integer that is greater.

The term "aliphatic", as used herein, includes non-aromatic and acyclic, saturated and unsaturated, straight chain (i.e., unbranched) and branched hydrocarbons. The term "aliphatic group" refers to a group resulting from the removal of one hydrogen from aforementioned aliphatic hydrocarbon. In some embodiments, the aliphatic group may be substituted by one or more substituents and/or functional groups. As one of ordinary skill in the art will clearly recognize, "aliphatic" is intended herein to include alkyl, alkenyl, and alkynyl.

As used herein, the term "heteroaliphatic" refers to an aliphatic moiety comprising one or two or more oxygen, sulfur, nitrogen, phosphorous, or silicon atoms in place of, for example, a carbon atom. The heteroaliphatic moiety can be branched or unbranched, but is nonaromatic and acyclic. The term "heteroaliphatic group" refers to a group generated by removing one hydrogen from the heteroaliphatic. In a certain embodiment, a heteroaliphatic group is independently and optionally substituted with one or two or more substituents. Examples of the substituent include, but are not limited to, an aliphatic group, a heteroaliphatic group, carbocyclyl, heterocyclyl, aryl, heteroaryl, arylalkyl, heteroarylalkyl, alkoxy, aryloxy, heteroalkoxy, heteroaryloxy, alkylthio, arylthio, heteroalkylthio, heteroarylthio, —F, —Cl, —Br, —I, —OH, —$NO_2$, —CN, —$CF_3$, —$CH_2CF_3$, —$CHCl_2$, —$CH_2OH$, —$CH_2CH_2OH$, —$CH_2NH_2$, —$CH_2SO_2CH_3$, —C(O)$R_{xa}$, —$CO_2(R_{xa})$, —CON$(R_{xa})_2$, —OC(O)$R_{xa}$, —$OCO_2R_{xa}$, —OCON$(R_{xa})_2$, —N$(R_{xa})_2$, —$S(O)_2R_{xa}$, and —$NR_{xa}$(CO)$R_{xa}$. $R_{xa}$ each independently includes, but is not limited to, an aliphatic group, a heteroaliphatic group, carbocyclyl, heterocyclyl, aryl, heteroaryl, arylalkyl, or heteroarylalkyl. The aliphatic substituent, heteroaliphatic substituent, arylalkyl substituent, carbocyclyl substituent, heterocyclyl substituent, and heteroarylalkyl substituent described above and described herein are further optionally substituted. The aryl substituent and heteroaryl substituent described above and described herein are optionally substituted, or unsubstituted. Additional examples of generally applicable substituents are provided in a specific embodiments shown in the examples described herein.

As used herein, "alkyl" refers to a radical of a straight-chain or branched saturated hydrocarbon group having from 1 to 30 carbon atoms ("$C_{1-30}$ alkyl"). In some embodiments, an alkyl group has 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

"Perhaloalkyl" is a substituted alkyl group as defined herein, wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to a radical of a straight-chain or branched saturated hydrocarbon group having from 1 to 30 carbon atoms, and which further comprises 1-10 heteroatoms independently selected from oxygen, nitrogen, and sulfur included within the parent chain ("$C_{1-30}$ heteroalkyl"). In some embodiments, a heteroalkyl group has 1 to 20 carbon atoms and 1-10 heteroatoms, inclusive ("$C_{1-20}$ heteroalkyl"). In some embodiments, a heteroalkyl group has 1 to 10 carbon atoms and 1-10 heteroatoms, inclusive ("$C_{1-10}$ heteroalkyl"). In some embodiments, a heteroalkyl group has 1 to 9 carbon atoms and 1-6 heteroatoms, inclusive ("$C_{1-9}$ heteroalkyl"). In some embodiments, a heteroalkyl group has 1 to 8 carbon atoms and 1-5 heteroatoms, inclusive ("$C_{1-8}$ heteroalkyl"). In some embodiments, a heteroalkyl group has 1 to 7 carbon atoms, and 1-4 heteroatoms, inclusive ("$C_{1-7}$ heteroalkyl"). In some embodiments, a heteroalkyl group has 1 to 6 carbon atoms and 1-3 heteroatoms, inclusive ("$C_{1-6}$ heteroalkyl"). In some embodiments, a heteroalkyl group has 1 to 5 carbon atoms and 1-2 heteroatoms, inclusive ("$C_{1-5}$ heteroalkyl"). In some embodiments, a heteroalkyl group has 1 to 4 carbon atoms and 1-2 heteroatoms, inclusive ("$C_{1-4}$ heteroalkyl"). In some embodiments, a heteroalkyl group has 1 to 3 carbon atoms and 1-2 heteroatoms, inclusive ("$C_{1-3}$ heteroalkyl"). In some embodiments, a heteroalkyl group has 1 to 2 carbon atoms and 1 heteroatom, inclusive ("$C_{1-2}$ heteroalkyl"). In some embodiments, a heteroalkyl group has 1 carbon atom and 1 ("$C_1$ heteroalkyl"). In some heteroatom, inclusive embodiments, a heteroalkyl group has 2 to 6 carbon atoms and inclusive ("$C_{2-6}$ heteroalkyl"). Unless 1-3 heteroatoms, otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted $C_{1-10}$ alkyl. In certain embodiments, the heteroalkyl group is a substituted $C_{1-10}$ heteroalkyl.

As used herein, "alkenyl" refers to a radical of a straight-chain or branched hydrocarbon group having from 2 to 30 carbon atoms, one or more carbon-carbon double bonds, and no triple bonds ("$C_{2-30}$ alkenyl"). In some embodiments, an alkenyl group has 2 to 20 carbon atoms ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 3-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), 3-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to a radical of a straight-chain or branched hydrocarbon group having from 2 to 30 carbon atoms, one or more carbon-carbon double bonds, no triple bonds, and which further comprises 1-10 heteroatoms independently selected from oxygen, nitrogen, and sulfur included within the parent chain ("$C_{2-30}$ heteroalkenyl"). In some embodiments, a heteroalkenyl group has 2 to 20 carbon atoms and 1-10 heteroatoms, inclusive ("$C_{2-20}$ heteroalkenyl"). In some embodiments, a heteroalkenyl group has 2 to 10 carbon atoms and 1-10 heteroatoms, inclusive ("$C_{2-10}$ heteroalkenyl"). In some embodiments, a heteroalkenyl group has 2 to 9 carbon atoms and 1-6 heteroatoms, inclusive ("$C_{2-9}$ heteroalkenyl"). In some embodiments, a heteroalkenyl group has 2 to 8 carbon atoms and 1-5 heteroatoms, inclusive ("$C_{2-8}$ heteroalkenyl"). In some embodiments, a heteroalkenyl group has 2 to 7 carbon atoms, and 1-4 heteroatoms, inclusive ("$C_{2-7}$ heteroalkenyl"). In some embodiments, a heteroalkenyl group has 2 to 6 carbon atoms and 1-3 heteroatoms, inclusive ("$C_{2-6}$ heteroalkenyl"). In some embodiments, a heteroalkenyl group has 2 to 5 carbon atoms and 1-2 heteroatoms, inclusive ("$C_{2-5}$ heteroalkenyl"). In some embodiments, a heteroalkenyl group has 2 to 4 carbon atoms and 1-2 heteroatoms, inclusive ("$C_{2-4}$ heteroalkenyl"). In some embodiments, a heteroalkenyl group has 2 to 3 carbon atoms and 1-2 heteroatoms, inclusive ("$C_{2-3}$ heteroalkenyl"). In some embodiments, a heteroalkenyl group has 2 carbon atoms and 1 heteroatom, inclusive ("$C_2$ heteroalkenyl"). In some embodiments, a heteroalkenyl group has 2 to 6 carbon atoms and 1-3 heteroatoms, inclusive ("$C_{2-6}$ heteroalkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted $C_{2-10}$ heteroalkenyl. In certain embodiments, the heteroalkenyl group is a substituted $C_{2-10}$ heteroalkenyl.

As used herein, "alkynyl" refers to a radical of a straight-chain or branched hydrocarbon group having from 2 to 30 carbon atoms, one or more carbon-carbon triple bonds, and optionally one or more double bonds ("$C_{2-30}$ alkynyl"). In some embodiments, an alkynyl group has 2 to 20 carbon atoms ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 3-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_5$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to a radical of a straight-chain or branched hydrocarbon group having from 2 to 30 carbon atoms, one or more carbon-carbon triple bonds, optionally one or more double bonds, and which further comprises 1-10 heteroatoms independently selected from oxygen, nitrogen, and sulfur included within the parent chain ("$C_{2-30}$ heteroalkynyl"). In some embodiments, a heteroalkynyl group has 2 to 20 carbon atoms and 1-10 heteroatoms, inclusive ("$C_{2-20}$ heteroalkynyl"). In some embodiments, a heteroalkenyl group has 2 to 10 carbon atoms and 1-10 heteroatoms, inclusive ("$C_{2-10}$ heteroalkynyl"). In some embodiments, a heteroalkynyl group has 2 to 9 carbon atoms and 1-6 heteroatoms, inclusive ("$C_{2-9}$ heteroalkynyl"). In some embodiments, a heteroalkynyl group has 2 to 8 carbon atoms and 1-5 heteroatoms, inclusive ("$C_{2-8}$ heteroalkynyl"). In some embodiments, a heteroalkynyl group has 2 to 7 carbon atoms, and 1-4 heteroatoms, inclusive ("$C_{2-7}$ heteroalkynyl"). In some embodiments, a heteroalkynyl group has 2 to 6 carbon atoms and 1-3 heteroatoms, inclusive ("$C_{2-6}$ heteroalkynyl"). In some embodiments, a heteroalkynyl group has 2 to 5 carbon atoms and 1-2 heteroatoms, inclusive ("$C_{2-5}$ heteroalkynyl"). In some embodiments, a heteroalkynyl group has 2 to 4 carbon atoms and 1-2 heteroatoms, inclusive ("$C_{2-4}$ heteroalkynyl"). In some embodiments, a heteroalkynyl group has 2 to 3 carbon atoms and 1-2 heteroatoms, inclusive ("$C_{2-3}$ heteroalkynyl"). In some embodiments, a heteroalkynyl group has 2 carbon atoms and 1 heteroatom, inclusive ("$C_2$ heteroalkynyl"). In some embodiments, a heteroalkynyl group has 2 to 6 carbon atoms and 1-3 heteroatoms, inclusive ("$C_{2-6}$ heteroalkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted $C_{2-10}$ heteroalkynyl. In certain embodiments, the heteroalkynyl group is a substituted $C_{2-10}$ heteroalkynyl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl as well groups as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ Carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "nonaromatic carbocycle" refers to a nonaromatic ring having three or more cyclic carbon atoms and zero heteroatoms in a ring system, including cyclic structures of a carbon ring radical exemplified as carbocyclyl. In some embodiments, if two substituents (e.g., a combination of $R^{X11}$ and $R^{X12}$ or $R^{X21}$ and $R^{X22}$), together with the carbon atom to which they are attached, form a nonaromatic carbocycle, examples of the cyclic structure include, but are not limited to, cyclopropane, cyclopropene, cyclobutane, cyclobutene, cyclopentane, cyclopentene, cyclohexane, cyclohexene, cyclohexadiene, cycleheptane, cycloheptene, cycloheptadiene, cycloheptatriene, cyclooctane, cyclooctene, bicyclo[2.2.1]heptane, bicyclo[2.2.2]octane, cyclononane, cyclononene, cyclodecane, cyclodecene, octahydro-1H-indene, decahydronaphthalene, spiro[4.5]decane, and the like.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiorenyl. Exemplary 4-membered heterocyclyl groups include, without limitation, containing 1 heteroatom azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl, and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups without 2 heteroatoms include, limitation, containing triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl, and thiocanyl. Exemplary bicyclic heterocyclyl groups include, without limitation, indolinyl, isoindolinyl, dihydrobenzofuranyl, tetrahydrobenzothienyl, dihydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl,5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

In one embodiment, if $R^{X11}$ and $R^{X12}$, or $R^{X21}$ and $R^{X22}$ together with the carbon atom to which they are attached, form saturated 4- to 6-membered heterocyclyl comprising a nitrogen atom substituted with two methyl groups, the nitrogen atom is quaternary.

As used herein, "nonaromatic heterocycle" refers to a nonaromatic ring having a cyclic carbon atom and 1 to 4 cyclic heteroatoms, including cyclic structures of a heterocyclic radical exemplified as heterocyclyl. In some embodiments, if two substituents (e.g., a combination of $R^{X11}$ and $R^{X12}$ or $R^{X21}$ and $R^{X22}$), together with the carbon atom to which they are attached, form a nonaromatic heterocycle, examples of the cyclic structure include, but are not limited to, aziridine, oxirane, thiirane, azetidine, oxetane, thietane, tetrahydrofuran, dihydrofuran, tetrahydrothiophene, dihydrothiophene, pyrrolidine, dihydro-1H-pyrrole, 1H-pyrrole-2,5-dione, dioxolane, oxathiolane, dithiolane, triazole, oxadiazole, thiadiazole, piperidine, tetrahydropyran, dihydropyridine, thiane, piperazine, morpholine, dithiane, dioxane, triazine, azepane, oxepane, thiepane, azocane, oxecane, thiocane, and the like.

As used herein, "aryl" refers to a radical of a monocyclic or polycyclic (e.g., bicyclic or tricyclic) 4n+2 aromatic ring system (e.g., having 6, 10, or 14 electrons shared in a cyclic array) having 6-14 ring carbon atoms and zero heteroatoms provided in the aromatic ring system ("$C_6$-14 aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl group. In certain embodiments, the aryl group is a substituted $C_{6-14}$ aryl group.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic or tricyclic) 4n+2 aromatic ring system (e.g., having 6, 10, or 14 electrons shared in a cyclic array) having ring carbon atoms and 1-4 ring heteroatoms provided in the aromatic ring system, wherein each heteroatom is independently selected from nitrogen, and oxygen, sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a group that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e. g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of the present disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, $—NO_2$, $—N_3$, $—SO_2H$, $—SO_3H$, —OH, $—OR^{aa}$, $—ON(R^{bb})_2$, $—N(R^{bb})_2$, $—N(R^{bb})_3{}^+X^—$, $—N(OR^{C})R^{bb}$, —SH, $—SR^{aa}$, $—SSR^{cc}$, $—C(=O)R^{aa}$, $—CO_2H$, —CHO, $—C(OR^{cc})_2$, $—CO_2R^{aa}$, $—OC(=O)R^{aa}$, $—OCO_2R^{aa}$, $—C(=O)N(R^{bb})_2$, $—OC(=O)N(R^{bb})_2$, $—NR^{bb}C(=O)R^{aa}$, $—NR^{bb}CO_2R^{aa}$, $—NR^{bb}C(=O)N(R^{bb})_2$, $—C(=NR^{bb})R^{aa}$, $—C(=NR^{bb})OR^{aa}$, $—OC(=NR^{bb})R^{aa}$, $—OC(=NR^{bb})OR^{aa}$, $—C(=NR^{bb})N(R^{bb})_2$, $—OC(=NR^{bb})N(R^{bb})_2$, $NR^{bb}C(=NR^{bb})N(R^{bb})_2$, $—C(=O)NR^{bb}SO_2R^{aa}$, $—NR^{bb}SO_2R^{aa}$, $—SO_2N(R^{bb})_2$, $—SO_2R^{aa}$, $—SO_2OR^{aa}$, $—OSO_2R^{aa}$, $—S(=O)R^{aa}$, $—OS(=O)R^{aa}$, $—Si(R^{aa})_3$, $—OSi(R^{aa})_3—C(=S)N(R^{bb})_2$, $—C(=O)SR^{aa}$, $—C(=S)SR^{aa}$, $—SC(=S)SR^{aa}$, $—SC(=O)SR^{aa}$, $—OC(=O)SR^{aa}$, $—SC(=O)OR^{aa}$, $—SC(=O)R^{aa}$, $—P(=O)_2R^{aa}$, $—OP(=O)_2R^{aa}$, $—P(=O)(R^{aa})_2$, $—OP(=O)(R^{aa})_2$, $—OP(=O)(OR^{cc})_2$, $—P(=O)_2N(R^{bb})_2$, $—OP(=O)_2N(R^{bb})_2$, $—P(=O)(NR^{bb})_2$, $—OP(=O)(NR^{bb})_2$, $—NR^{bb}P(=O)(OR^{cc})_2$, $—NR^{bb}P(=O)(NR^{bb})_2$, $—P(R^{cc})_2$, $—P (R^{cc})_3$, $—OP(R^{cc})_2$, $—OP(R^{cc})_3$, $—B(R^{aa})_2$, $—B(OR^{cc})_2$, $—BR^{aa}(OR^{cc})$, $C_{1-10}$ alkyl, $C_{1-10}$ perhaloalkyl, $C_{2-10}$ alkenyl, $C_{2-10}$ alkynyl, $C_3$-14 carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; or two geminal hydrogens on a carbon atom are replaced with the group =O, =S, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$; each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{cc}$) $OR^{aa}$, —C(═$NR^{cc}$)$N(R^{cc})_2$, —$SO_2N(R^{cc})_2$, —$SO_2R^{cc}$, —$SO_2OR^{aa}$, —$SOR^{aa}$, —C(═S)$N(R^{cc})_2$, —C(═O)$SR^{cc}$, —C(═S)$SR^{cc}$, —P(═$O)_2R^{aa}$, —P(═O)$(R^{aa})_2$, —P(═$O)_2N(R^{cc})_2$, —P(═O)$(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_6$-14 aryl, and 5-14 membered heteroaryl, or two Roc groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3{}^+X^-$, —N($OR^{ee}$) $R^{ff}$, —SH, —$SR^{ee}$, —$SSR^{ee}$, —C(═O)$R^{ee}$, —$CO_2H$, —$CO_2R^{ee}$, —OC(═O)$R^{ee}$, —$OCO_2R^{ee}$, —C(═O)N$(R^{ff})_2$, —OC(═O)$N(R^{ff})_2$, —$NR^{ff}$C(═O)$R^{ee}$, —$NR^{ff}CO_2R^{ee}$, —$NR^{ff}$C(═O)$N(R^{ff})_2$, —C(═$NR^{ff}$) $OR^{ee}$, —OC(═$NR^{ff}$) $R^{ee}$, —OC(═$NR^{ff}$)$OR^{ee}$, —C(═$NR^{ff}$)$N(R^{ff})_2$, —OC(═$NR^{ff}$)$N(R^{ff})_2$, —$NR^{ff}$C(═$NR^{ff}$) $N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(═O)$R^{ee}$, —$Si(R^{ee})_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═$O)_2R^{ee}$, —P(═O)$(R^{ee})_2$, —OP(═O)$(R^{ee})_2$, —OP(═O)$(OR^{ee})_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{qq}$ groups, or two geminal $R^{dd}$ substituents can be joined to form ═O or ═S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups; each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl)$_2$, —N($C_{1-6}$ alkyl)$_3{}^+X^-$, —NH($C_{1-6}$ alkyl)$_2{}^+X^-$, —$NH_2$($C_{1-6}$ alkyl)$^+$ $X^-$, —$NH_3{}^+X^-$, —N($OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(═O)($C_{1-6}$ alkyl), —$CO_2H$, —$CO_2$ ($C_{1-6}$ alkyl), —OC(═O)($C_{1-6}$ alkyl), —$OCO_2$ ($C_{1-6}$ alkyl), —C(═O)$NH_2$, —C(═O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2$ ($C_{1-6}$ alkyl), —NHC(═O)N($C_{1-6}$ alkyl)$_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)$OC_{1-6}$ alkyl, —C(═NH)N($C_{1-6}$ alkyl)$_2$, —C(═NH)NH($C_{1-6}$ alkyl), —C(═NH)$NH_2$, —OC(═NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(═NH)$NH_2$, —$NHSO_2$($C_{1-6}$ alkyl), —$SO_2$N($C_{1-6}$ alkyl)$_2$, —$SO_2$NH ($C_{1-6}$ alkyl), —$SO_2NH_2$, —$SO_2C_{1-6}$ alkyl, —$SO_2$OC alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$—C(═S)N($C_{1-6}$ alkyl)$_2$, C(═S)NH($C_{1-6}$ alkyl), —C(═S)$NH_2$, —C(═O)S ($C_{1-6}$ alkyl), —C(═S)$SC_{1-6}$ alkyl, —SC(═S)$SC_{1-6}$ alkyl, —P(═$O)_2$($C_{1-6}$ alkyl), —P(═O)($C_{1-6}$ alkyl)$_2$, —OP(═O)($C_{1-6}$ (alkyl)$_2$, —OP(═O)($OC_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ Carbocyclyl, $C_{6-10}$ aryl, 3-10 membered heterocyclyl, 5-10 membered heteroaryl; or two geminal $R^{gg}$ substituents can be joined to form ═O or ═S; wherein $X^-$ is a counterion.

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON$(R^{bb})_2$, —OC(═O)$SR^{aa}$, —OC(═O)$R^{aa}$, —$OCO_2R^{aa}$, —OC(═O)$N(R^{bb})_1$, —OC(═$NR^{bb}$)$R^{aa}$, —OC(═$NR^{bb}$) $OR^{aa}$, —OC(═$NR^{bb}$)$N(R^{bb})_2$, —$OSO_2R^{aa}$, —$OSi(R^{aa})_3$, —$OP(R^{cc})_2$, —$OP(R^{cc})_3$, —OP(═$O)_2R^{aa}$, —OP(═O)$(R^{aa})_2$, —OP(═O)$(OR^{cc})_2$, —OP(═$O)_2N(R^{bb})_2$, and —OP(═O)$(NR^{bb})_2$, wherein $R^{aa}$, $R^{bb}$, and $R^{cc}$ are as defined herein.

As used herein, the term "thiol" or "thio" refers to the group-SH. The term "substituted thiol" or "substituted thio," by extension, refers to a thiol group wherein the sulfur atom directly attached to the parent molecule is substituted with a group other than hydrogen, and includes groups selected from —$SR^{aa}$, —S═$SR^{cc}$, —SC(═S)$SR^{aa}$, —SC(═O)$SR^{aa}$, —SC(═O)$OR^{aa}$, and —SC(═O)$R^{aa}$, wherein $R^{aa}$, and Rec are as defined herein.

As used herein, the term, "amino" refers to the group —$NH_2$. The term "substituted amino," by extension, refers to a monosubstituted amino, a disubstituted amino, or a trisubstituted amino, as defined herein.

As used herein, the term "monosubstituted amino" refers to an amino group wherein the nitrogen atom directly attached to the parent molecule is substituted with one hydrogen and one group other than hydrogen, and includes groups selected from —NH$(R^{bb})$, —NHC(═O)$R^{aa}$, —$NHCO_2R^{aa}$, —NHC(═O)$N(R^{bb})_2$, —NHC(═$NR^{bb}$)N$(R^{bb})_2$, —$NHSO_2R^{aa}$, —NHP(═O)$(OR^{cc})_2$, and NHP(═O)$(NR^{bb})_2$, wherein $R^{aa}$, $R^{bb}$, and Rec are as defined herein, and wherein $R^{bb}$ of the group —NH$(R^{bb})$ is not hydrogen.

As used herein, the term "disubstituted amino" refers to an amino group wherein the nitrogen atom directly attached to the parent molecule is substituted with two groups other than hydrogen, and includes groups selected from —$N(R^{bb})_2$, —$NR^{bb}$ C(═O)$R^{aa}$, —$NR^{bb}CO_2$, $R^{aa}$, —$NR^{bb}$C(═O)$N(R^{bb})_2$, —$NR^{bb}$C(═$NR^{bb}$) $N(R^{bb})_2$, —$NR^{bb}SO_2R^{aa}$, —$NR^{bb}$P(═O)$(OR^{cc})_2$, and —$NR^{bb}$P(═O)$(NR^{bb})_2$, wherein $R^{aa}$, $R^{bb}$, and $R^{cc}$ are as defined herein, with the proviso that the nitrogen atom directly attached to the parent molecule is not substituted with hydrogen.

As used herein, the term "trisubstituted amino" or a "quaternary amino salt" or a "quaternary salt" refers to a nitrogen atom covalently attached to four groups such that the nitrogen is cationic, wherein the cationic nitrogen atom is further complexed with an anionic counterion, e.g., such as groups of the Formula —$N(R^{bb})_3{}^+X^-$ and —$N(R^{bb})_2$—$^+$ $X^-$, wherein $R^{bb}$ and $X^-$ are as defined herein.

As used herein, a "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, the term "sulfonyl" refers to a group selected from —$SO_2N(R^{bb})_2$, —$SO_2R^{aa}$, and —$SO_2OR^{aa}$, wherein $R^{aa}$ and $R^{bb}$ are as defined herein.

As used herein, the term "sulfinyl" refers to the group —S(═O)$R^{aa}$, wherein $R^{aa}$ is as defined herein.

As used herein, the term "acyl" refers a group wherein the carbon directly attached to the parent molecule is $sp^2$ hybridized, and is substituted with an oxygen, nitrogen or sulfur atom, e.g., a group selected from ketones (—C(═O)$R^{aa}$), carboxylic acids (—$CO_2H$), aldehydes (—CHO), esters (—$CO_2$, $R^{aa}$), thioesters (—C(═O)$SR^{aa}$, —C(═S)$SR^{aa}$), amides (—C(═O)$N(R^{bb})_2$, —C(═O)$NR^{bb}SO_2R^{aa}$), thioamides (—C(═S)$N(R^{bb})_2$), and imines (—C(═$NR^{bb}$)$R^{aa}$, —C(═$NR^{bb}$)$OR^{aa}$, —C(═$NR^{bb}$)$N(R^{bb})_2$), wherein $R^{aa}$ and $R^{bb}$ are as defined herein.

As used herein, the term "azido" refers to a group of the formula: —$N_3$.

As used herein, the term "cyano" refers to a group of the formula: —CN.

As used herein, the term "isocyano" refers to a group of the formula: —NC.

As used herein, the term "nitro" refers to a group of the formula: —$NO_2$.

As used herein, the term "halo" or "halogen" refers to fluorine (fluoro, —F), chlorine (chloro, —$C_1$), bromine (bromo, —Br), or iodine (iodo, —I).

As used herein, the term "oxo" refers to a group of the formula: ═O.

As used herein, the term "thiooxo" refers to a group of the formula: ═S.

As used herein, the term "imino" refers to a group of the formula: ═$N(R^b)$.

As used herein, the term "silyl" refers to the group-Si$(R^{aa})_3$, wherein $R^{aa}$ is as defined herein.

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$_2R^{aa}$, —P(═O)$(R^{aa})_2$, —P(═O)$_2N(R^{cc})_2$, —P(═O)$(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two Rec groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an amino protecting group (also referred to herein as a "nitrogen protecting group"). Amino protecting groups include, but are not limited to, —OH, —$OR^{aa}$, —$N(R^{cc})_2$, —C(═O)$R^{aa}$, —C(═O)$N(R^{cc})_2$, —$CO_2R^{aa}$, —$SO_2R^{aa}$, —C(═$NR^{cc}$)$R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Amino protecting groups are well known in the art and include those described in detail in Protecting Groups in Organic Synthesis, T. W. Greene and P. G. M. Wuts, 3rd edition, John Wiley & Sons, 1999, incorporated herein by reference.

For example, amino protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and (benzoyloxymethyl)benzamide.

Amino protecting groups such as carbamate groups (e.g., —C(═O)$OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-carbamate (DB-t-BOC), 1,1-dimethyl-2,2,2-2,2-dibromoethyl carbamate (TCBOC), 1-methyl-1-(4-trichloroethyl biphenylyl) ethyl carbamate (Bpoc), 1-(3,5-di-t-butylphenyl)-1-methylethyl carbamate (t-Bumeoc), 2-(2'- and 4 1-pyridyl) ethyl carbamate (Pyoc), 2-(N, N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, t-amyl carbamate, S-benzyl thiocarbamate, p-cyanobenzyl carbamate, cyclobutyl carbamate, cyclohexyl carbamate, carbamate, cyclopentyl cyclopropylmethyl carbamate, p-decyloxybenzyl carbamate, 2,2-dimethoxyacylvinyl carbamate, O—(N, N-dimethylcarboxamido)benzyl carbamate, 1,1-dimethyl-3-(N, N-dimethylcarboxamido) propyl carbamate, 1,1-dimethylpropynyl carbamate, di(2-pyridyl) methyl carbamate, 2-furanylmethyl carbamate, 2-iodoethyl carbamate, isoborynl carbamate, isobutyl carbamate, isonicotinyl carbamate, p-(p'-carbamate, 1-methylcyclobutyl methoxyphenylazo)benzyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2, 4,6-trimethylbenzyl carbamate.

Amino protecting groups such as sulfonamide groups (e.g., $—S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2, 5, 7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2, 5-dimethylpyrrole, N-1, 1, 4,4-tetramethyldisilylazacyclopentane adduct (STABASE), 5-substituted 1,3-dimethyl-1, 3,5-triazacyclohexan-2-one, 5-substituted 1,3-dibenzyl-1, 3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, “quaternary ammonium salts, N-benzylamine, N-di(4-methoxyphenyl)methylamine, N-5-dibenzosuberylamine, N-triphenylmethylamine (Tr), N-[(4-methoxyphenyl) diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N1,1-dimethylthiomethyleneamine, N-benzylideneamine, N-p-methoxybenzylideneamine, N-diphenylmethyleneamine, N-[(2-pyridyl) mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten) acyl]amine, N-copper chelate, N-zinc chelate, N-nitroamine, N-nitrosoamine, amine N-oxide, (Dpp), diphenylphosphinamide dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-pentachlorobenzenesulfenamide, dinitrobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is a hydroxyl protecting group (also referred to herein as an “oxygen protecting group”). Hydroxyl protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3$, $—P(=O)_2R^{aa}$, $—P(=O)(R^{aa})_2$, $—P(=O)(OR^{cc})_2$, $—P(=O)_2N(R^{bb})_2$, and $—P(=O)(NR^{bb})_2$, wherein $R^{aa}$, $R^{bb}$, and $R^{cc}$ are as defined herein. Hydroxyl protecting groups are well known in the art and include those described in detail in Protecting Groups in Organic Synthesis, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy methyl (p-AOM), guaiacolmethyl (GUM), t-butoxymethyl, 4-pentenyloxymethyl (POM), siloxymethyl, 2-methoxyethoxymethyl (MEM), 2, 2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S, S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a, 4,5,6,7,7a-octahydro-7, 8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2, 2,2-trichloroethyl, 2-trimethylsilylethyl, 2-(phenylselenyl) ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p, p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4)-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4" dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo) anthryl, 1,3-benzodithiolan-2-yl, benzisothiazolyl S, S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio) pentanoate (levulinoyldithioacetal), pivaloate, adamantoate, crotonate, 4-methoxycrotonate, benzoate, p-phenylbenzoate, 2, 4,6-trimethylbenzoate (mesitoate), methyl carbonate, 9-fluorenylmethyl carbonate (Fmoc), ethyl carbonate, 2, 2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy) butyrate, 2-(methylthiomethoxymethyl)benzoate, 2,6-dichloro-4-methylphenoxyacetate, 2,6-dichloro-4-(1, 1, 3,3-tetramethylbutyl) phenoxyacetate, 2,4-bis(1,1-dimethylpropyl) phenoxyacetate, chlorodiphenylacetate, isobutyrate, monosuccinoate, (E)-2-methyl-2-butenoate, o-(methoxyacyl)benzonate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

A "thiol protecting group" is well known in the art and include those described in detail in Protecting Groups in Organic Synthesis, T. W. Greene and P. G. M. Wuts, 3rd edition, John Wiley & Sons, 1999, the entirety of which is incorporated herein by reference. Examples of protected further include, but are not limited to, thiol groups thioesters, carbonates, sulfonates allyl thioethers, thioethers, silyl thioethers, alkyl thioethers, arylalkyl thioethers, and alkyloxyalkyl thioethers. Examples of ester groups include carbonates, formates, acetates, proprionates, valerate, crotonates, and benzoates. Specific examples of ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benylbenzoate, 2, 4,6-trimethylbenzoate. Examples of carbonates include 9-fluorenylmethyl, ethyl, 2, 2,2-trichloroethyl, 2-(trimethylsilyl)ethyl, 2-(phenylsulfonyl)ethyl, vinyl, allyl, and p-nitrobenzyl carbonate. Examples of silyl groups include trimethylsilyl, triethylsilyl, t-butyldimethylsilyl, t-butyldiphenylsilyl, triisopropylsilyl ether, and other trialkylsilyl ethers. Examples of alkyl groups include methyl, benzyl, p-methoxybenzyl, 3,4-dimethoxybenzyl, trityl, t-butyl, and allyl ether, or derivatives thereof. Examples of arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

The term "amino acid" refers to a molecule that contains both an amino group and a carboxyl group. Amino acids include, as non-limiting examples, α-amino acids, β-amino acids, γ-amino acids, δ-amino acids, etc. (Depending on the position of the amino group, there are various names for amino acids, all of which may be covered by the present disclosure), and include both D-amino acids and L-amino acids. As typical examples, the structures of α-amino acids, β-amino acids, and γ-amino acids are shown below.

[Chemical Formula 163]

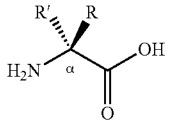

α-amino acid

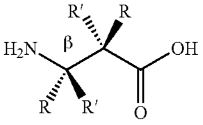

β-amino acid

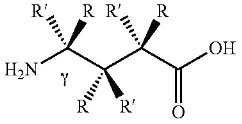

γ-amino acid

In some embodiments, the amino acid is an α-amino acid. In some embodiments, the amino acid is an L-D-amino acid. In some embodiments, the amino acid is a natural amino acid. In some embodiments, the amino acid is a non-natural amino acid. In some embodiments, the amino acid is an artificial amino acid. Artificial amino acids are a type of non-natural amino acid and can be used synonymously with natural amino acids.

In the present specification, as for the positions of the carbon atoms in the side chain of an amino acid, for example, as in

[Chemical Formula 164]

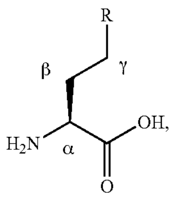

the carbon atom (or carbon chain) to which the carboxyl and amino groups are connected and the group of the side chain is connected is referred to as the α-position, and in order from the α-position toward the end of the side chain, the positions are referred to as β-position, γ-position, and δ-position (Subsequent positions will also be named based on the technical common sense of the field.). In the present specification, they may be referred to as side chain α-position, side chain β-position, side chain γ-position, side chain δ-position, etc. Exemplary amino acids include, without limitation, natural α-amino acids, e.g., D and L isomers of the 20 common naturally occurring α-amino acids found in peptides, unnatural α-amino acids, artificial α-amino acids, natural β-amino acids (e.g., β-alanine), unnatural β-amino acids, and artificial β-amino acids. The amino acids used to construct the peptides of the present disclosure can be prepared by organic synthesis or obtained by other routes, such as degradation of natural sources or isolation therefrom. Amino acids can be commercially available or can be synthesized.

A "peptide" or "polypeptide" comprises a polymer of amino acid residues linked together by peptide (amide) bonds. The term(s), as used herein, refers to proteins, polypeptides, and peptide of any size, structure, or function. The term(s), as used herein, include bridged and unbridged polypeptides. Typically, a peptide or polypeptide is at least 3 amino acids in length. A peptide or polypeptide may refer to an individual protein or a series of proteins. Proteins of the present disclosure preferably contain only natural amino acids, although non-natural amino acids (i.e., compounds that do not occur in nature but that can be incorporated into a polypeptide chain) and/or amino acid analogs as are known in the art may alternatively be employed. One or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof. In the present specification, a peptide or polypeptide can be cross-linked by side chains of amino acids in the peptide or polypeptide. A bridge peptide or bridge polypeptide refers to a peptide or polypeptide in which the side chains of amino acids in the peptide or polypeptide are cross-linked by metathesis reactions, click chemistry, and reductive amination etc.

As used herein, the term "bridge peptide" refers to a peptide that has a bridge portion at least partially within the peptide. Crosslinking can be accomplished by any cross-linking reaction in the field. Such cross-linking reactions can be achieved by using any technique known in the field, such as olefin metathesis, alkyne metathesis, reductive amination, click chemistry, Michael addition, carbamate formation, etc. and they are illustrated in the examples herein. In one embodiment, cross-linking of a peptide refers to cross-linking the side chains of a polypeptide chain by covalently linking the olefin moieties together using an olefin metathesis reaction. Cross-linking of peptides destabilizes structures other than the β-strand of the polypeptide. The present disclosure provides bridge polypeptides having a cross-link connecting the α carbons of two amino acids in a β-strand. The present disclosure further provides pharmaceutical compositions of bridge polypeptides, methods of preparing the bridge peptides of the present disclosure, and methods of using the bridge peptides of the present disclosure. The present disclosure also provides click chemistry and reductive amination as a means of stabilizing the structure of a polypeptide.

As used herein, the term "bridge moiety", when used in a bridge peptide, refers to any chemical entity portion that joins amino acids at least at different positions of the peptide in a bridge peptide, and is also referred to as a "cross-link" and encompasses the entire cross-link that joins one α-amino acid, β-amino acid, or other amino acid to a second α-amino acid, β-amino acid, or other amino acid, but excludes the α carbon of each amino acid and the polypeptide chain of which they are a part. The bridge moiety can adopt any structure that results from any crosslinking technique in the field, or any structure that can be modified or derived from the structure as long as the desired structure (e.g., β-strand structure, etc.) is not destroyed. As for the modification reaction after cross-linking, any method known in the field can be employed. The post-crosslinking modification reactions include, for example, reduction of triple bonds to double bonds (including E or Z selective reduction); reduction of double bonds to single bonds (Schafmeister C E et al., "An All-Hydrocarbon Cross-Linking System for Enhancing the Helicity and Metabolic Stability of Peptides", J. Am. Chem. Soc. 2000, 122, 5891-5892;), etc., and reactions using 1) Pd/C, H2,2) 2, 4,6-triisopropyl benzenesulphonyl hydrazide and piperidine are examples. Examples of olefin reduction include the following reactions:

Material and Quantity

Resin 30 μmol 2, 4,6-triisopropylbenzenesulfonyl hydrazide 90 mg (300 μmol)

Piperidine 59 μl (600 μmol)

NMP 430 μl 2, 4,6-trisopropylbenzenesulfonyl hydrazide is adjusted to 0.7 M.

One Example of a Procedure

The mixture of 2, 4,6-trisopropylbenzenesulfonyl hydrazide, Piperidine and NMP is added to Resin, and stirred at 47° C. for 2 hours. This process is repeated 4 times.

In addition, the following reactions are also possible as a post-crosslinking modification reaction.

A) Dibromination of triple bonds (below) (Orthogonal ring-closing alkyne and olefin metathesis for the synthesis of small GTPase-targeting bicyclic peptides)

[Chemical Formula 165]

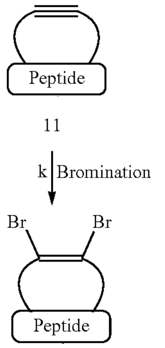

11

12

2-2) Dihydroxylation of Double Bonds

[Chemical Formula 166]

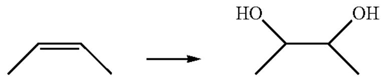

2-3) Epoxidation of Double Bonds

[Chemical Formula 167]

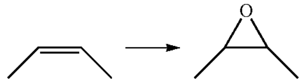

2-4) Aziridination

[Chemical Formula 168]

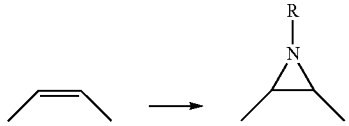

where R=PRO, PRO is a protecting group, etc.

Hydroboration→Addition of OH or $NH_2$ (may include triple bonds)

[Chemical Formula 169]

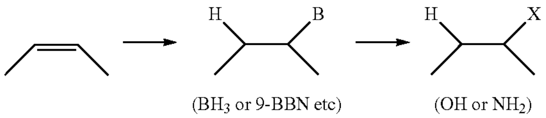

The above is an example and other derivatization methods may be used in the present disclosure.

As used herein, the term "salt" or "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds, amino acids, and polypeptides of the present disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, gluconate, hemisulfate, heptanoate, glycerophosphate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary ammmonium salts, e.g., trisubstituted amino groups defined herein.

The aforementioned and other exemplary functional groups are described in more detail in description of embodiments, examples, and scope of claims. The present disclosure is not intended to be limited in any manner by the above exemplary listing of substituents.

As used herein, the phrase "β-position when the carbon at which the bridge moiety attaches to the peptide is in the α-position" refers to the β-position (Cβ) when the carbon atom at which the bridge moiety in the bridge peptide attaches to the polypeptide in the main chain is in the α-position (Cα) according to the definition of amino acids used in the field.

As used herein, the phrase "no hydrogen bonds to induce or maintain secondary structure" refers to the absence of hydrogen bonds to induce or maintain secondary structure in a polypeptide or peptide moiety, and the absence of intramolecular hydrogen bonds. It is known that there are hydrogen bonds to induce or maintain the secondary structure in the β-hairpin structure, etc., whereas there are no such hydrogen bonds in the β-strand structure.

As used herein, the term "β-strand structure" is used in the same sense as it is normally used in the field, and refers to the secondary structure of a protein. The β-strand structure is usually present in lengths of 5-10 residues in a protein, polypeptide or peptide structure, and adopts an almost fully extended conformation. Therefore, β-strand structure refers to a structure that the amide group in the main chain cannot form hydrogen bonds with neighboring residues.

As used herein, the term "tertiary" refers to the state in which an atom is bonded to one hydrogen and three atoms other than hydrogen. Typically, if a carbon atom is single bonded to one hydrogen and three non-hydrogen atoms, e.g., one hydrogen atom and three carbon atoms, respectively, then the central carbon atom is tertiary.

As used herein, the term "quaternary" refers to the state in which an atom is bonded to four atoms other than hydrogen. Typically, if a carbon atom is single bonded to each of the four non-hydrogen atoms, e.g., four carbon atoms, then the central carbon atom is quaternary. In the case of a nitrogen atom, typically an ammonium cation that is tetrasubstituted with an alkyl or aryl, etc., is quaternary.

As used herein, the term "van der Waals radius" is one of the measures used to describe the size of an atom. It is calculated by dividing the distance between adjacent atoms by two in elements that form a single crystal by van der Waals forces. The distance between atoms is measured using X-ray diffraction and other techniques. As used herein, the term "van der Waals volume" refers to the volume occupied by the atoms that make up a protein and the volume calculated based on the van der Waals radius. Both values can be calculated using techniques known in the field.

As used herein, the term "A Value" is a general expression of steric bulk, as well as a numerical value used for the determination of the most stable orientation of atoms in a molecule, and means the change (difference) in Gibbs free energy of equilibrium between eq-substituted cyclohexane and ax-substituted cyclohexane in monosubstituted cyclohexane, reported by Winstein and Holness in 1955. The A-value can also be calculated using methods known in the field.

As used herein, the term "functional group bulkier than or equal to a methyl group" refers to any functional group bulkier than or equal to a methyl group and can be determined by comparison with van der Waals radius, van der Waals volume and/or A Value.

PREFERRED EMBODIMENTS

The preferred embodiments of the present disclosure are described hereinafter. It is understood that the embodiments provided hereinafter are provided for the better understanding of the present disclosure, so that the scope of the present disclosure should not be limited to the following descriptions. Thus, it is apparent that those skilled in the art can refer to the descriptions herein to make appropriate modifications within the scope of the present disclosure. It is also understood that the following embodiments of the present disclosure can be used individually or as a combination.

The present disclosure provides compounds or bridge peptides comprising one or more β-strand structures. In the present disclosure, at least one of a compound or bridge peptide comprises a substituent wherein position β, when carbon at which a bridge moiety attaches to a peptide is position α based on a nomenclature for amino acids, is tertiary or quaternary. The presence of a tertiary or quaternary substituent at position β in a bridge peptide promotes crosslinking by destabilizing the conformation other than a β-strand of a peptide and eliciting a β-strand structure. The present disclosure also provides a pharmaceutical composition comprising the bridge polypeptide of the present disclosure and a method of preparing and using the bridge peptide of the present disclosure. A β-strand bridge peptide achieved by the technology of the present disclosure is a technology for eliciting a β-strand. The present disclosure can be applied not only to a β-strand alone, but also to β-strands comprised in a β hairpin, β-sheet, β-α-β structure, or the like, and can elicit one β-strand for each crosslink. In another embodiment, it can be preferable to comprise a secondary substituent at position β.

The bridge polypeptides of the present disclosure, as described herein, may be useful, for example, as therapeutic agents, biological probes, or drug delivery agents in all cases where the secondary structural motifs covered by the present disclosure are advantageous. The bridge polypeptides of the present disclosure may function as modulators of interactions related to biological macromolecules such as interactions between biological macromolecules, for example, protein-protein, protein-ligand, protein-polynucleotides, protein-mRNA, cell-cell, or protein-receptor binding interactions etc.

"Interactions related to biological macromolecules" means any interaction between two or more entities, wherein at least one of the entities includes a biological macromolecule (e.g., peptide, lipid, polysaccharide, protein, nucleic acid, sugar, their derivatives, molecules that combine them, complexes thereof, entities containing complexes thereof (e.g., cells), etc.). In certain embodiments, these bridge polypeptides are useful in the treatment of a disorder in a subject, e.g., a disorder selected from the group consisting of proliferative disorders, neurological disorders, immunological disorders, endocrinologic disorders, cardiovascular disorders, hematologic disorders, inflammatory disorders, and disorders characterized by premature or unwanted cell death. The present disclosure also contemplates use of the bridge peptides of the present disclosure as research tools, e.g., in cellular or biochemical studies.

The bridge polypeptide of the present disclosure described herein comprises a stabilized β-strand structure, so that the polypeptide can materialize what an α helix described below cannot or what is challenging with an α helix, and enables materialization of what conventional bridge peptides or other peptides could not or what would be substantially challenging therewith.

In one embodiment, the bridge polypeptide of the present disclosure described herein can materialize creation of an aggregate of a peptide or protein. Although not wishing to be bound by any theory, such a polypeptide can, for example, aggregate proteins or the like involved in aggregation of β-strands such as β amyloid involved in Alzheimer's or TDP-43 or prion involved in amyotrophic lateral sclerosis (ALS), and achieve or enhance a biological effect due to aggregation.

In one embodiment, the bridge polypeptide of the present disclosure described herein can be used as an aggregation initiator. For example, prion and TDP-43 are known to aggregate due to a change in the structure from a helix to β-strand. For this reason, the β-strand bridge peptide of the present disclosure can be intended for use as an aggregation initiator for eliciting such a structural change. In this manner, such a polypeptide can be utilized in research or pathological studies in the protein field, and thus the treatment, diagnosis, or prevention of a disease.

In one embodiment, the bridge polypeptide of the present disclosure described herein can be used for controlling the size of an aggregate. For example, it is understood that a smaller aggregate is actually more toxic than a larger aggregate for β amyloid and TDP-43, but it is considered challenging to control the size of aggregates with current technologies. Meanwhile, use of the bridge peptide of the present disclosure allows the size of an aggregate to be controlled by, for example, mixing a β-strand bridge peptide with a wild-type β amyloid peptide. For this reason, use of a β-strand bridge peptide is envisioned in order to prepare aggregates of different sizes for each of the various crosslinking sites. This can also be utilized in research or pathological studies in the protein field, and thus the treatment, diagnosis, or prevention of a disease.

In another embodiment, the bridge polypeptide of the present disclosure described herein can be used for inhibiting an interaction related to a biopolymer associated with an organism within a cell or the like that can be inhibited only by a β-strand and not a helix, e.g., interactions between biopolymers such as Protein-Protein Interaction (PPI). Such an interaction related to a biopolymer such as PPI is involved in various biological phenomena and diseases. Such inhibition can be used in the biological regulation and treatment or prevention of a disease.

For example, a study published a result showing that PPI in which a β-strand is involved accounts for 20% or more of all PPI (estimated to be 130 to 650 thousand). Research and development can be conducted and pharmaceutical products can be provided based on inhibition by a β-strand, which could not be materialized in the past.

(Polypeptide)

In a representative aspect, the present disclosure provides a bridge peptide comprising a bridge moiety and a peptide moiety, wherein position β, when carbon at which the bridge moiety attaches to the peptide is position α, is tertiary or quaternary. Conventional bridge peptides use position β without bulk (no substituent). A secondary structure such as an α helix was immobilized by reducing the bulk at position β. Meanwhile, it was found in the present disclosure that introducing bulk can surprisingly stabilize an unstable secondary structure. In the field of bridge peptides, retention of a secondary structure is important, but strategies other than immobilization of the conformation were nonexistent. Thus, the concept of reproducing the conformation for β-strand, random coils, loops, etc. which could not be materialized from immobilization of the conformation was: nonexistent. Meanwhile, the present disclosure has found a stabilization method. Specifically, a β-strand is secondary structure that cannot be a materialized from immobilization of the conformation due to the lack of an intramolecular hydrogen bond. For this reason, a concept other than immobilization of the conformation was needed, but the present disclosure materialized this by eliminating conformation, which was not practiced in the past in the field of bridge peptides.

Although not wishing to be bound by any theory, the bridge peptide of the present disclosure is a molecule in a straight line, so that the efficiency in the number of atoms is high with respect to binding with a target. In comparison to a helix or β sheet, such a peptide can bind more strongly to a target theoretically with fewer number of atoms, i.e., less molecular weight. Although not wishing to be bound by any theory, the bridge peptide of the present disclosure can utilize an amide group of the parent chain for binding to a target due to the lack of a hydrogen bond in the amide group of the parent chain. Theoretically, such a peptide can bind more strongly to a target compared to an α helix or the like, and thus can have an advantageous effect in biological activity or the like.

Although not wishing to be bound by any theory, the bridge peptide of the present disclosure has many available atoms on a single surface and high efficiency in the number of atoms with respect to binding to a target because it is a molecule in a straight line. Since an amide group of the parent chain does not have a hydrogen bond, such amide groups can also be utilized in binding to a target. Specifically, compared to an α helix or β sheet, such a peptide can bind more strongly to a target with theoretically fewer number of atoms, i.e., less molecular weight, and thus can have an advantageous effect in biological activity or the like.

Although not wishing to be bound by any theory, prior to the present disclosure, a general synthesis method of an artificial amino acid introduced with a substituent at position α was established and actively applied to drug research and development or the like. For example, 5 to 10 types of bridge peptides, including those that are not suitable for drug development and research, have been reported, and the number should increase in the future. However, a crosslinking technology for an α helix cannot be directly applied to a β-strand structure, and rather was understood as not successfully achievable. This is because it was generally understood that introduction of a substituent to position β without formation of a racemate at position α of an amino acid or amino acid derivative is difficult. Prior to the present disclosure, there was no general synthesis method of an artificial amino acid with position β that is tertiary or quaternary, and studies using such an amino acid was considered difficult.

Although not wishing to be bound by any theory, a multi-stage synthesis method of artificial amino acids, which can introduce various substituents into position β, each with the number of carbons differing by one carbon, was successfully established in the development of the bridge peptide of the present disclosure. The structure of the olefin site of the artificial amino acid provided by the present disclosure can be converted into, for example, a terminal azide or alkyne that is suitable for click chemistry, or alkyne that is suitable for alkyne metathesis.

Although not wishing to be bound by any theory, a β-strand structure of the bridge peptide of the present disclosure does not have an intramolecular hydrogen bond for eliciting or maintaining a secondary structure, unlike an α helix or the like. For this reason, this was not achievable by conventional strategies for bridge peptides, i.e., immobilization of the conformation, so that there were no precedence for conventional bridge peptides. (Classification based on an intramolecular hydrogen bond for eliciting or maintaining a secondary structure: 1) peptides with an intramolecular hydrogen bond involved in a secondary structure: α-helix, β-sheet, $3_{10}$-helix, π-helix, α-turn, β-turn, γ-turn, and other turns; 2) peptides without an intramolecular hydrogen bond involved in a secondary structure: β-strand, random coil, and loop).

The present disclosure focused on elimination of conformations such as α helices or random coils, which is the opposite concept of immobilization of the conformation, to provide the synthesis method and bridge peptide of the present disclosure.

Although not wishing to be bound by any theory, the present disclosure can achieve a significant effect that could not have been expected from conventional art by configuring position β to be tertiary or quaternary. As an example thereof, it was found that an unexpectedly significant ability to elicit a β-strand is imparted by configuring position β to be tertiary or quaternary. As shown in the Examples, a significant ability to elicit a β-strand was observed by conformation analysis using CD (e.g., BP 4-6 1st peptide). It could not have been expected that such a significant ability to elicit a β-strand would be observed with a methyl group at position β. For example, a result showing that a combination of βDM4 and βDM6 shown in the Examples is preferable was also completely unexpected at first.

Thus, although not wishing to be bound by any theory, the bridge peptide of the present disclosure provides an application of creating an aggregate of a peptide and protein as described above. The bridge peptide of the present disclosure can be used as a medicament.

Although not wishing to be bound by any theory, the bridge peptide of the present disclosure can be used as an aggregation initiator that elicits a change in the structure of prion and TDP-43. It is known in the art that prion and TDP-43 aggregate due to a change in the structure from an α helix to a β-strand. For this reason, the bridge peptide of the present disclosure can be used as an aggregation initiator for eliciting a structure change in prion and TDP-43.

Although not wishing to be bound by any theory, the bridge peptide of the present disclosure can be used, for example, to control the size of an aggregate of β amyloid and TDP-43. A smaller aggregate of β amyloid and TDP-43 can have more toxicity than a larger aggregate. However, it is challenging to control the size of an aggregate with current technologies. It is expected that the size of an aggregate can be controlled by, for example, mixing a β-strand bridge peptide with a wild-type β amyloid peptide. Thus, the β-strand bridge peptide of the present disclosure can be used in order to prepare aggregates with different sizes for each of the various crosslinking site.

Thus, in one embodiment, the peptide in the present disclosure comprises a peptide moiety that does not have a hydrogen bond to induce or maintain a secondary structure. In another embodiment, the peptide in the present disclosure comprises a β-strand structure.

In a preferred embodiment, position β is quaternary. The bulk can be ensured by being quaternary, and a β-strand can be stabilized by destabilizing the conformation other than the β-strand of a molecule.

In one embodiment, at least one substituent at position β comprises a functional group with a size equal to or greater than a methyl group. Having such a functional group promotes crosslinking by eliciting a β-strand structure while destabilizing the conformation other than a β-strand of a polypeptide. More preferably, two substituents at position β comprise an independently selected functional group with a size equal to or greater than a methyl group. This is because destabilization of the conformation other than a β-strand can be materialized more efficiently.

In another embodiment, a functional group that attaches to position β in the bridge peptide in the present disclosure has: a) a van der Waals volume of 7.24 $Å^3$ or greater; or b) a van der Waals radius of 1.2 Å or greater. More preferably, at least of the functional groups that attach to position β has: a) a van der Waals volume of 21.6 $Å^3$ or greater; b) a van der Waals radius of 2.00 Å or greater; or c) an A-value of 1.74 (kcal/mol) or greater.

In another embodiment, substituents at position β are each independently hydrogen, optionally substituted alkyl, alkene, alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or two substituents, together with the carbon atom to which they are a attached, may form an optionally substituted nonaromatic carbocycle, an optionally substituted nonaromatic heterocycle, optionally substituted aryl, or optionally substituted heteroaryl, provided that two substituents are not both hydrogen.

Alternatively, in another embodiment, substituents at position β are each independently substituted alkyl, substituted alkene, substituted alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or two substituents, together with the carbon atom to which they are attached, may form an optionally substituted nonaromatic carbocycle, an optionally substituted nonaromatic heterocycle, optionally substituted aryl, or optionally substituted heteroaryl, provided that two substituents are not both hydrogen.

In a preferred embodiment, substituents are each independently hydrogen, methyl, methoxy, methoxymethyl, secondary amine substituted with methyl or Boc, tertiary amine (substituted with methyl), quaternary ammonium substituted with methyl, or methyl substituted with halogen, or two substituents, together with the carbon atom to which they are attached, may form an unsubstituted saturated $C_{3-12}$ nonaromatic carbocycle or an optionally substituted saturated 3- to 12-membered nonaromatic heterocycle, provided that two substituents are not both hydrogen.

In a preferred embodiment, substituents are each independently methoxy, methoxymethyl, secondary amine substituted with methyl or Boc, tertiary amine (substituted with methyl), quaternary ammonium substituted with methyl, or methyl substituted with halogen, or two substituents, together with the carbon atom to which they are attached, may form an unsubstituted saturated $C_{3-12}$ nonaromatic carbocycle or an optionally substituted saturated 3- to 12-membered nonaromatic heterocycle, provided that two substituents are not both hydrogen.

In one embodiment, the bridge peptide has a crosslink formed by a crosslinking method selected from the group consisting of olefin metathesis, alkyne metathesis, click chemistry, reductive amination, Michael addition, and carbamate formation. In one embodiment, the bridge peptide has a crosslink formed by a crosslinking method selected from the group consisting of olefin metathesis, alkyne metathesis, reductive amination, Michael addition, and carbamate formation.

For a substituent at position β of the present disclosure, a nonaromatic carbocycle, a nonaromatic heterocycle, or the like generally can be a 3- to 10-membered ring, preferably a 3- to 8-membered ring, more preferably a 3- to 7-membered ring, and more preferably a a 3- to 6-membered ring, although there is no upper limit as long as it is bulky.

The bridge peptide of the present disclosure formed by olefin metathesis can be preferable. Although not wishing to be bound by any theory, the bridge peptide preferably has a crosslink highly capable of permeating through a cell membrane. This can be useful because passive diffusion is generally selected as a strategy when a bridge peptide is orally administered. Use of olefin metathesis can be advantageous because a reaction proceeds more cleanly than click chemistry, so that screening can be performed without purification.

In one embodiment, position α in a bridge peptide is hydrogen or halogen (e.g., fluorine).

In another aspect, a novel use of the bridge peptide of the present disclosure is provided. The bridge peptide of the present disclosure can be used as a medicament.

In another aspect, the bridge peptide of the present disclosure provides an application for creating an aggregate of a peptide and protein. The bridge peptide of the present disclosure can be used as a medicament.

In one embodiment, the bridge peptide of the present disclosure can be used as an aggregation initiator for eliciting a structural change in prion and TDP-43. It is known in the art that prion and TDP-43 aggregate due to a change in the structure from an α helix to a β-strand. For this reason, the bridge peptide of the present disclosure can be used as an aggregation initiator for eliciting a structural change in prion and TDP-43.

In another embodiment, the bridge peptide of the present disclosure can be used to control the size of an aggregate of β amyloid and TDP-43. A smaller aggregate of β amyloid and TDP-43 can have more toxicity than a larger aggregate. However, it is challenging to control the size of an aggregate with current technologies. It is expected that the size of an aggregate can be controlled by, for example, mixing a β-strand bridge peptide with a wild-type β amyloid peptide. Thus, the β-strand bridge peptide of the present disclosure can be used in order to prepare aggregates with different sizes for each of the various crosslinking site.

In another aspect, the present disclosure provides a composition for permeation through a cell membrane, comprising the bridge peptide of the present disclosure.

In another aspect, the present disclosure provides a method comprising: providing a bridge peptide having a β-strand structure or a raw material thereof; processing, or introducing a substituent into, the bridge peptide or raw material thereof so that position β, when carbon at which the bridge moiety of the bridge peptide attaches to the peptide is position α, is tertiary and/or quaternary; and optionally generating the bridge peptide using the raw material.

In another aspect, the present disclosure provides a compound moiety for crosslinking a peptide moiety comprising a β-strand structure, wherein the compound moiety has an amino acid structure, and position β in the amino acid structure has a tertiary or quaternary structure, a compound providing such a compound moiety, or a combination thereof. Such a compound moiety can be a moiety comprised in the bridge peptide of the present disclosure. A compound providing such a compound moiety or a combination thereof can comprise a raw material of the bridge peptide of the present disclosure or a combination thereof.

In another aspect, the present disclosure provides a bridge peptide comprising a compound moiety for crosslinking a peptide moiety comprising a β-strand structure, wherein the compound moiety has an amino acid structure, and position β in the amino acid structure has a tertiary or quaternary structure. Such a compound moiety can be a moiety comprised in the bridge peptide of the present disclosure. A compound providing such a compound moiety or a combination thereof can comprise a raw material of the bridge peptide of the present disclosure or a combination thereof.

In still another aspect, the present disclosure provides a composition comprising a bridge peptide material for cross-linking a peptide moiety comprising a β-strand structure, wherein the bridge peptide material is a material that comprises an amino acid structure or forms an amino acid structure after synthesis, and position β in the amino acid structure has a tertiary or quaternary structure. Such a compound moiety can be a moiety comprised in the bridge peptide of the present disclosure. A compound providing such a compound moiety or a combination thereof can comprise a raw material of the bridge peptide of the present disclosure or a combination thereof.

The present disclosure provides a bridge polypeptide having a feature set forth in the following formula in at least one crosslink. In one embodiment, the present disclosure is a polypeptide of formula (I)

[Chemical Formula 170]

(I)

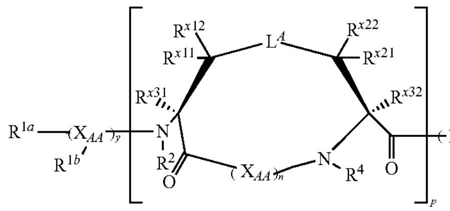

or a pharmaceutically acceptable salt thereof or a stereoisomer thereof, wherein $R^{1a}$ and $R^{1b}$ are independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or $R^{1a}$ and $R^{1b}$ together form an optionally substituted nonaromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently hydrogen, optionally substituted alkyl, optionally substituted alkene, optionally substituted alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or $R^{X11}$ and $R^{X12}$, together with the carbon atom to which they are attached, may form an optionally substituted nonaromatic carbocycle, an optionally substituted nonaromatic heterocycle, optionally substituted aryl, or optionally substituted heteroaryl, $R^{X21}$ and $R^{X22}$, together with the carbon atom to which they are attached, may form an optionally substituted nonaromatic carbocycle, an substituted optionally nonaromatic heterocycle, optionally substituted aryl, or optionally substituted heteroaryl, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxy, or two $R^B$ groups together form an optionally substituted nonaromatic carbocycle, an optionally substituted nonaromatic heterocycle, optionally substituted aryl, or an optionally substituted heteroaryl ring, $L^A$ is each independently-(optionally substituted $C_{0-k}$ alkylene)-[optionally substituted alkylene, optionally substituted alkenylene, optionally substituted alkynylene, optionally substituted cycloalkylene, optionally substituted cycloalkenylene, optionally substituted cycloalkynylene, optionally substituted heteroalkylene, optionally substituted heteroalkenylene, optionally substituted heteroalkynylene, optionally substituted heterocycloalkylene, optionally substituted heterocycloalkenylene, optionally substituted heterocycloalkynylene, optionally substituted arylene, or optionally substituted heteroarylene]-(optionally substituted $C_{0-k}$ alkylene)-, wherein k is an integer that is 5 or greater, y and z are each independently an integer from 0 to 100 (preferably 0 to 10), $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is an integer (preferably n is 1), and p is an integer from 1 to 100 (preferably 1 to 10).

The present disclosure provides a bridge polypeptide having a feature set forth in the following formula in at least one crosslink. In one embodiment, the present disclosure is a polypeptide of formula (I)

[Chemical Formula 171]

(I)

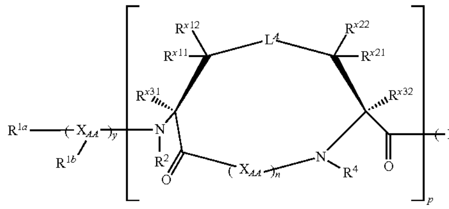

or a pharmaceutically acceptable salt thereof or a stereoisomer thereof, wherein $R^{1a}$ and $R^{1b}$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or $R^{1a}$ and $R^{1b}$ together form an optionally substituted non-aromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently hydrogen, methyl, methoxy, methoxymethyl, secondary amine substituted with methyl or Boc, tertiary amine (substituted with methyl), quaternary ammonium substituted with methyl, or methyl substituted with halogen, or $R^{X11}$ and $R^{X12}$, together with the carbon atom to which they are attached, may unsubstituted saturated $C_{3-10}$ nonaromatic carbocycle or an optionally substituted saturated 3- to 10-membered nonaromatic heterocycle, $R^{X21}$ and $R^{X22}$, together with the carbon atom to which they are attached, may form an unsubstituted saturated $C_{3-10}$ nonaromatic carbocycle or an optionally substituted saturated 3- to 10-membered nonaromatic heterocycle, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic heterocycle or an optionally substituted heteroaryl ring, $L^A$ is each independently-(optionally substituted $C_{0-k}$ alkylene)-[optionally substituted alkylene, optionally substituted alkenylene, optionally substituted alkynylene, optionally substituted cycloalkylene, optionally substituted cycloalkenylene, optionally substituted cycloalkynylene, optionally substituted heteroalkylene, optionally substituted heteroalkenylene, optionally substituted heteroalkynylene, optionally substituted heterocycloalkylene, optionally substituted heterocycloalkenylene, optionally substituted heterocycloalkynylene, optionally substituted arylene, or optionally substituted heteroarylene]-(optionally substituted $C_{0-k}$ alkylene)-, wherein k is an integer that is 5 or greater, y and z are each independently an integer from 0 to 10, $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is 1, and p is an integer from 1 to 10.

In one embodiment, the present disclosure is a polypeptide of formula (I),

[Chemical Formula 172]

(I)

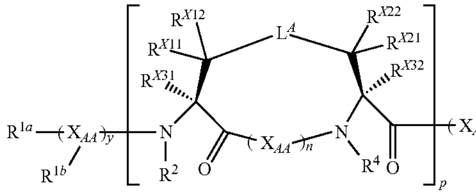

or a pharmaceutically acceptable salt thereof or a stereoisomer thereof, wherein $R^{1a}$ and $R^{1b}$ are each independently hydrogen, an optionally substituted aliphatic group, an optionally substituted heteroaliphatic group, optionally substituted carbocyclyl, optionally substituted heterocyclyl, optionally substituted substituted aryl, optionally heteroaryl, optionally substituted acyl, or hydroxyl, or $R^{1a}$ and $R^{1b}$ together form an optionally substituted non-aromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently hydrogen, methyl, methoxy, methoxymethyl, secondary amine substituted with methyl or Boc, tertiary amine substituted with methyl or Boc, quaternary ammonium substituted with methyl, or methyl substituted with halogen, preferably hydrogen, methyl, or methyl substituted with halogen, or $R^{X11}$ and $R^{X12}$, together with the carbon atom to which they are attached, may form an unsubstituted saturated $C_{3-10}$ nonaromatic carbocycle or an optionally substituted saturated 3- to 10-membered nonaromatic heterocycle, $R^{X21}$ and $R^{X22}$, together with the carbon atom to which they are attached, may form an unsubstituted saturated $C_{3-10}$ nonaromatic carbocycle or an optionally substituted saturated 3- to 10-membered nonaromatic heterocycle, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic heterocycle or an optionally substituted heteroaryl ring, $L^A$ is each independently-(optionally substituted $C_{0-k}$ alkylene)-[optionally substituted alkylene, optionally substituted alkenylene, optionally substituted alkynylene, optionally substituted cycloalkylene, optionally substituted cycloalkenylene, optionally substituted cycloalkynylene, optionally substituted heteroalkylene, optionally substituted heteroalkenylene, optionally substituted heteroalkynylene, optionally substituted heterocycloalkylene, optionally substituted heterocycloalkenylene, optionally substituted heterocycloalkynylene, optionally substituted arylene, or optionally substituted heteroarylene]-(optionally substituted $C_{0-k}$ alkylene)-, wherein k is an integer that is 6 or greater (or 5 or greater), y and z are each independently an integer from 0 to 100 (preferably 0 to 100), $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is an integer, preferably 1, and p is an integer from 1 to 10.

In one embodiment, a substituent formed by click chemistry may be excluded from LA.

In one embodiment, $R^{X11}$, $R^{X12}$, $R^{X21}$, and $R^{X22}$ are each independently alkyl substituted with halogen or alkyl of $C_2$ or greater, or $R^{X11}$ and $R^{X12}$, together with the carbon atom to which they are attached, may form an unsubstituted saturated $C_{3-10}$ nonaromatic carbocycle or an optionally substituted saturated 3- to 10-membered nonaromatic heterocycle, $R^{X21}$ and $R^{X22}$, together with the carbon atom to which they are attached, may form an unsubstituted saturated $C_{3-10}$ nonaromatic carbocycle or an optionally substituted saturated 3- to 10-membered nonaromatic heterocycle.

The present disclosure provides a bridge polypeptide having at least one crosslink having a feature set forth in the following structure. In one aspect, the present disclosure is a polypeptide of formula (II)

[Chemical Formula 173]

(II)

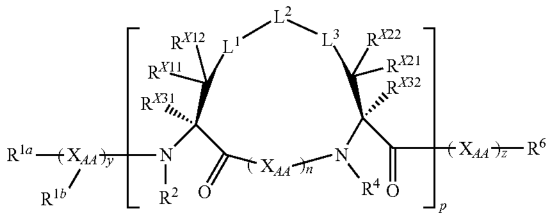

or a pharmaceutically acceptable salt thereof or a stereoisomer thereof, wherein $R^{1a}$ and $R^{1b}$ are each independently hydrogen, an substituted aliphatic group, an optionally optionally substituted heteroaliphatic group, optionally substituted carbocyclyl, optionally substituted heterocyclyl, optionally substituted aryl, optionally substituted heteroaryl, optionally substituted acyl, or hydroxyl, or $R^{1a}$ and $R^{1b}$ together form an optionally substituted nonaromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently hydrogen, optionally substituted alkyl, optionally substituted alkene, optionally substituted alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or $R^{X11}$ and $R^{X12}$, together with the carbon atom to which they are attached, may form an optionally substituted nonaromatic carbocycle, an optionally substituted nonaromatic heterocycle, optionally substituted aryl, or optionally substituted heteroaryl, $R^{X21}$ and $R^{X22}$, together with the carbon atom to which they are attached, may form an optionally substituted nonaromatic carbocycle, an optionally substituted nonaromatic heterocycle, optionally substituted aryl, or optionally substituted heteroaryl, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic carbocycle, an optionally substituted nonaromatic heterocycle, optionally substituted aryl, or an optionally substituted heteroaryl ring, $L^1$ and $L^3$ are each independently optionally substituted $C_{0-k}$ alkylene, wherein k is an integer that is 6 or greater, $L^2$ is optionally substituted alkylene, optionally substituted alkenylene, optionally substituted alkynylene, optionally substituted cycloalkylene, optionally substituted cycloalkenylene, optionally substituted cycloalkynylene, optionally substituted heteroalkylene, optionally substituted heteroalkenylene, optionally substituted heteroalkynylene, optionally substituted heterocycloalkylene, optionally substituted heterocycloalkenylene, optionally substituted heterocycloalkynylene, optionally substituted arylene, or optionally substituted heteroarylene, y and z are each independently an integer from 0 to 100 (preferably 0 to 10), $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is an integer (preferably n is 1), and p is an integer from 1 to 100 (preferably 1 to 10).

Alternatively, the present disclosure is a peptide of formula (II)

[Chemical Formula 174]

(II)

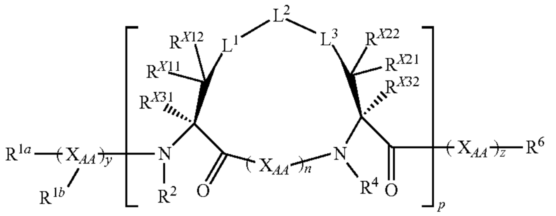

or a pharmaceutically acceptable salt thereof or a stereoisomer thereof, wherein $R^{1a}$ and $R^{1b}$ are each independently hydrogen, an optionally substituted aliphatic group, an optionally substituted heteroaliphatic group, optionally substituted carbocyclyl, optionally substituted heterocyclyl, optionally substituted heteroaryl, substituted aryl, optionally optionally substituted acyl, or hydroxyl, or $R^{1a}$ and $R^{1b}$ together form an optionally substituted nonaromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently substituted alkyl, optionally substituted alkene, optionally substituted alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or $R^{X11}$ and $R^{X12}$, together with the carbon atom to which they are attached, may form an optionally substituted nonaromatic carbocycle, an optionally substituted nonaromatic heterocycle, optionally substituted aryl, or optionally substituted heteroaryl, $R^{X21}$ and $R^{X22}$, together with the carbon atom to which they are attached, may form an optionally substituted nonaromatic carbocycle, an optionally substituted nonaromatic heterocycle, optionally substituted aryl, or optionally substituted heteroaryl, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic carbocycle, an optionally substituted nonaromatic heterocycle, optionally substituted aryl, or an optionally substituted heteroaryl ring, $L^1$ and $L^3$ are each independently optionally substituted $C_{0-k}$ alkylene, wherein k is an integer that is 6 or greater, $L^2$ is optionally substituted alkylene, optionally substituted alkenylene, optionally substituted alkynylene, optionally substituted cycloalkylene, optionally substituted cycloalkenylene, optionally substituted cycloalkynylene, optionally substituted heteroalkylene, optionally substituted heteroalkenylene, optionally substituted heteroalkynylene, optionally substituted heterocycloalkylene, optionally substituted heterocycloalkenylene, optionally substituted heterocycloalkynylene, optionally substituted arylene, or optionally substituted heteroarylene, y and z are each independently an integer from 0 to 100 (preferably 0 to 10), $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is an integer (preferably n is 1), and p is an integer from 1 to 100 (preferably 1 to 10).

Alternatively, the present disclosure is a polypeptide of formula (II)

[Chemical Formula 174-2]

(II)

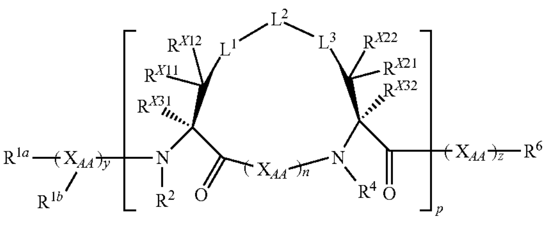

or a pharmaceutically acceptable salt thereof or a stereoisomer thereof, wherein $R^{1a}$ and $R^{1b}$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or $R^{1a}$ and $R^{1b}$ together form an optionally substituted nonaromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently hydrogen, methyl, methoxy, methoxymethyl, secondary amine substituted with methyl or Boc, tertiary amine (substituted with methyl), quaternary ammonium substituted with methyl, or methyl substituted with halogen, or $R^{X11}$ and $R^{X12}$, together with the carbon atom to which they are attached, may form an unsubstituted saturated $C_{3-10}$ nonaromatic carbocycle or an optionally substituted saturated 3- to 10-membered nonaromatic heterocycle, $R^{X21}$ and $R^{X22}$, together with the carbon atom to which they are attached, may form an unsubstituted saturated $C_{3-10}$ nonaromatic carbocycle or an optionally substituted saturated 3- to 10-membered nonaromatic heterocycle, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic heterocycle or an optionally substituted heteroaryl ring, $L^1$ and $L^3$ are each independently optionally substituted $C_{0-k}$ alkylene, wherein k is an integer that is 6 or greater, $L^2$ is optionally substituted alkylene, optionally substituted alkenylene, optionally substituted alkynylene, optionally substituted cycloalkylene, optionally substituted cycloalkenylene, optionally substituted cycloalkynylene, optionally substituted heteroalkylene, optionally substituted heteroalkenylene, optionally substituted heteroalkynylene, optionally substituted heterocycloalkylene, optionally substituted heterocycloalkenylene, optionally substituted heterocycloalkynylene, optionally substituted arylene, or optionally substituted heteroarylene, y and z are each independently an integer from 0 to 10, $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is 1, and p is an integer from 1 to 10.

Alternatively, the present disclosure is a polypeptide of formula (II)

[Chemical Formula 174-3]

(II)

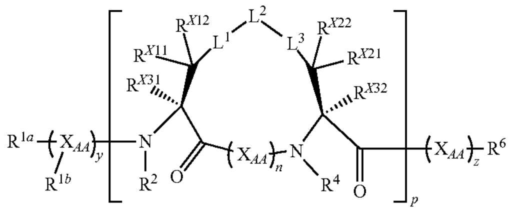

or a pharmaceutically acceptable salt thereof or a stereoisomer thereof, wherein $R^{1a}$ and $R^{1b}$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or $R^{1a}$ and $R^{1b}$ together form an optionally substituted nonaromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently methoxy, methoxymethyl, secondary amine substituted with methyl or Boc, tertiary amine (substituted with methyl), quaternary ammonium substituted with methyl, or methyl substituted with halogen, or $R^{X11}$ and $R^{X12}$, together with the carbon atom to which they are attached, may form an unsubstituted saturated $C_{3-10}$ nonaromatic carbocycle or an optionally substituted saturated 3- to 10-membered nonaromatic heterocycle, $R^{X21}$ and $R^{X22}$, together with the carbon atom to which they are attached, may form an unsubstituted saturated $C_{3-10}$ nonaromatic carbocycle or an optionally substituted saturated 3-10-membered nonaromatic heterocycle, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic heterocycle or an optionally substituted heteroaryl ring, $L^1$ and $L^3$ are each independently optionally substituted $C_{0-k}$ alkylene, wherein k is an integer that is 6 or greater, $L^2$ is optionally substituted alkylene, optionally substituted alkenylene, optionally substituted alkynylene, optionally substituted cycloalkylene, optionally substituted cycloalkenylene, optionally substituted cycloalkynylene, optionally substituted heteroalkylene, optionally substituted heteroalkenylene, optionally substituted heteroalkynylene, optionally substituted heterocycloalkylene, optionally substituted heterocycloalkenylene, optionally substituted heterocycloalkynylene, optionally substituted arylene, or optionally substituted heteroarylene, y and z are each independently an integer from 0 to 10, $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is 1, and p is an integer from 1 to 10.

The present disclosure provides a bridge peptide having at least one crosslink having a feature set forth in the following structure. In one aspect, the present disclosure is a polypeptide of formula (II)

[Chemical Formula 174-4]

(II)

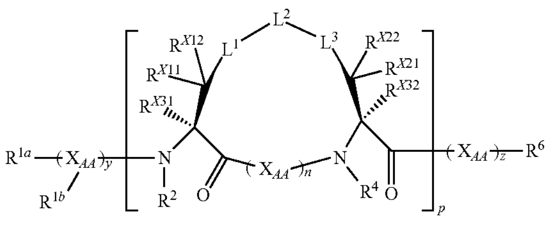

or a pharmaceutically acceptable salt thereof or a stereoisomer thereof, wherein $R^{1a}$ and $R^{1b}$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or $R^{1a}$ and $R^{1b}$ together form an optionally substituted nonaromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently hydrogen, optionally substituted alkyl, alkene, alkyne, optionally substituted heteroalkyl, imine, nitrile, optionally substituted secondary amine, tertiary amine, quaternary ammonium, sulfone ($SO_2$), or sulfoxide, or $R^{X11}$ and $R^{X12}$, together with the carbon atom to which they are attached, may form an optionally substituted nonaromatic carbocycle, an optionally substituted nonaromatic heterocycle, optionally substituted aryl, or optionally substituted heteroaryl, $R^{X21}$ and $R^{X22}$, together with the carbon atom to which they are attached, may form an optionally substituted nonaromatic carbocycle, an optionally substituted nonaromatic heterocycle, optionally substituted aryl, or optionally substituted heteroaryl, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic heterocycle or an optionally substituted heteroaryl ring, $L^1$ and $L^3$ are each independently optionally substituted $C_{0-k}$ alkylene, wherein k is an integer that is 6 or greater, $L^2$ is optionally substituted alkylene, optionally substituted alkenylene, optionally substituted alkynylene, optionally substituted cycloalkylene, optionally substituted substituted cycloalkynylene, cycloalkenylene, optionally optionally substituted heteroalkylene, optionally substituted heteroalkenylene, optionally substituted heteroalkynylene, optionally substituted heterocycloalkylene, optionally substituted heterocycloalkenylene, optionally substituted heterocycloalkynylene, optionally substituted arylene, or optionally substituted heteroarylene, y and z are each independently an integer from 0 to 100, $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is 1, and p is an integer from 1 to 10.

Each variable of formula (II) can be any combination of variables of formula (I), and $L_1$ can be any variable of a substituent in the center of $L_4$.

In one embodiment, the present disclosure is a polypeptide represented by the following formula:

[Chemical Formula 174-5]

(II)

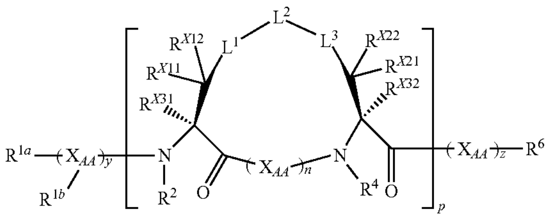

or a pharmaceutically acceptable salt thereof or a stereoisomer thereof, wherein $R^{1a}$ and $R^{1b}$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or $R^{1a}$ and $R^{1b}$ together form an optionally substituted nonaromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently hydrogen, methyl, methoxy, methoxymethyl, secondary amine substituted with methyl or Boc, tertiary amine (substituted with methyl), quaternary ammonium substituted with methyl, or methyl substituted with halogen, or $R^{X11}$ and $R^{X12}$, together with the carbon atom to which they an unsubstituted saturated $C_{3-10}$ are attached, may form nonaromatic carbocycle or an optionally substituted saturated 3- to 10-membered nonaromatic heterocycle, $R^{X21}$ and $R^{X22}$, together with the carbon atom to which they are attached, may form an unsubstituted saturated $C_{3-10}$ nonaromatic carbocycle or an optionally substituted saturated 3- to 10-membered nonaromatic heterocycle, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is $—R^B$, $—OR^B$, $—N(R^B)_2$, or $—SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic heterocycle or an optionally substituted heteroaryl ring, $L^1$ and $L^3$ are each independently optionally substituted $C_{0-k}$ alkylene, wherein k is an integer that is 6 or greater, $L^2$ is optionally substituted alkylene, optionally substituted alkenylene, optionally substituted alkynylene, optionally substituted cycloalkylene, optionally substituted cycloalkenylene, optionally substituted cycloalkynylene, optionally substituted heteroalkylene, optionally substituted heteroalkenylene, optionally substituted heteroalkynylene, optionally substituted heterocycloalkylene, optionally substituted heterocycloalkenylene, optionally substituted heterocycloalkynylene, optionally substituted arylene, or optionally substituted heteroarylene, y and z are each independently an integer from 0 to 10, $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is 1, and p is an integer from 1 to 10.

In one embodiment, $L^2$ is optionally substituted alkylene, optionally substituted alkenylene, optionally substituted alkynylene, optionally substituted cycloalkylene, optionally substituted cycloalkenylene, optionally substituted cycloalkynylene, optionally substituted heteroalkylene, substituted optionally heteroalkenylene, optionally substituted heteroalkynylene, optionally substituted heterocycloalkylene, optionally substituted heterocycloalkenylene, optionally substituted heterocycloalkynylene, or optionally substituted arylene.

In one embodiment, the present disclosure is a polypeptide of formula (II):

[Chemical Formula 174-6]

(II)

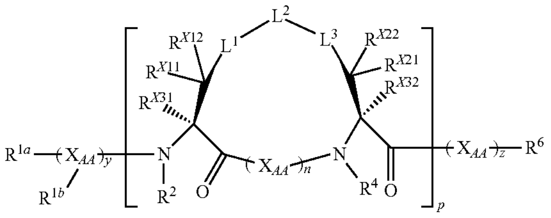

or a pharmaceutically acceptable salt thereof or a stereoisomer thereof, wherein $R^{1a}$ and $R^{1b}$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or $R^{1a}$ and $R^{1b}$ together form an optionally substituted nonaromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently hydrogen, methyl, methoxy, methoxymethyl, optionally substituted (e.g., Boc-substituted) secondary amine, tertiary amine substituted with methyl or Boc, quaternary ammonium substituted with methyl, or methyl substituted with halogen, preferably hydrogen, methyl, or methyl substituted with halogen, or $R^{X11}$ and $R^{X12}$, together with the carbon atom to which they are attached, may form an unsubstituted saturated $C_{3-10}$ nonaromatic carbocycle or an optionally substituted saturated 3- to 10-membered nonaromatic heterocycle, preferably an unsubstituted $C_{3-6}$ nonaromatic carbocycle or an optionally substituted 4- to 6-membered nonaromatic heterocycle, $R^{X21}$ and $R^{X22}$, together with the carbon atom to which they are attached, may form an unsubstituted saturated $C_{3-10}$ nonaromatic carbocycle an or optionally substituted saturated 3- to 10-membered nonaromatic heterocycle, preferably an unsubstituted $C_{3-6}$ nonaromatic carbocycle or an optionally substituted to 4-6-membered nonaromatic heterocycle, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic heterocycle or an optionally substituted heteroaryl ring, $L^1$ and $L^3$ are each independently optionally substituted $C_{0-k}$ alkylene, wherein k is an integer that is 6 or greater, $L^2$ is optionally substituted alkylene, optionally substituted alkenylene, optionally substituted alkynylene, optionally substituted cycloalkylene, optionally substituted cycloalkenylene, optionally substituted cycloalkynylene, optionally substituted heteroalkylene, optionally substituted heteroalkenylene, optionally substituted heteroalkynylene, optionally substituted heterocycloalkylene, optionally substituted heterocycloalkenylene, optionally substituted heterocycloalkynylene, optionally substituted arylene, or optionally substituted heteroarylene, y and z are each independently an integer from 0 to 100, $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is 1, and p is an integer from 1 to 10.

In one embodiment, $L^2$ is optionally substituted alkylene, optionally substituted alkenylene, optionally substituted alkynylene, optionally substituted cycloalkylene, optionally substituted cycloalkenylene, optionally substituted cycloalkynylene, optionally substituted heteroalkylene, optionally substituted heteroalkenylene, optionally substituted heteroalkynylene, optionally substituted heterocycloalkylene, optionally substituted heterocycloalkenylene, optionally substituted heterocycloalkynylene, or optionally substituted arylene.

The present disclosure provides a bridge polypeptide having a double bond or a triple bond in at least one crosslink. In one aspect, the present disclosure provides a polypeptide of formula (III):

[Chemical Formula 175]

(III)

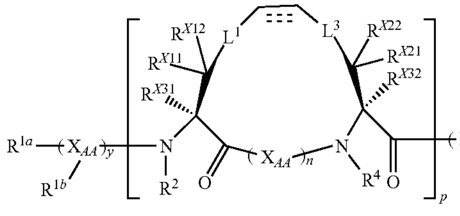

or a pharmaceutically acceptable salt thereof, wherein each instance of

[Chemical Formula 176]

independently represents a single bond, a double bond, or a triple bond, $R^{1a}$ and $R^{1b}$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or $R^{1a}$ and $R^{1b}$ together form an optionally substituted nonaromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted optionally aryl, substituted heteroaryl, optionally substituted acyl, or a nitrogen protecting group, $R^{X11}$, $R^{X12}$, $R^{X21}$, and $R^{X22}$ are each independently hydrogen, optionally substituted alkyl, optionally substituted alkene, optionally substituted alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or $R^{X11}$ and $R^{X12}$, together with the carbon atom to which they are attached, may form an optionally substituted nonaromatic carbocycle, an optionally substituted nonaromatic heterocycle, optionally substituted aryl, or optionally substituted heteroaryl, $R^{X21}$ and $R^{X22}$, together with the carbon atom to which they are attached, may form an optionally substituted nonaromatic carbocycle, an optionally substituted non-aromatic heterocycle, optionally substituted aryl, or optionally substituted heteroaryl, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic an optionally substituted heteroaliphatic group, group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic carbocycle, "an optionally substituted nonaromatic heterocycle, optionally substituted aryl, or an optionally substituted heteroaryl ring, $L^1$ is independently a bond, optionally substituted $C_{1-10}$ alkylene, —$COR^{L1}$—, —$C(=O)R^{L1}$—, —$C(=O)OR^{L1}$—, —$C(=NR^{L1A})R^{L1}$—, or —$C(=NOH)R^{L1}$, wherein $R^{L1}$ and $R^{L1A}$ are each independently optionally substituted $C_{1-10}$ alkylene, $L^3$ is independently a bond, optionally substituted $C_{1-10}$ alkylene, —$COR^{L1}$—, —$C(=O)R^{L1}$—, —$C(=O)OR^{L1}$—, —$C(=NR^{L1A})R^{L1}$—, or —$C(=NOH)R^{L1}$—, $R^{L1}$, $R^{L1A}$, and $R^2$ are each independently optionally substituted $C_{1-10}$ alkylene, y and z are each independently an integer from 0 to 100 (preferably 0 to 10), $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is an integer (preferably n is 1), and p is an integer from 1 to 100 (preferably 1 to 10).

Alternatively, y and z are each independently an integer from 0 to 100 (preferably 0 to 10), $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is an integer (preferably n is 1), and p is an integer from 1 to 100 (preferably 1 to 10).

Alternatively, the present disclosure provides a bridge polypeptide having a double bond or a triple bond in at least one crosslink. In one aspect, the present disclosure is a polypeptide of formula (III):

[Chemical Formula 177]

(III)

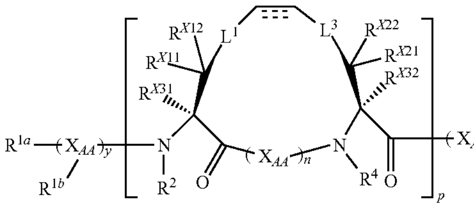

or a pharmaceutically acceptable salt thereof, wherein each instance of

[Chemical Formula 178]

independently represents a single bond, a double bond, or a triple bond, $R^{1a}$ and $R^{1b}$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or $R^{1a}$ and $R^{1b}$ form together an optionally substituted non-aromatic heterocycle or an optionally substituted heteroaryl ring, $R^2$ and $R^4$ are each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or a nitrogen protecting group, $R^{X11}$, $R^{X12}$, $R^{X21}$, and $R^{X22}$ are each independently substituted alkyl, optionally substituted alkene, optionally substituted alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or $R^{X11}$ and $R^{X12}$, together with the carbon atom to which they are attached, may form an optionally substituted nonaromatic carbocycle, an optionally substituted non-aromatic heterocycle, optionally substituted aryl, or optionally substituted heteroaryl, $R^{X21}$ and $R^{X22}$, together with the carbon atom to which they are attached, may form an optionally substituted nonaromatic carbocycle, an optionally substituted non-aromatic heterocycle, optionally substituted aryl, or optionally substituted heteroaryl, provided that $R^{X11}$ and $R^{X12}$ are not both hydrogen, and $R^{X21}$ and $R^{X22}$ are not both hydrogen, $R^{X31}$ and $R^{X32}$ are each independently hydrogen or halogen, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic carbocycle, an optionally substituted nonaromatic heterocycle, optionally substituted aryl, or an optionally substituted heteroaryl ring, $L^1$ is independently a bond, optionally substituted $C_{1-10}$ alkylene, —$COR^{L1}$—, —C(=O)$R^{L1}$—, —C(=O)$OR^{L1}$—, —C(=$NR^{L1A}$)$R^{L1}$—, or —C(=NOH)$R^{L1}$—, wherein $R^{L1}$ and $R^{L1A}$ are each independently optionally substituted $C_{1-10}$ alkylene, $L^3$ is independently a bond, optionally substituted $C_{1-10}$ alkylene, —$COR^{L1}$—, —C(=O)$R^{L1}$—, —C(=O)$OR^{L1}$—, —C(=$NR^{L1A}$)$R^{L1}$—, or —C(=NOH)$R^{L1}$—, $R^{L1}$, $R^{L1A}$, and $R^{L2}$ are each independently optionally substituted $C_{1-10}$ alkylene, y and z are each independently an integer from 0 to 100 (preferably 0 to 10), $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is an integer (preferably n is 1), and p is an integer from 1 to 100 (preferably 1 to 10).

Alternatively, y and z are each independently an integer from 0 to 100 (preferably 0 to 10), $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is an integer (preferably n is 1), and p is an integer from 1 to 100 (preferably 1 to 10).

Alternatively, the present disclosure provides a bridge polypeptide having a double bond or a triple bond in at least one crosslink. In one aspect, the present disclosure provides a polypeptide of formula (III):

[Chemical Formula 178-2]

(III)

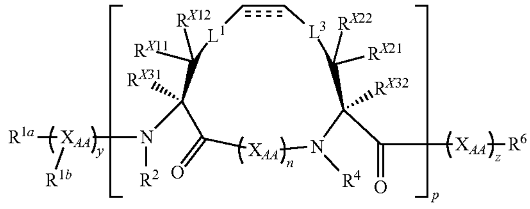

or a pharmaceutically acceptable salt thereof, wherein each instance of

[Chemical Formula 178-3]

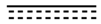

represents a single bond, a double bond, or a triple bond, $R^2$ and $R^4$ are each independently hydrogen, acyl, optionally substituted $C_{1-6}$ alkyl, or an amino protecting group, $R^{X31}$ and $R^{X32}$ are each independently hydrogen or halogen, $R^{X11}$, $R^{X12}$, $R^{X21}$, and $R^{X22}$ are each independently hydrogen, optionally substituted alkyl, alkene, alkyne, optionally substituted heteroalkyl, imine, nitrile, optionally substituted secondary amine, tertiary, quaternary ammonium, sulfone ($SO_2$), or methyl substituted with sulfoxide, $R^{X11}$ and $R^{X12}$, together with the carbon atom to which they are attached, may form an optionally substituted nonaromatic carbocycle, an optionally substituted nonaromatic heterocycle, optionally substituted aryl, or optionally substituted heteroaryl, $R^{X21}$ and $R^{X22}$, together with the carbon atom to which they are attached, may form an optionally substituted nonaromatic carbocycle, an optionally substituted nonaromatic heterocycle, optionally substituted aryl, or optionally substituted heteroaryl, provided that $R^{X11}$ and $R^{X12}$ are not both hydrogen, and $R^{X21}$ and $R^{X22}$ are not both hydrogen, $L^1$ is independently a bond, optionally substituted $C_{1-10}$ alkylene, —$COR^{L1}$—, —C(=O)$R^{L1}$—, —C(=O)$OR^{L1}$—, —C(=$NR^{L1A}$)$R^{L1}$—, or —C(=NOH)$R^{L1}$—, wherein $R^{L1}$ and $R^{L1A}$ are each independently optionally substituted $C_{1-10}$ alkylene, $L^3$ is independently a bond, optionally substituted $C_{1-10}$ alkylene, —$COR^{L1}$—, —C(=O)$R^{L1}$—, —C(=O)$OR^{L1}$—, —C(=$NR^{L1A}$)$R^{L1}$—, or —C(=NOH)$R^{L1}$—, $R^{L1}$, $R^{L1A}$, and $R^{L2}$ are each independently optionally substituted $C_{1-10}$ alkylene, $R^{1a}$ and $R^{1b}$ are each independently —$R^B$, —$OR^B$, —$N(R^B)_2$, or —$SR^B$, wherein $R^B$ is each independently hydrogen, a branched or unbranched aliphatic group, a branched or unbranched heteroaliphatic group, carbocyclyl, heterocyclyl, aryl, heteroaryl, acyl, resin, or hydroxyl, amino, or thiol protecting group, $R^6$ is —$R^B$, —$OR^B$, —$N(R^B)_2$, or —$SR^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic heterocycle or an optionally substituted heteroaryl ring, y and z are each independently an integer from 0 to 100, $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is 1, and p is an integer from 1 to 10.

In one embodiment, the present disclosure provides a polypeptide of formula (III):

[Chemical Formula 178-4]

(III)

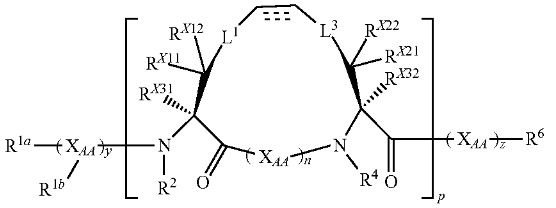

or a pharmaceutically acceptable salt thereof, wherein each instance of

[Chemical Formula 178-5]

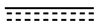

independently represents a single bond, a double bond, or a triple bond, $R^2$ and $R^4$ are each independently hydrogen, acyl, optionally substituted $C_{1-6}$ alkyl, or an amino protecting group, $R^{X31}$ and $R^{X32}$ are each independently hydrogen or halogen, $R^{X11}$, $R^{X12}$, $R^{X21}$, and $R^{X22}$ are each independently hydrogen, methyl, methoxy, methoxymethyl, optionally substituted secondary amine (with methyl, Boc, or the like), tertiary amine substituted with methyl or Boc, quaternary ammonium substituted with methyl or Boc, or methyl substituted with halogen, $R^{X11}$ and $R^{X12}$, together with the carbon atom to which they are attached, may form an unsubstituted saturated $C_{3-10}$ nonaromatic carbocycle or an optionally substituted saturated 3- to 10-membered nonaromatic heterocycle, preferably an unsubstituted $C_{3-6}$ nonaromatic carbocycle or an optionally substituted 4- to 6-membered nonaromatic heterocycle, $R^{X21}$ and $R^{X22}$, together with the carbon atom to which they are attached, may form an unsubstituted saturated $C_{3-10}$ nonaromatic carbocycle an or optionally substituted saturated 3- to 10-membered nonaromatic heterocycle, or may form an unsubstituted $C_{3-6}$ nonaromatic carbocycle or an optionally substituted 4- to 6-membered nonaromatic heterocycle, provided that $R^{X11}$ and $R^{X12}$ are not both hydrogen, and $R^{X21}$ and $R^{X22}$ are not both hydrogen, $L^1$ is independently a bond, optionally substituted $C_{1-10}$ alkylene, or —C(═O)O$R^{L1}$—, $L^3$ is independently a bond, optionally substituted $C_{1-10}$ alkylene, or —C(═O)O$R^{L2}$—, $R^{L1}$ and $R^{L2}$ are each independently optionally substituted $C_{1-10}$ alkylene, $R^{1a}$ and $R^{1b}$ are each independently —$R^B$, —O$R^B$, —N($R^B$)$_2$, or —S$R^B$, wherein $R^B$ is each independently hydrogen, a branched or unbranched aliphatic group, a branched or unbranched heteroaliphatic group, carbocyclyl, heterocyclyl, aryl, heteroaryl, acyl, resin, or hydroxyl, amino, or thiol protecting group, $R^6$ is —$R^B$, —O$R^B$, —N($R^B$)$_2$, or —S$R^B$, wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together form an optionally substituted nonaromatic heterocycle or an optionally substituted heteroaryl ring, y and z are each independently an integer from 0 to 100, $(X_{AA})_y$ is a peptide comprised of y amino acids selected from the group consisting of naturally occurring amino acids and non-naturally occurring amino acids, and derivatives thereof, wherein the y amino acids may be the same or different from one another, $(X_{AA})_z$ is a peptide comprised of z amino acids selected from the group consisting of naturally occurring amino acids and non-naturally occurring amino acids, and derivatives thereof, wherein the z amino acids may be the same or different from one another, n is 1, and p is an integer from 1 to 10.

As generally described above, $L^1$ is independently a bond, optionally substituted $C_{1-10}$ alkylene, —CO$R^{L1}$—, —C(═O)$R^{L1}$—, —C(═O)O$R^{L1}$—, —C(═N$R^{L1A}$) $R^{L1}$—, —C(═NOH) $R^{L1}$—, —C(═O)NR$R^{L1}$, or —C(═O) S$R^{L1}$—, wherein $R^{L1}$ and $R^{L1A}$ are each independently optionally substituted $C_{1-10}$ alkylene. In some embodiments, $L^1$ is optionally substituted $C_{1-10}$ alkylene. In some embodiments, $L^1$ is substituted $C_{1-10}$ alkylene. In some embodiments, $L^1$ is —$(CH_2)_g$—, wherein g is 0 or an integer from 1 to 10. In some embodiments, g is 0, and $L^1$ is a bond. In some embodiments, g is 1. In some embodiments, g is 2. In some embodiments, g is 3. In some embodiments, g is 4. In some embodiments, g is 5. In some embodiments, g is 6. In some embodiments, g is 7. In some embodiments, g is 8. In some embodiments, g is 9. In some embodiments, g is 10. In a certain embodiment, $R^{L1}$ is substituted $C_{1-10}$ alkylene. In a certain embodiment, $R^{L1}$ is —$(CH_2)_{g1}$—, wherein g1 is an integer from 1 to 10. In some embodiments, g1 is 1. In some embodiments, g1 is 2. In some embodiments, g1 is 3. In some embodiments, g1 is 4. In some embodiments, g1 is 5. In some embodiments, g1 is 6. In some embodiments, g1 is 7. In some embodiments, g1 is 8. In some embodiments, g1 is 9. In some embodiments, g1 is 10.

As generally described above, $L^3$ is independently a bond, optionally substituted $C_{1-10}$ alkylene, or —C(═O)O$R^{L3}$—, and $R^{L3}$ is optionally substituted $C_{1-10}$ alkylene. In some embodiments, is optionally substituted $C_{1-10}$ alkylene. In some embodiments, $L^3$ is substituted $C_{1-10}$ alkylene. In some embodiments, $L^3$ is —$(CH_2)_h$—, wherein h is 0 or an integer from 1 to 10. In some embodiments, h is 0, and $L^3$ is a bond. In some embodiments, h is 1. In some embodiments, h is 2. In some embodiments, h is 3. In some embodiments, h is 4. In some embodiments, h is 5. In some embodiments, h is 6. In some embodiments, h is 7. In some embodiments, h is 8. In some embodiments, h is 9. In some embodiments, h is 10. In a certain embodiment, $R^2$ is substituted $C_{1-10}$ alkylene. In a certain embodiment, $R^{L3}$ is —$(CH_2)_{h1}$—, wherein h1 is an integer from 1 to 10. In some embodiments, h1 is 1. In some embodiments, h1 is 2. In some embodiments, h1 is 3. In some embodiments, h1 is 4. In some embodiments, h1 is 5. In some embodiments, h1 is 6. In some embodiments, h1 is 7. In some embodiments, h1 is 8. In some embodiments, h1 is 9. In some embodiments, h1 is 10.

In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8. In certain embodiments, p is 9. In certain embodiments, p is 10.

In a certain embodiment, —[$X^{AA}$]-corresponds to formula

[Chemical Formula 179]

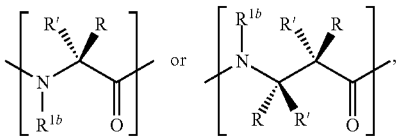

wherein R and R' are each independently hydrogen or a suitable amino acid side chain defined herein, and $R^{1a}$ and $R^{1b}$ are the same as defined herein. Suitable amino acid side chains include, but are not limited to, both naturally occurring and non-naturally occurring amino acids that are provided in Tables 1 to 3 and those that are described herein. In a certain embodiment, each $X^{AA}$ is an α-amino acid. In a certain embodiment, each $X^{AA}$ is a naturally occurring L-amino acid provided in Table 1. In a certain embodiment, $X^{AA}$ is each independently a naturally occurring L-amino acid provided in Table 1, or a non-naturally occurring D-amino" acid provided in Table 2. Fisher B F, J. Am. Chem. Soc. 2016, 138, 10766-10769 or the like can be referred for an example of γ amino acid. Of course, δ amino acid and any amino acid defined by other nomenclatures are within the scope of the present disclosure.

In a certain embodiment, each $X^{AA}$ is a naturally occurring amino acid. In a certain embodiment, each $X^{AA}$ is an α-amino acid. In a certain embodiment, each $X^{AA}$ is a naturally occurring L-amino acid provided in Table 1. In a certain embodiment, $X^{AA}$ is each independently a naturally occurring L-amino acid provided in Table 1, or a non-naturally occurring amino acid provided in Table 2, 3, and/or 4.

TABLE 1

| Exemplary naturally occuring α amino acid | R | R' |
|---|---|---|
| L-alanine (A) | —$CH_3$ | —H |
| L-arginine (R) | —$CH_2CH_2CH_2$—NHC(=NH)$NH_2$ | —H |
| L-asparagine (N) | —$CH_2C$(=O)$NH_2$ | —H |
| L-aspartic acid (D) | —$CH_2CO_2H$ | —H |
| L-cysteine (C) | —$CH_2SH$ | —H |
| L-glutamic acid (E) | —$CH_2CH_2CO_2H$ | —H |
| L-glutamine (Q) | —$CH_2C$(=O)$NH_2$ | —H |

TABLE 1-continued

| Exemplary naturally occuring α amino acid | R | R' |
|---|---|---|
| Glycine (G) | —H | —H |
| L-histidine (H) | —$CH_2$-2-(1H-imidazole) | —H |
| L-isoleucine (I) | -sec-butyl | —H |
| L-leucine (L) | -isobutyl | —H |
| L-lysine (K) | —$CH_2CH_2CH_2CH_2NH_2$ | —H |
| L-methionine (M) | —$CH_2CH_2SCH_3$ | —H |
| L-phenylalanine (F) | —$CH_2Ph$ | —H |
| L-proline (P) | -2-(pyrrolidine) | —H |
| L-serine (S) | —$CH_2OH$ | —H |
| L-threonine (T) | —$CH_2CH(OH)(CH_3)$ | —H |
| L-tryptophan (W) | —$CH_2$-3-(1H-indole) | —H |
| L-tyrosine (Y) | —$CH_2$-3-(p-hydroxyphenyl) | —H |
| L-valine (V) | -isopropyl | —H |

TABLE 2

| Exemplary non-naturally occurring α amino acid | R | R' |
|---|---|---|
| D-alanine | —H | —$CH_3$ |
| D-arginine | —H | —$CH_2CH_2CH_2$—NHC(=NH)$NH_2$ |
| D-asparagine | —H | —$CH_2C$(=O)$NH_2$ |
| D-aspartic acid | —H | —$CH_2CO_2H$ |
| D-cysteine | —H | —$CH_2SH$ |
| D-glutamic acid | —H | —$CH_2CH_2CO_2H$ |
| D-glutamine | —H | —$CH_2CH_2C$(=O)$NH_2$ |
| D-histidine | —H | —$CH_2$-2-(1H-imidazole) |
| D-isoleucine | —H | -sec-butyl |
| D-leucine | —H | -isobutyl |
| D-lysine | —H | —$CH_2CH_2CH_2CH_2NH_2$ |
| D-methionine | —H | —$CH_2CH_2SCH_3$ |
| D-phenylalanine | —H | —$CH_2Ph$ |
| D-proline | —H | -2-(pyrrolidine) |
| D-serine | —H | —$CH_2OH$ |
| D-threonine | —H | —$CH_2CH(OH)(CH_3)$ |
| D-tryptophan | —H | —$CH_2$-3-(1H-indole) |
| D-tyrosine | —H | —$CH_2$-3-(p-hydroxyphenyl) |
| D-valine | —H | -isopropyl |
| Divinyl | —CH=$CH_2$ | —CH=$CH_2$ |

TABLE 3

| Exemplary non-naturally occurring α amino acid | R and R' are equal to the following | |
|---|---|---|
| α-methyl-alanine (Aib, 2-amino-2-methylpropanoic acid) | $—CH_3$ | $—CH_3$ |
| α-methyl-arginine | $—CH_3$ | $—CH_2CH_2CH_2—NHC({=}NH)NH_2$ |
| α-methyl-asparagine | $—CH_3$ | $—CH_2C({=}O)NH_2$ |
| α-methyl-aspartic acid | $—CH_3$ | $—CH_2CO_2H$ |
| α-methyl-cysteine | $—CH_3$ | $—CH_2SH$ |
| α-methyl-glutamic acid | $—CH_3$ | $—CH_2CH_2CO_2H$ |
| α-methyl-glutamine | $—CH_3$ | $—CH_2CH_2C({=}O)NH_2$ |
| α-methyl-histidine | $—CH_3$ | $—CH_2$-2-(1H-imidazole) |
| α-methyl-isoleucine | $—CH_3$ | -sec-butyl |
| α-methyl-leucine | $—CH_3$ | -isobutyl |
| α-methyl-lysine | $—CH_3$ | $—CH_2CH_2CH_2CH_2NH_2$ |
| α-methyl-methionine | $—CH_3$ | $—CH_2CH_2SCH_3$ |
| α-methyl-phenylalanine | $—CH_3$ | $—CH_2Ph$ |
| α-methyl-proline | $—CH_3$ | -2-(pyrrolidine) |
| α-methyl-serine | $—CH_3$ | $—CH_2OH$ |
| α-methyl-threonine | $—CH_3$ | $—CH_2CH(OH)(CH_3)$ |
| α-methyl-tryptophan | $—CH_3$ | $—CH_2$-3-(1H-indole) |
| α-methyl-tyrosine | $—CH_3$ | $—CH_2$-3-(p-hydroxyphenyl) |
| α-methyl-valine | $—CH_3$ | -isopropyl |
| Divinyl | $—CH{=}CH_2$ | $—CH{=}CH_2$ |
| Norleucine | —H | $—CH_2CH_2CH_2CH_3$ |

TABLE 4

| Exemplary non-naturally occurring α amino acid | R and R' are equivalent to hydrogen or $—CH_3$, and the following |
|---|---|
| Terminally unsaturated α-amino acids and bis α-amino acids (e.g., modified cysteine, modified lysine, modified tryptophan, modified serine, modified threonine, modified proline, modified histidine, modified alanine, and similar amino acids) | $—(CH_2)_g—S—(CH_2)_gCH{=}CH_2$,<br>$—(CH_2)_g—O—(CH_2)_gCH{=}CH_2$,<br>$—(CH_2)_g—NH—(CH_2)_gCH{=}CH_2$,<br>$—(CH_2)_g—(C{=}O)—S—(CH_2)_gCH{=}CH_2$,<br>$—(CH_2)_g—(C{=}O)—O—(CH_2)_gCH{=}CH_2$,<br>$—(CH_2)_g—(C{=}O)—NH—(CH_2)_gCH{=}CH_2$,<br>$—CH_2CH_2CH_2CH_2—NH—(CH_2)_gCH{=}CH_2$,<br>$—(C_6H_5)$-p$—O—(CH_2)_gCH{=}CH_2$,<br>$—CH(CH_3)—O—(CH_2)_gCH{=}CH_2$,<br>$—CH_2CH(—O—CH{=}CH_2)(CH_3)$,<br>-histidine- $N((CH_2)_gCH{=}CH_2)$,<br>-tryptophan- $N((CH_2)_gCH{=}CH_2)$, and<br>$—(CH_2)_g(CH{=}CH_2)$,<br>g is each independently 0-10 |

There are many known unnatural amino acids any of which may be included in the peptides of the present disclosure. See, for example, S. Hunt, *The Non-Protein Amino Acids: In Chemistry and Biochemistry of the Amino Acids*, edited by G. C. Barrett, Chapman and Hall, 1985. Some additional examples of unnatural amino acids are 4-hydroxyproline, desmosine, γ-aminobutyric acid, β-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with $—C({=}O)C_6H_5$; $—CF_3$; —CN; -halo; $—NO_2$; $—CH_3$), disubstituted phenylalanines, substituted tyrosines (e.g., further substituted with $—C({=}O)C_6H_5$; $—CF_3$; —CN; -halo; $—NO_2$; $—CH_3$), and statine. Furthermore, the amino acids for use in the present disclosure may be derivatized to include amino acid residues that are hydroxylated, phosphorylated, sulfonated, acylated, alkylated, farnesylated, geryanylated, and/or glycosylated.

Groups $R^{1a}$ and $R^{1b}$ correspond to the N-terminus of a polypeptide. If, for example, $—[X^{AA}]—$ corresponds to an α-amino acid of the formula

[Chemical Formula 180]

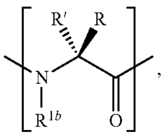, as a result, in a certain embodiment, $R^{1a}$—$(X^{AA})_y$— corresponds to the formula

[Chemical Formula 181]

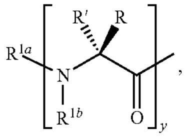

and y, R, and R' are the same as defined herein, and $R^{1a}$ and $R^{1b}$ are each independently —$R^B$, —$OR^B$, —$N(R^B)_2$, or —$SR^B$, wherein $R^B$ is each independently hydrogen, a branched or unbranched aliphatic group, a branched or unbranched heteroaliphatic group, carbocyclyl, heterocyclyl, aryl, heteroaryl, acyl, resin, hydroxyl, amino, or thiol protecting group.

In some embodiments, $R^{1a}$ and $R^{1b}$ are each independently hydrogen. In some embodiments, $R^{1a}$ and $R^{1b}$ are each independently $C_{1-6}$alkyl. In some embodiments, $R^{1a}$ and $R^{1b}$ are each independently —$CH_3$. In some embodiments, $R^{1a}$ and $R^{1b}$ are each independently an amino protecting group. In some embodiments, $R^{1a}$ and $R^{1b}$ are each independently -Boc. In some embodiments, $R^{1a}$ and $R^{1b}$ are each independently -Fmoc. In some embodiments, $R^{1a}$ and $R^{1b}$ are each independently an acyl. In some embodiments, $R^{1a}$ and $R^{1b}$ are each independently —(C═O)$CH_3$. In some embodiments, $R^{1a}$ and $R^{1b}$ are each independently label. In some embodiments $R^1$ is a resin and a solid carrier. $R^{1a}$ and $R^{1b}$ may be any combination of the above.

In certain embodiments, $R^{1a}$ and $R^{1b}$ are each independently a label joined by a linker, if necessary, wherein the linker is substituted or unsubstituted, cyclic or acyclic, branched or unbranched alkylene; substituted or unsubstituted, cyclic or acyclic, branched or unbranched alkenylene; substituted or unsubstituted, cyclic or acyclic, branched or unbranched alkynylene; substituted or unsubstituted, cyclic or acyclic, branched or unbranched heteroalkylene; substituted or unsubstituted, cyclic or acyclic, branched or unbranched heteroalkenylene; substituted or unsubstituted, cyclic or acyclic, branched or unbranched heteroalkynylene; substituted or unsubstituted arylene; substituted or unsubstituted heteroarylene; or substituted or unsubstituted acylene.

As generally described above, group $R^6$ corresponds to the C-terminus of a peptide chain, and corresponds to variable —$R^B$, —$OR^B$, —$N(R^B)_2$, or —$SR^B$. $R^B$ is the same as defined herein. If, for example, —$[X^{AA}]$— corresponds to an α-amino acid of the formula

[Chemical Formula 182]

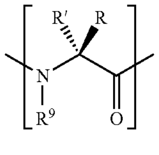

(wherein $R^9$ is defined the same as $R^2$), as a result, in a certain embodiment, —$[X^{AA}]_z$—$R^6$ corresponds to the formula

[Chemical Formula 183]

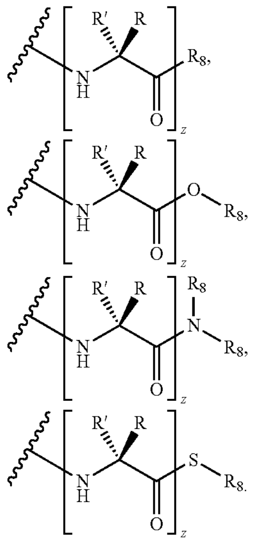

or wherein $R^B$ is each independently hydrogen, an optionally substituted aliphatic group, an optionally substituted heteroaliphatic group, optionally substituted carbocyclyl, optionally substituted heterocyclyl, optionally substituted aryl, optionally substituted heteroaryl, optionally substituted acyl, or hydroxyl, or two $R^B$ groups together can form an optionally substituted nonaromatic heterocycle or an optionally substituted heteroaryl ring.

In some embodiments, $R^6$ is —$OR^B$, wherein $R^B$ is independently hydrogen, a substituted or unsubstituted aliphatic group, a substituted or unsubstituted heteroaliphatic group, a substituted or unsubstituted carbocyclic group, a substituted or unsubstituted heterocyclic group, a substituted or unsubstituted aryl group, a substituted or unsubstituted heteroaryl group, a substituted or unsubstituted acyl group, or a substituted or unsubstituted hydroxyl group.

In some embodiments, $R^B$—$SR^B$, wherein $R^B$ is independently hydrogen, a substituted or unsubstituted aliphatic group, a substituted or unsubstituted heteroaliphatic group, a substituted or unsubstituted carbocyclic group, a substituted or unsubstituted heterocyclic group, a substituted or unsubstituted aryl group, a substituted or unsubstituted heteroaryl group, a substituted or unsubstituted acyl group, or a substituted or unsubstituted hydroxyl group.

In some embodiments, $R^B$ is —$N(R^B)_2$, and $R^B$ is independently hydrogen, a substituted or unsubstituted aliphatic group, a substituted or unsubstituted heteroaliphatic group, a substituted or unsubstituted carbocyclic group, a substituted or unsubstituted heterocyclic group, a substituted or unsubstituted aryl group, a substituted or unsubstituted heteroaryl group, a substituted or unsubstituted acyl, a substituted or unsubstituted hydroxyl group, or two $R^B$ groups together form a substituted or unsubstituted nonaromatic heterocyclic ring or a substituted or unsubstituted heteroaryl ring.

As used herein, a "label" refers to a moiety that has at least one element, isotope, or functional group incorporated into the moiety which enables detection of the polypeptide of the present disclosure to which the label is attached. Labels encompass moieties that are directly attached (i.e., via a bond) to the polypeptide or such moieties that attached to the polypeptide by a linking group. It will be appreciated that the label may be attached to the polypeptide at any position that does not interfere with the biological activity or characteristic of the polypeptide of the present disclosure that is being detected. In general, a label can fall into any one (or more) of five classes: a) a label which contains isotopic moieties, which may be radioactive or heavy isotopes, including, but not limited to, $^{2}H$, $^{3}H$, $^{13}C$, $^{14}C$, $^{15}N$, $^{18}F$, $^{31}p$, $^{32}p$, $^{35}S$, $^{67}Ga$, $^{99}mTc$ (Tc-99m), $^{111}In$, $^{123}T$, $^{125}I$, $^{169}Yb$, and $^{186}Re$; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label FITC); d) a label which has one or more photoaffinity moieties; and e) a label which has a ligand moiety with one or more known binding partners (such as biotin-streptavidin, FK506-FKBP). Any of these types of labels as described above may also be referred to as "diagnostic agents" as defined herein. Exemplary labels include, but are not limited to, FITC, 5-carboxyfluorescein (FAM) and biotin.

[Chemical Formula 184]

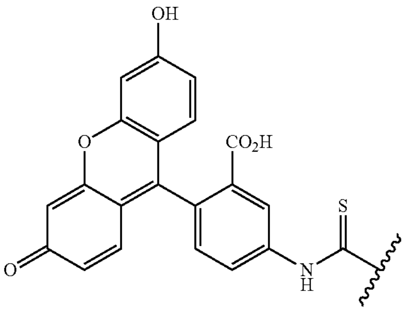

FITC

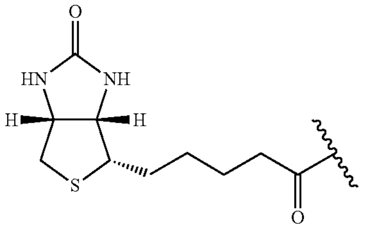

Biotin

In certain embodiments, the label is directly attached to the bridge peptide of the present disclosure (i.e., through a bond). In certain embodiments, the label is indirectly attached to the bridge peptide of the present disclosure (i.e., through a linker). In certain embodiments, the linker is a substituted or unsubstituted, cyclic or acyclic, branched or unbranched alkylene. In certain embodiments, the linker is a substituted or unsubstituted, cyclic or acyclic, branched or unbranched alkenylene. In certain embodiments, the linker is a substituted or unsubstituted, cyclic or acyclic, branched or unbranched alkynylene. In certain embodiments, the linker is a substituted or unsubstituted, cyclic or acyclic, branched or unbranched heteroalkylene. In certain embodiments, the linker is a substituted or unsubstituted, cyclic or acyclic, branched or unbranched heteroalkenylene. In certain embodiments, the linker is a substituted or unsubstituted, cyclic or acyclic, branched or unbranched heteroalkynylene. In certain embodiments, the linker is a substituted or unsubstituted arylene. In certain embodiments, the linker is a substituted or unsubstituted heteroarylene. In certain embodiments, the linker is a substituted or unsubstituted acylene. In certain embodiments, the linked is a β-alanine (β-Ala) linker. In certain embodiments, the linked is a PEG linker. In certain embodiments, the PEG linker is Fmoc-NH—(PEG) —COOH or Fmoc-NH— $(PEG)_2$—COOH).

As used herein, a "diagnostic agent" refers to imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); and contrast agents.

In certain embodiments, such as in the identification of a biological target, the label comprises a radioactive isotope, preferably an isotope which emits detectable particles, such as β particles. In certain embodiments, the label comprises one or more photoaffinity moieties for the direct elucidation of intermolecular interactions in biological systems. A variety of known photophores can be employed, most relying on photoconversion of diazo compounds, azides, or diazirines to nitrenes or carbenes. (see, Bayley, H., Photogenerated Reagents in Biochemistry and Molecular Biology (1983), Elsevier, Amsterdam, the entire contents of which are incorporated herein by reference). In certain embodiments of the present disclosure, the photoaffinity labels employed are o-, m- and p-azidobenzoyls, substituted with one or more halogen moieties, including, but not limited to 4-azido-2, 3, 5,6-tetrafluorobenzoic acid. In certain embodiments, the label comprises one or more fluorescent moieties. In certain embodiments, the label is the fluorescent label FITC. In certain embodiments, the label comprises a ligand moiety with one or more known binding partners. In certain embodiments, the label comprises the ligand moiety biotin.

As used herein, a "solid support" includes, but is not limited to, solid insoluble surface to which the polypeptide is attached. Solid supports include, but are not limited to, glass slides, glass beads, resins, and the like.

As used herein, a "resin" refers to a material useful in solid phase synthesis, wherein the polypeptide is attached thereto. Solid phase synthesis is a well-known synthetic technique; see generally, Atherton, E., Sheppard, R. C. *Solid Phase Peptide Synthesis: A Practical Approach*, IRL Press, 20 Oxford, England, 1989, and Stewart J. M., Young, J. D. *Solid Phase Peptide Synthesis,* 2nd edition, Pierce Chemical Company, Rockford, 1984, the entire contents of each of which are hereby incorporated herein by reference. Exemplary resins which may be employed by the present disclosure include, but are not limited to, alkenyl resins, amine functionalized resins, benzhydrylamine (BHA) resins, Br-functionalized resins, Chloromethyl resins, CHO-functionalized resins, Cl-functionalized resins, $CO_2H$ functionalized resins, Hypo-Gel resins, I-functionalized resins, MBHA resins, OH-functionalized resins, oxime resins, PEG resins, Boc-Biz peptide synthesis resins, Fmoc-tBu peptide synthesis resins, thiol-functionalized resins, and Wang resins.

Exemplary alkenyl resins include, but are not limited to, REM resin, vinyl sulfone polymer-bound resin, and vinyl-polystyrene resin.

Exemplary amine functionalized resins include, but are not limited to, amidine resin, N-(4-benzyloxybenzyl hydroxylamine polymer bound, (aminomethyl) polystyrene, polymer bound (R)-(+)-α-methylbenzylamine, 2-chlorotrityl Knorr resin, 2-N-Fmoc-amino-dibenzocyclohepta-1,4-diene (polymer-bound resin), 4-[4-(1-Fmoc-aminoethyl)-2-methoxy-5-nitrophenoxy]butyramidomethyl-polystyrene resin, 4-benzyloxybenzylamine (polymer-bound), 4-Carboxybenzenesulfonamide (polymer-bound), bis(tert-butoxycarbonyl)thiopseudourea (polymer-bound), dimethylaminomethyl-polystyrene, Fmoc-3-amino-3-(2-nitrophenyl) propionic acid (polymer-bound), N-methyl aminomethylated polystyrene, PAL resin, Sieber amide resin, tert-butyl N-(2-mercaptoethyl) carbamate (polymer-bound), and triphenyl-chloromethane-4-carboxamide polymer bound resin.

Exemplary benzhydrylamine (BHA) resins include, but are not limited to, 2-chlorobenzhydryl chloride (polymer bound), HMPB-benzhydrylamine (polymer bound), 4-m (polymer-bound), benzhydryl chloride (polymer-bound), and benzhydrylamine polymer-bound resin.

Exemplary PEG resins include, but are not limited to, ethylene glycol polymer bound resin.

As used herein, "crosslink" is synonymous with "bridge moiety", which encompass the entire crosslink in which one α-amino acid, β-amino acid, γ-amino acid, or another amino acid is attached to a second α-amino acid, β-amino acid, γ-amino acid, or another amino acid, but excludes a carbon of each amino acid and polypeptide chains in which they constitute a part thereof.

In a certain embodiment, two amino acids in a crosslink are associated by (i, i+2), including a carbon to a carbon (exclusive of both ends) of a crosslink provided in the bridge peptide of the present disclosure, e.g., 15 or less (such as 1, 2, 3, 4, 5, 6, 7, 8, 9, 10, 11, 12, 13, 14, or 15) consecutively attached atoms. Alternatively, more than 15 carbons may be included.

As generally defined above, each instance of y and z is, independently, 0 or an integer between 1 and 100, inclusive.

In certain embodiments, y is 0 or an integer between 1 and 100, inclusive. In certain embodiments, y is 0. In certain embodiments, y is an integer between 1 and 100, inclusive. In certain embodiments, y is an integer between 75 and 100, inclusive. In certain embodiments, y is an integer between 50 and 100, inclusive. In certain embodiments, y is an integer between 25 and 100, inclusive. In certain embodiments, y is an integer between 15 and 100, inclusive. In certain embodiments, y is an integer between 10 and 100, inclusive. In certain embodiments, y is an integer between 5 and 100, inclusive. In certain embodiments, y is an integer between 10 and 75, inclusive. In certain embodiments, y is an integer between 25 and 50, inclusive. In certain embodiments, y is an integer between 1 and 10, inclusive. In certain embodiments, y is an integer between 3 and 6, inclusive.

In certain embodiments, z is 0 or an integer between 1 and 100, inclusive. In certain embodiments, z is 0. In certain embodiments, z is an integer between 1 and 100, inclusive. In certain embodiments, z is an integer between 75 and 100, inclusive. In certain embodiments, z is an integer between 50 and 100, inclusive. In certain embodiments, z is an integer between 25 and 100, inclusive. In certain embodiments, z is an integer between 15 and 100, inclusive. In certain embodiments, z is an integer between 10 and 100, inclusive. In certain embodiments, z is an integer between 5 and 100, inclusive. In certain embodiments, z is an integer between 10 and 75, inclusive. In certain embodiments, z is an integer between 25 and 50, inclusive. In certain embodiments, z is an integer between 1 and 10, inclusive. In certain embodiments, z is an integer between 1 and 5, inclusive.

As generally defined above, p is an integer between 1 and 10, inclusive. In certain embodiments, p is an integer between 1 and 9, inclusive. In certain embodiments, p is an integer between 1 and 8, inclusive. In certain embodiments, p is an integer between 1 and 7, inclusive. In certain embodiments, p is an integer between 1 and 6, inclusive. In certain embodiments, p is an integer between 1 and 5, inclusive. In certain embodiments, p is an integer between 1 and 4, inclusive. In certain embodiments, p is an integer between 1 and 3, inclusive. In certain embodiments, p is an integer between 1 and 2, inclusive. In certain embodiments, p is 10. In certain embodiments, p is 9. In certain embodiments, p is 8. In certain embodiments, p is 7. In certain embodiments, p is 6. In certain embodiments, p is 5. In certain embodiments, p is 4. In certain embodiments, p is 3. In certain embodiments, p is 2. In certain embodiments, p is 1.

In some embodiments, n is any integer (e.g., more than or equal to 1 or more than or equal to 2, etc.), preferably n is 1. In some embodiments, the polypeptide has a crosslink having one tertiary amine. In some embodiments, the polypeptide has a crosslink having two tertiary amines. In some embodiments, the polypeptide has a crosslink with one carbamate. In some embodiments, the polypeptide has a crosslink with two carbamates. In some embodiments, the polypeptide contains crosslinks having both E and Z isomers. In some embodiments, the crosslink has a double bond with an E isomer. In some embodiments, the cross-link has a double bond with a Z isomer.

As generally defined above, y is an integer between 1 and 10. In certain embodiments, y is 10. In certain embodiments, y is 9. In certain embodiments, y is 8. In certain embodiments, y is 7. In certain embodiments, y is 6. In certain embodiments, y is 5. In certain embodiments, y is 4. In certain embodiments, y is 3. In certain embodiments, y is 2. In certain embodiments, y is 1.

As generally defined above, z is an integer between 1 and 10. In certain embodiments, z is 10. In certain embodiments, z is 9. In certain embodiments, z is 8. In certain embodiments, z is 7. In certain embodiments, z is 6. In certain embodiments, z is 5. In certain embodiments, z is 4. In certain embodiments, z is 3. In certain embodiments, z is 2. In certain embodiments, z is 1.

In certain embodiments, y is 1 and z is 1.

Exemplary secondary structural motifs of polypeptides and proteins can be secondary structures that do not form intramolecular hydrogen bonds between amide groups of the main chain, and include, but are not limited to, β-strand. In some embodiments, the primary secondary structural motif of the bridge peptides of the present disclosure is the β-strand.

In some embodiments, the polypeptide of formulae (I)-(III) above or a subset thereof is a β-strand polypeptide. In some embodiments, the polypeptides of formulae (I)-(III) above or a subset thereof are substantially β-strand polypeptides. β-strand does not form intramolecular hydrogen bonds between the amide groups of the main chain (as do α-helices and β-sheets) and is a polypeptide in which at least one of the amino acids provided in the polypeptide chain has a β-strand structure. There may be more than one β-strand structure (e.g., two or more, three or more, four or more, five or more, ten or more, twenty or more, fifty or more, one hundred or more). The β-strand secondary structure of the polypeptide can be confirmed by well-known analytical techniques, such as x-ray crystallography, electron crystallography, fiber diffraction, fluorescence anisotropy, circular dichroism (CD), and nuclear magnetic resonance spectroscopy.

In a certain embodiment, the amino acid sequence of the peptide chain portion of the bridge peptide of the present disclosure is homologous to a known β-strand polypeptide. In a certain embodiment, the amino acid sequence of the peptide chain portion of the bridge peptide of the present disclosure is at least 80%, 85%, 90%, or 95% homologous to a known β-strand polypeptide.

In some embodiments, cross-links are prepared using two amino acids selected from the exemplary amino acids shown herein (e.g., β-DM3, β-DM4, β-DM5, and β-DM6 as described in the examples). In some embodiments, the amino acid used is an analog of one of the exemplary amino acids shown herein.

(The Method of Manufacturing the Compound of the Present Disclosure)

Hereinafter, the method of manufacturing the compound of the present disclosure is described, but the method of manufacturing the compound of the present disclosure is not limited thereto.

The compound of the present disclosure can be produced by, for example, but is not limited to, the production methods described below. These production methods can be appropriately improved based on the knowledge of those who are familiar with synthetic organic chemistry. In the following production methods, the compound used as a raw material may be a salt thereof as long as it does not interfere with the reaction.

In the production methods of the present disclosure, even if use of a protecting group is not specifically described, a functional group other than those at the reaction point can be protected as needed and deprotected after the completion of a reaction or after a series of reactions to obtain a compound of interest if any functional groups other than the reaction point is changed under the reaction condition or if it is unsuitable for post-reaction processing. Common protecting groups described in the document (T. W. Greene and P. G. M. Wuts, "Protective Group in Organic Synthesis", 3rd Ed., John Wiley and Sons, Inc., New York (1999)) or the like can be adopted as the protecting groups used in these processes. A protecting group can be introduced or removed by a method that is commonly used in organic synthetic chemistry (e.g., method described in the aforementioned document or the like) or a method in accordance therewith.

Starting materials and intermediates in the following production methods can be purchased as commercially available products, or can be obtained by the method described in the known literature or by synthesis from known compounds according to known methods. In addition, salts of these starting materials and intermediates may be used as long as they do not interfere with the reaction.

The intermediate and target compound in the production method of the present disclosure can also be converted into another compound included in the present disclosure by appropriately converting their functional groups. Conversion of functional groups in that case can be performed by the method conventionally used in organic synthetic chemistry (for example, the method described in RC Larock, "Comprehensive Organic Transformations", 2 nd Ed., John Wiley and Sons, Inc., New York (1999) or the like) or a method similar thereto.

The inert solvent in the following production method means a solvent that does not react with the raw materials, reagents, bases, acids, catalysts, ligands and the like used in the reaction (hereinafter also referred to as "raw materials used in the reaction"). Furthermore, even when the solvent used in each step reacts with the raw materials used in the reaction, it can be used as an inert solvent as long as the desired reaction proceeds and the desired compound is obtained.

Synthetic Scheme.

The present disclosure also relates to methods for preparing polypeptides of Formula (I) and salts thereof. The present disclosure also provides intermediates for the synthesis of the bridge peptides of the present disclosure.

As an example, an example of a synthetic scheme includes the olefin metathesis reaction shown in FIG. 8. A.

Thus, the olefin metathesis reaction is a catalytic reaction in which bond recombination occurs between two olefins. Two olefins in a molecule react with each other by a carbene complex to afford a cyclic alkene along with a volatile alkene by the following mechanism.

Mechanism

[Chemical Formula 186]

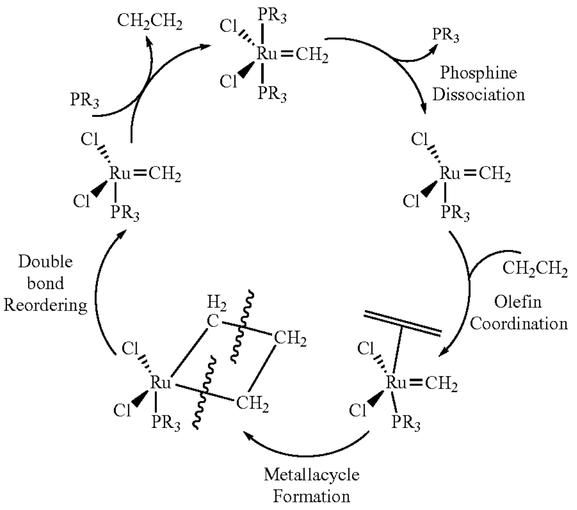

Synthesis typically involves the preparation of non-bridged polypeptide precursors or their salts of formulae (i) to (v) shown below.

[Chemical Formula 187]

Formula (i)

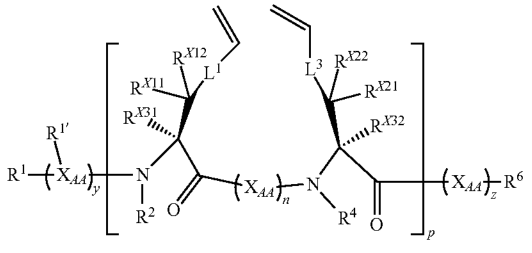

$R^1$, $R^2$, $R^4$, $R^6$, $R^{X31}$, $R^{X11}$, $R^{X12}$, $R^{X32}$, $R^{X21}$, $R^{X22}$, $L^1$, $L^3$, p, n, Y, z, and $X^{AA}$ are defined in the same manner as for formula (III). A non-bridge polypeptide precursor is then treated with an olefin metathesis catalyst to provide a bridge polypeptide of the present disclosure of formula (II).

[Chemical Formula 188]

Formula (ii)

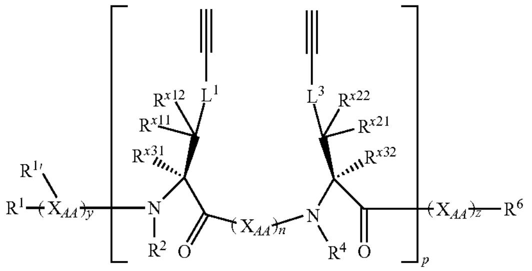

$R^1$, $R^6$, $R^2$, $R^4$, $R^{X31}$, $R^{X11}$, $R^{X12}$, $R^{X32}$, $R^{X21}$, $R^{X22}$, $L^1$, $L^3$, p, n, Y, z, and $X^{AA}$ are defined in the same manner as for formula (III). A non-bridge polypeptide precursor is then treated with an alkyne metathesis catalyst to provide a bridge polypeptide of the present disclosure of formula (II) (see, for example, https://www.chem-station.com/odos/2009/07/-alkyne-metathesis.html).

[Chemical Formula 189]

Formula (iii)

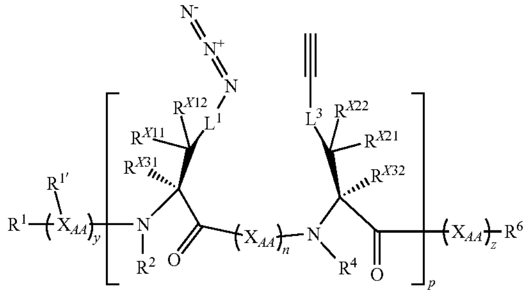

and

[Chemical Formula 190]

formula (iv)

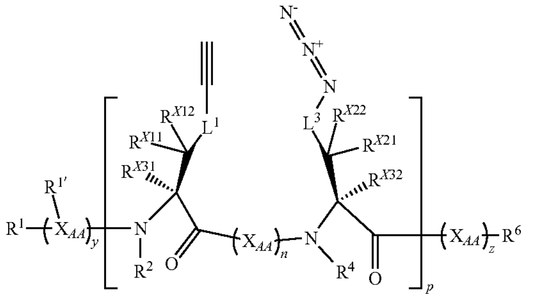

$R^1$, $R^6$, $R^2$, $R^4$, $R^{X31}$, $R^{X11}$, $R^{X12}$, $R^{X32}$, $R^{X21}$, $R^{X22}$, $L^1$, $L^3$, p, n, y, z, and $X^{AA}$ are defined in the same manner as for formula (III). A non-bridge polypeptide precursor is then treated with a click chemistry catalyst to provide a bridge polypeptide of the present disclosure of formula (II). In this manner, click chemistry is a [3+2] cycloaddition reaction from a reaction between alkyne and an azide compound. For example, click chemistry of Cu(I) and Ru(II) which is known in the art or the like can be used in the present disclosure.

[Chemical Formula 191]

Formula (v)

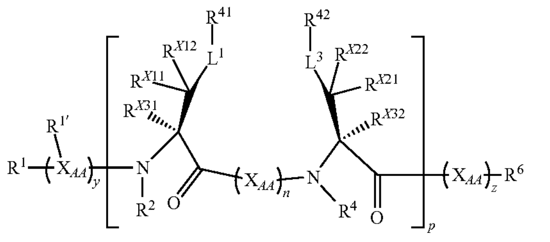

$R^1$, $R^6$, $R^2$, $R^4$, $R^{X31}$, $R^{X11}$, $R^{X12}$, $R^{X32}$, $R^{X21}$, $R^{X22}$, $L^1$, $L^3$, p, n, y, z, and $X^{AA}$ are defined in the same manner as for formula (III). $R^{41}$ and $R^{42}$ is a combination of functional groups resulting in reductive amination. Those skilled in the art readily understand such a combination. For example, $R^{41}$ is a group including a ketone group or aldehyde group, and $R^{42}$ is a group including an amine group. A non-bridge polypeptide precursor is then treated with a reductive amination catalyst to provide a bridge polypeptide of the present disclosure of formula (II) (see, for example, https://ja.wikipedia.org/wiki/% E9%82%84% E5%85%83% E7%9A %84% E 3% 82% A2% E3% 83% 9F % E3% 83% 8E % E5%80%96).

In this manner, reductive amination is the general term for chemical reactions that convert aldehyde or ketone into amine. Such reactions are divided into the following two stages. First, a carbonyl group reatsreatsreatsreacts with amine to produce imine (iminium cation when using secondary amine). Subsequently, amine is obtained by using a reducing agent such as sodium cyanoborohydride. Examples of the reducing agent include, but are not limited to, formic acid, borohydride reagents, sodium cyanoborohydride ($NaBH_3CN$), and sodium triacetoxyborohydride ($NaBH(OAc)_3$).

Synthesis of a non-bridge polypeptide of the present disclosure first includes selection of the desired sequence and number of amino acids and amino acid analogs. While it is obvious to those skilled in the art, the number, stereochemistry, and form of the selected amino acid structures (naturally-occurring or non-naturally-occurring) are dependent on the size of the polypeptide to be prepared, the ability of a specific amino acid to produce a desired structural motif (e.g., β-strand), and any specific peptide sequence that is desirable to mimic.

Once amino acids have been selected, synthesis of the non-bridged polypeptides of the present disclosure can be accomplished using standard deprotection and coupling reactions. Peptide bond formation and polypeptide synthesis are well known techniques in the art, and encompass both solid-phase and solution-phase methods. See generally, Bodanszky and Bodanszky, The Practice of Peptide Synthesis, Springer-Verlag, Berlin, 1984, Atherton and Sheppard, Solid Phase Peptide Synthesis: A Practical Approach, IRL Press at Oxford University Press Oxford, England, 1989, and Stewart and Young, Solid Phase Peptide Synthesis, 2nd edition, Pierce Chemical Company, Rockford, 1984, the entire contents of which are incorporated herein by reference. In both solution-phase and solid-phase technologies, the selection of protecting groups, as well as the specific coupling technology adopted, must be considered. For a detailed discussion of peptide synthesis techniques for solution-phase and solid-phase reactions, see Hecht, Bioorganic chemistry: Peptides and Proteins, Oxford University Press, New York: 1998, which is incorporated herein in its entirety by reference.

In a certain embodiment, the method comprises linking the bridge peptide of the present disclosure to another polypeptide or protein by ligation in accordance with the strategy described in International Publication No. PCT/US2010/001952 (which is also incorporated herein by reference).

In a certain embodiment, a synthesis method of polypeptides comprises synthesis of a liquid phase of a non-bridge polypeptide precursor of formula (i). The aforementioned synthesis of a liquid phase is a technology that is well known for constructing a polypeptide. Exemplary liquid phase synthesis comprises (1) providing an amino acid with the N-terminus protected with an amino protecting group, (2) providing an amino acid with the C-terminus protected with an oxygen protecting group, (3) coupling the N-protected amino acid to the C-protected amino acid, (4) deprotecting a product of a coupling reaction at the N-terminus or C-terminus, and (5) repeating steps (3) to (4) until a desired polypeptide is obtained, wherein at least two of the amino acids coupled by one of the above steps comprise artificial amino acid, wherein the artificial amino acid comprises a terminal unsaturated amino acid side chain, a terminal azide group-containing amino acid side chain, and at least one e selected from the group consisting of (reductively aminated ketone group or aldehyde group and other functional groups used in any crosslinking method described herein), and comprises a terminal unsaturated amino acid side chain, a terminal alkyne-containing amino acid side chain, and at least one selected from the group consisting of (reductively aminated amine group and other functional groups used in any crosslinking method described herein). In the process of the above synthesis, various parameters (including, but are not limited to, arrangement of artificial amino acids, stereochemistry of amino acids, length and functionality of an artificial amino acid side chain, and amino acid residue used) can be changed.

In a certain embodiment, the method comprises solid phase synthesis of a non-bridge polypeptide precursor of formula (i) or (ii). The aforementioned solid phase synthesis is a technology that is well known for constructing a polypeptide. Exemplary solid phase synthesis comprises (1) providing a resin-bound amino acid, (2) deprotecting the resin-bound amino acid, (3) coupling an amino acid to the deprotected resin-bound amino acid, and (4) repeating step (3) until a desired peptide is obtained, wherein at least two of the amino acids coupled by one of the above steps comprise an artificial amino acid, wherein the artificial amino acid comprises a terminal unsaturated amino acid side chain, a terminal azide group-containing amino acid side chain, and at least one selected from the group consisting of (reductively aminated ketone group or aldehyde group and other functional groups used in any crosslinking method described herein), and comprises a terminal unsaturated amino acid side chain, a terminal alkyne-containing amino acid side chain, and at least one selected from the group consisting of (reductively aminated amine group and other functional groups used in any crosslinking method described herein). In the process of the above synthesis, various parameters (including, but are not limited to, arrangement of artificial amino acids, stereochemistry of amino acids, length and functionality of an artificial amino acid side chain, and amino acid residue used) can be changed.

After a desired polypeptide is synthesized, polypeptides of formulas (i) to (V) are contacted with a specific catalyst to promote crosslinking to provide polypeptides of formulas (I) to (III). For example, a resin-bound polypeptide can be contacted with a catalyst to promote crosslinking, or can be first cleaved from resin and then contacted with a catalyst to promote crosslinking. In this regard, an amino acid comprising a terminal unsaturated amino acid side chain, a terminal azide group-containing amino acid side chain, or (reductively aminated ketone group or aldehyde group and other functional groups used in any crosslinking method described herein) is incorporated into a polypeptide chain in order to provide a proximal terminal unsaturated amino acid side chain, a terminal alkyne-containing amino acid side chain, or (reductively aminated amine group and other functional groups used in any crosslinking method described herein). The side chains can be within the same plane or on the same side of a polypeptide chain with respect to each other in any given conformation of polypeptides. By treating with a catalyst, the proximal side chains thereof react with each other by crosslinking to provide a conformationally stabilized polypeptide. In a certain embodiment, a proximal side chain is arranged so that the resulting crosslink does not interfere with biological/therapeutic activity of the bridge polypeptide of the present disclosure.

After cross-linking of the bridge peptides of the present disclosure, the method may further include additional synthetic modification(s). Any of the chemical or biological modifications can be made to the bridge polypeptide.

Intermediates and target compounds in the above production method can be isolated and purified by appropriately combining methods used in ordinary organic synthesis, for example, neutralization, filtration, extraction, washing, drying, concentration, crystallization, various chromatography, and the like. In addition, the intermediates can be subjected to the next reaction without any particular purification.

Optically active forms of the compound of the present disclosure can be produced by using an optically active starting material or intermediate, or by optically resolving a racemate of the intermediate or final product. Examples of optical resolution methods include, but are not limited to, a separation method using an optically active column and a separation method such as fractional crystallization method. A diastereomer of the compound of the present disclosure can be produced by, for example, a separation method such as column chromatography or fractional crystallization, but the method is not limited thereto.

A pharmaceutically acceptable salt of a bridge peptide or a compound provided in the present disclosure can be produced by, for example, mixing a bridge peptide or a compound provided in the present disclosure with a pharmaceutically acceptable acid or base in a solvent such as water, methanol, ethanol, 2-propanol, ethyl acetate, or acetone, but the production method is not limited thereto.

In some embodiments, additional modifications of the bridge peptide include reduction, oxidation, and nucleophilic or electrophilic addition to the double bond provided by the metathesis reaction and provide a synthetically modified polypeptide. Other modifications anywhere in the bridge polypeptide backbone, such as the N-terminus of a bridge polypeptide, the C-terminus of a bridge polypeptide, and an amino acid side chain of a bridge polypeptide, or in one or more modified or unmodified crosslinking sites etc may include complexation of the bridge polypeptide with a therapeutically active agent, label, or diagnostic agent, or synthetic modification of the bridge polypeptide. Such modifications may be useful in the delivery of peptides or therapeutically active agents to cells, tissues, or organs. Such modifications may allow for targeting to specific types of cells or tissues in some embodiments.

In certain embodiments, the coupling step comprises the use of a coupling reagent. Exemplary coupling reagents include, but are not limited to, benzotriazol-1-yloxy-tris (dimethylamino)-phosphonium hexafluorophosphate (BOP), benzotriazole-1-yl-oxy-tris-pyrrolidino-phosphonium hexafluorophosphate (PyBOP), bromo-tris-pyrrolidino phosphonium hexafluorophosphate (PyBroP), 1-ethyl-3-(3-dimethyllaminopropyl) carbodiimide (EDC), N,N'-carbonyldiimidazole (CDI), 3-(diethoxyphosphoryloxy)-1, 2, 3-benzotriazin-4 (3H)-one (DEPBT), 1-hydroxy-7-azabenzotriazole (HOAt), 1-hydroxy-7-benzotriazole (HOBt), 2-(7-aza-1H-benzotriazole-1-yl)-1, 1, 3,3-tetramethyluronium hexafluorophosphate (HATU), 2-(6-chloro-1H-benzotriazole-1-yl)-1,1,3,3-tetramethylaminium hexafluorophosphate (HCTU), 2-(1H-benzotriazole-1-yl)-1,1,3,3-tetramethyluronium hexafluorophosphate (HBTU), O-(7-azabenzotriazole-1-yl)-N, N,N',N'-tetramethyluronium tetrafluoroborate (TATU), 2-(1H-benzotriazole-1-yl)-1, 1, 3,3-tetramethyluronium tetrafluoroborate (TBTU), N, N,N', N'-tetramethyl-O-(3,4-dihydro-4-oxo-1,2,3-benzotriazin-3-yl) uranium tetrafluoroborate (TDBTU), (1-Cyano-2-ethoxy-2-oxoethylidenaminooxy)dimethylamino-morpholino-carbenium hexafluorophosphate (COMU), and O—(N-succinimidyl)-1,1,3,3-tetramethyl uranium tetrafluoroborate (TSTU).

In certain embodiments, the coupling step comprises a base. Exemplary bases include, but are not limited to, potassium carbonate, potassium hydroxide, sodium hydroxide, tetrabutylammonium hydroxide, benzyltrimethylammonium hydroxide, triethylbenzylammonium hydroxide, 1,1,3, 3-tetramethylguanidine, 1,8-diazabicyclo[5.4.0]undec-7-ene (DBU), N-methylmorpholine, diisopropylethylamine (DIPEA), tetramethylethylenediamine (TMEDA), pyridine (Py), 1,4-diazabicyclo[2.2.2]octane (DABCO), N, N-dimethylamino pyridine (DMAP), or triethylamine (NEt3).

In some embodiments, coupling step is performed in a medium. A medium is a solvent or a solvent mixture that, in combination with the combined reacting partners and reagents, facilitates the progression of the reaction therebetween. A solvent may solubilize one or more of the reaction components, or, alternatively, the solvent may facilitate the suspension of or one more of the reaction components; see generally, March's Advanced Organic Chemistry: Reactions, Mechanisms, and Structure, M. B. Smith and J. March, $5^{th}$ Edition, John Wiley & Sons, 2001, and Comprehensive Organic Transformations, R. C. Larock, $2^{nd}$ Edition, John Wiley & Sons, 1999, the entire contents of each of which are incorporated herein by reference. Solvents include ethers, halogenated hydrocarbons, aromatic solvents, polar aprotic solvents, or mixtures thereof. In other embodiments, the solvent is diethyl ether, dioxane, tetrahydrofuran (THF), dichloromethane (DCM), dichloroethane (DCE), acetonitrile (ACN), chloroform, toluene, benzene, dimethylformamide (DMF), dimethylacetamide (DMA), dimethylsulfoxide (DMSO), N-methyl pyrrolidinone (NMP), or mixtures thereof.

In some embodiments, coupling step is performed at a temperature between about 0° C. and about 100° C., inclusive.

In some embodiments, the coupling step comprises a coupling reagent, a base, and a medium, and is performed at temperature between about 0° C. and about 100° C., inclusive.

In some embodiments, the method further includes the step of providing polypeptides of Formula (III-i) which are obtained by treating polypeptides of formula (i) or (ii) with an olefin metathesis catalyst or an alkyne metathesis catalyst,

[Chemical Formula 192]

(III-i)

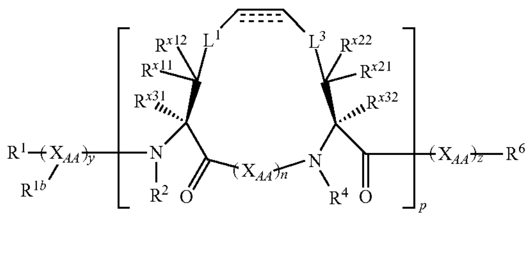

or includes the step of providing a salt thereof.

In certain embodiments, the olefin metathesis catalyst is a tungsten (W), molybdenum (Mo), or ruthenium (Ru) catalyst. In certain embodiments, the olefin metathesis catalyst is a ruthenium catalyst. Examples of suitable olefin metathesis catalyst include, but are not limited to, Schrock catalyst, Grubbs Catalyst $1^{st}$ generation, or benzylidene-bis(tricyclohexylphosphine)dichlororuthenium, Grubbs Catalyst 2nd Generation, or benzylidene[1,3-bis(2,4,6-trimethylphenyl)-2-midazolidinylidene]dichloro-(tricyclohexylphosphine) ruthenium, and Hoveyda-Grubbs Catalyst 2nd Generation, or 1,3-bis-(2, 4,6-trimethylphenyl)-2-imidazolidinylidene) dichloro (o-isopropoxyp-phenylmethylene) ruthenium. Olefin metathesis catalysts employable by the above synthetic method are described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299; the entire contents of each of which are incorporated herein by reference.

In another embodiment, the present disclosure can use Grubbs Catalyst 3rd Generation, as well as the cationic type of Grubbs catalysts. The Grubbs catalysts listed in Aldrich can also be used (For example, https://www.sigmaaldrich-.com/japan/chemistry/chemical-synthesis/technology-spotlights/metathesis.html).

In certain embodiments, the alkyne metathesis catalyst is a tungsten (W), molybdenum (Mo) catalysts, etc. In certain embodiments, the alkyne metathesis catalyst is a molybdenum (Mo) catalyst. Examples of suitable alkyne metathesis catalyst include, but are not limited to. Examples of alkyne catalysts employable by the above synthetic method are described in Cromm, P. M. et al. Orthogonal ring-closing alkyne and olefinmetathesis for the synthesis of small GTPase-targeting bicyclic peptides. Nat. Commun. 7:11300 doi: 10.1038/ncomms11300 (2016). Heppekausen J et al., Chem. Eur. J. 2012, 18, 10281-10299 etc, and all of these can be used. The entire contents of each of them are incorporated herein by reference.

In some embodiments, the click chemistry catalyst is a copper(I) (Cu(I)) or ruthenium(II) (Ru(II)) catalyst. Examples of suitable click chemistry catalysts include, but are not limited to, $Cp^*RuCl(PPh_3)_2$ or $Cp^*RuCl(cod)$.

In some embodiments, the reductive amination catalyst is $NaBH_3CN$, $NaBH(OAc)_3$, nickel (Ni) catalyst, copper (II) (Cu(II)) catalyst, palladium (Pd) catalyst, platinum (Pt)

catalyst, ruthenium (Ru) catalyst, rhodium (Rh) catalyst, iron (Fe) catalyst, cobalt (Co) catalyst, manganese (Mn) catalyst, or iridium (Ir) catalyst. Examples of suitable reductive amination catalysts include, but are not limited to, $NaBH_3CN$, $NaBH(OAc)_3$, Raney Ni, $Cu(OAc)_2$, Pd/C, Pt/C, $RuCl_2(PPh_3)_3$, or Rh. Each of these is incorporated herein by reference in their entirety.

The metathesis catalyst, click chemistry catalyst, or reductive amination catalyst may be provided in any suitable form that enables it to promote polymerisation. For example, the catalyst may be combined with a suitable carrier material such as a solvent or perhaps a solid and formed into a tablet. It will be appreciated that any such carrier material should be compatible with other components of the curable systems.

In addition to olefin metathesis catalysts, alkyne metathesis catalysts, click chemistry catalysts, or reductive amination catalysts, other reagents capable of promoting carbon-carbon bond or carbon-heteroatom bond formation can also be utilized. For example, other reactions that can be utilized, include, but are not limited to, palladium coupling reactions, transition metal catalyzed cross coupling reactions, pinacol couplings (terminal aldehydes), hydrozirconation (terminal alkynes), nucleophilic addition reactions, NHK (Nozaki-Hiyama-Kishi (Furstner et al., *J. Am. Chem. Soc.* 1996, 118, 12349)) coupling reactions, Michael addition, and carbamate formation. Examples of the carbon-carbon bond or carbon-heteroatom bond formations are shown in FIG. 9. Thus, the appropriate reactive moieties are first incorporated into the desired amino acids, and then the peptide is subjected to reaction disorders that results in the formation of one or more cross-links.

In certain embodiments, the cross-linking step generates one bridged product as a preferred product. As used herein, a "preferred product" refers to one constitutional isomer present as the major constituent in a mixture of isomers. In certain embodiments, a "preferred product" refers to one constitutional isomer present as a component in at least about 50%, 55%, 60%, 65%, 70%, 75%, 80%, 85%, 90%, 95%, 98%, or 99% of an isomeric mixture.

In a certain embodiment, the method further comprises the step of (vii) modifying a double bond of a polypeptide of formula (I-x) to provide a polypeptide of formula (I-y)

[Chemical Formula 194]

(I-y)

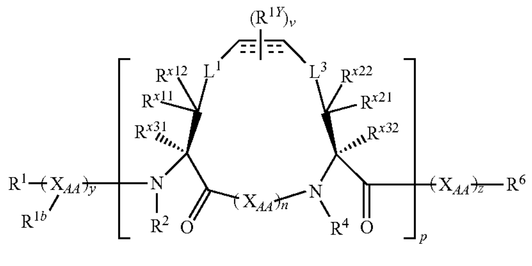

or a salt thereof, wherein $R^{1a}$, $R^{1b}$, $R^2$, $R^4$, $R^6$, $R^{X31}$, $R^{X11}$, $R^{X12}$, $R^{X32}$, $R^{X21}$, $R^{X22}$, $L^1$, $L^3$, p, n, y, z, and $X^{AA}$ are as defined above, $R^{1Y}$ is each independently hydrogen, halogen, hydroxyl, nitro, alkoxy, $—N(R^2)_2$, or an optionally substituted aliphatic group, and v is 0, 1, or 2.

One of ordinary skill in the art will appreciate that a wide variety of reactions, disorders, and reactive agents may be employed to promote such a transformation, therefore, a wide variety of reactions, disorders, and reactive agents are envisioned; see generally, *March's Advanced Organic Chemistry: Reactions, Mechanisms, and Structure*, M. B. Smith and J. March, 5th Edition, John Wiley & Sons, 2001; *Advance Organic Chemistry, Part B: Reactions and Synthesis*, Carey and Sundberg, 3rd Edition, Plenum Press, New York, 1993; and *Comprehensive Organic Transformations*, R. C. Larock, 2nd Edition, John Wiley & Sons, 1999, the entirety of each of which is hereby incorporated herein by reference. Exemplary reactive agents may be any agent reactive with double bond. In certain embodiments, reactive agents are able to react with a double bond, for example, via hydrogenation, osmylation, hydroxylation (mono- or di-), amination, halogenation, cycloaddition (e.g., cyclopropanation, aziridination, epoxidation), oxy-mercuration, and/or a hydroboration reaction, to provide a functionalized bridge structure. As one of ordinary skill in the art will clearly recognize, these above-described transformations will introduce functional groups compatible with the particular stabilized structures and the desired biological interactions. In particularly preferred embodiments, in but one example, the hydrophilicity of stabilized structures may be increased by the introduction of hydroxyl moieties. As one of ordinary skill in the art will realize, these synthetic modifications will be selected to introduce functionalities compatible with the particular stabilized structures and the desired biological interactions.

In certain embodiments, the bridging method can be any one listed in FIG. X.

In another aspect, in certain embodiments, the method above further includes providing polypeptide of Formula (I) complexed with a therapeutically active agent by activating the bridge peptide of the present disclosure of Formula (I) and then by complexation with a therapeutically active agent.

Furthermore, in another aspect, in certain embodiments, the method above further includes providing polypeptide of Formula (I) complexed with a label by treating the polypeptide of Formula (I) with a label.

In another aspect, in certain embodiments, the method above further includes providing polypeptide of Formula (I) complexed with a diagnostic agent by treating the polypeptide of Formula (I) with a diagnostic agent.

As used herein, when two entities are "conjugated" to one another, they are linked by a direct or indirect covalent or non-covalent interaction. In some embodiments, the association is covalent. In other embodiments, the association is non-covalent. Non-covalent interactions include hydrogen bonds, van der Waals interactions, hydrophobic interactions, magnetic interactions, and electrostatic interactions. An indirect covalent interaction means that two entities are covalently connected through a linker group, if necessary.

Conjugation of an agent (e.g., a label, a diagnostic agent, a therapeutically active agent) to the bridge peptide of the present disclosure may be achieved in a variety of different ways. The agent may be covalently conjugated, directly or indirectly, to the polypeptide at the site of bridging, or to the N-terminus or the C-terminus of the polypeptide chain. Alternatively, the agent may be noncovalently conjugated, directly or indirectly, to the polypeptide at the site of bridging, or to the N-terminus or the C-terminus of the polypeptide chain. Indirect covalent conjugation is by means of one or more covalent bonds. Indirect noncovalent conjugation is by means of one or more noncovalent bonds. Conjugation may also be via a combination of non-covalent and covalent forces/bonds. The agent may also be conjugated through a covalent or non-covalent linking group.

Any bond may be used in the conjugation of a therapeutically active agent, label, and/or diagnostic agent to the bridge peptide of the present disclosure. Such bonds include amide linkages, ester linkages, disulfide linkages, carbon-carbon bonds, carbamate, carbonate, urea, hydrazide, and the like. In some embodiments, the bond is cleavable under physiological disorders (e.g., enzymatically cleavable, cleavable with a high or low pH, with heat, light, ultrasound, X-ray). However, in some embodiments, the bond is not cleavable.

It will also be appreciated by one of ordinary skill in the art that the synthetic method as described above can also be applied to combinatorial synthesis of the bridge peptide of the present disclosure. Although combinatorial synthesis techniques can be applied in solution, it is more typical that combinatorial techniques are performed on the solid phase using split-and-pool techniques. During the course of the combinatorial synthesis, various parameters can be varied, including, but is not limited to, placement of amino acids with terminally unsaturated side chains, stereochemistry of amino acids, terminally unsaturated side-chain length and functionality, and amino acid residues utilized.

Methods of Use and Treatment

The present disclosure provides a method of treating a disorder in a subject in need thereof, comprising administering to the subject an effective amount of a polypeptide of Formula (I)-(III), or a salt thereof.

The present disclosure provides a method of treating a disorder in a subject in need thereof, comprising instructing the subject to take an effective amount of a polypeptide of Formula (I)-(III), or a salt thereof.

The present disclosure also provides a polypeptide of Formula (I)-(III), or salt thereof, for use in treating a disorder.

As used herein, a "disease" or "disorder" are used interchangeably.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In some embodiments, the non-human animal is a mammal. The non-human animal may be a male or female at any stage of development. A non-human animal may be a transgenic animal.

As used herein, and unless otherwise specified, the terms "treat," "treating" and "treatment" contemplate an action that occurs while a subject is suffering from a disorder and that reduces the severity of the disorder or retards or slows the progression of the disorder ("therapeutic treatment"), and also contemplates an action that occurs before a subject begins to suffer from the disorder and that inhibits or reduces the severity of the disorder ("prophylactic treatment").

In general, the "effective amount" of a compound refers to an amount sufficient to elicit the desired biological response, i.e., treating the disorder. As will be appreciated by those of ordinary skill in this art, the effective amount of a compound of the present disclosure may vary depending on such factors as the desired biological endpoint, the pharmacokinetics of the compound, the disorder being treated, the mode of administration, and the age, health, and the subject. An effective amount encompasses therapeutic and prophylactic treatment.

As used herein, and unless otherwise specified, a "therapeutically effective amount" of a compound is an amount sufficient to provide a therapeutic benefit in the treatment of a disorder or to delay or minimize one or more symptoms associated with a disorder. A therapeutically effective amount of a compound means an amount of a therapeutic agent, alone or in combination with other therapies, which provides a therapeutic benefit in the treatment of a disorder. The term "therapeutically effective amount" can encompass an amount that improves overall therapy, reduces or prevents symptoms or causes of a disorder, or enhances the therapeutic efficacy of another therapeutic agent.

As used herein, and unless otherwise specified, a "prophylactically effective amount" of a compound is an amount sufficient to prevent a disorder, or one or more symptoms associated with a disorder or to prevent its recurrence. A prophylactically effective amount of a compound means an amount of a therapeutic agent, alone or in combination with other agents, which provides a prophylactic benefit in the prevention of a disorder. The term "prophylactically effective amount" can encompass an amount that improves overall prophylaxis or enhances the prophylactic efficacy of another prophylactic agent.

Exemplary disorders are, but are not limited to, proliferative disorders, neurological disorders, immunological disorders, endocrinologic disorders, cardiovascular disorders, hematologic disorders, inflammatory disorders, and disorders characterized by premature or unwanted cell death.

As used herein a proliferative disorder includes, but is not limited to, cancer, hematopoietic neoplastic disorders, proliferative breast disease, proliferative disorders of the lung, proliferative disorders of the colon, proliferative disorders of the liver, and proliferative disorders of the ovary.

Examples of cancers include, but are not limited to, carcinoma, sarcoma, or metastatic disorders, breast cancer, ovarian cancer, colon cancer, lung cancer, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Exemplary hematopoietic neoplastic disorders include, but are not limited to, disorders involving hyperplastic/neoplastic cells of hematopoietic origin, e.g., arising from myeloid, lymphoid or erythroid lineages, or precursor cells thereof. In certain embodiments, the disorders arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML). Lymphoid malignancies include, but are not limited to, acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to, non-Hodgkin lymphoma and variants thereof, peripheral T-cell lymphomas, adult T cell leukemia/lymphoma (ATL), cutaneous T-cell lymphoma (CTCL), large granular lymphocytic leukemia (LGF), Hodgkin's disease, and Reed-Stemberg disease.

Exemplary proliferative breast diseases include, but are not limited to, epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal in situ carcinoma (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular papillary carcinoma, and carcinoma, and invasive miscellaneous malignant neoplasms. Disorders in the male breast include, but are not limited to, gynecomastia and carcinoma.

Exemplary proliferative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Exemplary proliferative disorders of the colon include, but are not limited to, non-neoplastic polyps, adenomas, familial syndromes, colorectal carcinogenesis, colorectal carcinoma, and carcinoid tumors.

Exemplary proliferative disorders of the liver include, but are not limited to, nodular hyperplasias, adenomas, and malignant tumors, including primary carcinoma of the liver and metastatic tumors.

Exemplary proliferative disorders of the ovary include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

The bridge peptides described herein can also be used to treat, prevent or diagnose disorders characterized by overactive cell death or cellular death due to physiologic insult. Some examples of disorders characterized by premature or unwanted cell death, or alternatively unwanted or excessive cellular proliferation, include, but are not limited to hypocellular/hypoplastic, acellular/aplastic, or hypercellular/hyperplastic disorders. Such disorders include, but not limited to, fanconi anemia, aplastic anemia, thalaessemia, congenital neutropenia, myelodysplasia. The polypeptides of the present disclosure that act to decrease apoptosis can be used to treat disorders associated with an undesirable level of cell death. Thus, the anti-apoptotic peptides of the present disclosure can be used to treat disorders such as those that lead to cell death associated with viral infection, e.g., infection associated with infection with human immunodeficiency virus (HIV).

A wide variety of neurological diseases are characterized by the gradual loss of specific sets of neurons, and the anti-apoptotic peptides can be used in the treatment of these disorders. Such disorders include Alzheimer's disease, Parkinson's disease, amyotrophic lateral sclerosis (ALS), retinitis pigmentosa, spinal muscular atrophy, and various forms of cerebellar degeneration. The cell loss in these disorders does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. The anti-apoptotic peptides of the present disclosure can be used to treat all such disorders associated with undesirable cell death.

Some examples of neurologic disorders that can be treated with the bridge peptides described herein include, but are not limited to, Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, Bovine Spongiform Encephalitis, a Prion-mediated disease, Huntington's Disease, Pick's Disease, Amyotrophic Lateral Schlerosis (ALS), Parkinson's Disease, and Lewy Body Disease.

Some examples of endocrinologic disorders that can be treated with the bridge peptides described herein include, but are not limited to, diabetes, hypothyroidism, hypopituitarism, hypoparathyroidism, hypogonadism, and fertility disorders.

Some examples of immunologic disorders that can be treated with the bridge peptides described herein include, but are not limited to, organ transplant rejection, arthritis, lupus, inflammatory bowel disease (IBD), Crohn's disease, asthma, multiple sclerosis, diabetes, graft versus host diseases, autoimmune diseases, psoriasis, and rheumatoid arthritis.

Examples of cardiovascular disorders that can be treated or prevented with the bridge peptides described herein include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolernia, hyperlipidemia, xanthomatosis, asthma, hypertension, emphysema and chronic pulmonary disease; or a cardiovascular disorder associated with interventional procedures ("procedural vascular trauma"), such as restenosis following angioplasty, placement of a shunt, stent, synthetic or natural excision grafts, indwelling catheter, valve or other implantable devices.

In addition, the bridge peptides of the present disclosure may be useful in the area of materials science. For example, molecules such as lipids and other polymeric molecules may be attached to the peptides and thus generate biomaterials.

In addition to the above-mentioned uses, the bridge peptides of the present disclosure may be used for studies in bioinorganic chemistry or in catalysis, either as a ligand for a transition metal capable of mimicking an important biological environment, or by acting in concert with a particular transition metal catalyst to achieve a desired chemical reaction.

The present disclosure further provides a method of modifying a biological pathway inside a cell, comprising treating the cell with a bridge peptide of the present disclosure, or salt thereof. Such a method comprises in vitro or in vivo methods. A bridge peptide of the present disclosure may be useful as a research tool, e.g., for cellular assays.

The present disclosure provides pharmaceutical compositions comprising a bridge peptide of the present disclosure, or a salt thereof, and a pharmaceutically acceptable additive. Pharmaceutical compositions comprise compositions for therapeutic use as well as cosmetic compositions. Such compositions may optionally comprise one or more additional therapeutically active agents. In accordance with some embodiments, a method of administering a pharmaceutical composition comprising a composition of the present disclosure to a subject in need thereof is provided. In some embodiments, the composition of the present disclosure is administered to humans. For the purposes of the present disclosure, the "active ingredient" generally refers to such as a bridge peptide and compound, as described herein.

Although the descriptions of pharmaceutical compositions provided herein are principally directed to pharmaceutical compositions for administration to humans, it artisan that such will be understood by the skilled compositions are generally suitable for administration to animals of all sorts. Modification of pharmaceutical compositions for administration to various animals is well understood, and the ordinarily skilled veterinary pharmacologist can design and/or perform such modification with merely ordinary, if any, experimentation.

Pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition of the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient, and/or any additional ingredients in a pharmaceutical composition of the present disclosure will vary, depending upon the identity, size, and/or disorder of the subject treated and further depending upon, the route by which the composition is to be administered. By way of example, the composition may comprise between 0.1% and 100% (w/w) active ingredient.

As used herein, a pharmaceutically acceptable excipient includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy,* 21$^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional carrier medium is incompatible with a substance or its derivatives, such as by producing any undesirable biological effect or otherwise interacting in a deleterious manner with any other component(s) of the pharmaceutical composition, its use is contemplated to be within the scope of the present disclosure.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by the United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable additives used in the manufacture of pharmaceutical compositions include, but are diluents, dispersing and/or not limited to, inert granulating agents, surface active agents and/or emulsifiers, disintegrating agents, binding agents, preservatives, buffering agents, lubricating agents, and/or oils. Such additives may optionally be included in the formulations of the present disclosure. Additives such as cocoa butter and suppository waxes, coloring agents, coating agents, sweetening, flavoring, and perfuming agents can be present in the composition, according to the judgment of the Formulator.

Exemplary diluents include, but are not limited to, calcium carbonate, sodium carbonate, calcium phosphate, dicalcium phosphate, calcium sulfate, calcium hydrogen phosphate, sodium phosphate, lactose, sucrose, cellulose, microcrystalline cellulose, kaolin, mannitol, sorbitol, inositol, sodium chloride, dry starch, cornstarch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary surface active agents and/or emulsifiers include, but are not limited to, natural emulsifiers (e.g. acacia, agar, alginic acid, sodium alginate, tragacanth, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, ghatti gum, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, a tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium, D-glubionate, calcium gluceptate, calcium gluconate, gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the present disclosure are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions be may formulated according to the known art using dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution (U.S. P.), and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of the present disclosure with non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art.

In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a conjugate of the present disclosure may include ointments, pastes, creams, lotions, gels, powders, solutions, sprays, inhalants and/or patches. Generally, the active component is admixed under sterile disorders with a pharmaceutically acceptable carrier and/or any needed preservatives and/or buffers as may be required. Additionally, the present disclosure contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537;

5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4, 940, 460; and PCT publications WO 97/37705 and WO 97/13537. Alternatively or additionally, conventional syringes may be used in the classical mantoux method of intradermal administration.

Formulations for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the present disclosure may be prepared, packaged, and/or sold in a formulation for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the present disclosure formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surfactant, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the present disclosure. Another formulation for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the present disclosure may be prepared, packaged, and/or sold in a formulation for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the present disclosure may be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of the present disclosure.

General considerations in the formulation and/or manufacture of pharmaceutical agents may be found, for example, in *Remington: The Science and Practice of Pharmacy* 21st ed., Lippincott Williams & Wilkins, 2005.

The bridge peptides of the present disclosure provided herein are typically formulated in dosage unit form for ease of administration and uniformity of dosage. It will be understood, however, that the total daily usage of the compositions of the present disclosure will be decided by the attending physician within the scope of sound medical judgment. The specific therapeutically effective dose level for any particular subject will depend upon a variety of factors including the disease, disorder, or disorder being treated and the severity of the disorder; the activity of the specific active ingredient employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The polypeptide of Formula (I)-(III), salt thereof, or pharmaceutical composition thereof, may be administered by any route. In some embodiments, the polypeptide of Formula (I), salt thereof, or pharmaceutical composition thereof, are administered by a variety of routes, including oral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, sublingual; nasal, bucal, enteral, by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general, the most appropriate route of administration will depend upon a variety of factors including the nature of the agent (e.g., its stability in the environment of the gastrointestinal tract), and/or the disorder of the subject (e.g., whether the subject is able to tolerate oral administration). At present the oral and/or nasal spray and/or aerosol route is most commonly used to deliver therapeutic agents directly to the lungs and/or respiratory system. However, the present disclosure encompasses the delivery of the pharmaceutical composition of the present disclosure by any appropriate route taking into consideration likely advances in the sciences of drug delivery.

In certain embodiments, polypeptide of Formula (I), salt thereof, or pharmaceutical composition thereof, may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. The exact amount of a bridge peptide of the present disclosure required to achieve an effective amount will vary from subject to subject, depending, for example, on species, age, and general disorder of a subject, severity of the side effects or disorder, identity of the particular compound(s), mode of administration, and the like.

In some embodiments, the present disclosure encompasses "therapeutic cocktails" comprising bridge peptides of the present disclosure. In some embodiments, the bridge peptide of the present disclosure comprises a single species which can bind to multiple targets. In some embodiments, different bridge peptides of the present disclosure comprise different targeting moiety species, and all of the different targeting moiety species bind to the same target. In some embodiments, different bridge peptides of the present disclosure comprise different targeting moiety species, and all of the different targeting moiety species can bind to different targets. In some embodiments, such different targets may be associated with the same cell type. In some embodiments, such different targets may be associated with different cell types.

It will be appreciated that bridge peptides of the present disclosure and pharmaceutical compositions of the present disclosure can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, a conjugate of the present disclosure useful for detecting tumors may be administered concurrently with another agent useful for detecting tumors), or they may achieve different effects (e.g., control of any adverse effects).

Pharmaceutical compositions of the present disclosure may be administered either alone or in combination with one or more therapeutically active agents. By "in combination with," it is not intended to imply that the agents must be administered at the same time and/or formulated for delivery together, although these methods of delivery are within the scope of the present disclosure. The compositions can be administered concurrently with, prior to, or subsequent to, one or more other desired therapeutics or medical procedures. In general, each agent will be administered at a dose and/or on a time schedule determined for that agent. Additionally, the present disclosure encompasses the delivery of the pharmaceutical compositions of the present disclosure in combination with agents that may improve their bioavailability, reduce and/or modify their metabolism, inhibit their excretion, and/or modify their distribution within the body. It will further be appreciated that therapeutically active agent and the bridge peptides of the present disclosure utilized in this combination may be administered together in a single composition or administered separately in different compositions.

The particular combination employed in a combination regimen will take into account compatibility of the therapeutically active agent and/or procedures with the bridge peptide of the present disclosure and/or the desired therapeutic effect to be achieved. It will be appreciated that the combination employed may achieve a desired effect for the same disorder (for example, a bridge peptide of the present disclosure may be administered concurrently with another therapeutically active agent used to treat the same disorder), and/or they may achieve different effects (e.g., control of any adverse effects).

As used herein, a "therapeutically active agent" refers to any substance used as a medicine for treatment, prevention, delay, reduction or amelioration of a disorder, and refers to a substance that is useful for therapy, including prophylactic and therapeutic treatment. A therapeutically active agent also includes a compound that increases the effect or effectiveness of another compound, for example, by enhancing potency or reducing adverse effects of the compound of Formula (I).

In certain embodiments, a therapeutically active agent is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, anti-neoplastic antihistamine, immunosuppressant agent, agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), or inhibitors/intercalators of DNA, RNA, protein-protein interactions, or protein-receptor interactions.

In some embodiments, pharmaceutical compositions of the present disclosure may be administered in combination with any therapeutically active agent or procedure (e.g., surgery, radiation therapy) that is useful to treat, alleviate, ameliorate, relieve, delay onset of, inhibit progression of, reduce severity of, and/or reduce incidence of one or more symptoms or features of cancer.

Kits

The present disclosure also provides a variety of kits comprising one or more of the bridge peptides of the present disclosure. For example, the present disclosure provides a kit comprising a bridge peptide of the present disclosure and instructions for use. A kit may comprise multiple different polypeptides. A kit may comprise any of a number of additional components or reagents in any combination. All of the various combinations are not set forth explicitly but each combination is included in the scope of the present disclosure.

According to certain embodiments of the present disclosure, a kit may include, for example, (i) one or more bridge peptides of the present disclosure and, optionally, one or more particular therapeutically active agents to be delivered; (ii) instructions for administration to a subject in need thereof.

Kits typically include instructions which may, for example, comprise protocols and/or describe disorders for production of bridge peptides of the present disclosure, administration of bridge peptides of the present disclosure to a subject in need thereof, design of novel bridge peptides of the present disclosure. Kits will generally include one or more vessels or containers so that some or all of the individual components and reagents may be separately housed. Kits may also include a means for enclosing individual containers in relatively close confinement for commercial sale, e.g., a plastic box, in which instructions, packaging materials such as styrofoam (Registered trademark), may be enclosed. An identifier, e.g., a bar code, radio frequency identification (ID) tag, may be present in or on the kit or in or one or more of the vessels or containers included in the kit. An identifier can be used, e.g., to uniquely identify the kit for purposes of quality control, inventory control, tracking, movement between workstations.

In order that the invention described herein may be more fully understood, the following examples are set forth. It should be understood that these examples are for illustrative purposes only and are not to be construed as limiting the present disclosure in any manner.

As used herein, "or" is used when "at least one or more" of the listed matters enumerated in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present disclosure has been described while showing preferred embodiments to facilitate understanding. While the present disclosure is described hereinafter based on the examples, the above descriptions and the following examples are provided for the sole purpose of exemplification, not limitation of the present disclosure. Thus, the scope of the present disclosure is not limited to the embodiments and examples that are specifically described herein and is limited only by the scope of claims.

EXAMPLES

Examples are shown below. It is understood that any reagents, drugs, etc. that can be used in the examples can be obtained from reagent vendors such as Aldrich, Wako Pure Chemicals, etc.

In the examples, the abbreviations shown above and below may be used for simplicity of description.

s: singlet
d: doublet
t: triplet
m: multiplet
dd: double doublet
J: coupling constant
Hz: Hertz
d: chemical shift
min: min
RT: retention time
$CDCl_3$: deuterated chloroform
Me: methyl
Et: ethyl
Pr: propyl
i-Pr: isopropyl
i-Bu: isobutyl
s-Bu or sec-Bu: secondary butyl
tBu or tBu or tert-Bu: tertiary butyl
i-Pnt: isopentyl
Hxy: n-hexyl
P Ac: acetyl
Bz: benzoyl
Bnzl: benzyl
Boc or tBOC or tBOC: tert-butoxycarbonyl
Alloc: allyloxycarbonyl
Fmoc: 9-fluorenylmethoxycarbonyl
DTFM: DiTriFluoroMethyl

Example 1: Synthesis of Artificial Amino Acids

In this example, an example of synthesis of artificial amino acids is shown.

Synthesis of β-di(trifluoromethyl)-substituted compounds

Here, the synthesis of β-di(trifluoromethyl)-substituted compounds is illustrated below. Here, bridge lengths of 3-6 are described below.

Synthetic scheme is shown below.

The synthesis of(S)-βDTFM3 and (R)-βDTFM3

[Chemical Formula 195]

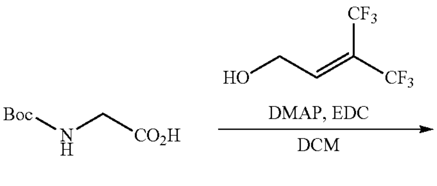

-continued
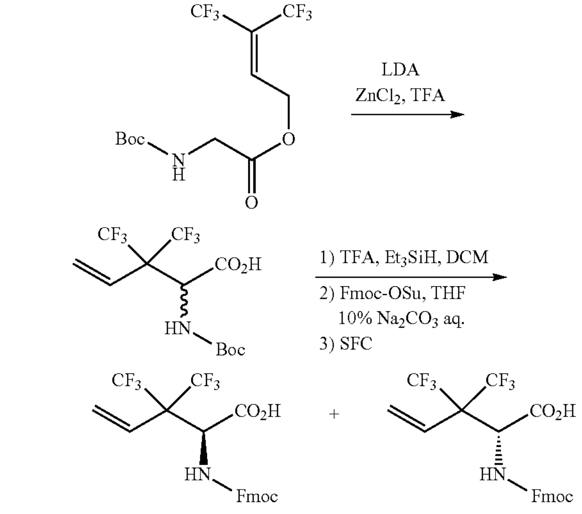
The synthesis of(S)-βDTFM4 and (R)-βDTFM4
[Chemical Formula 196]
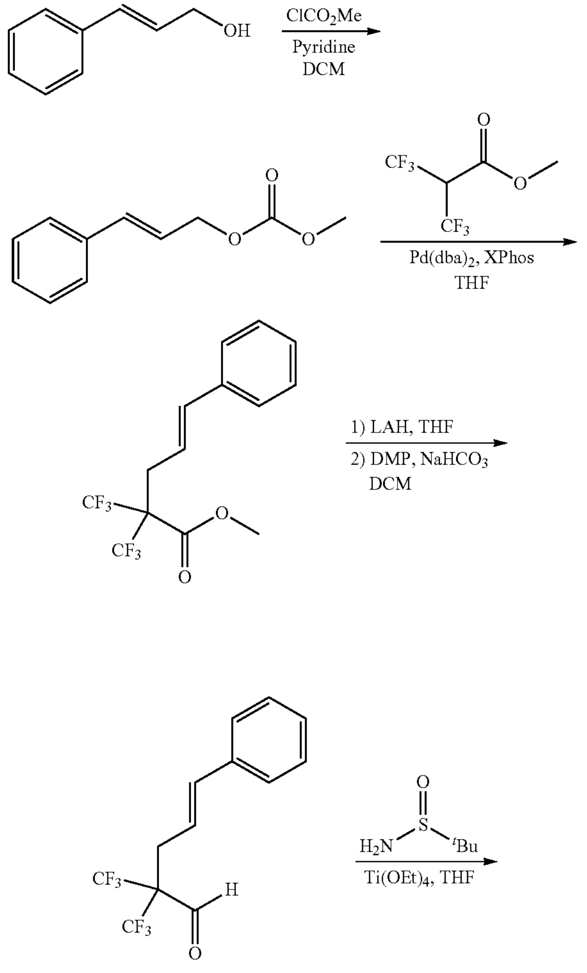
-continued
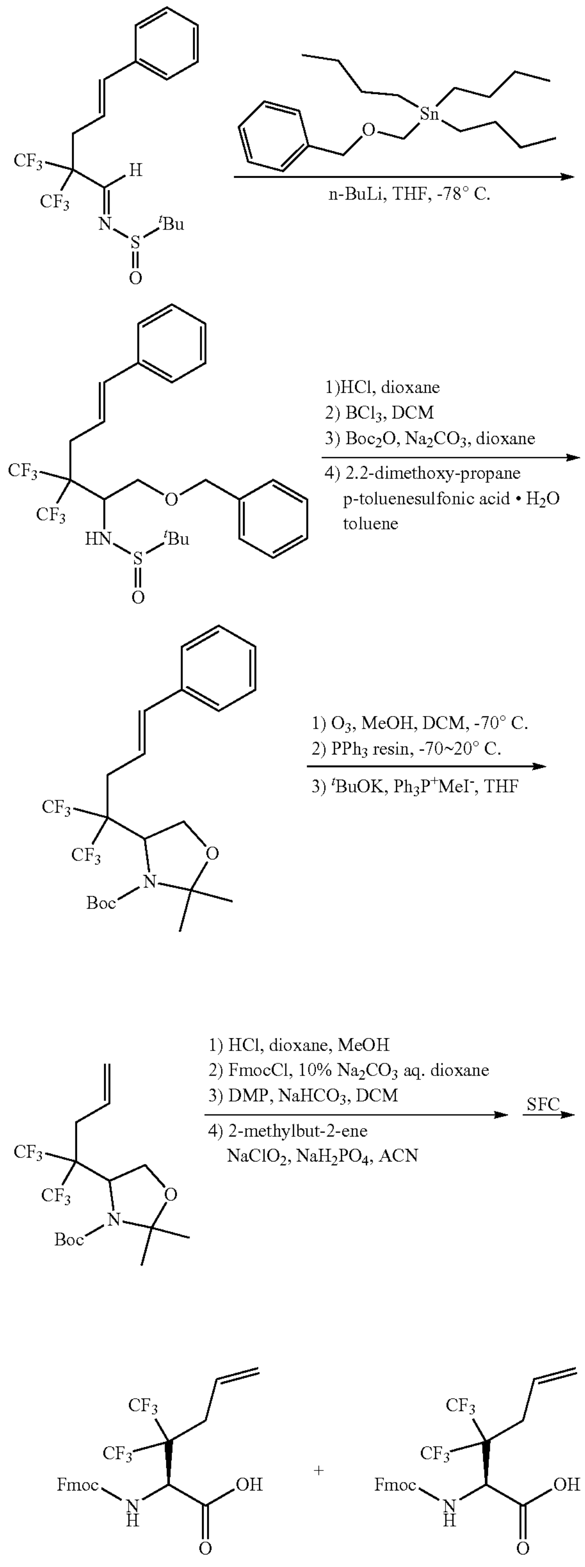
(S)-βDTFM4
(R)-βDTFM4

The synthesis of(S)-βDTFM5 and (R)-βDTFM5

[Chemical Formula 196-2]

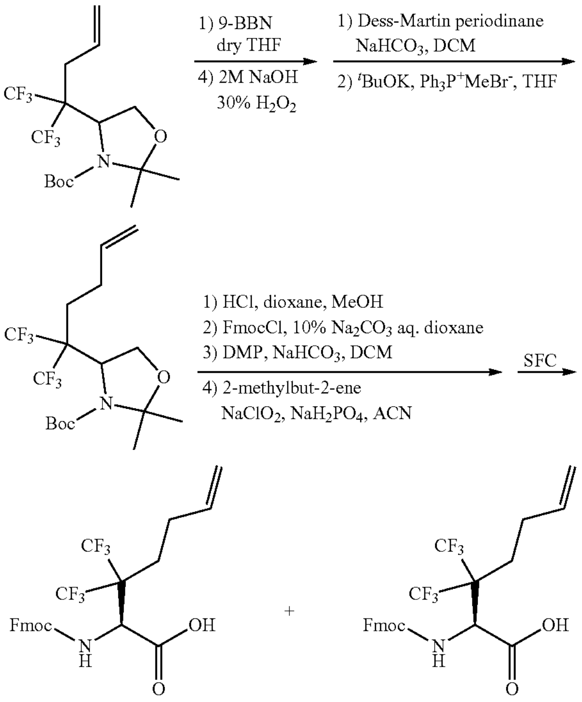

(S)-βDTFM5 + (R)-βDTFM5

The synthesis of(S)-βDTFM6 and (R)-βDTFM6

[Chemical Formula 197]

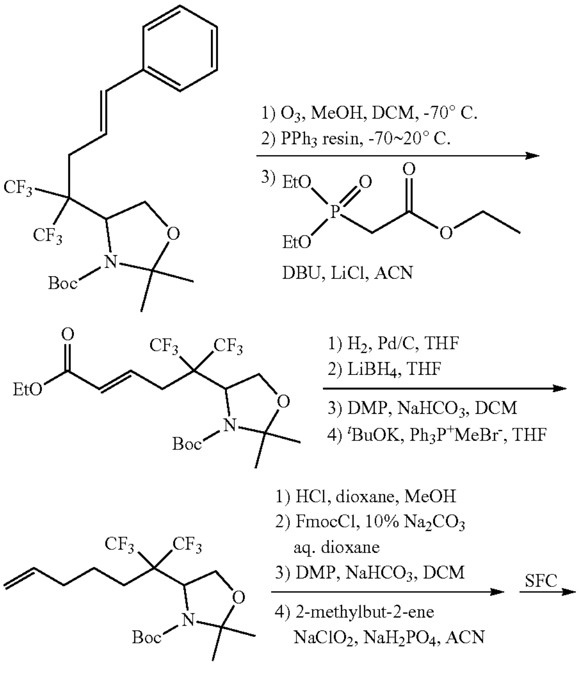

-continued

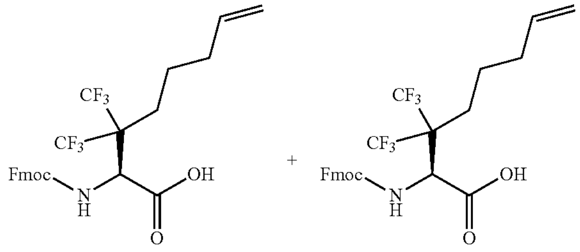

(S)-βDTFM6 + (R)-βDTFM6

(Result)

Artificial amino acids can be produced by performing the scheme shown above.

Schemes of artificial amino acids' synthesis are described below as another examples.

[Chemical Formula 198]

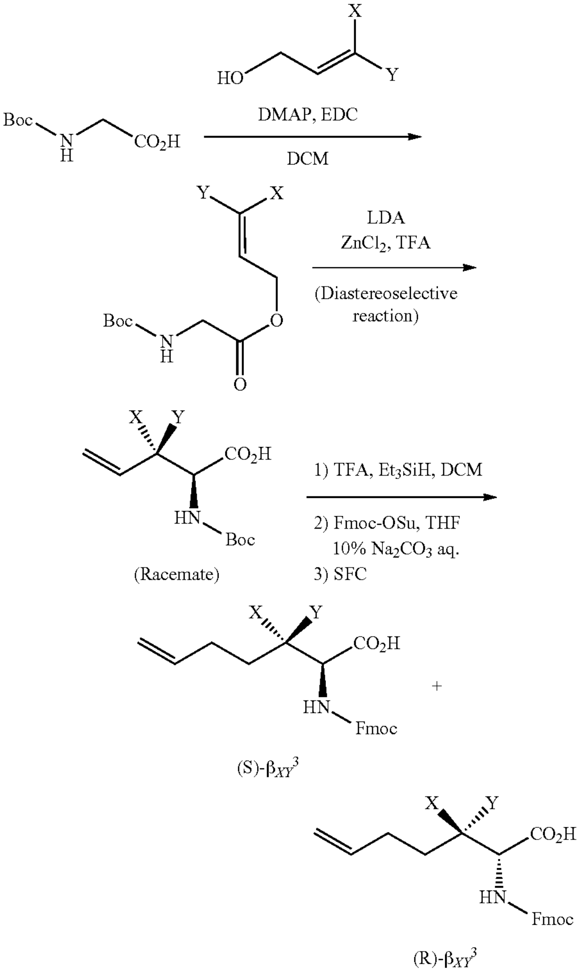

(Racemate)

(S)-$\beta_{XY}^3$ +

(R)-$\beta_{XY}^3$

[Chemical Formula 199]
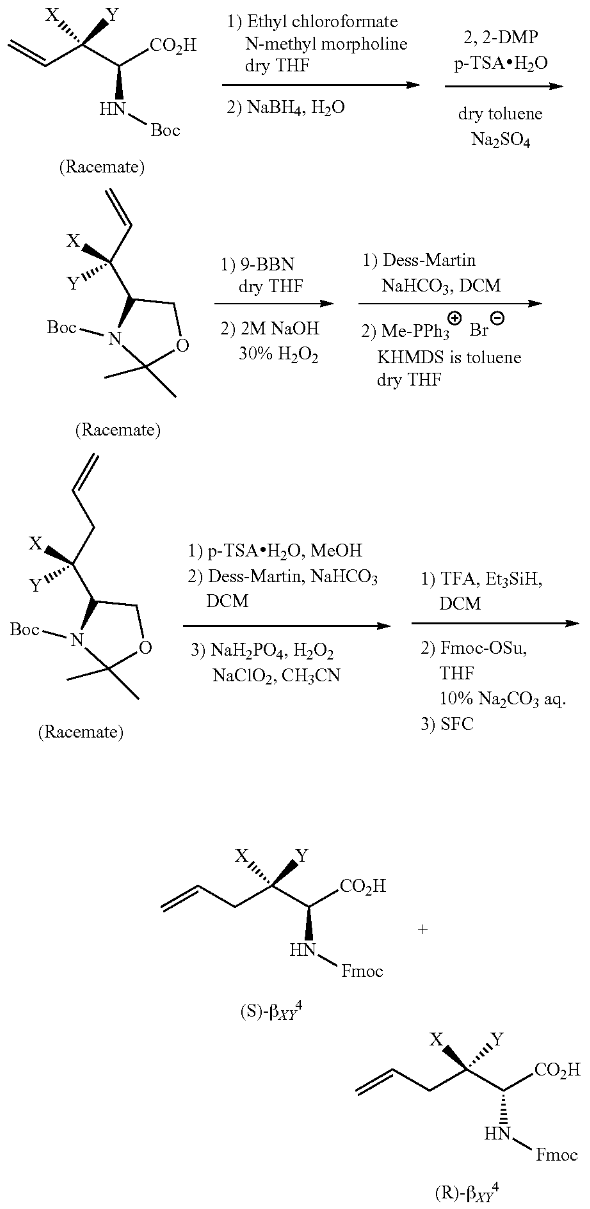
(Result)
Artificial amino acids can be produced by performing the scheme shown above.
Here, X and Y can be any substituents in the β-position of the bridge peptide of the present disclosure.
Another Examples
In the present disclosure, artificial amino acids can also be synthesized by the following scheme.
[Chemical Formula 200]
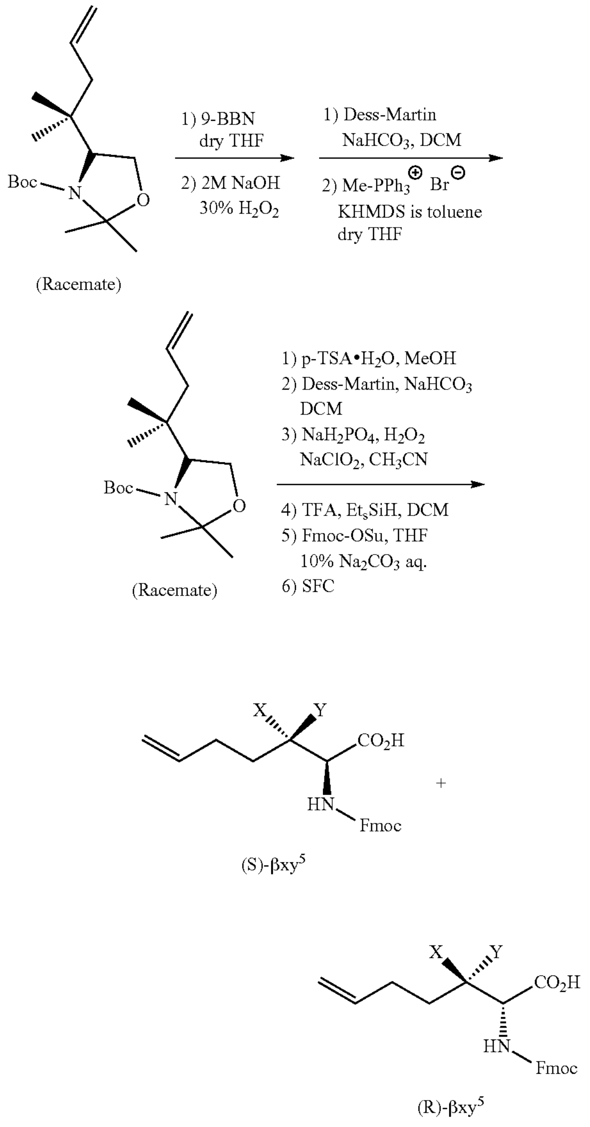
[Chemical Formula 201]
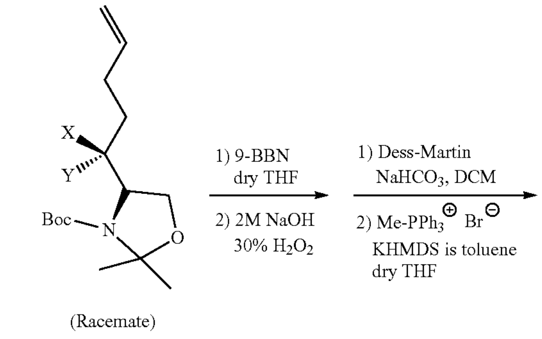

-continued

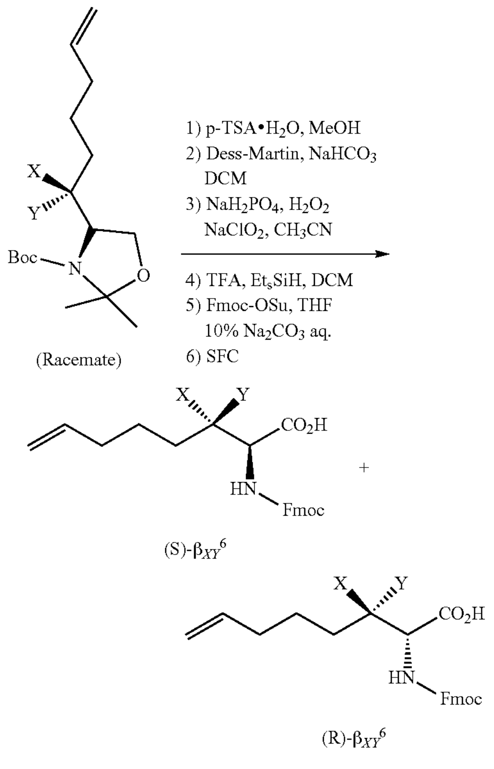

(Racemate)

(S)-$\beta_{XY}{}^{6}$ (R)-$\beta_{XY}{}^{6}$ (Result)

Artificial amino acids can be produced by performing the scheme shown above.

Here, X and Y can be any substituents in the β-position of the bridge peptide of the present disclosure.

The synthetic routes of(S)-βDM3, (S)-βDM4, (S)-βDM5, and(S)-βDM6 are shown below.

The synthetic route for (S)-βDM3

[Chemical Formula 202]

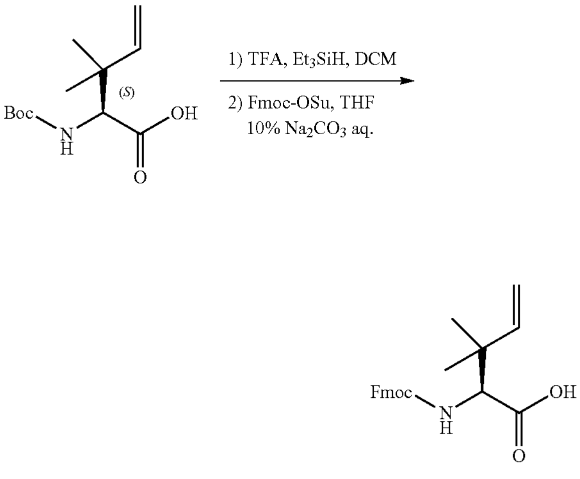

(S)-βDM3

The synthetic route for (*S*)-βDM4

[Chemical Formula 203]

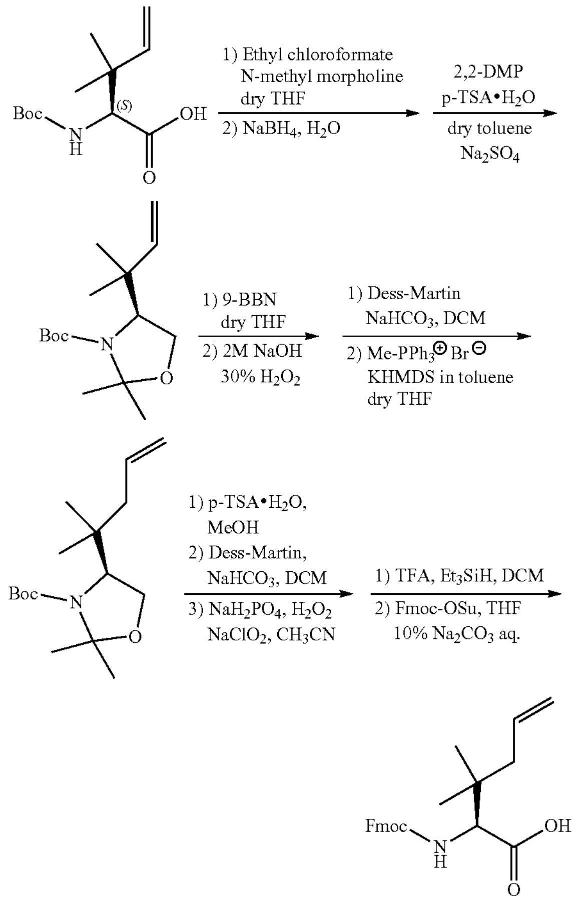

(*S*)-βDM4

The synthesis of (*S*)-βDM5 and (*S*)-βDM6 by one-carbon extension

[Chemical Formula 204]

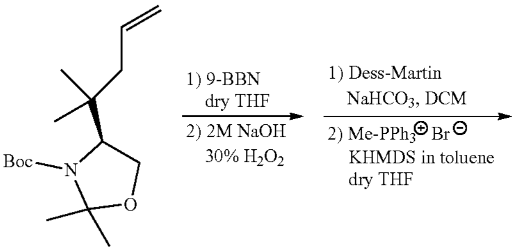

-continued

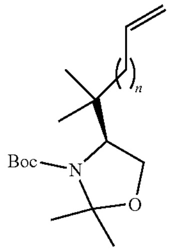

Once: n = 2 ((*S*)-βDM5)
Repeated twice: n = 3 ((*S*)-βDM6)

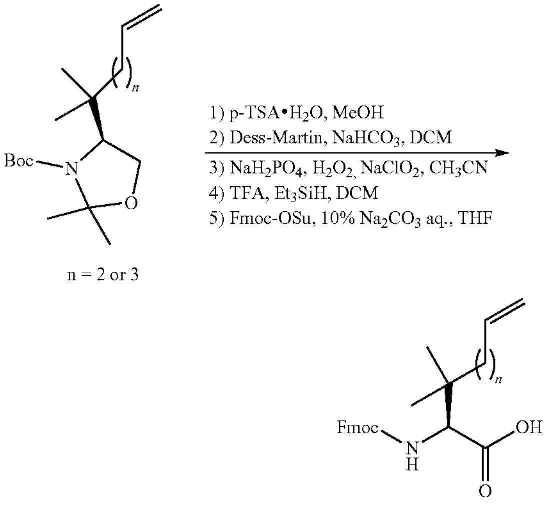

(*S*)-βDM5 (n = 2)
(*S*)-βDM6 (n = 3)

(Result)

Artificial amino acids can be produced by performing the scheme shown above.

Example 2: Synthesis of(S)-βDM3

[Chemical Formula 205]

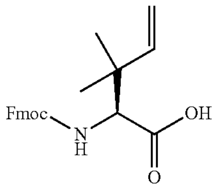

(S)-βDM3

(S)-2-((tert-butoxycarbonyl)amino)-3,3-dimethylpent-4-enoic acid was prepared by following the reported paper (Paul A. Bartlett et al., J. Org. Chem., 1982, 47, 393303941).

Nuclear magnetic resonance (NMR) spectra were measured by JEOL ECX-400 (400 MHz). Tetramethylsilane (TMS) (0.00 ppm) was used as internal standard in $^1$H-NMR measurement.

[Chemical Formula 206]

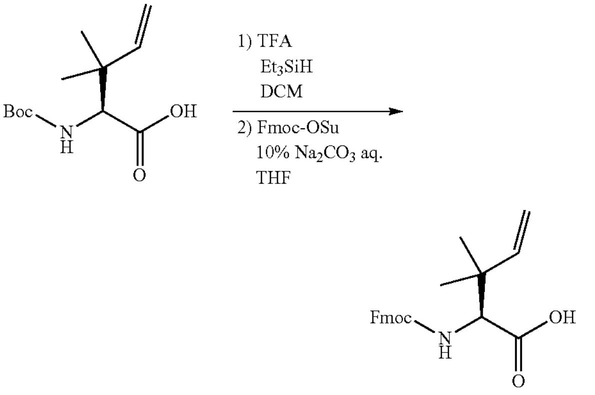

(S)-βDM3

Trifluoroacetic acid (8 mL) and triethylsilane (0.64 mL) was added to the mixture of(S)-2-((tert-butoxycarbonyl) amino)-3,3-dimethylpent-4-enoic acid (217 mg, 0.892 mmol) in dichloromethane (10 mL) at 0° C. The mixture was stirred at r.t. for 3 h, and the solvent and trifluoroacetic acid were removed under reduced pressure by using toluene to give crude product. The crude product was dissolved in 10% $Na_2CO_3$ aq. (7 mL).

N-(9-Fluorenylmethoxycarbonyloxy)succinimide (Fmoc-OSu, 306 mg, 0.91 mmol) was dissolved into THE (7 mL), and the THF solution was added into the $Na_2CO_3$ aqueous solution. The mixture was stirred for 12 h at room temperature, and the THF was removed under reduced pressure. The water phase was adjusted to a pH value of 3 with 1N HCl at 0° C. and extracted with chloroform. The combined organic extracts were washed by sat. NaCl aqueous solution, dried over $Na_2SO_4$, filtered and evaporated in vacuo. Purification of the residue by flash column chromatography (Hexane: Ethyl Acetate=3:1) afforded(S)-βDM3 (248 mg, 76%, 2 steps).

$^1$H-NMR (400 MHz, $CDCl_3$): δ 7.76 (d, J=7.3 Hz, 2H), 7.58 (d, J=7.3 Hz, 2H), 7.40 (t, J=7.3 Hz, 2H), 7.31 (t, J=7.3 Hz, 2H), 5.86 (dd, J=17.4, 11.0 Hz, 1H), 5.26 (d, J=9.2 Hz, 1H), 5.15 (d, J=11.0 Hz, 1H), 5.10 (d, J=17.4 Hz, 1H), 4.50-4.31 (m, 2H), 4.30-4.18 (m, 2H), 3.54 (br s, 1H), 1.17 (s, 2.5H), 1.14 (s, 2.5H), 1.05 (s, 1H).

Example 3: Synthesis of(S)-βDM4

[Chemical Formula 207]

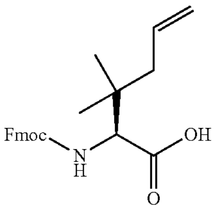

(S)-βDM4

Step 3-1 to 3-2: The Synthesis of Tert-Butyl(S)-2,2-dimethyl-4-(2-methylbut-3-en-2-yl)oxazolidine-3-carboxylate Step 3-1

[Chemical Formula 208]

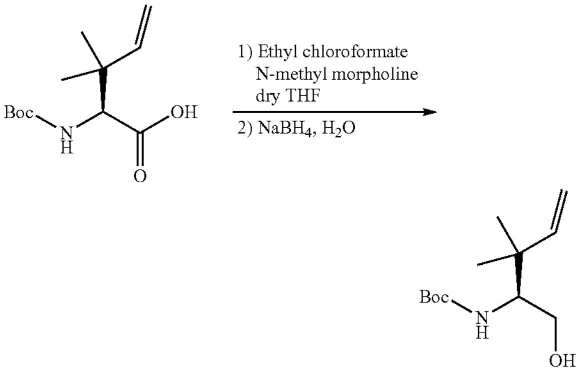

(S)-2-((tert-butoxycarbonyl)amino)-3,3-dimethylpent-4-enoic acid (2.2 g, 9.0 mmol) was dissolved in dry THF (92 mL), and N-methylmorpholine (1.2 mL, 10.9 mmol) and Ethyl chloroformate (1.02 mL, 10.7 mmol) were then added at −10° C. The mixture was stirred at −10° C. for 30 min. $NaBH_4$ (1.02 g, 27.0 mmol) in $H_2O$ (26 mL) and then $H_2O$ (384 mL) were added at −10° C. The mixture was stirred for 1 h at r.t., neutralized with 1N HCl, and the THF was removed in vacuo. The organic layer was extracted with $CHCl_3$, washed by sat. NaCl aqueous solution, and dried over $Na_2SO_4$, and concentrated in vacuo to afford the crude product. The residual oil was loaded on a silica gel column and eluted with Hexane/Ethyl acetate (3/1) to afford the product as colorless oil (1.9 g, 92% yield).

$^1$H-NMR (400 MHz, $CDCl_3$): δ 5.84 (dd, J=17.4, 11.0 Hz, 1H), 5.09 (d, J=11.0 Hz, 1H), 5.05 (dd, J=17.4, 0.92 Hz, 1H), 4.66 (br s, 1H), 3.80 (d, J=8.7 Hz, 1H), 3.59-3.44 (m, 2H), 2.24 (br s, 1H), 1.45 (s, 9H), 1.07 (s, 3H), 1.05 (s, 3H).

Step 3-2

[Chemical Formula 209]

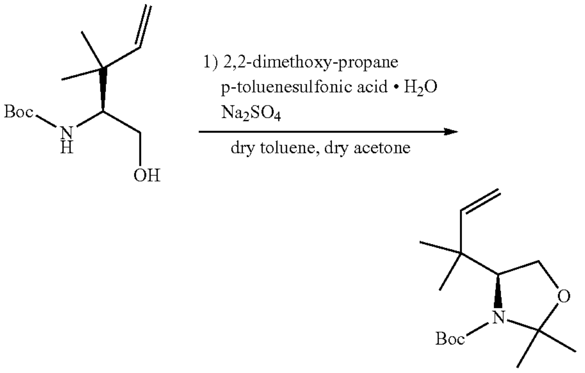

Toluene (130 mL), acetone (59 mL), and 2,2-dimethoxy-propane (164 mL, 1.34 mol) were dried over $Na_2SO_4$ and filtered through a filter paper before the reaction. tert-butyl (S)-(1-hydroxy-3,3-dimethylpent-4-en-2-yl) carbamate (3.9 g, 16.9 mmol) was dissolved in toluene (130 mL), acetone (59 mL), and 2,2-dimethoxy-propane (164 mL, 1.34 mol). p-toluenesulfonic acid monohydrate (6.4 g, 33.6 mmol), and $Na_2SO_4$ (150 g) were added and the mixture was stirred at 80° C. for 5 h under Ar atmosphere. Sat. $NaHCO_3$ aq. was added and toluene, acetone, and 2,2-dimethoxy-propane were removed under reduced pressure. The organic layer was extracted with $CHCl_3$, dried over $Na_2SO_4$, and concentrated in vacuo to afford the crude product. The residual oil was loaded on a silica gel column and eluted with Hexane/Ethyl acetate (30/1) to afford the product as colorless oil (3.2 g, 73% yield).

$^1$H-NMR (400 MHz, $CDCl_3$): δ 5.86 (dd, J=17.4, 10.6 Hz, 1H), 4.987 (d, J=10.6 Hz, 1H), 4.985 (d, J=17.4 Hz, 1H), 4.00-3.72 (m, 3H), 1.60 (br s, 3H), 1.48 (s, 12H), 1.02 (s, 3H), 1.01 (s, 3H).

Step 3-3 to 3-5: The Synthesis of Tert-Butyl(S)-2,2-dimethyl-4-(2-methylpent-4-en-2-yl)oxazolidine-3-carboxylate Step 3-3

[Chemical Formula 210]

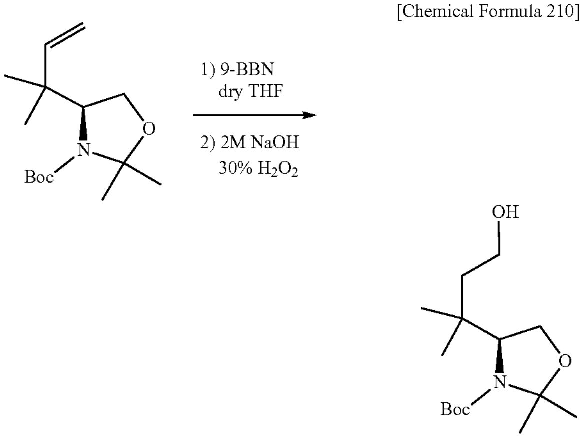

tert-butyl(S)-2,2-dimethyl-4-(2-methylbut-3-en-2-yl) oxazolidine-3-carboxylate (3.8 g, 14.0 mmol) was dissolved in dry THF (117 mL). 9-Borabicyclo[3.3.1]nonane (9-BBN) solution in THF (0.5 M, 84 mL) was added at 0° C. under Ar atmosphere and then stirred for 3 h at r.t. 2M NaOH (72 mL) and 30% $H_2O_2$ (24 mL) were added at 0° C. The mixture was stirred vigorously for 30 min at r.t. Sat. $NH_4Cl$ aq. and sat. $Na_2S_2O_3$ aq. were added and the organic layer was extracted with $CHCl_3$, washed by sat. NaCl aq., dried over $Na_2SO_4$, and concentrated in vacuo to afford the crude product. The residual oil was loaded on a silica gel column and eluted with Hexane/Ethyl acetate (3/1) to afford the product as colorless oil (3.9 g, 96% yield).

$^1$H-NMR (400 MHz, $CDCl_3$): δ 4.15-4.01 (m, 1H), 3.99-3.83 (m, 2H), 3.82-3.67 (m, 2H), 2.67 (br s, 1H), 1.72-1.55 (m, 2H), 1.61 (br s, 3H), 1.49 (s, 12H), 0.94 (s, 3H), 0.92 (s, 3H).

Step 3-4 and 3-5

[Chemical Formula 211]

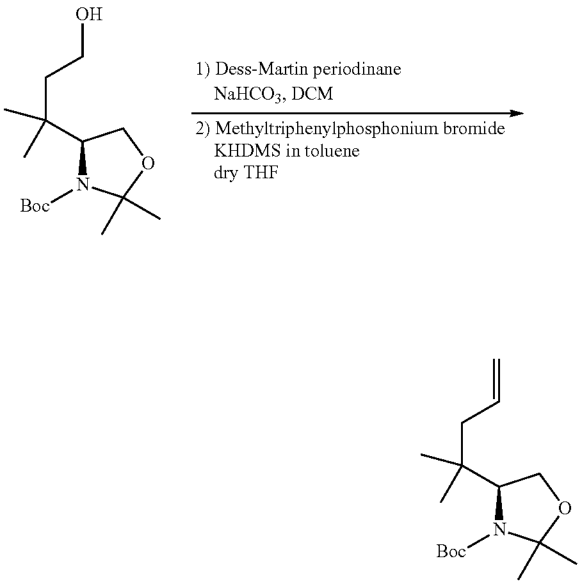

tert-butyl(S)-4-(4-hydroxy-2-methylbutan-2-yl)-2,2-dimethyloxazolidine-3-carboxylate (3.6 g, 12.5 mmol) was dissolved in DCM (111 mL). Dess-Martin periodinane (9.0 g, 21.1 mmol) and $NaHCO_3$ (15.7 g, 187 mmol) were added at 0° C. and then stirred for 3 h at 0° C. Sat. $NaHCO_3$ aq. and sat. $Na_2S_2O_3$ aq. were added at 0° C. and the mixture was stirred for 10 min at r.t. until both phases are clear. The organic layer was extracted with $CHCl_3$, washed by sat. NaCl aq., dried over $Na_2SO_4$, and concentrated in vacuo to afford the crude product. The residual oil was loaded on a silica gel column and eluted with Hexane/Ethyl acetate (20/1) to afford the desired aldehyde derivative. The crude product including the aldehyde derivative was used immediately after the purification.

Methyltriphenylphosphonium bromide (9.9 g, 27.7 mmol) was dissolved in dry THF (150 mL). KHMDS solution in toluene (0.5 M, 50 mL) was added to the mixture at 0° C. and then stirred for 1 h at 0° C. The prepared ylide solution in dry THF (173 mL) was added to the crude product including the aldehyde derivative in dry THF (16 mL) at −78° C. and then stirred for 2 h at r.t. Sat. $NH_4Cl$ aq. was added and the THF was removed in vacuo. The organic layer was extracted with $CHCl_3$, washed by sat. NaCl aq., dried over $Na_2SO_4$, and concentrated in vacuo to afford the crude product. The residual oil was loaded on a silica gel column and eluted with Hexane/Ethyl acetate (40/1) to afford the product as colorless oil (2.7 g, 76% yield, 2 steps).

$^1$H-NMR (400 MHz, $CDCl_3$): δ 5.93-5.74 (m, 1H), 5.04 (d, J=10.1 Hz, 1H), 5.00 (dd, J=17.2, 0.92 Hz, 1H), 4.00-3.70 (m, 3H), 2.09-1.94 (m, 2H), 1.62 (br s, 3H), 1.49 (s, 3H), 1.48 (s, 9H), 0.89 (s, 3H), 0.87 (s, 3H).

Step 3-6 to 3-10: The Synthesis of(S)-2-((((9H-fluoren-9-yl) methoxy) carbonyl)amino)-3,3-dimethylhex-5-enoic acid Step 3-6

[Chemical Formula 212]

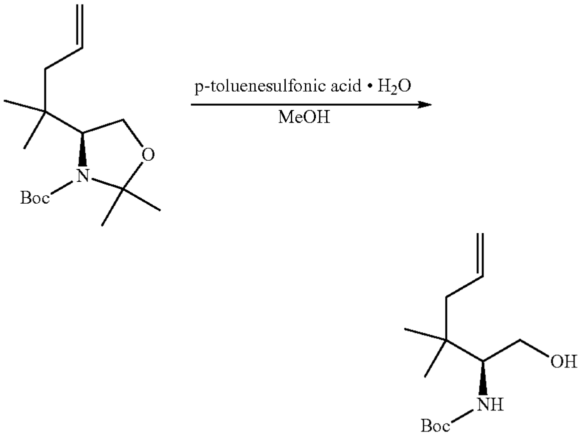

tert-butyl(S)-2,2-dimethyl-4-(2-methylpent-4-en-2-yl) oxazolidine-3-carboxylate (283 mg, 1.0 mmol) was dissolved in methanol (10 mL). p-toluenesulfonic acid monohydrate (20 mg, 0.105 mmol) was added to the mixture and then stirred for 2.5 h at r.t. Sat. $NaHCO_3$ aq. was added and methanol was removed under reduced pressure. The organic layer was extracted with $CHCl_3$, washed by sat. NaCl aq., dried over $Na_2SO_4$, and concentrated in vacuo to afford the crude product. The residual oil was loaded on a silica gel column and eluted with Hexane/Ethyl acetate (20/1) to afford the product (211 mg, 87% yield).

$^1$H-NMR (400 MHz, $CDCl_3$): δ 5.90-5.77 (m, 1H), 5.09 (dd, J=10.6, 1.84 Hz, 1H), 5.05 (dd, J=16.9, 1.84 Hz, 1H), 4.73-4.57 (m, 1H), 3.92-3.76 (m, 1H), 3.64-3.44 (m, 2H), 2.13-1.95 (m, 3H), 1.45 (s, 9H), 0.924 (s, 3H), 0.919 (s, 3H).

Step 3-7 to 3-10

[Chemical Formula 213]

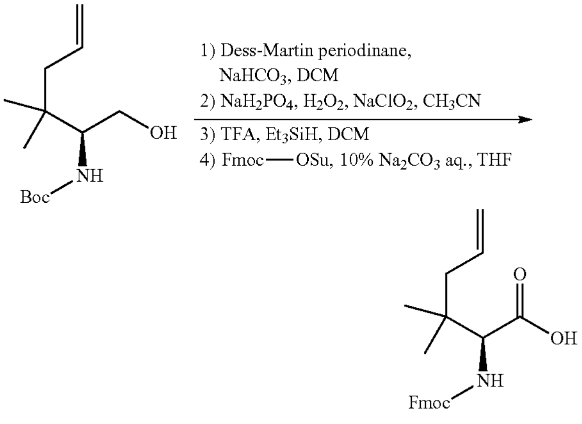

(S)-βDM4 tert-butyl(S)-(1-hydroxy-3,3-dimethylhex-5-en-2-yl) carbamate (211 mg, 0.87 mmol) was dissolved in DCM (7.7 mL). Dess-Martin periodinane (624 mg, 1.46 mmol) and $NaHCO_3$ (1.09 g, 13 mmol) were added at 0° C. and then stirred for 3 h at 0° C. Sat. $NaHCO_3$ aq. and sat. $Na_2S_2O_3$ aq. were added at 0° C. and the mixture was stirred for 10 min at r.t. until both phases are clear. The organic layer was extracted with $CHCl_3$, washed by sat. NaCl aq., dried over $Na_2SO_4$, and concentrated in vacuo to afford the crude product. The residual oil was loaded on a silica gel column and eluted with Hexane/Ethyl acetate (20/1) to afford the desired aldehyde derivative. The crude product including the aldehyde derivative was used immediately after the purification.

The crude product was dissolved in acetonitrile (16 mL). $NaH_2PO_4$ (215 mg, 1.79 mmol), 30% $H_2O_2$ aq. (6.8 mL), and $NaClO_2$ (125 mg, 1.38 mmol) were added at 0° C. and then stirred for 35 min at r.t. $Na_2SO_3$ (125 mg, 0.99 mmol) was added to the mixture and then stirred for 1 h at r.t. Acetonitrile was removed under reduced pressure and sat. $NaHCO_3$ aq. was added to the mixture. The water phase was washed by ether, adjusted to a pH value of 2 with 1N HCl at 0° C. and extracted with chloroform. The combined organic extracts were washed by sat. NaCl aqueous solution, dried over $Na_2SO_4$, filtered and evaporated in vacuo. Purification of the residue by flash column chromatography (Hexane: Ethyl Acetate=2:1) afforded the desired carboxylic acid derivative. The crude product including carboxylic acid derivative was used immediately after the purification.

Trifluoroacetic acid (15.6 mL) and triethylsilane (1.0 mL) was added to the mixture of the crude product in dichloromethane (18 mL) at 0° C. The mixture was stirred at r.t. for 3 h, and the solvent and trifluoroacetic acid were removed under reduced pressure by using toluene to give the crude product which was used immediately in next reaction.

The crude product was dissolved in 10% $Na_2CO_3$ aq. (5.2 mL). N-(9-Fluorenylmethoxycarbonyloxy)succinimide (Fmoc-OSu, 243 mg, 0.72 mmol) was dissolved into THE (5.2 mL), and the THE solution was added into the $Na_2CO_3$ aqueous solution. The mixture was stirred for 12 h at room temperature, and the THF was removed under reduced pressure. The water phase was adjusted to a pH value of 3 with 1N HCl at 0° C. and extracted with chloroform. The combined organic extracts were washed by sat. NaCl aqueous solution, dried over $Na_2SO_4$, filtered and evaporated in vacuo. Purification of the residue by flash column chromatography (Hexane: Ethyl Acetate=3:1) afforded(S)-βDM4 (239 mg, 73%, 4 steps).

$^1$H-NMR (400 MHz, $CDCl_3$): δ 7.76 (d, J=7.3 Hz, 2H), 7.59 (d, J=7.3 Hz, 2H), 7.40 (t, J=7.3 Hz, 2H), 7.31 (t, J=7.3 Hz, 2H), 5.92-5.77 (m, 1H), 5.34 (d, J=9.6 Hz, 1H), 5.12 (d, J=9.2 Hz, 1H), 5.09 (d, J=16.0 Hz, 1H), 4.55-4.34 (m, 2H), 4.29 (d, J=9.6 Hz, 1H), 4.23 (t, J=6.9 Hz, 1H), 2.11 (d, J=7.3 Hz, 2H), 1.01 (s, 2.5H), 0.99 (s, 2.5H), 0.92 (s, 0.5H), 0.88 (s, 0.5H).

Example 4: Synthesis of(S)-βDM5

[Chemical Formula 214]

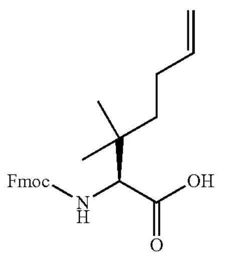

(S)-βDM5

Step 4-1 to 4-3: The Synthesis of tert-butyl(S)-2,2-dimethyl-4-(2-methylhex-5-en-2-yl) oxazolidine-3-carboxylate

Step 4-1

[Chemical Formula 215]

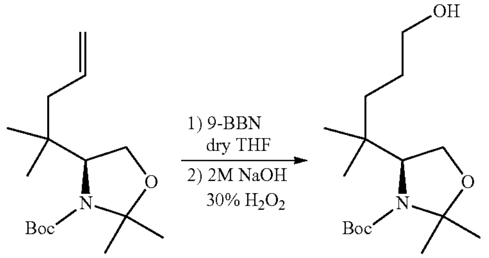

tert-butyl(S)-2,2-dimethyl-4-(2-methylpent-4-en-2-yl) oxazolidine-3-carboxylate (2.4 g, 8.43 mmol) was dissolved in dry THF (71 mL). 9-Borabicyclo[3.3.1]nonane (9-BBN) solution in THF (0.5 M, 51 mL) was added at 0° C. under Ar atmosphere and then stirred for 3 h at r.t. 2M NaOH (44 mL) and 30% $H_2O_2$ (14.5 mL) were added at 0° C. The mixture was stirred vigorously for 30 min at r.t. Sat. $NH_4Cl$ aq. and sat. $Na_2S_2O_3$ aq. were added and the organic layer was extracted with $CHCl_3$, washed by sat. NaCl aq., dried over $Na_2SO_4$, and concentrated in vacuo to afford the crude product. The residual oil was loaded on a silica gel column and eluted with Hexane/Ethyl acetate (3/1) to afford the product as colorless oil (2.5 g, 98% yield).

$^1$H-NMR (400 MHz, $CDCl_3$): δ 3.97-3.83 (m, 3H), 3.74-3.62 (m, 1H), 3.61-3.49 (m, 1H), 1.89 (br s, 1H), 1.72-1.42 (m, 4H), 1.60 (br s, 3H), 1.49 (s, 3H), 1.48 (s, 9H), 0.90 (s, 3H), 0.88 (s, 3H).

Step 4-2 and 4-3

[Chemical Formula 216]

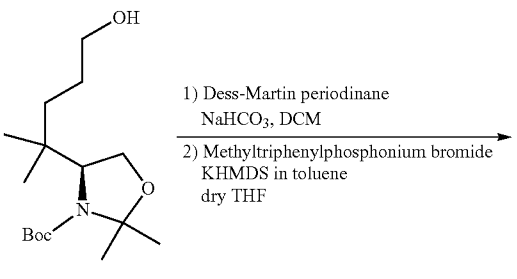

-continued

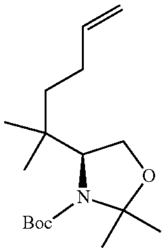

tert-butyl(S)-4-(5-hydroxy-2-methylpentan-2-yl)-2,2-dimethyloxazolidine-3-carboxylate (1.3 g, 4.2 mmol) was dissolved in DCM (37 mL). Dess-Martin periodinane (3.0 g, 7.0 mmol) and $NaHCO_3$ (5.2 g, 62 mmol) were added at 0° C. and then stirred for 3 h at 0° C. Sat. $NaHCO_3$ aq. and sat. $Na_2S_2O_3$ aq. were added at 0° C. and the mixture was stirred for 10 min at r.t. until both phases are clear. The organic layer was extracted with $CHCl_3$, washed by sat. Nacl aq., dried over $Na_2SO_4$, and concentrated in vacuo to afford the crude product. The residual oil was loaded on a silica gel column and eluted with Hexane/Ethyl acetate (20/1) to afford the desired aldehyde derivative. The crude product including the aldehyde derivative was used immediately after the purification.

Methyltriphenylphosphonium bromide (3.3 g, 9.2 mmol) was dissolved in dry THF (50 mL) at 0° C. KHMDS solution in toluene (0.5 M, 17 mL) was added to the mixture at 0° C. and then stirred for 1 h at 0° C. The prepared ylide solution in dry THF (57 mL) was added to the crude product including the aldehyde derivative in dry THF (6 mL) at −78° C. and then stirred for 2 h at r.t. Sat. $NH_4Cl$ aq. was added and the THF was removed in vacuo. The organic layer was extracted with $CHCl_3$, washed by sat. NaCl aq., dried over $Na_2SO_4$, and concentrated in vacuo to afford the crude product. The residual oil was loaded on a silica gel column and eluted with Hexane/Ethyl acetate (40/1) to afford the product as colorless oil (0.9 g, 73% yield, 2steps).

$^1$H-NMR (400 MHz, $CDCl_3$): δ 5.88-5.75 (m, 1H), 4.99 (d, J=17.0 Hz, 1H), 4.92 (d, J=10.1 Hz, 1H), 4.00-3.70 (m, 3H), 2.15-1.94 (m, 2H), 1.61 (br s, 3H), 1.49 (s, 3H), 1.48 (s, 9H), 1.40-1.25 (m, 2H), 0.89 (s, 3H), 0.88 (s, 3H).

Step 4-4 to 4-8: The Synthesis of(S)-2-((((9H-fluoren-9-yl) methoxy) carbonyl)amino)-3,3-dimethylhept-6-enoic acid

Step 4-4

[Chemical Formula 217]

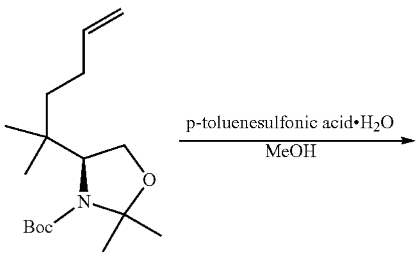

-continued

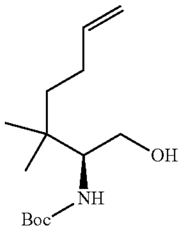

tert-butyl(S)-2,2-dimethyl-4-(2-methylhex-5-en-2-yl) oxazolidine-3-carboxylate (288 mg, 0.97 mmol) was dissolved in methanol (10 mL). p-toluenesulfonic acid monohydrate (20 mg, 0.105 mmol) was added to the mixture and then stirred for 2.5 h at r.t. Sat. $NaHCO_3$ aq. was added and methanol was removed under reduced pressure. The organic layer was extracted with $CHCl_3$, washed by sat. NaCl ag., dried over $Na_2SO_4$, and concentrated in vacuo to afford the crude product. The residual oil was loaded on a silica gel column and eluted with Hexane/Ethyl acetate (20/1) to afford the product (238 mg, 96% yield).

$^1$H-NMR (400 MHz, $CDCl_3$): δ 5.86-5.73 (m, 1H), 5.01 (dd, J=17.4, 1.84 Hz, 1H), 4.94 (d, J=10.1 Hz, 1H), 4.61 (d, J=8.2 Hz, 1H), 3.89-3.79 (m, 1H), 3.65-3.45 (m, 2H), 2.15-1.96 (m, 3H), 1.45 (s, 9H), 1.43-1.23 (m, 2H), 0.92 (s, 3H), 0.91 (s, 3H).

Step 4-5 to 4-8

[Chemical Formula 218]

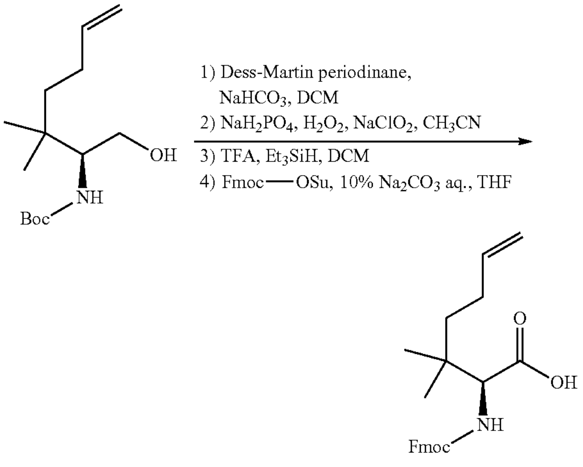

(S)-βDM5 tert-butyl(S)-(1-hydroxy-3,3-dimethylhept-6-en-2-yl) carbamate (238 mg, 0.93 mmol) was dissolved in DCM (8.2 mL). Dess-Martin periodinane (666 mg, 1.56 mmol) and $NaHCO_3$ (1.16 g, 13.8 mmol) were added at 0° C. and then stirred for 3 h at 0° C. Sat. $NaHCO_3$ aq. and sat. $Na_2S_2O_3$ aq. were added at 0° C. and the mixture was stirred for 10 min at r.t. until both phases are clear. The organic layer was extracted with $CHCl_3$, washed by sat. NaCl aq., dried over $Na_2SO_4$, and concentrated in vacuo to afford the crude product. The residual oil was loaded on a silica gel column and eluted with Hexane/Ethyl acetate (20/1) to afford the desired aldehyde derivative. The crude product i including the aldehyde derivative was used immediately after the purification.

The crude product was dissolved in acetonitrile (17 mL). $NaH_2PO_4$ (229 mg, 1.91 mmol), 30% $H_2O_2$ aq. (7.3 mL), and $NaClO_2$ (133 mg, 1.47 mmol) were added at 0° C. and then stirred for 35 min at r.t. $Na_2SO_3$ (133 mg, 1.05 mmol) was added to the mixture and then stirred for 1 h at r.t. Acetonitrile was removed under reduced pressure and sat. $NaHCO_3$ aq. was added to the mixture. The water phase was washed by ether, adjusted to a pH value of 2 with 1N HCl at 0° C. and extracted with chloroform. The combined organic extracts were washed by sat. NaCl aqueous solution, dried over $Na_2SO_4$, filtered and evaporated in vacuo. Purification of the residue by flash column chromatography (Hexane: Ethyl Acetate=2:1) afforded the desired carboxylic acid derivative. The crude product including carboxylic acid derivative was used immediately after the purification.

Trifluoroacetic acid (21 mL) and triethylsilane (1.32 mL) was added to the mixture of the carboxylic acid derivative in dichloromethane (24 mL) at 0° C. The mixture stirred at r.t. for 3 h, and the solvent and was trifluoroacetic acid were removed under reduced pressure by using toluene to give the crude product which was used immediately in next reaction.

The crude product was dissolved in 10% $Na_2CO_3$ aq. (6.9 mL). N-(9-Fluorenylmethoxycarbonyloxy) succinimide (Fmoc-OSu, 321 mg, 0.95 mmol) was dissolved into THE (6.9 mL), and the THE solution was added into the $Na_2CO_3$ aqueous solution. The mixture was stirred for 12 h at room temperature, and the THF was removed under reduced pressure. The water phase was adjusted to a pH value of 3 with 1N HCl at 0° C. and extracted with chloroform. The combined organic extracts were washed by sat. NaCl aqueous solution, dried over $Na_2SO_4$, filtered and evaporated in vacuo. Purification of the residue by flash column chromatography (Hexane: Ethyl Acetate=3:1) afforded(S)-βDM5 (256 mg, 70%, 4 steps).

$^1$H-NMR (400 MHz, $CDCl_3$): δ 7.76 (d, J=7.3 Hz, 2H), 7.58 (d, J=7.3 Hz, 2H), 7.40 (t, J=7.3 Hz, 2H), 7.31 (t, J=7.3 Hz, 2H), 5.87-5.67 (m, 1H), 5.31 (d, J=9.6 Hz, 1H), 5.02 (d, J=17.4 Hz, 1H), 4.94 (dd, J=10.1, 1.84 Hz, 1H), 4.50-4.33 (m, 2H), 4.31 (d, J=9.6 Hz, 1H), 4.23 (t, J=6.9 Hz, 1H), 2.17-2.03 (m, 2H), 1.43 (t, J=8.2 Hz, 2H), 1.014 (s, 2.5H), 1.006 (s, 2.5H), 0.90 (s, 0.5H), 0.84 (s, 0.5H).

Example 5: Synthesis of(S)-βDM6

[Chemical Formula 219]

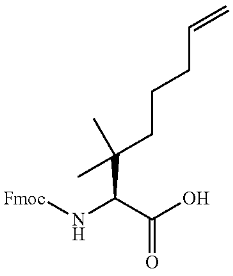

(S)-βDM6

Step 5-1 to 5-3: The Synthesis of tert-butyl(S)-2,2-dimethyl-4-(2-methylhept-6-en-2-yl) oxazolidine-3-carboxylate (Step 5-1)

[Chemical Formula 220]

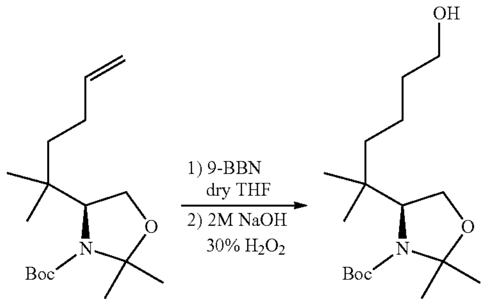

tert-butyl(S)-2,2-dimethyl-4-(2-methylhex-5-en-2-yl) oxazolidine-3-carboxylate (547 mg, 1.84 mmol) was dissolved in dry THF (16 mL). 9-Borabicyclo[3.3.1]nonane (9-BBN) solution in THF (0.5 M, 11 mL) was added at 0° C. under Ar atmosphere and then stirred for 3 h at r.t. 2M NaOH (9.6 mL) and 30% $H_2O_2$ (3.2 mL) were added at 0° C. The mixture was stirred vigorously for 30 min at r.t. Sat. $NH_4Cl$ aq. and sat. $Na_2S_2O_3$ aq. were added and the organic layer was extracted with $CHCl_3$, washed by sat. NaCl aq., dried over $Na_2SO_4$, and concentrated in vacuo to afford the crude product. The residual oil was loaded on a silica gel column and eluted with Hexane/Ethyl acetate (3/1) to afford the product as colorless oil (569 mg, 98% yield).

$^1$H-NMR (400 MHz, $CDCl_3$): δ 3.97-3.81 (m, 3H), 3.78-3.56 (m, 2H), 1.95-1.78 (m, 1H), 1.72-1.44 (m, 4H), 1.60 (br s, 3H), 1.49 (s, 3H), 1.48 (s, 9H), 1.36-1.21 (m, 2H), 0.88 (s, 3H), 0.87 (s, 3H).

Step 5-2 and 5-3

[Chemical Formula 221]

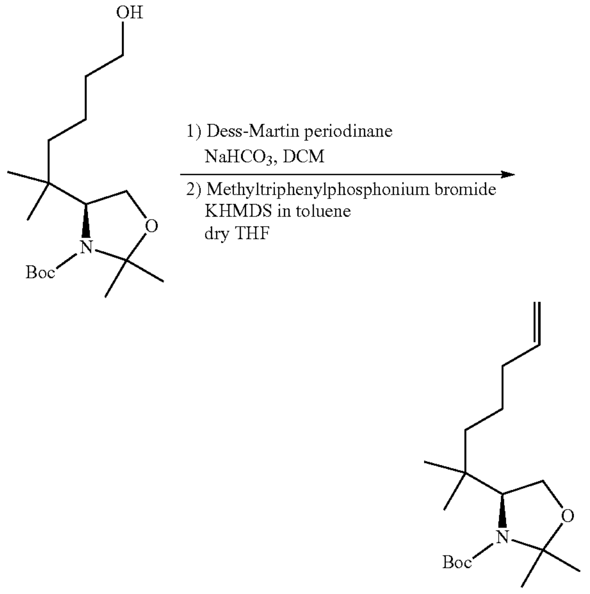

tert-butyl(S)-4-(6-hydroxy-2-methylhexan-2-yl)-2,2-dimethyloxazolidine-3-carboxylate (360 mg, 1.1 mmol) was dissolved in DCM (10 mL). Dess-Martin periodinane (1.24 g, 2.9 mmol) and $NaHCO_3$ (2.2 g, 26 mmol) were added at 0° C. and then stirred for 3 h at 0° C. Sat. $NaHCO_3$ aq. and sat. $Na_2S_2O_3$ aq. were added at 0° C. and the mixture was stirred for 10 min at r.t. until both phases are clear. The organic layer was extracted with $CHCl_3$, washed by sat. NaCl aq., dried over $Na_2SO_4$, and concentrated in vacuo to afford the crude product. The residual oil was loaded on a silica gel column and eluted with Hexane/Ethyl acetate (20/1) to afford the desired aldehyde derivative. The crude product including the aldehyde derivative was used immediately after the purification.

Methyltriphenylphosphonium bromide (0.91 g, 2.54 mmol) was dissolved in dry THF (14 mL) at 0° C. KHMDS solution in toluene (0.5 M, 4.6 mL) was added to the mixture at 0° C. and then stirred for 1 h at 0° C. The prepared ylide solution in dry THF (15.7 mL) was added to the crude product including the aldehyde derivative in dry THF (1.7 mL) at −78° C. and then stirred for 2 h at r.t. Sat. $NH_4Cl$ aq. was added and the THF was removed in vacuo. The organic layer was extracted with $CHCl_3$, washed by sat. NaCl aq., dried over $Na_2SO_4$, and concentrated in vacuo to afford the crude product. The residual oil was loaded on a silica gel column and eluted with Hexane/Ethyl acetate (40/1) to afford the product as colorless oil (230 mg, 65% yield, 2steps).

$^1$H-NMR (400 MHz, $CDCl_3$): δ 5.87-5.74 (m, 1H), 4.99 (d, J=17.4 Hz, 1H), 4.93 (d, J=10.1 Hz, 1H), 3.96-3.70 (m, 3H), 2.08-1.96 (m, 2H), 1.60 (br s, 3H), 1.484 (s, 3H), 1.475 (s, 9H), 1.42-1.18 (m, 4H), 0.87 (s, 3H), 0.86 (s, 3H).

Step 5-4 to 5-8: The Synthesis of(S)-2-((((9H-Fluoren-9-yl) methoxy) carbonyl)amino)-3,3-dimethyloct-7-enoic acid Step 5-4

[Chemical Formula 217]

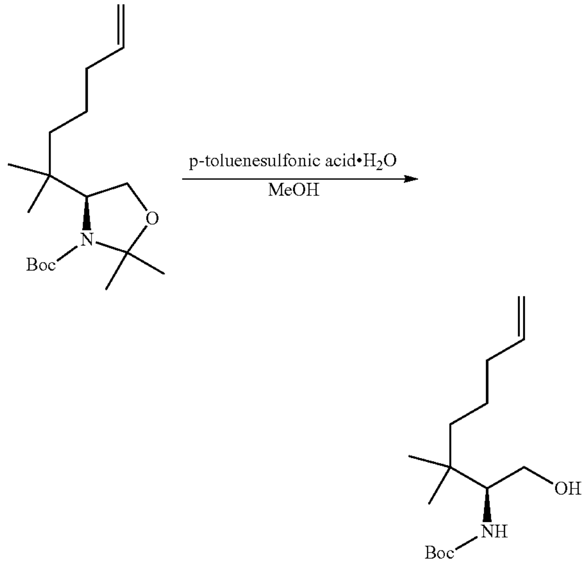

tert-butyl(S)-2,2-dimethyl-4-(2-methylhept-6-en-2-yl) oxazolidine-3-carboxylate (230 mg, 0.74 mmol) was dissolved in methanol (8 mL). p-toluenesulfonic acid monohydrate (16 mg, 0.084 mmol) was added to the mixture and then stirred for 2.5 h at r.t. Sat. $NaHCO_3$ aq. was added and methanol was removed under reduced pressure. The organic layer was extracted with $CHCl_3$, washed by sat. Nacl aq., dried over $Na_2SO_4$, and concentrated in vacuo to afford the crude product. The residual oil was loaded on a silica gel column and eluted with Hexane/Ethyl acetate (20/1) to afford the product (195 mg, 97% yield).

$^1$H-NMR (400 MHz, $CDCl_3$): δ 5.85-5.72 (m, 1H), 5.40-4.90 (m, 2H), 4.60 (d, J=8.7 Hz, 1H), 3.89-3.77 (m, 1H), 3.64-3.41 (m, 2H), 2.15 (t, J=5.5 Hz, 1H), 2.06-1.97 (m, 2H), 1.45 (s, 9H), 1.44-1.15 (m, 4H), 0.90 (s, 3H), 0.89 (s, 3H).

Step 5-5 to 5-8

[Chemical Formula 223]

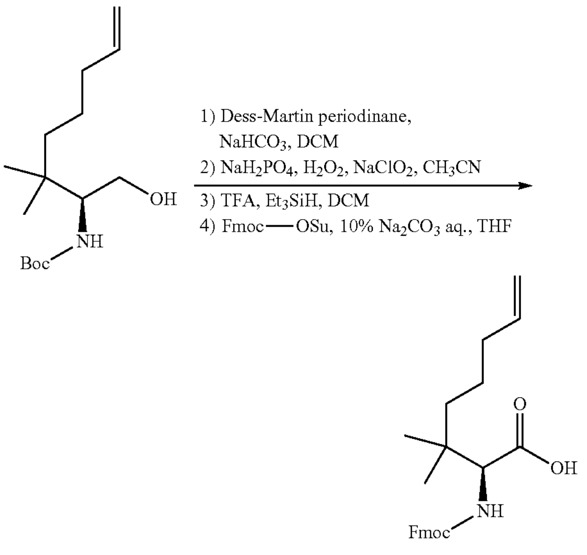

(S)-βDM6 tert-butyl(S)-(1-hydroxy-3,3-dimethyloct-7-en-2-yl) carbamate (195 mg, 0.72 mmol) was dissolved in DCM (6.5 mL). Dess-Martin periodinane (800 mg, 1.87 mmol) and $NaHCO_3$ (1.43 g, 17.0 mmol) were added at 0° C. and then stirred for 3 h at 0° C. Sat. $NaHCO_3$ aq. and sat. $Na_2S_2O_3$ aq. were added at 0° C. and the mixture was stirred for 10 min at r.t. until both phases are clear. The organic layer was extracted with $CHCl_3$, washed by sat. Nacl aq., dried over $Na_2SO_4$, and concentrated in vacuo to afford the crude product. The residual oil was loaded on a silica gel column and eluted with Hexane/Ethyl acetate (20/1) to afford the desired aldehyde derivative. The crude product including the aldehyde derivative was used immediately after the purification.

The crude product was dissolved in acetonitrile (14 mL). $NaH_2PO_4$ (183 mg, 1.53 mmol), 30% $H_2O_2$ aq. (5.84 mL), and NaCl02 (106 mg, 1.17 mmol) were added at 0° C. and then stirred for 35 min at r.t. $Na_2SO_3$ (106 mg, 0.84 mmol) was added to the mixture and then stirred for 1 h at r.t. Acetonitrile was removed under reduced pressure and sat. $NaHCO_3$ aq. was added to the mixture. The water phase was washed by ether, adjusted to a pH value of 2 with 1N HCl at 0° C. and extracted with chloroform. The combined organic extracts were washed by sat. NaCl aqueous solution, dried over $Na_2SO_4$, filtered and evaporated in vacuo. Purification of the residue by flash column chromatography (Hexane: Ethyl Acetate=2:1) afforded the desired carboxylic acid derivative. The crude product including carboxylic derivative was used immediately after the purification.

Trifluoroacetic acid (16.5 mL) and triethylsilane (1.0 mL) was added to the mixture of the carboxylic acid derivative in dichloromethane (19 mL) at 0° C. The mixture was stirred at r.t. for 3 h, and the solvent and trifluoroacetic acid were removed under reduced pressure by using toluene to give the crude product which was used immediately in next reaction.

The crude product was dissolved in 10% $Na_2CO_3$ aq. (5.5 mL). N-(9-Fluorenylmethoxycarbonyloxy)succinimide (Fmoc-OSu, 257 mg, 0.76 mmol) was dissolved into THF (5.5 mL), and the THF solution was added into the $Na_2CO_3$ aqueous solution. The mixture was stirred for 12 h at room temperature, and the THF was removed under reduced pressure. The water phase was adjusted to a pH value of 3 with 1N HCl at 0° C. and extracted with chloroform. The combined organic extracts were washed by sat. NaCl aqueous solution, dried over $Na_2SO_4$, filtered and evaporated in vacuo. Purification of the residue by flash column chromatography (Hexane: Ethyl Acetate=3:1) afforded(S)-βDM6 (212 mg, 70%, 4 steps).

$^1$H-NMR (400 MHz, $CDCl_3$): δ 7.76 (d, J=7.3 Hz, 2H), 7.65-7.51 (m, 2H), 7.40 (t, J=7.3 Hz, 2H), 7.31 (t, J=7.3 Hz, 2H), 5.86-5.71 (m, 1H), 5.33 (d, J=9.6 Hz, 1H), 5.00 (dd, J=17.4, 1.84 Hz, 1H), 4.94 (d, J=10.1 Hz, 1H), 4.51-4.34 (m, 2H), 4.30 (d, J=9.6 Hz, 1H), 4.23 (t, J=6.9 Hz, 1H), 2.09-1.95 (m, 2H), 1.54-1.18 (m, 4H), 1.00 (s, 2.4H), 0.99 (s, 2.4H), 0.91 (s, 0.6H), 0.86 (s, 0.6H).

Example 6: The Synthesis of(S)-βDTFM4, (R)-βDTFM4, (S)-βDTFM6, and (R)-βDTFM6

Nuclear magnetic resonance (NMR) spectra were measured by Bruker Advance Neo (400 MHz for $^1$H NMR, 100 MHz for 13C NMR, 376 MHz for 19F NMR). Tetramethylsilane (TMS) (0.00 ppm) was used as internal standard in $^1$H-NMR measurement.

Example 6-1: The Synthesis of(S)-βDTFM4 and (R)-βDTFM4

[Chemical Formula 224]

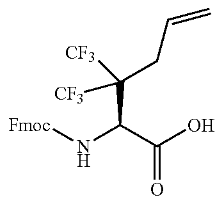

Step 6-1A to 6-1B: The Synthesis of methyl (E)-5-phenyl-2,2-bis(trifluoromethyl) pent-4-enoate

Step 6-1A

[Chemical Formula 224-2]

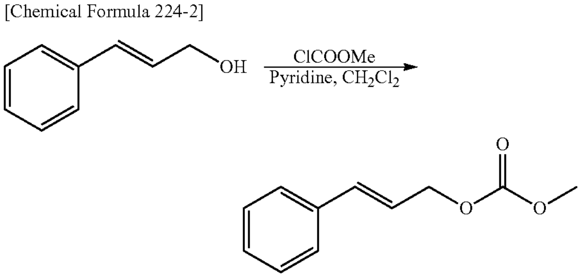

To a mixture of pyridine (120.00 g, 1.52 mol), cinnamyl alcohol (30 g, 223.59 mmol) and dichloromethane (300 mL) was added methyl chloroformate (51.24 g, 542.24 mmol) dropwise at 0° C. The reaction mixture was allowed to warm to room temperature (15° C.) and then refluxed for 15 h. The reaction was cooled to 0° C., then 2N HCl aq. (200 mL) was added. The two phases were separated and the aqueous phase was extracted with DCM. Combined organic phase was washed with brine successively, dried over $Na_2SO_4$, concentrated to give a yellow oil. The crude oil was purified by flash silica gel chromatography (Eluent: ethyl acetate in petroleum from 0 to 10% at flowrate 100 mL/min) to afford desired product (38 g, 88%).

$^1$H NMR (400 MHz, $CDCl_3$): δ 7.45-7.38 (m, 2H), 7.37-7.31 (m, 2H), 7.30-7.25 (m, 1H), 6.70 (d, J=16.1 Hz, 1H), 6.31 (td, J=6.5, 15.9 Hz, 1H), 4.81 (dd, J=1.3, 6.5 Hz, 2H), 3.82 (s, 3H).

Step 6-1B

[Chemical Formula 224-3]

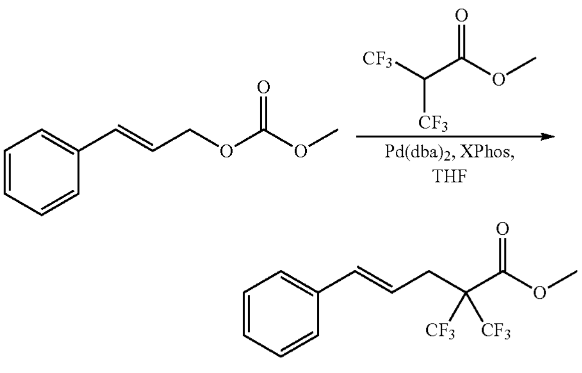

A solution of Pd (dba) 2 (2.51 g, 4.37 mmol) and XPhos (6.25 g, 13.11 mmol) in THF (200 mL) was stirred under $N_2$ atmosphere for 30 min, then [(E)-cinnamyl]methyl carbonate (21 g, 109.26 mmol) in THF (50 mL) was added dropwise under $N_2$ atmosphere. After 10 min, methyl 3,3,3-trifluoro-2-(trifluoromethyl)propanoate (22.95 g, 109.26 mmol) in THF (50 mL) was added to the mixture dropwise, and the mixture was allowed to react for 12 h. The mixture was concentrated in reduced pressure to afford a crude, which was purified by flash silica gel chromatography (Eluent: ethyl acetate in petroleum from 0 to 10% at flowrate 100 mL/min) to afford the desired product (30.6 g, 86%).

$^1$H-NMR (400 MHz, $CDCl_3$): δ=7.37-7.30 (m, 4H), 7.28-7.26 (m, 1H), 6.60 (d, J=15.8 Hz, 1H), 6.11-6.03 (m, 1H), 3.91 (s, 3H), 3.10 (d, J=7.5 Hz, 2H).

$^{19}$F-NMR (376 MHz, $CDCl_3$): δ=−66.03 (s, 6F).

Step 6-1C to 6-1E: The Synthesis of 2-methyl-N-((1E, 4E)-5-phenyl-2,2-bis(trifluoromethyl)pent-4-en-1-ylidene)propane-2-sulfinamide Step 6-1C

[Chemical Formula 224-4]

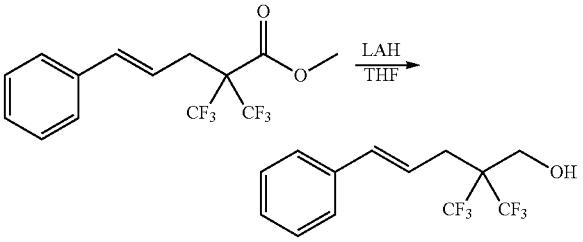

Methyl (E)-5-phenyl-2,2-bis(trifluoromethyl)pent-4-enoate (30.6 g, 93.80 mmol) in THF (300 mL) was dropwise added into a suspension of LAH (3.56 g, 93.80 mmol) in THF (300 mL) and stirred under $N_2$ atmosphere for 30 min at 0° C., then at r.t. for 30 min. The reaction was quenched with $H_2O$ (4 mL), aq. NaOH (15%, 4 mL) and $H_2O$ (12 mL) then diluted with $H_2O$ (100 mL) and ethyl acetate (100 mL), followed with addition of Rochelle's salt (30 g) and the solution was stirred vigorously for 3 h. Then phases were separated and aqueous phase was extracted with ethyl acetate. Combined organic phase was washed by sat. NaCl aq., dried over $Na_2SO_4$ and concentrated in reduced pressure to afford a crude, which was purified by flash silica gel chromatography (Eluent: ethyl acetate in petroleum from 0 to 10% at flowrate 100 mL/min) to afford the desired product (25.2 g, 90%).

$^1$H-NMR (400 MHz, DMSO-$d_6$): δ=7.41 (d, J=7.2 Hz, 2H), 7.33 (t, J=7.2 Hz, 2H), 7.25 (t, J=7.2 Hz, 1H), 6.62 (d, J=15.6 Hz, 1H), 6.27-6.19 (m, 1H), 5.70 (t, J=5.6 Hz, 1H), 3.90 (br d, J=6.0 Hz, 2H), 2.79 (br d, J=7.6 Hz, 2H).

$^{19}$F-NMR (376 MHz, CHLOROFORM-d): δ=−66.73 (br s, 6F).

MS (ESI): 281.3 ($M-OH^+$)

Step 6-1D

[Chemical Formula 224-5]

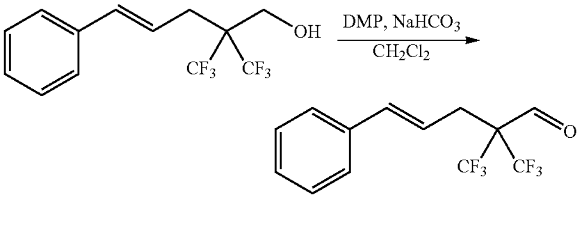

To a stirred solution of (E)-5-phenyl-2,2-bis(trifluoromethyl) pent-4-en-1-ol (25.2 g, 84.5 mmol) in DCM (200 mL) was added Dess-Martin periodinane (53.8 g, 126.8 mmol) and $NaHCO_3$ (32.5 g, 387.1 mmol). The reaction mixture was kept stirring for 1.5 h. The reaction was quenched with sat. $NaHCO_3$ (aq.) (200 mL) and $NaHSO^3$ (26 g), extracted with DCM and organic phase was washed with $Na_2CO_3$ (26 g in 100 mL $H_2O$), dried over $Na_2SO_4$, filtered and the filtrate was concentrated in reduced pressure to afford the product (23 g, 91.9%) which was used in next step directly without further purification.

$^1$H-NMR (400 MHz, $CDCl_3$): δ 9.72 (s, 1H), 7.39-7.24 (m, 5H), 6.58 (d, J=15.6 Hz, 1H), 6.09-6.01 (m, 1H), 3.04 (d, J=7.2 Hz, 2H).

$^{19}$F-NMR (376 MHz, DMSO-$d_6$): δ −64.71 (s, 6F).

Step 6-1E

[Chemical Formula 224-6]

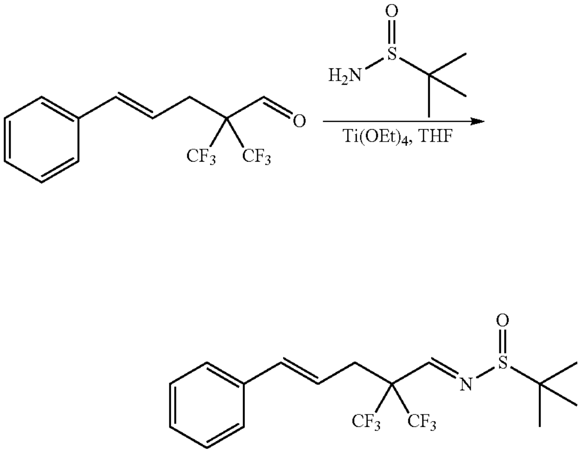

To a mixture of 2-methylpropane-2-sulfinamide (7.0 g, 57.4 mmol) and (E)-5-phenyl-2,2-bis(trifluoromethyl)pent-4-enal (10 g, 33.8 mmol) in THF (100 mL) was added $Ti(OEt)_4$ (12.3 g, 54.0 mmol, 11.2 mL) and stirred at 60° C. for 8 h. The reaction was quenched by addition of water (50 mL) and Rochelle's salt (18 g), and diluted with ethyl acetate (150 mL). Two phases were separated after vigorous stirring for 2 h. The organic phase was separated and concentrated to give a residue, which was purified by flash silica gel chromatography (Eluent: ethyl acetate in petroleum from 0 to 100% at flowrate 80 mL/min) to afford the desired product (12 g, 89%).

$^1$H-NMR (400 MHz, $CDCl_3$) δ=8.08 (s, 1H), 7.32 (d, J=4.5 Hz, 4H), 7.29-7.23 (m, 1H), 6.58 (d, J=15.6 Hz, 1H), 6.14-6.06 (m, 1H), 3.23-3.02 (m, 2H), 1.24 (s, 9H).

$^{19}$F-NMR (376 MHz, $CDCl_3$) δ=−66.56 (td, J=8.7, 27.7 Hz, 6F).

MS (ESI): 399.9 $(M+H)^+$.

Step 6-1F to 6-1J: The Synthesis of tert-butyl (E)-2,2-dimethyl-4-(1, 1,1-trifluoro-5-phenyl-2-(trifluoromethyl) pent-4-en-2-yl) oxazolidine-3-carboxylate Step 6-1F

[Chemical Formula 224-7]

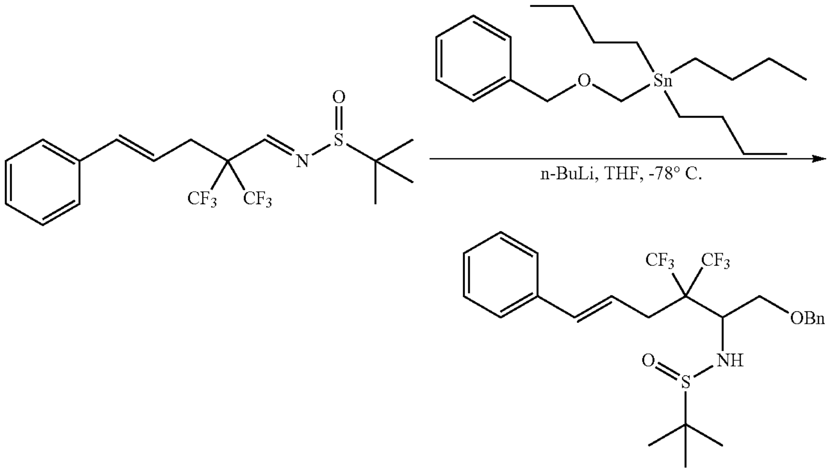

To a solution of benzyloxymethyl(tributyl) stannane (2.0 g, 4.9 mmol) in THF (20 mL) was added n-butyllithium (2.5 M, 1.95 mL) dropwise at −78° C. under $N_2$ atmosphere. After 10 min, a solution of 2-methyl-N-((1E,4E)-5-phenyl-2, 2-bis(trifluoromethyl) pent-4-en-1-ylidene) propane-2-sulfinamide (1.5 g, 3.76 mmol) in THF (5 mL) was added dropwise at −78° C. and the mixture was stirred at −78° C. for 80 min. The reaction was quenched by addition of saturated $NH_4Cl$ (aq.) (10 mL). The mixture was extracted with ethyl acetate and concentrated in reduced pressure to afford a crude, which was purified by flash silica gel chromatography (Eluent: ethyl acetate in petroleum from 0 to 100% at flowrate 50 mL/min) to afford the desired product (0.46 g, 23.4%).

$^1$H-NMR (400 MHz, $CDCl_3$): δ 7.34-7.21 (m, 10H), 6.72 (d, J=15.3 Hz, 1H), 6.18-6.14 (m, 1H), 4.50-4.36 (m, 2H), 3.97-3.90 (m, 1H), 3.80-3.68 (m, 2H), 3.58-3.50 (m, 1H), 3.13 (dd, J=7.9, 14.7 Hz, 1H), 2.80 (dd, J=6.8, 15.1 Hz, 1H), 1.14 (s, 9H)

$^{19}$F-NMR (376 MHz, $CDCl_3$): δ −63.62 (q, J=10.4 Hz, 3F), −64.00 (q, J=9.2 Hz, 3F)

MS (ESI): 522.2 $(M+H)^+$.

Step 6-1G and H

[Chemical Formula 224-8]

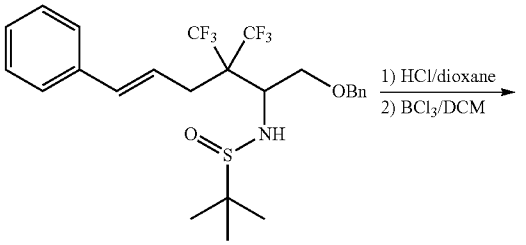

-continued

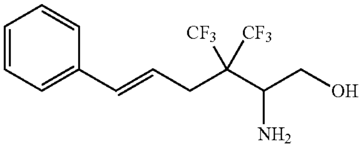

To a solution of (E)-N-(1-(benzyloxy)-6-phenyl-3, 3-bis (trifluoromethyl) hex-5-en-2-yl)-2-methylpropane-2-sulfinamide (4.1 g, 7.9 mmol) in MeOH (15 mL) was added HCl/dioxane (4 M, 18 mL) and kept for 2 hr. The solvent was removed in reduced pressure to give a crude, which was diluted with sat. $NaHCO_3$ (aq.) (40 mL) and extracted with ethyl acetate. The organic phase was combined, dried over $Na_2SO_4$, and concentrated to afford the crude product, which was used in next step directly.

The crude product was dissolved in DCM (40 mL). To the mixture was added $BCl_3$ (1 M, 17.7 mL) and stirred for 30 min at −78° C. Then the reaction was allowed to room temperature for 1.5 hr. The solution was quenched with sat. $NaHCO_3$ (aq.) (30 mL) and extracted with DCM, organic phase was washed with brine, dried over $Na_2SO_4$ and concentrated in reduced pressure to give a crude, which was purified by flash silica gel chromatography (Eluent: ethyl acetate in petroleum from 0 to 80% at flow rate 50 mL/min) to afford the desired product (2.04 g, 73%).

$^1$H-NMR (400 MHz, $CDCl_3$): δ 7.31-7.18 (m, 5H), 6.51 (d, J=15.6 Hz, 1H), 6.10-6.02 (m, 1H), 3.80 (dd, J=3.1, 10.7 Hz, 1H), 3.41 (br t, J=10.4 Hz, 1H), 3.25 (br d, J=9.5 Hz, 1H), 2.84 (dd, J=7.2, 14.9 Hz, 1H), 2.66 (br dd, J=8.0, 15.1 Hz, 1H)

$^{19}$F-NMR (376 MHz, $CDCl_3$): δ −63.75–63.93 (m, 3F), −64.94 (q, J=9.2 Hz, 3F)

MS (ESI): 327.9 $(M+H)^+$.

Step 6-1I

[Chemical Formula 224-9]

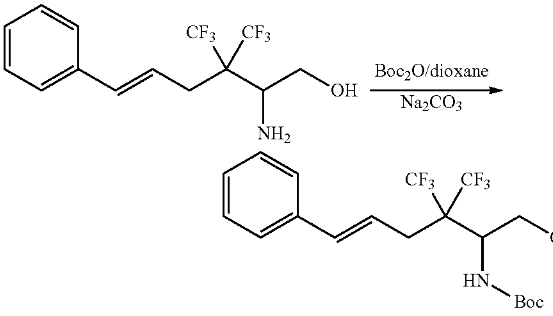

To a solution of (E)-2-amino-6-phenyl-3, 3-bis(trifluoromethyl) hex-5-en-1-ol (1.2 g, 3.7 mmol) in dioxane (20 mL) and $H_2O$ (20 mL) was added $Na_2CO_3$ (800 mg, 7.6 mmol) and $Boc_2O$ (1.60 g, 7.3 mmol) at 0° C. The solution was kept stirring at 20° C. for 36 h. The reaction was extracted with ethyl acetate, organic phase was concentrated and purified by flash silica gel chromatography (Eluent: ethyl acetate in petroleum from 0 to 70% at flowrate 25 mL/min) to afford the desired product (1.2 g, 76.6%).

$^1$H-NMR (400 MHz, $CDCl_3$): δ=7.33-7.29 (m, 2H), 7.28-7.22 (m, 2H), 7.21-7.19 (m, 1H), 6.50 (d, J=15.6 Hz, 1H), 6.27-6.05 (m, 1H), 4.79 (br d, J=11.0 Hz, 1H), 4.47-4.30 (m, 1H), 4.01-3.91 (m, 1H), 3.71-3.57 (m, 1H), 2.91-2.69 (m, 2H), 1.38 (s, 9H)

$^{19}$F-NMR (376 MHz, $CDCl_3$): δ=−64.70 (q, J=8.1 Hz, 3F), −65.10 (q, J=10.4 Hz, 3F).

Step 6-1J

[Chemical Formula 224-10]

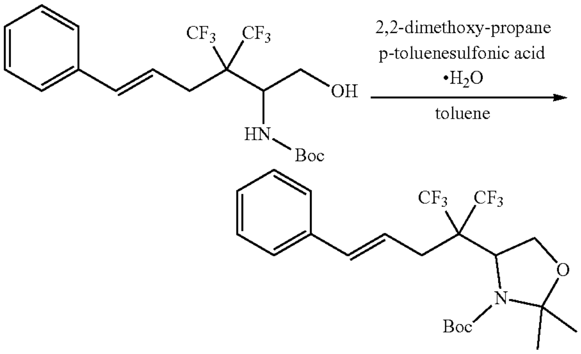

To a solution of tert-butyl (E)-(1-hydroxy-6-phenyl-3, 3-bis(trifluoromethyl) hex-5-en-2-yl) carbamate (850 mg, 1.99 mmol) in toluene (8 mL) and 2, 2-dimethoxypropane (3.61 g, 34.7 mmol, 4.25 mL) was added TsOH·$H_2O$ (85.0 mg, 0.447 mmol) and kept in 84° C. for 12 h. The reaction was quenched with sat. $NaHCO_3$ aq. (5 mL), extracted with chloroform, concentrated under reduced pressure and purified by flash silica gel chromatography (Eluent: ethyl acetate in petroleum ether from 0% to 50% gradient at flowrate 45 mL/min) to afford the desired product (1.04 g, 83% yield).

$^1$H-NMR (400 MHz, $CDCl_3$): δ 7.33-7.21 (m, 4H), 7.18-7.13 (m, 1H), 6.45 (br d, J=15.6 Hz, 1H), 6.33-6.15 (m, 1H), 4.64 (s, 1H), 4.32 (d, J=10.5 Hz, 1H), 3.96 (dd, J=6.5, 10.8 Hz, 1H), 2.90 (br t, J=6.5 Hz, 2H), 1.58 (br s, 3H), 1.46 (s, 3H), 1.42 (s, 9H)

$^{19}$F-NMR (376 MHz, $CDCl_3$): δ −63.52 (br d, J=10.4 Hz, 3F), −66.23 (br d, J=10.4 Hz, 3F).

Step 6-1K to 6-1P: The Synthesis of 2-((((9H-fluoren-9-yl)methoxy)carbonyl)amino)-3, 3-bis(trifluoromethyl)hex-5-enoic acid (βDTFM4)

Step 6-1K and L

[Chemical Formula 224-11]

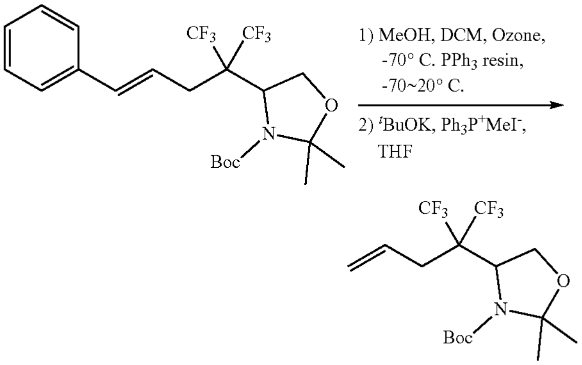

A solution of tert-butyl 2, 2-dimethyl-4-[(E)-4-phenyl-1, 1-bis(trifluoromethyl)but-3-enyl]oxazolidine-3-carboxylate (0.5 g, 1.1 mmol) in a mixed solvent of DCM (10 mL) and MeOH (10 mL) was seated in dry ice-EA bath (−70° C.). Then Ozone was blew into the mixture till the solution turned blue. Excessive $O_3$ was purged with 02 and successively added $PPh_3$ resin (3 mmol/g, 570 mg). The reaction was stirred at −70° C. for 20 min then allowed to r.t. The $PPh_3$ residue was filtered and then concentrated to afford the crude product, which was used in next step directly.

TO THF (10 mL) was added methyl triphenyl phosphonium iodide (1.8 g, 4.5 mmol) and followed with $^t$BuOK (1 M in THE, 5.1 mL) at 0° C. under $N_2$ atmosphere, and the mixture was stirred at r.t. for 0.5 h. A THF solution (5 mL) of the crude product obtained in previous step was added and the solution was further stirred for 12 hr. The reaction was quenched with sat. $NH_4Cl$ aq. (10 mL) and extracted with DCM. Organic phase was dried over $Na_2SO_4$ and concentrated in reduced pressure to afford a crude oil. The residue was purified by flash silica gel chromatography (Eluent: ethyl acetate in petroleum ether from 0% to 70% gradient flow at 45 mL/min) to afford the desired product (510 mg, 64% yield).

$^1$H-NMR (400 MHz, $CDCl_3$): δ 5.88 (m, 1H), 5.19-5.03 (m, 2H), 4.66 (m, 1H), 4.28 (d, J=10.8 Hz, 1H), 3.94 (dd, J=6.6, 10.6 Hz, 1H), 2.73 (br t, J=7.3 Hz, 2H), 1.49 (s, 3H), 1.44 (s, 3H), 1.42 (s, 9H).

$^{19}$F-NMR (376 MHz, $CDCl_3$): δ −63.63 (br d, J=8.5 Hz, 3F), −66.08 (br d, J=8.5 Hz, 3F).

Step 6-1M and N

[Chemical Formula 224-12]

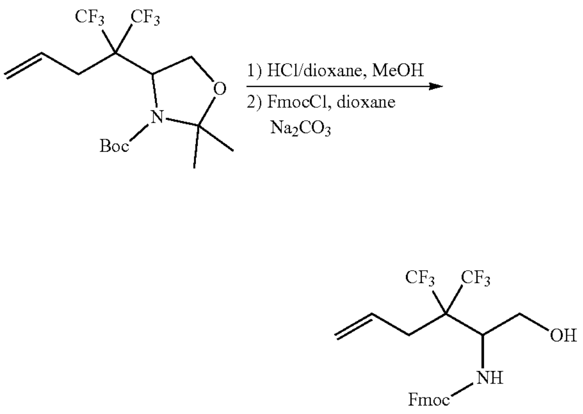

To a solution of tert-butyl 2, 2-dimethyl-4-(1, 1, 1-trifluoro-2-(trifluoromethyl) pent-4-en-2-yl) oxazolidine-3-carboxylate (400 mg, 1.02 mmol) in MeOH (5 mL) was added HCl/dioxane (4 M, 16 mL) and the mixture was kept stirring for 3 h at r.t. The solution was then concentrated under reduced pressure to give the crude product, which was used in next step directly.

To a solution of the crude product in 10% $Na_2CO_3$ aq. (10 mL) at 0° C. was slowly added a solution of 9H-fluoren-9-ylmethyl carbonochloridate (Fmoc-$C_1$) (521.7 mg, 2.0 mmol) in dioxane (10 mL) and the reaction mixture was stirred for 18 h at r.t. The reaction was diluted with ethyl acetate (20 mL) and $H_2O$ (20 mL), and the organic phase was concentrated to afford a crude oil. The residue was purified by flash silica gel chromatography (Eluent: ethyl acetate in petroleum ether from 0% to 70% gradient flowrate at 25 mL/min) to afford the product (360 mg, 75%).

$^1$H-NMR (400 MHz, $CDCl_3$): δ 7.68 (d, J=7.5 Hz, 2H), 7.53-7.45 (m, 2H), 7.36-7.29 (m, 2H), 7.27-7.19 (m, 2H), 6.03-5.60 (m, 1H), 5.25-5.13 (m, 2H), 5.07-4.97 (m, 1H), 4.45 (br dd, J=6.8, 10.7 Hz, 1H), 4.39-4.24 (m, 2H), 4.13 (br t, J=6.7 Hz, 1H), 3.89 (br dd, J=3.4, 11.7 Hz, 1H), 3.65-3.50 (m, 1H), 2.69-2.49 (m, 2H), 2.05-1.85 (br s, 1H).

$^{19}$F-NMR (376 MHz, $CDCl_3$): δ −64.64 (q, J=8.5 Hz, 3F), −65.33 (q, J=8.5 Hz, 3F).

MS (ESI): 496.2 $(M+Na)^+$, 474.2 $(M+H)^+$.

Step 6-10 and P

[Chemical Formula 224-13]

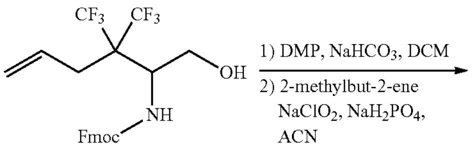

-continued

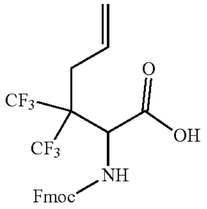

To a solution of (9H-fluoren-9-yl)methyl (1-hydroxy-3, 3-bis(trifluoromethyl) hex-5-en-2-yl) carbamate (360 mg, 0.76 mmol) in DCM (20 mL) was added Dess-Martin periodinane (806.3 mg, 1.90 mmol) and $NaHCO_3$ (575 mg, 6.8 mmol) successively. The mixture was stirred for 4 h at r.t. After addition of sat. $NaHCO_3$ aq. (20 mL) and sat. $Na_2S_2O_3$ aq. (20 mL) at 0° C., the mixture was stirred at room temperature for 10 minutes, and then extracted with DCM, washed by sat. NaCl aq., dried over anhydrous $Na_2SO_4$ and concentrated under reduced pressure to afford the crude product, which was quickly used in next step.

To a mixture of the crude product and MeCN (20 mL), was added dropwise 2-methylbut-2-ene (2.60 g, 37.1 mmol, 3.9 mL), $NaH_2PO_4$ (890.8 mg, 7.4 mmol) and sodium chlorite (201.5 mg, 2.2 mmol) in $H_2O$ (10 mL) at 0° C. and the mixture was stirred at r.t. for 1 h. The reaction was quenched with $Na_2SO_3$ (aq.) (5 mL) and 2M HCl to pH<3, then diluted with EtOAc. The organic phase was extracted, washed with brine, dried over $Na_2SO_4$, concentrated under reduced pressure to afford a crude oil. The crude was purified by Prep HPLC (column: Welch Xtimate C18 150*25 mm*5 μm; mobile phase: [water (TFA)-MeCN]; B %: 48%-78%, 10 min) and then separated by SFC (column: DAICEL CHIRALPAK IC (250 mm*30 mm, 10 mm); mobile phase: [0.1% $NH_3 \cdot H_2O$ IPA]; B %: 15%-15%, 4.8 min) to afford βDTFM4_1st_peak (80 mg, 44%, 2 steps) and βDTFM4_2nd_peak (92 mg, 50%, 2 steps). βDTFM4 (Racemate): $^1$H-NMR (400 MHz, $CDCl_3$) δ=7.79 (d, J=7.6 Hz, 2H), 7.59 (br dd, J=2.3, 6.9 Hz, 2H), 7.43 (t, J=7.4 Hz, 2H), 7.36-7.31 (m, 2H), 5.98-5.82 (m, 1H), 5.63 (br d, J=10.8 Hz, 1H), 5.49 (br d, J=16.8 Hz, 1H), 5.42 (br d, J=9.5 Hz, 1H), 5.12 (br d, J=11.0 Hz, 1H), 4.55-4.45 (m, 1H), 4.42-4.35 (m, 1H), 4.32-4.23 (m, 1H), 3.09-2.97 (m, 1H), 2.82 (br dd, J=5.8, 14.8 Hz, 1H).

$^{19}$F-NMR (376 MHz, $CDCl_3$) δ=−64.05 (q, J=8.5 Hz, 3F), −67.13 (q, J=8.5 Hz, 3F).

MS (ESI): 510.1 $(M+Na)^+$.

βDTFM4_1st_peak and βDTFM4_2nd_peak:

$^1$H-NMR (400 MHz, $CD_3OD$): δ 7.80 (d, J=7.5 Hz, 2H), 7.65 (br d, J=7.1 Hz, 2H), 7.39 (t, J=7.4 Hz, 2H), 7.30 (t, J=7.4 Hz, 2H), 6.00-5.87 (m, 1H), 5.42 (br d, J=16.8 Hz, 1H), 5.31 (br d, J=10.1 Hz, 1H), 4.94 (br s, 1H), 4.40 (dd, J=7.5, 10.4 Hz, 1H), 4.32 (dd, J=7.0, 10.5 Hz, 1H), 4.25 (t, J=7.3 Hz, 1H), 3.17 (dd, J=7.9, 14.5 Hz, 1H), 2.79 (br dd, J=6.8, 14.4 Hz, 1H). (Note: One proton was overlapped with water peak.)

$^{13}$C-NMR (100 MHz, $CD_3OD$): δ 169.28, 156.59, 143.70 (s, 2C), 141.15 (s, 2C), 129.30, 127.42 (s, 2C), 126.80 (s, 2C), 124.85 (s, 2C), 121.14, 128.36-120.28 (m, 2C), 119.53 (s, 2C), 67.14, 57.47-56.24 (m, 1C), 52.27, 46.86, 31.76.

$^{19}$F-NMR (376 MHz, $CD_3OD$): δ −65.31 (q, J=9.4 Hz, 3F), −68.00 (q, J=9.4 Hz, 3F)

MS (ESI): 510.1 $(M+Na)^+$.

Example 6-2: The Synthesis of(S)-βDTFM6 and (R)-βDTFM6

[Chemical Formula 225]

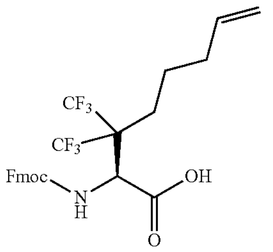

Step 6-2A to 6-2E: The Synthesis of tert-butyl 2, 2-dimethyl-4-(1, 1, 1-trifluoro-2-(trifluoromethyl) hept-6-en-2-yl) oxazolidine-3-carboxylate Step 6-2A

[Chemical Formula 225-2]

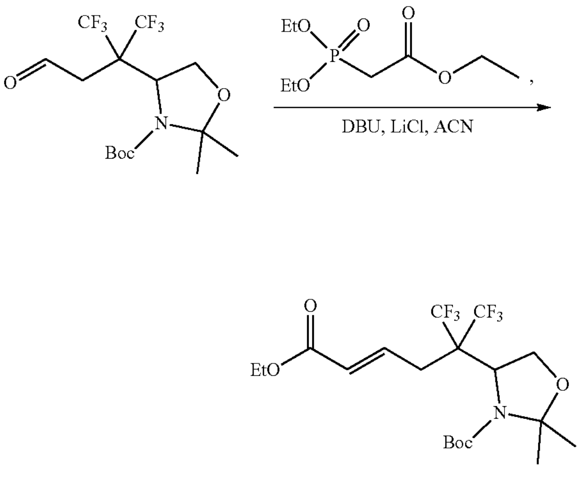

tert-Butyl 2, 2-dimethyl-4-[3-oxo-1, 1-bis(trifluoromethyl)propyl]oxazolidine-3-carboxylate (100 mg, 0.25 mmol) was dissolved in MeCN (3 mL). Ethyl 2-diethoxyphosphorylacetate (68.4 mg, 0.31 mmol, 0.061 mL), DBU (54.2 mg, 0.356 mmol, 0.054 mL) and LiCl (15.1 mg, 0.356 mmol) were added and the mixture was stirred for 3 h at r.t. The acetonitrile was removed under reduced pressure. The organic phase was extracted with ethyl acetate, washed with brine, dried over $Na_2SO_4$, and concentrated under reduced pressure to give a crude. The residue was purified by flash silica gel chromatography (Eluent: ethyl acetate in petroleum ether from 0% to 30% to afford the product (100 mg, 84.88% yield).

MS (ESI): 486.1 $(M+Na)^+$.

Step 6-2B, C, D and E

[Chemical Formula 225-3]

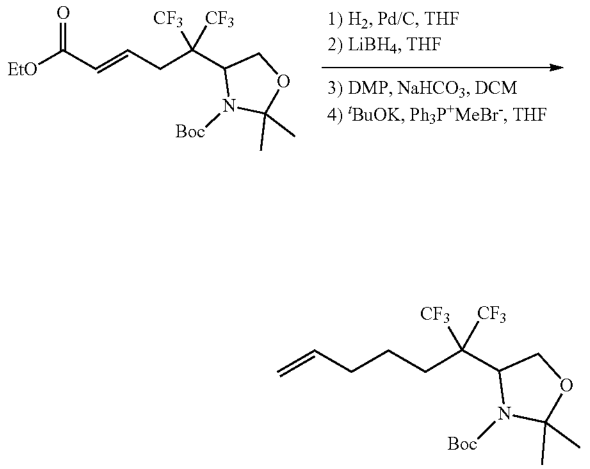

To a solution of tert-butyl (E)-4-(6-ethoxy-1, 1, 1-trifluoro-6-oxo-2-(trifluoromethyl) hex-4-en-2-yl)-2, 2-dimethyloxazolidine-3-carboxylate (116 mg, 0.25 mmol) in MeOH (8 mL) was added Pd/C (23.0 mg, 0.022 mmol, 10% wet) and kept in $H_2$ atmosphere (15 psi) for 3 h at r.t. The solution was filtered through a frit to afford the crude product, which was used in next step directly.

To a solution of the crude product in THF (3 mL) was added $LiBH_4$ (10.3 mg, 0.473 mmol) at r.t. and the reaction was kept stirring for 14 h. The reaction was quenched with diluted HCl (1M, 1 mL) at 0° C., extracted with DCM, dried over anhydrous sodium sulfate, and concentrated under reduced pressure to give the crude product (99 mg), which was used in next step directly.

To a solution of the crude product (99 mg) in DCM (6 mL) was added $NaHCO_3$ (180 mg, 2.1 mmol) and Dess-Martin periodinane (247.9 mg, 0.585 mmol). The mixture was stirred for 0.5 h. The reaction was quenched with sat. $NaHCO_3$ aq. (3 mL), extracted with DCM, and concentrated under reduced pressure to give the crude product (95 mg), which was used in next step directly.

TO THF (5 mL) was added methyl triphenyl phosphonium bromide (199.8 mg, 0.56 mmol) at 0° C. under $N_2$ atmosphere, and followed with tBuOK (1M in THF, 0.699 mL). The mixture was stirred at r.t. for 0.5 h, a THE solution (5 mL) of the crude product (95 mg) was added and the solution was further stirred for 2 h. The reaction was quenched with sat. $NH_4Cl$ aq. (5 mL) and extracted with DCM. Organic phase was dried over $Na_2SO_4$ and concentrated under reduced pressure to afford a crude oil. The residue was purified by flash silica gel chromatography (Eluent: ethyl acetate in petroleum ether from 0% to 70%) to afford the desired product (70 mg, 67% yield, 4 steps).

$^1H$-NMR (400 MHz, $CDCl_3$): δ 5.89-5.70 (m, 1H), 5.11-4.95 (m, 2H), 4.72 (br s, 1H), 4.34 (br d, J=10.4 Hz, 1H), 4.01 (dd, J=6.8, 10.5 Hz, 1H), 2.05 (q, J=6.8 Hz, 2H), 2.02-1.86 (m, 2H), 1.85-1.70 (m, 1H), 1.61 (m, 4H), 1.51 (br s, 3H), 1.48 (s, 9H).

$^{19}F$-NMR (376 MHz, $CDCl_3$): δ −63.94 (br d, J=8.5 Hz, 3F), −65.81 (br d, J=11.3 Hz, 3F).

Step 6-2F to 6-21: The Synthesis of 2-((((9H-fluoren-9-yl) methoxy) carbonyl)amino)-3, 3-bis(trifluoromethyl)oct-7-enoic acid (βDTFM6)

Step 6-2F and G

[Chemical Formula 225-4]

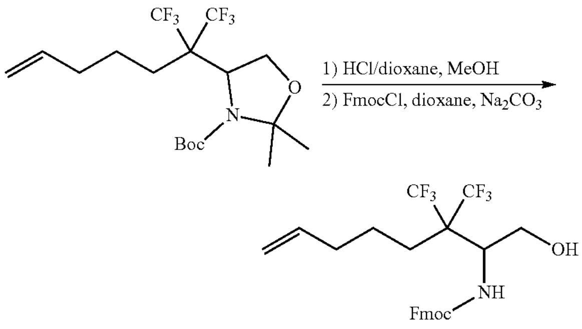

To a MeOH solution (1 mL) of tert-butyl 2, 2-dimethyl-4-(1, 1, 1-trifluoro-2-(trifluoromethyl) hept-6-en-2-yl) oxazolidine-3-carboxylate (65 mg, 0.155 mmol) was added HCl/dioxane (4 M, 2 mL), and the mixture was stirred for 3 h. The solvent was concentrated under reduced pressure to give the crude product (48 mg), which was used in next step directly.

To the crude product (48 mg) was added 10% $Na_2CO_3$ (3 mL) at 0° C. and was slowly added a solution of (9H-fluoren-9-yl)methyl carbonochloridate (Fmoc-Cl) (60 mg, 0.232 mmol) in dioxane (3 mL), and stirred for 3 h at r.t. The reaction was extracted with DCM, concentrated under reduced pressure, and was purified by flash silica gel chromatography (Eluent: ethyl acetate in petroleum ether from 0% to 80%) to afford the desired product (35 mg, 45% yield, 2 steps).

$^1$H-NMR (400 MHz, $CDCl_3$): δ 7.78 (d, J=7.5 Hz, 2H), 7.65-7.55 (m, 2H), 7.44-7.40 (m, 2H), 7.36-7.31 (m, 2H), 5.74 (m, 1H), 5.08-4.97 (m, 3H), 4.57-4.42 (m, 3H), 4.27-4.23 (m, 1H), 4.13-4.04 (m, 1H), 3.96 (br dd, J=2.8, 11.6 Hz, 1H), 3.72-3.63 (m, 1H), 2.12-2.06 (m, 2H), 1.92-1.82 (m, 2H), 1.75-1.62 (m, 2H).

$^{19}$F-NMR (376 MHz, $CDCl_3$): δ −64.80 (q, J=10.4 Hz, 1F), −65.09 (q, J=11.3 Hz, 1F).

MS (ESI): 502.1 $(M+H)^+$.

Step 6-2H and I

[Chemical Formula 225-5]

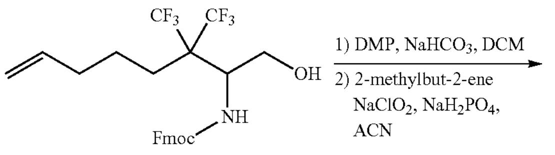

-continued

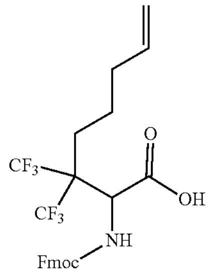

To a solution of (9H-fluoren-9-yl)methyl (1-hydroxy-3, 3-bis(trifluoromethyl) oct-7-en-2-yl) carbamate (35 mg, 0.0698 mmol) in DCM (4 mL) was added Dess-Martin periodinane (45 mg, 0.11 mmol) and $NaHCO_3$ (40 mg, 0.48 mmol) successively. The mixture was stirred for 4 h. After addition of sat. $NaHCO_3$ aq. (10 mL) at 0° C., the mixture was stirred at r.t. for 10 min, extracted with DCM, and concentrated under reduced pressure to afford the crude product (38 mg), which was quickly used in next step.

To a mixture of the crude product (38 mg) and MeCN (6 mL), 2-methylbut-2-ene (280.8 mg, 4.0 mmol, 0.42 mL), $NaH_2PO_4$ (96.1 mg, 0.80 mmol) and sodium chlorite (22 mg, 0.24 mmol) in $H_2O$ (3 mL) were added at 0° C. and the mixture was stirred at r.t. for 1 h. The reaction was quenched with $Na_2SO_3$ aq. (5 mL) and 2M HCl aq. to pH<3, then diluted with DCM. The organic phase was extracted and concentrated under reduced pressure to afford a crude oil. The crude was purified by silica gel column eluted by MeOH in DCM from 0 to 20% to afford the racemic βDTFM6 (35 mg, 97% yield, 2 steps).

$^1$H-NMR (400 MHz, $CD_3OD$): δ 7.80 (d, J=7.2 Hz, 2H), 7.66 (br d, J=6.8 Hz, 2H), 7.39 (t, J=7.6 Hz, 2H), 7.30 (t, J=7.6 Hz, 2H), 5.86-5.75 (m, 1H), 5.07-4.97 (m, 3H), 4.44-3.39 (m, 1H), 4.36-4.32 (m, 1H), 4.26 (t, J=7.2 Hz, 1H), 2.29-1.98 (m, 4H), 1.84-1.72 (m, 1H), 1.65-1.53 (m, 1H).

$^{19}$F-NMR (376 MHz, $CD_3OD$): δ −65.82 (m, 3F), −67.74 (m, 3F).

MS (ESI): 538.1 $(M+Na)^+$, 516.1 $(M+H)^+$.

Example 6-3: Separation of the enantiomers of βDTFM4 and βDTFM6, and determination of their absolute configuration Separation of the enantiomers by supercritical fluid chromatography (SFC) was performed, using SHIMADZU LC-30AD.

(Separation of the enantiomers of βDTFM4 by SFC)

[Chemical Formula 225-6]

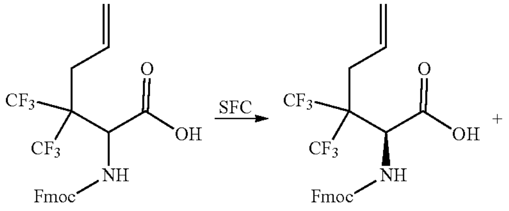

-continued

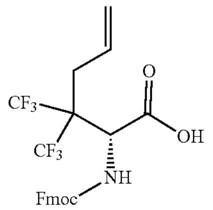

The crude product (350 mg) of racemic βDTFM4 was subjected to supercritical fluid chromatography (SFC) (column: DAICEL CHIRALPAK IC (250 mm*30 mm, 10 μm); mobile phase: [0.1% $NH_3 \cdot H_2O$ IPA]; B %: 15%-15%, 4.8 min) to afford βDTFM4_1st_peak (retention time: 1.21 min, 80 mg) and βDTFM4_2nd_peak (retention time: 1.33 min, 92 mg).

(Separation of the Enantiomers of βDTFM6 by SFC)

[Chemical Formula 225-7]

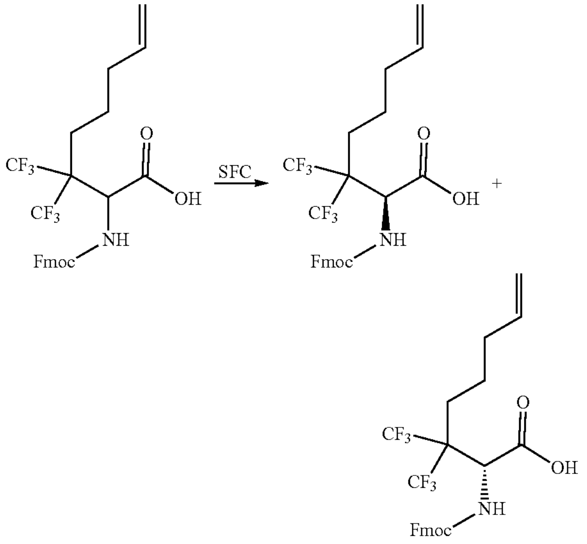

Racemic βDTFM6 (35 mg) was subjected to supercritical fluid chromatography (SFC) (column: DAICEL CHIRALPAK IC (250 mm*30 mm, 10 μm); mobile phase: [0.1% $NH_3 \cdot H_2O$ IPA]; B %: 30%-30%, Injection time: 6.0 min, Total time: 102 min) to separate the two enantiomers to obtain βDTFM6_1st_peak (retention time: 1.16 min) and βDTFM6_2nd_peak (retention time: 1.37 min). Each enantiomers were further subjected to preparative high-performance liquid chromatography (HPLC) (column: Welch Xtimate C18 150*25 mm*5 μm; mobile phase: [water (TFA)-MeCN]; B %: 57%-87%, 10 min) to afford βDTFM6_1st_peak (8 mg) and βDTFM6_2nd_peak (7 mg).

βDTFM6_1st_peak and βDTFM6_2nd_peak:

$^1$H-NMR (400 MHz, $CD_3OD$): δ 7.80 (d, J=7.2 Hz, 2H), 7.66 (br d, J=6.8 Hz, 2H), 7.39 (t, J=7.6 Hz, 2H), 7.30 (t, J=7.6 Hz, 2H), 5.86-5.75 (m, 1H), 5.07-4.97 (m, 3H), 4.44-3.39 (m, 1H), 4.36-4.32 (m, 1H), 4.32-4.22 (m, 1H), 4.32-4.22 (m, 1H). 07-4.97 (m, 3H), 4.44-3.39 (m, 1H), 4.36-4.32 (m, 1H), 4.32-4.22 (m, 1H), 2.29-1.9 8 (m, 4H), 1.84-1.72 (m, 1H), 1.65-1.53 (m, 1H). $^{19}$F-NMR (376 MHz, $CD_3OD$): δ −65.82 (m, 3F), −67.74 (m, 3F).

MS (ESI): 538.1 $(M+Na)^+$.

(Determination of the absolute configuration of βDTFM4 and βDTFM6 by VCD)

The experimental vibrational circular dichroism (VCD) spectra were measured by Biotools ChiralIR-2X spectrometer (BaF2 cell, Resolution: 4 $cm^{-1}$, Frequency range: 3000-800 $cm^{-1}$, PEM calibrated at 1400 $cm^{-1}$) using a sample (10 mg) dissolved in dimethyl sulfoxide (DMSO) (200 μl).

The theoretical VCD spectra were calculated by Gaussian16. The conformation was generated by GMMX calculation (Force field: MMFF94), and the geometry optimization and theoretical VCD spectra were calculated by density functional theory (DFT), B3LYP/6-311G (d, p), in DMSO. The results for βDTFM4_1st_peak and βDTFM4_2nd_peak were shown in FIG. 4.

The absolute configuration of βDTFM4_1st_peak and βDTFM4_2nd_peak was described below, and likewise the absolute configuration of βDTFM6 was determined in the same method. By comparing the experimental VCD spectra with the theoretical VCD spectra, βDTFM4_1st_peak was determined to be S isomer and βDTFM4_2nd_peak was determined to be R isomer.

In addition, in this example, the $CF_3$ derivatives with the bridge lengths from 3 to 6 carbons shown below can be synthesized in the same way.

[Chemical Formula 225-8]

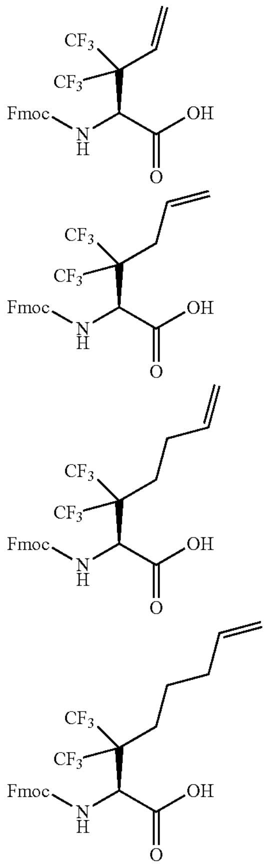

Example 7

The following amino acids are synthesized by the methods described in the examples shown above or in the literature elsewhere in the present specification.

The another synthetic scheme of an artificial amino acid (in the present specification, its entirety is described as artificial amino acid X) is described below.

[Chemical Formula 225-9]

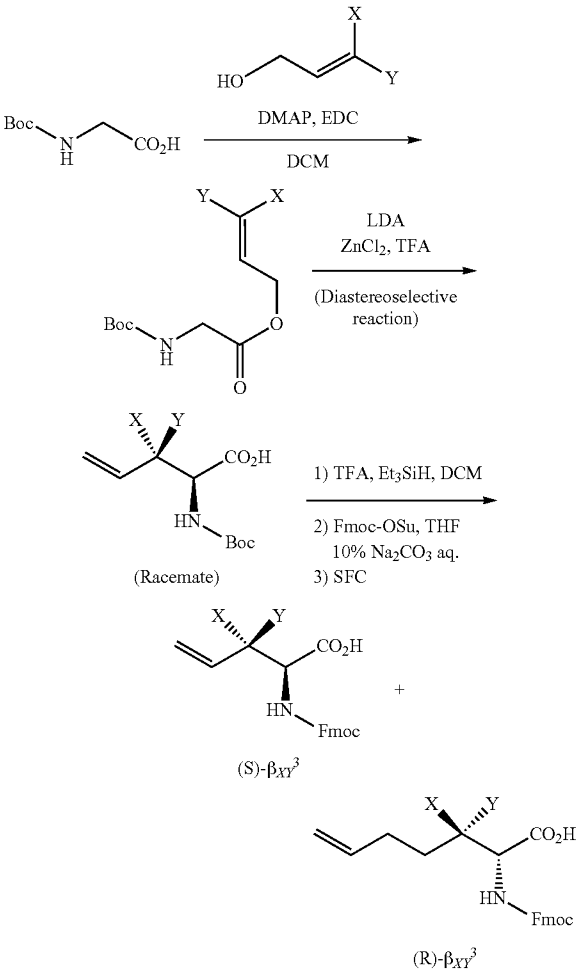

[Chemical Formula 225-10]

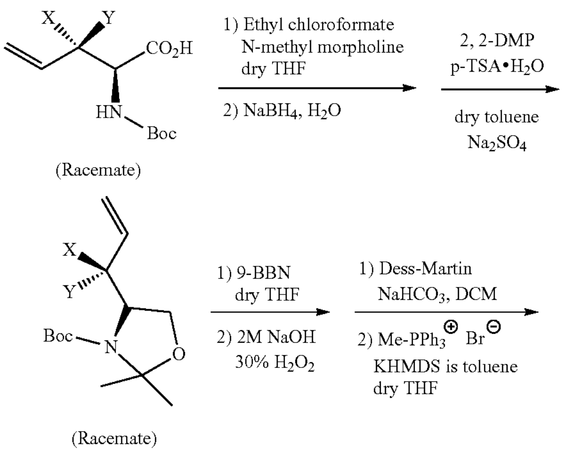

-continued

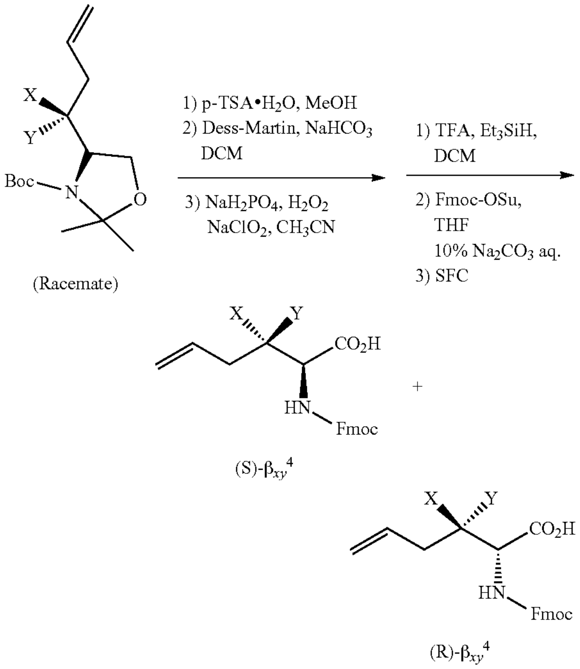

(Result)

Artificial amino acids can be produced by implementing the above scheme. Here, X and Y can be any substituents in the β-position of the bridge peptide of the present disclosure.

Another Example

In the present disclosure, artificial amino acids can also be synthesized by the following scheme.

[Chemical Formula 225-11]

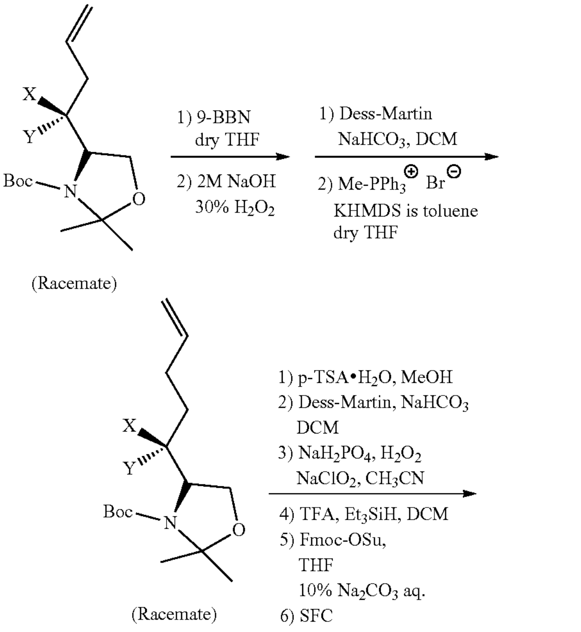

-continued

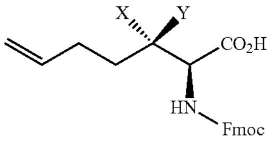

+

(S)-$\beta_{XY}^5$

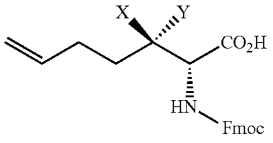

(R)-$\beta_{XY}^5$

[Chemical Formula 225-12]

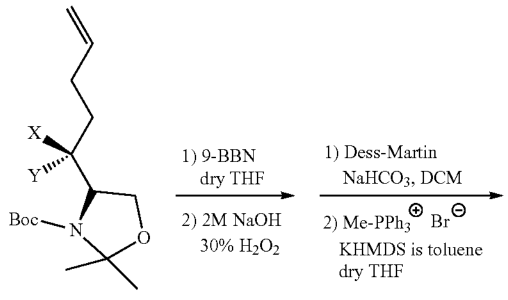

(Racemate)

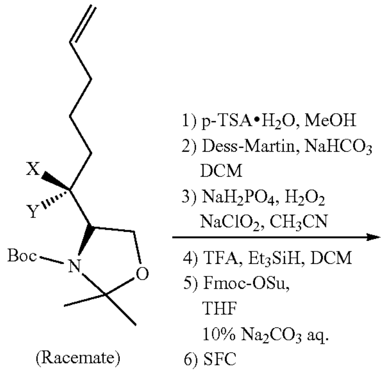

(Racemate)

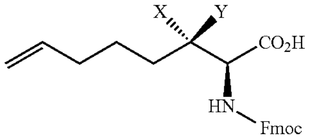

+

(S)-$\beta_{XY}^6$

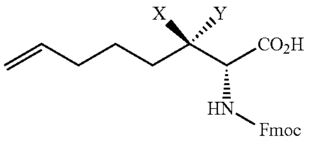

(R)-$\beta_{XY}^6$ (Result)

Artificial amino acids can be produced by implementing the above scheme. Here, X and Y can be any substituents in the β-position of the bridge peptide of the present disclosure.

The artificial amino acid X is shown below.

[Chemical Formula 226]

(S)-βDM3

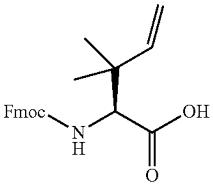

(S)-βDM4-8

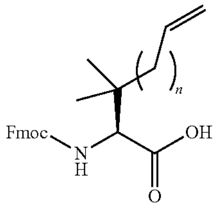

(n = 1-5)

(R)-βDM3

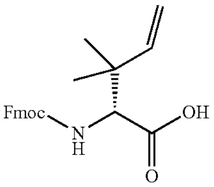

(R)-βDM4-8

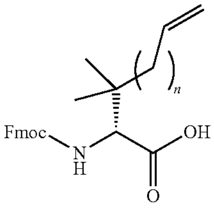

(n = 1-5)

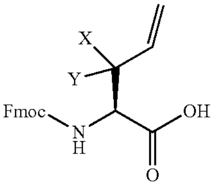

X = $CH_2F$, $CHF_2$, $CF_3$
Y = $CH_2F$, $CHF_2$, $CF_3$

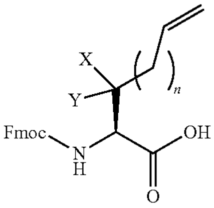

(n = 1-5)

-continued
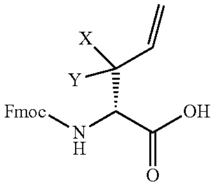
X = $CH_2F$, $CHF_2$, $CF_3$
Y = $CH_2F$, $CHF_2$, $CF_3$
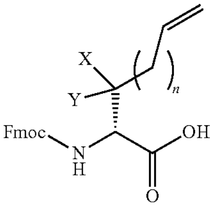
(n = 1-5)
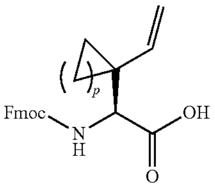
p = 1-10
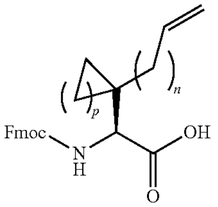
p = 1-10
(n = 1-5)
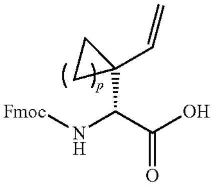
p = 1-10
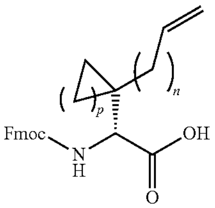
p = 1-10
(n = 1-5)
[Chemical Formula 227]
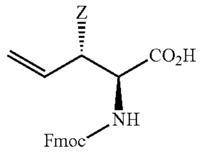
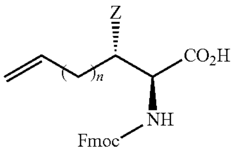
(n = 1-5)
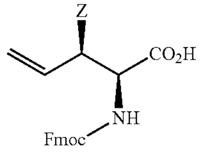
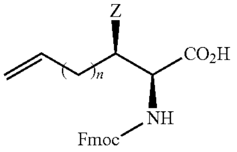
(n = 1-5)
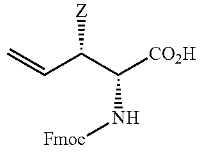
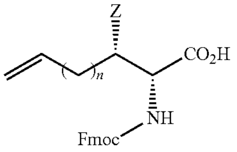
(n = 1-5)
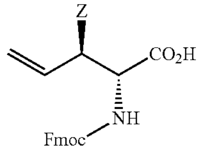
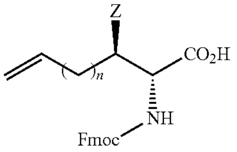
(n = 1-5)
Z = Me, $CH_2F$, $CHF_2$, $CF_3$, $^t$Bu,
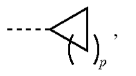
p = 1-10
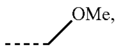
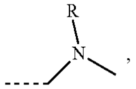
R = Me or Boc
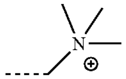
[Chemical Formula 228]
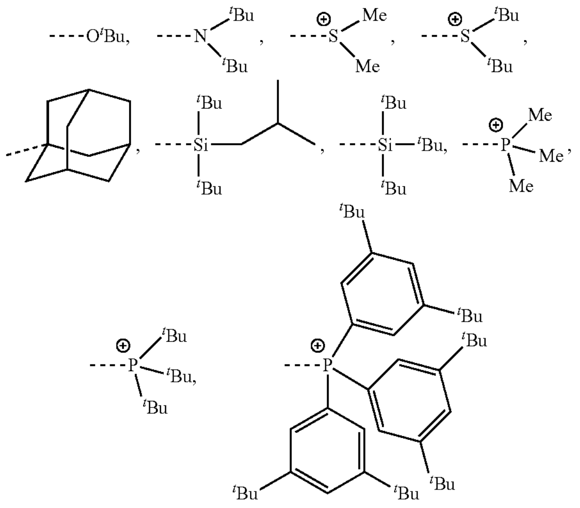

[Chemical Formula 229]
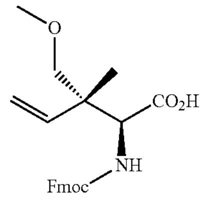
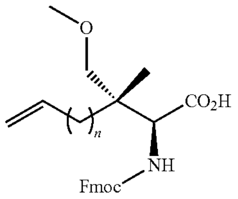
(n = 1-5)
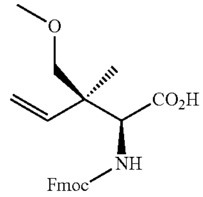
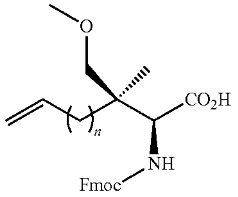
(n = 1-5)
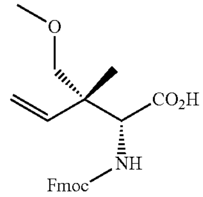
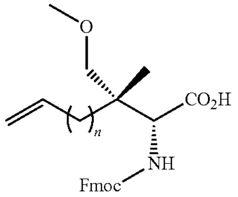
(n = 1-5)
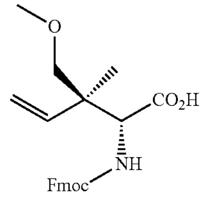
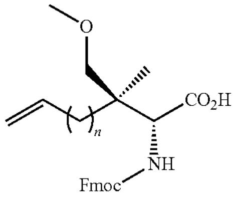
(n = 1-5)
[Chemical Formula 230]
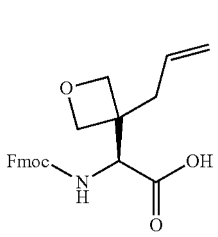
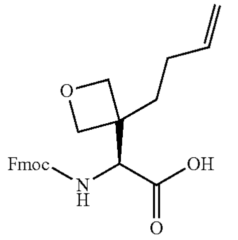
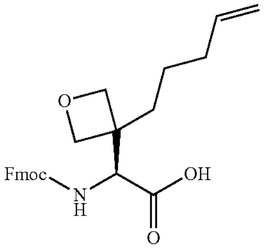
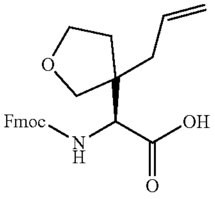
-continued
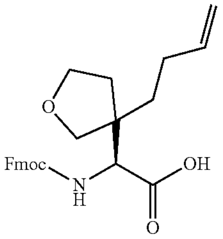
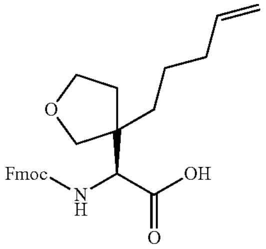
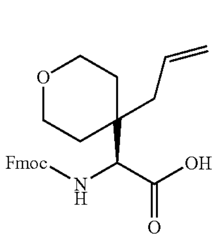
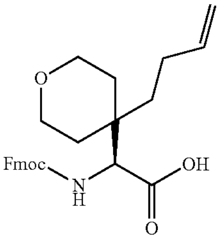
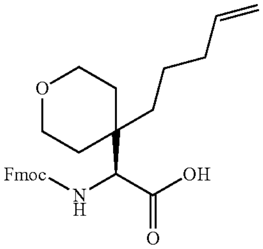
[Chemical Formula 231]
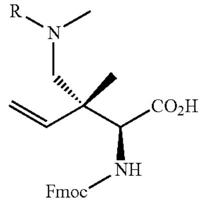
R = Me or Boc
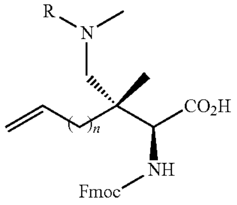
(n = 1-5)
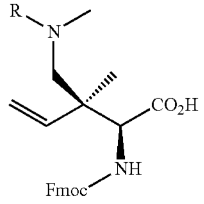
R = Me or Boc
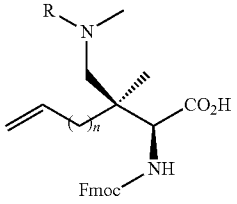
(n = 1-5)
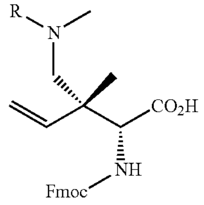
R = Me or Boc
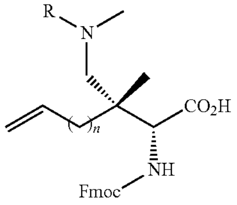
(n = 1-5)

-continued
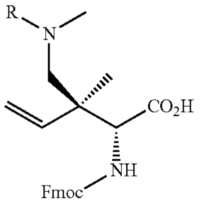
R = Me or Boc
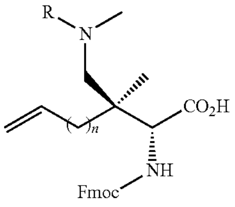
(n = 1-5)
[Chemical Formula 232]
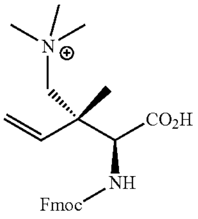
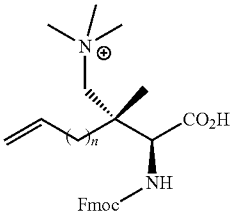
(n = 1-5)
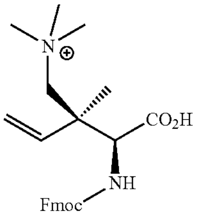
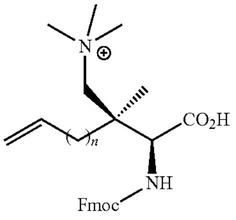
(n = 1-5)
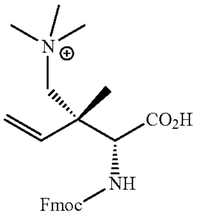
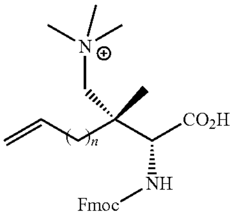
(n = 1-5)
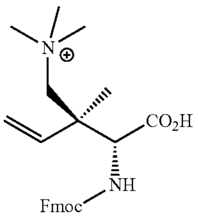
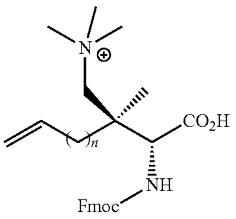
(n = 1-5)
[Chemical Formula 233]
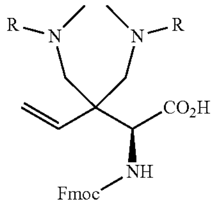
R = Me or Boc
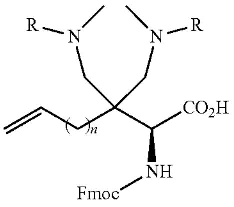
(n = 1-5)
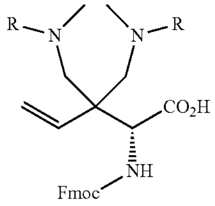
R = Me or Boc
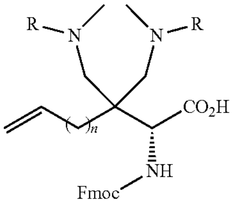
(n = 1-5)
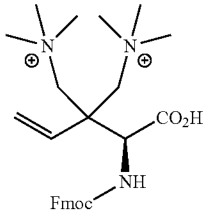
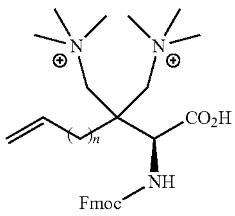
(n = 1-5)
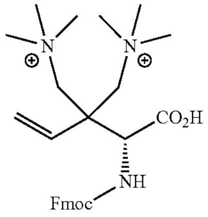
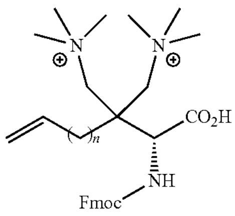
(n = 1-5)
[Chemical Formula 234]
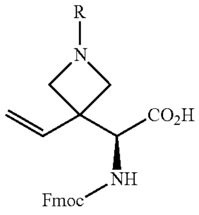
R = Me or Boc
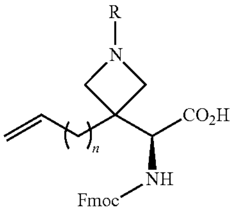
(n = 1-5)
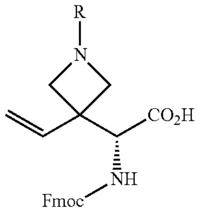
R = Me or Boc
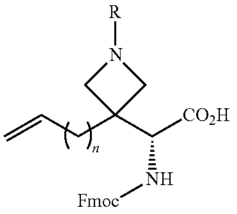
(n = 1-5)

-continued
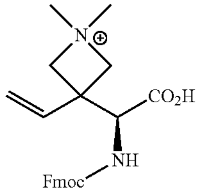
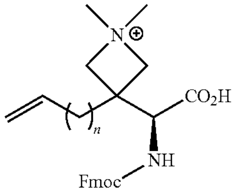
(n = 1-5)
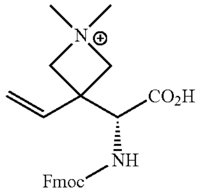
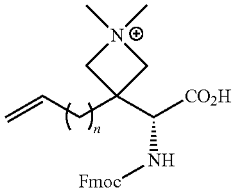
(n = 1-5)
[Chemical Formula 235]
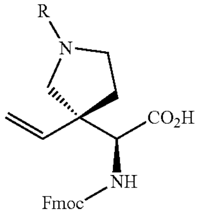
R = Me or Boc
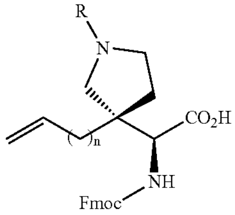
(n = 1 - 5)
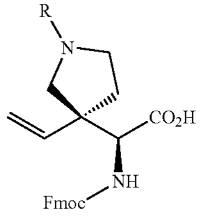
R = Me or Boc
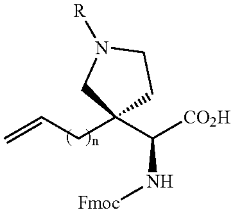
(n = 1 - 5)
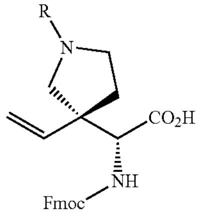
R = Me or Boc
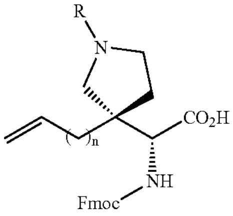
(n = 1 - 5)
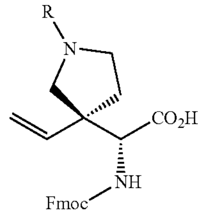
R = Me or Boc
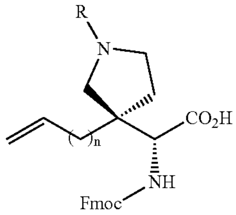
(n = 1 - 5)
[Chemical Formula 236]
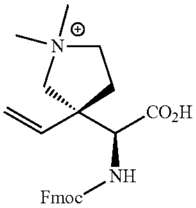
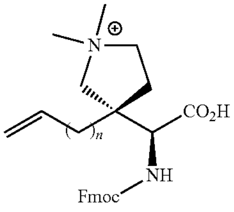
(n = 1-5)
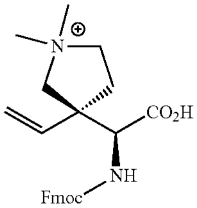
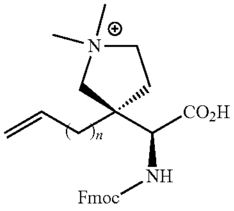
(n = 1-5)
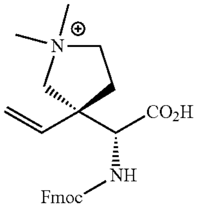
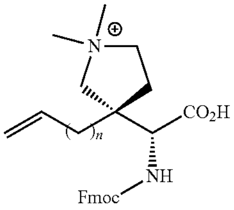
(n = 1-5)
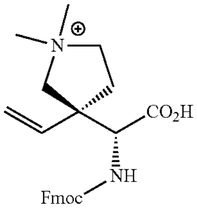

-continued
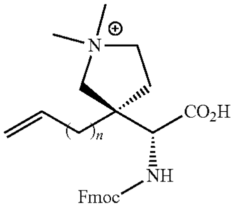
(n = 1-5)
[Chemical Formula 237]
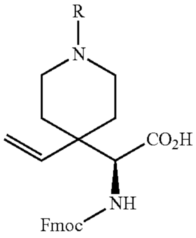
R = Me or Boc
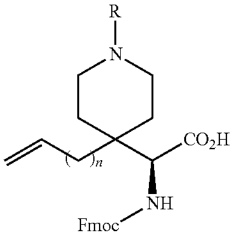
(n = 1-5)
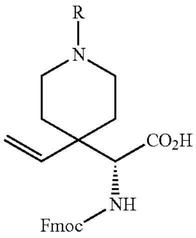
R = Me or Boc
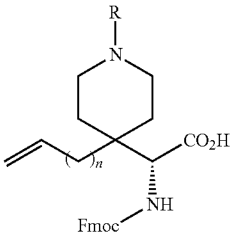
(n = 1-5)
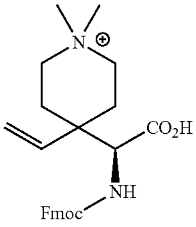
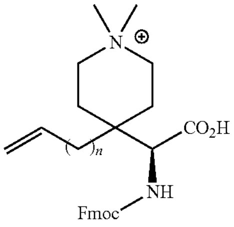
(n = 1-5)
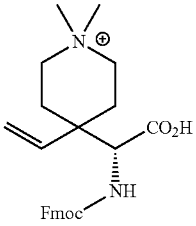
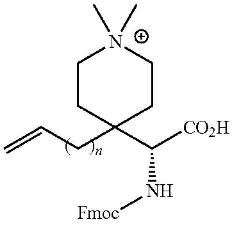
(n = 1-5)
[Chemical Formula 238]
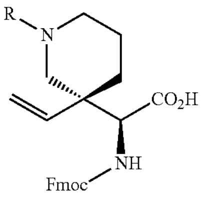
R = Me or Boc
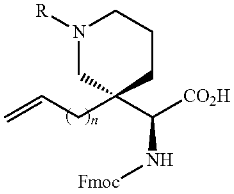
(n = 1-5)
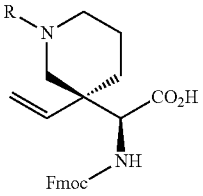
R = Me or Boc
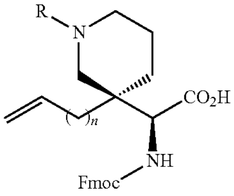
(n = 1-5)
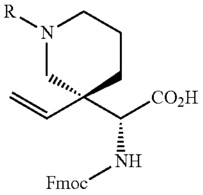
R = Me or Boc
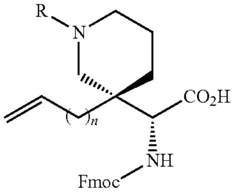
(n = 1-5)
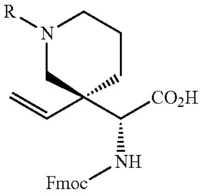
R = Me or Boc
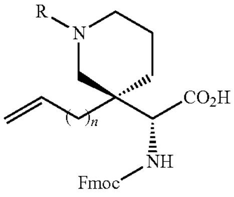
(n = 1-5)
[Chemical Formula 239]
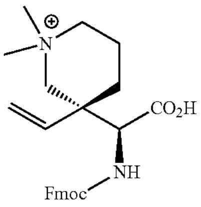
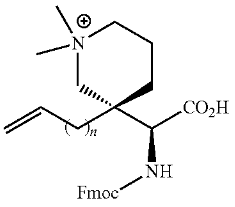
(n = 1-5)
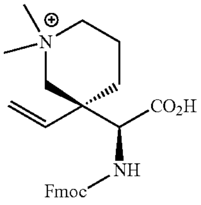
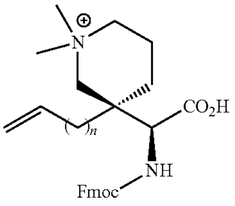
(n = 1-5)

-continued
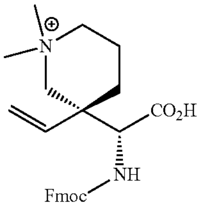
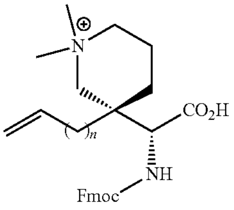
(n = 1-5)
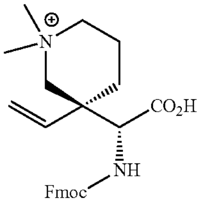
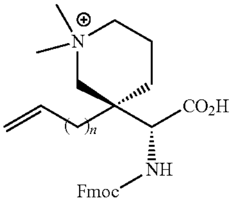
(n = 1-5)
[Chemical Formula 240]
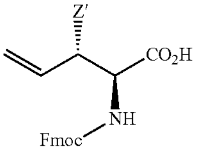
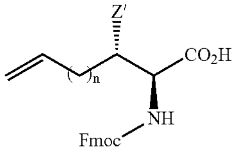
(n = 1-5)
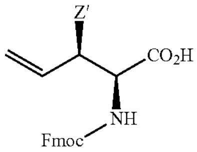
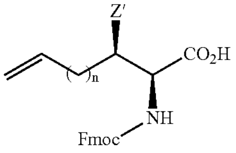
(n = 1-5)
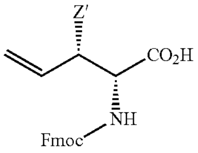
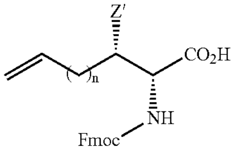
(n = 1-5)
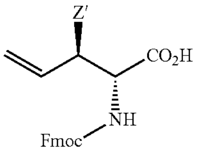
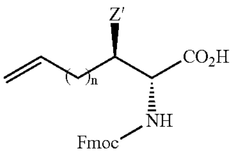
(n = 1-5)
Z' = 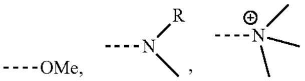
R = Me or Boc
[Chemical Formula 241]
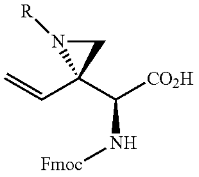
R = Me or Boc
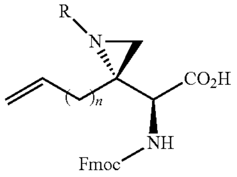
(n = 1-5)
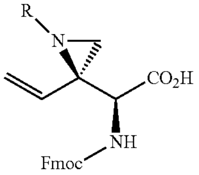
R = Me or Boc
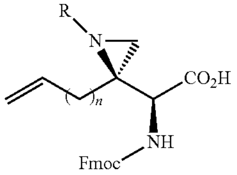
(n = 1-5)
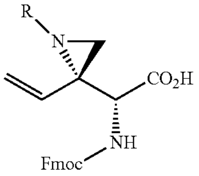
R = Me or Boc
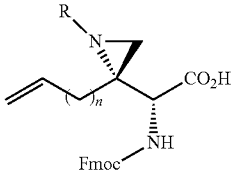
(n = 1-5)
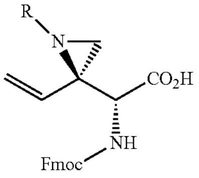
R = Me or Boc
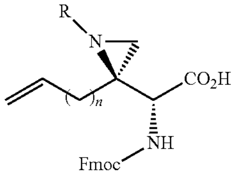
(n = 1-5)
[Chemical Formula 242]
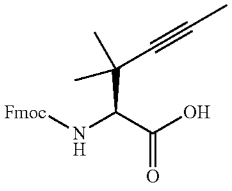
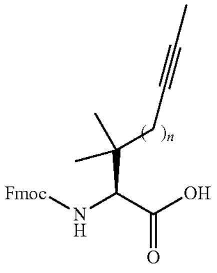
(n = 1 - 5)
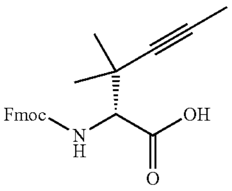
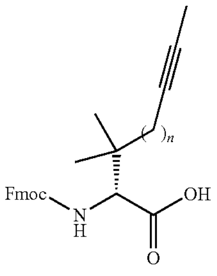
(n = 1 - 5)

-continued
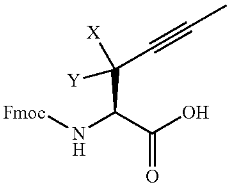
X = $CH_2F$, $CHF_2$, $CF_3$
Y = $CH_2F$, $CHF_2$, $CF_3$
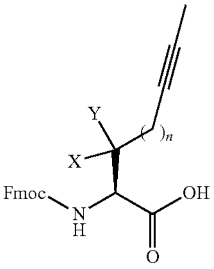
(n = 1 - 5)
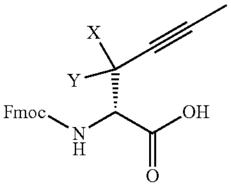
X = $CH_2F$, $CHF_2$, $CF_3$
Y = $CH_2F$, $CHF_2$, $CF_3$
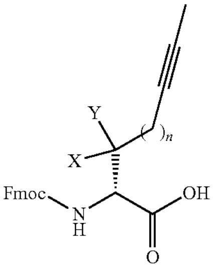
(n = 1 - 5)
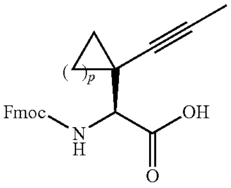
p = 1 - 10
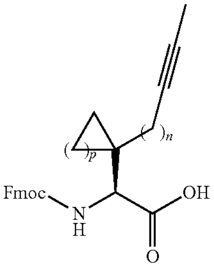
p = 1 - 10
(n = 1 - 5)
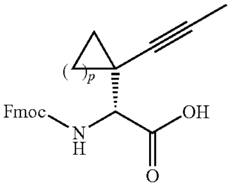
p = 1 - 10
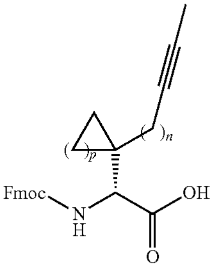
p = 1 - 10
(n = 1 - 5)
[Chemical Formula 243]
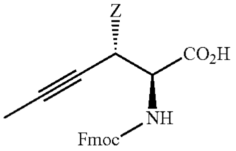
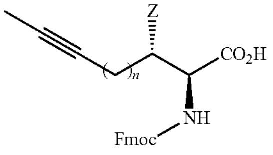
(n = 1-5)
-continued
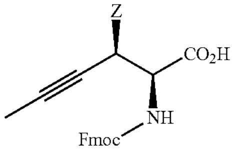
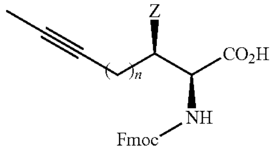
(n = 1-5)
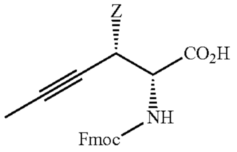
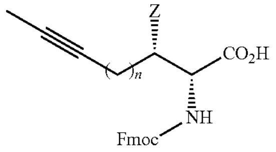
(n = 1-5)
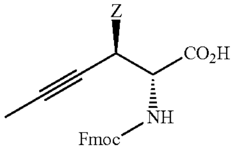
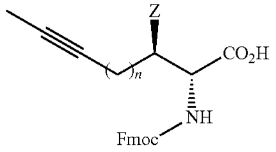
(n = 1-5)
Z = Me, $CH_2F$, $CHF_2$, $CF_3$, ${}^tBu$, 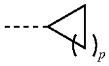,
p = 1-10
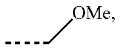 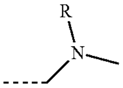, 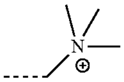
R = Me or Boc
[Chemical Formula 244]
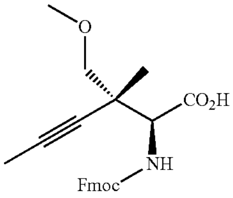
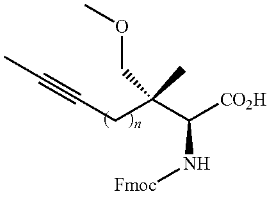
(n = 1-5)
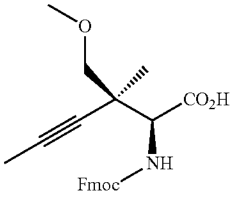
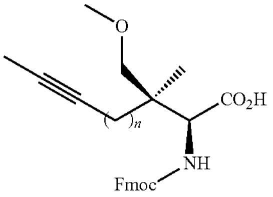
(n = 1-5)
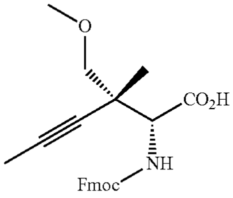
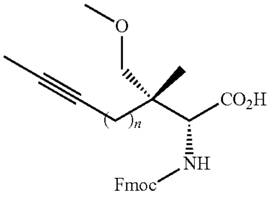
(n = 1-5)

-continued
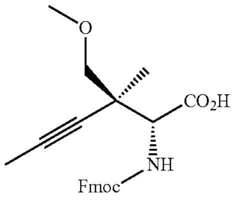
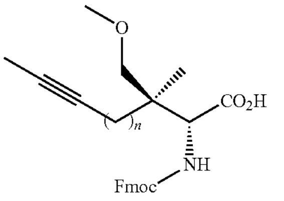
(n = 1-5)
[Chemical Formula 245]
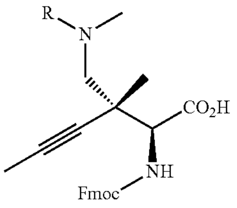
R = Me or Boc
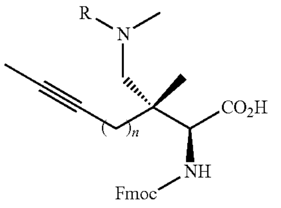
(n = 1-5)
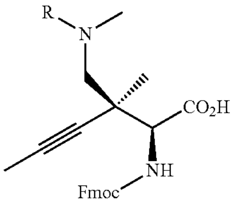
R = Me or Boc
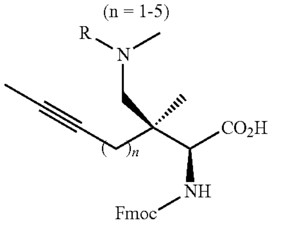
(n = 1-5)
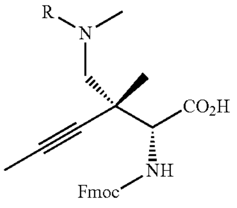
R = Me or Boc
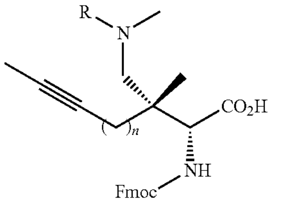
(n = 1-5)
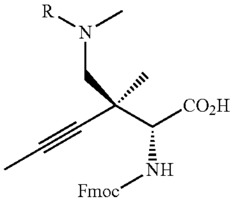
R = Me or Boc
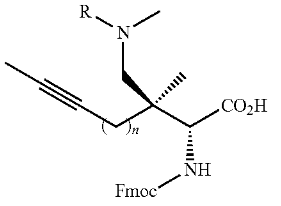
(n = 1-5)
[Chemical Formula 246]
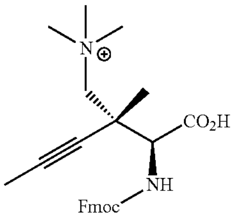
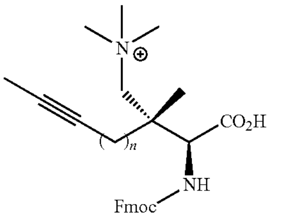
(n = 1-5)
-continued
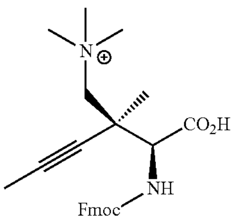
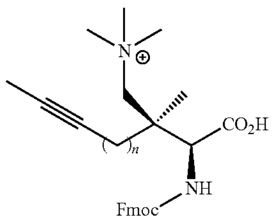
(n = 1-5)
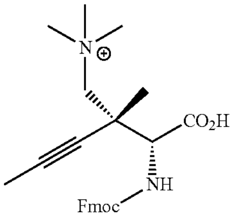
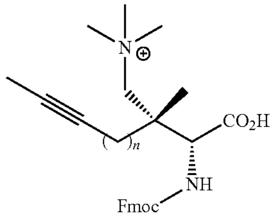
(n = 1-5)
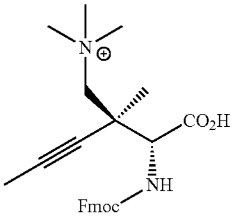
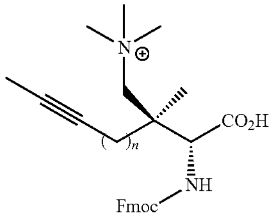
(n = 1-5)
[Chemical Formula 247]
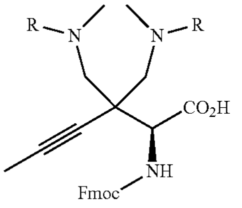
R = Me or Boc
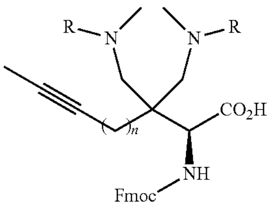
(n = 1-5)
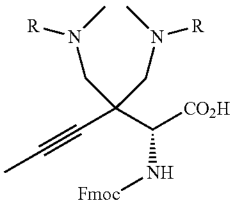
R = Me or Boc
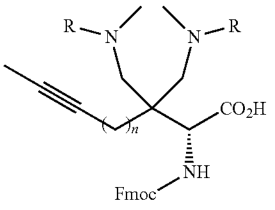
(n = 1-5)
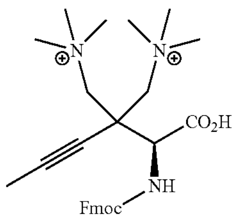
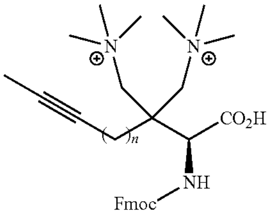
(n = 1-5)

-continued
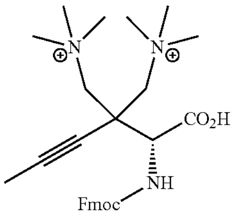
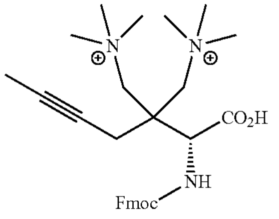
(n = 1-5)
[Chemical Formula 248]
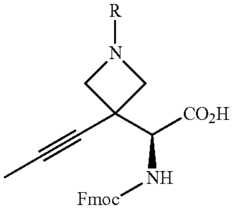
R = Me or Boc
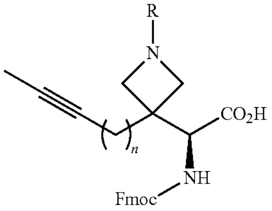
(n = 1-5)
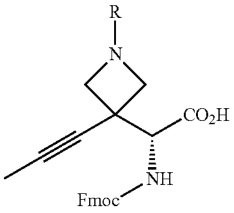
R = Me or Boc
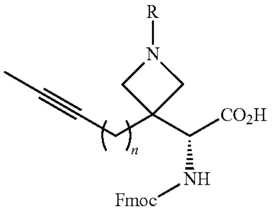
(n = 1-5)
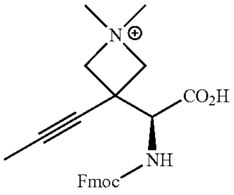
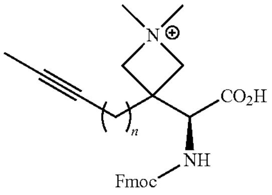
(n = 1-5)
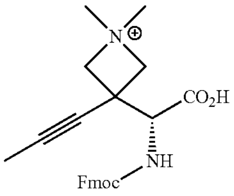
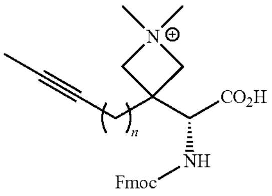
(n = 1-5)
[Chemical Formula 249]
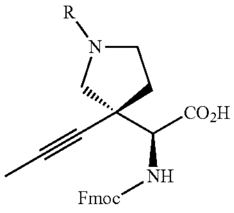
R = Me or Boc
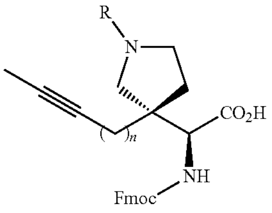
(n = 1-5)
-continued
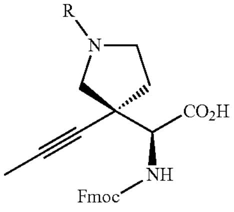
R = Me or Boc
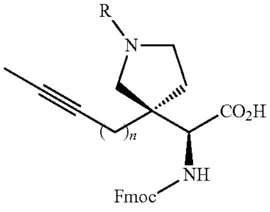
(n = 1-5)
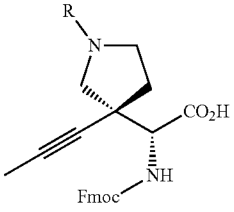
R = Me or Boc
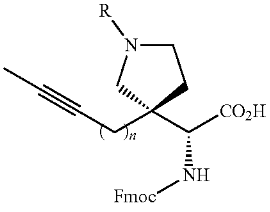
(n = 1-5)
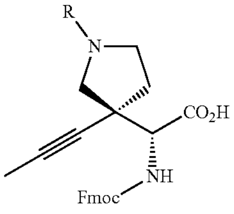
R = Me or Boc
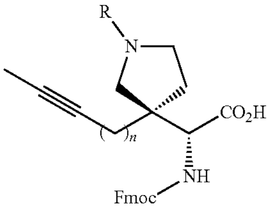
(n = 1-5)
[Chemical Formula 250]
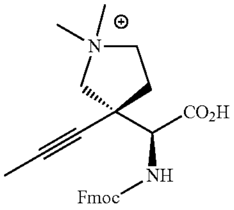
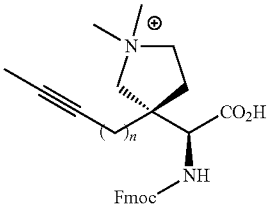
(n = 1-5)
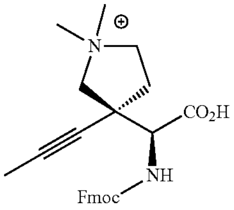
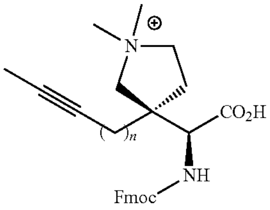
(n = 1-5)
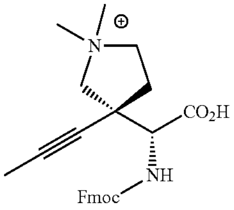
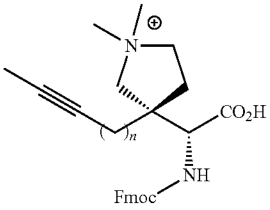
(n = 1-5)

-continued
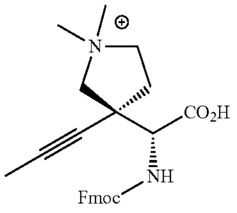
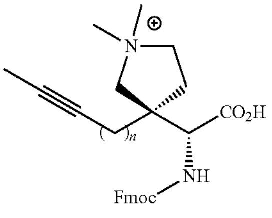
(n = 1-5)
[Chemical Formula 251]
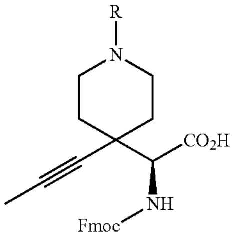
R = Me or Boc
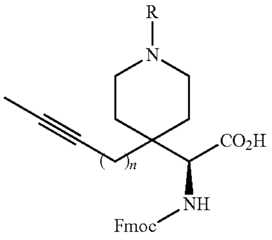
(n = 1-5)
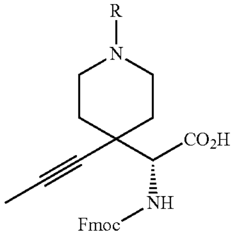
R = Me or Boc
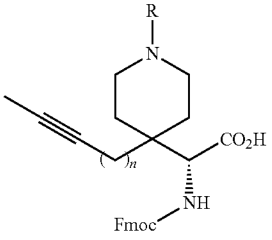
(n = 1-5)
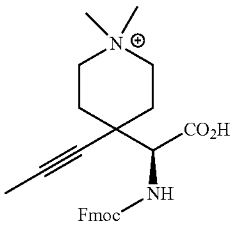
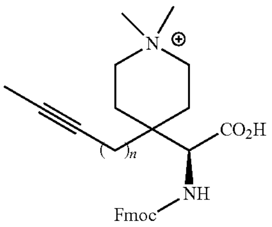
(n = 1-5)
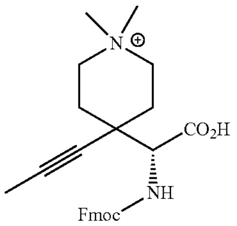
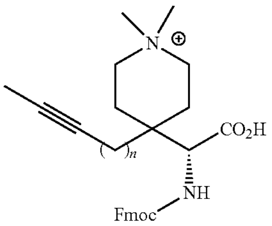
(n = 1-5)
[Chemical Formula 252]
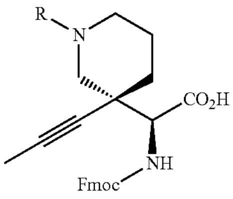
R = Me or Boc
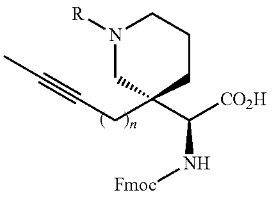
(n = 1-5)
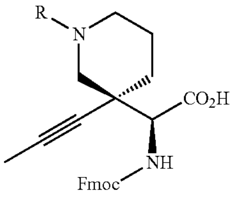
R = Me or Boc
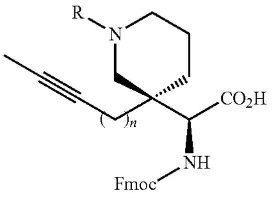
(n = 1-5)
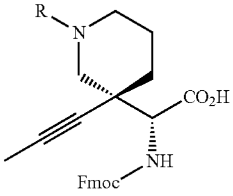
R = Me or Boc
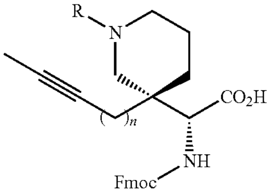
(n = 1-5)
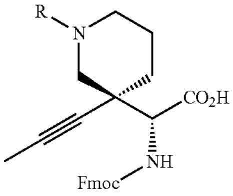
R = Me or Boc
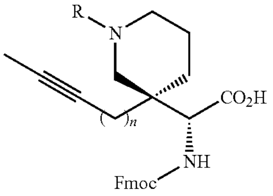
(n = 1-5)
[Chemical Formula 253]
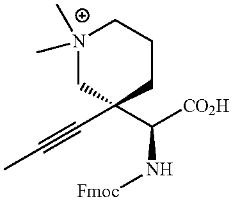
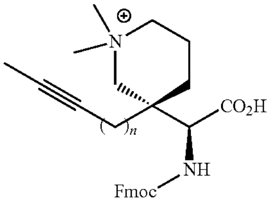
(n = 1-5)
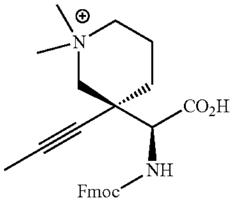
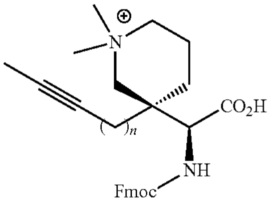
(n = 1-5)

-continued
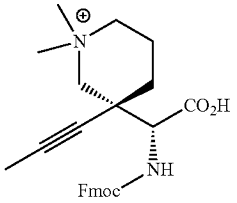
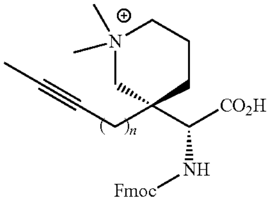
(n = 1-5)
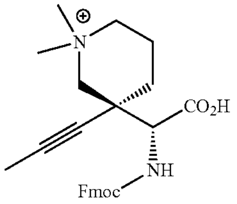
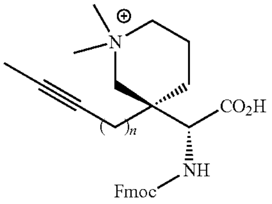
(n = 1-5)
[Chemical Formula 254]
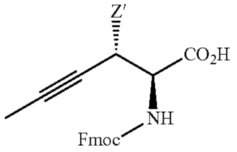
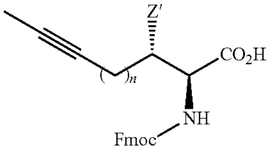
(n = 1-5)
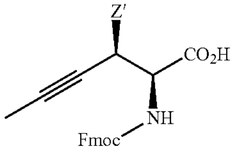
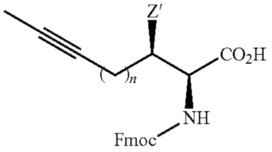
(n = 1-5)
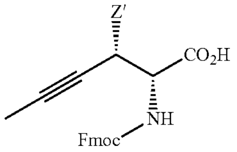
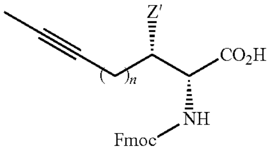
(n = 1-5)
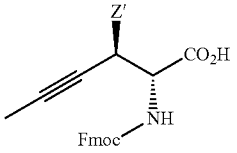
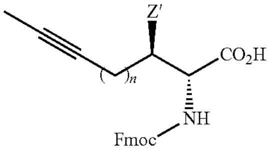
(n = 1-5)
Z′ =
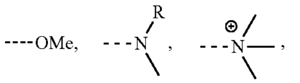
R = Me or Boc
[Chemical Formula 255]
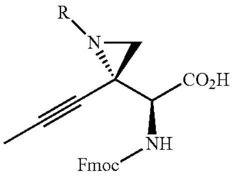
R = Me or Boc
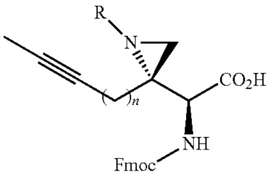
(n = 1-5)
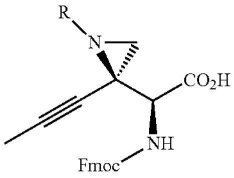
R = Me or Boc
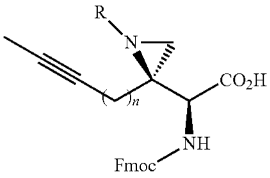
(n = 1-5)
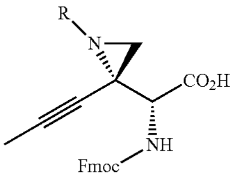
R = Me or Boc
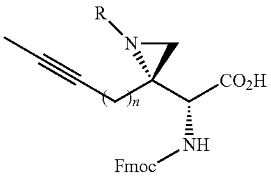
(n = 1-5)
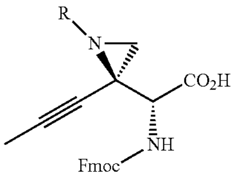
R = Me or Boc
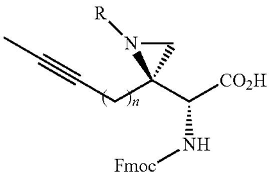
(n = 1-5)
[Chemical Formula 256]
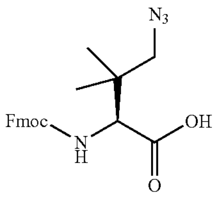
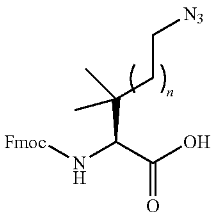
(n = 1-5)
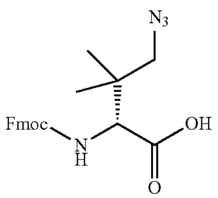
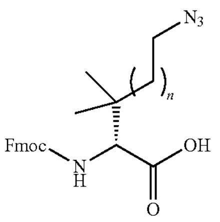
(n = 1-5)

-continued
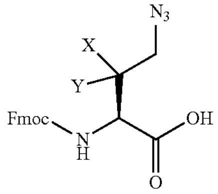
X = $CH_2F$, $CHF_2$, $CF_3$
Y = $CH_2F$, $CHF_2$, $CF_3$
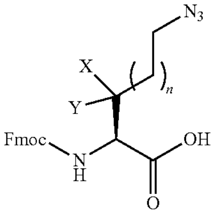
(n = 1-5)
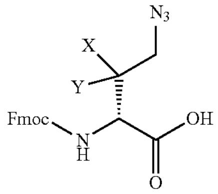
X = $CH_2F$, $CHF_2$, $CF_3$
Y = $CH_2F$, $CHF_2$, $CF_3$
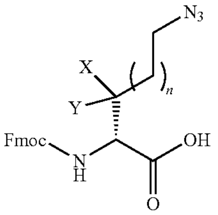
(n = 1-5)
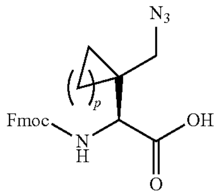
p = 1-10
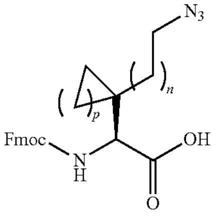
p = 1-10
(n = 1-5)
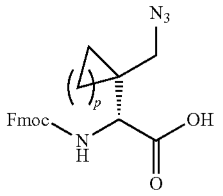
p = 1-10
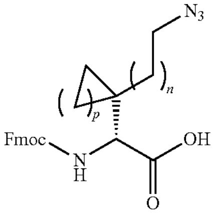
p = 1-10
(n = 1-5)
[Chemical Formula 257]
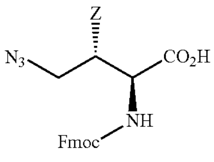
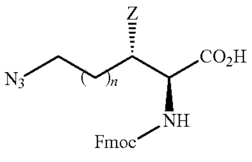
(n = 1-5)
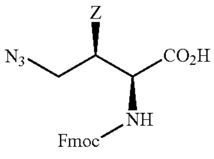
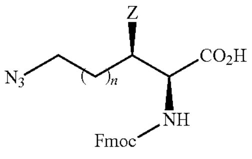
(n = 1-5)
-continued
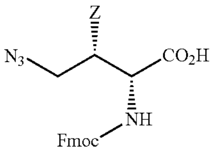
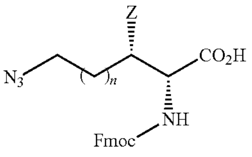
(n = 1-5)
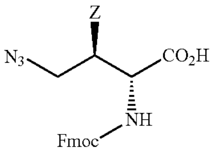
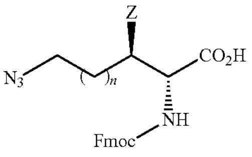
(n = 1-5)
Z = Me, $CH_2F$, $CHF_2$, $CF_3$, ${}^tBu$, 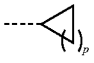, 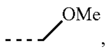,
p = 1-10
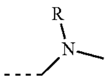, 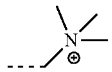,
R = Me or Boc
[Chemical Formula 258]
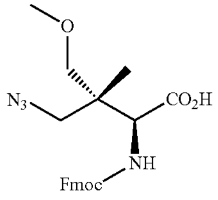
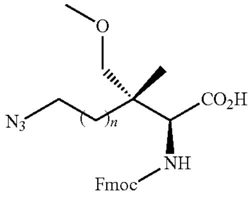
(n = 1-5)
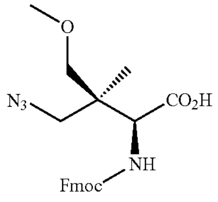
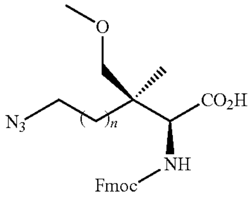
(n = 1-5)
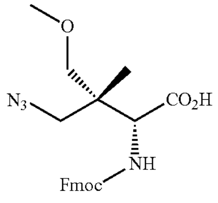
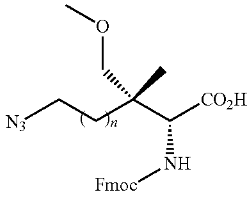
(n = 1-5)
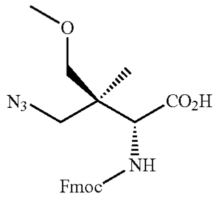
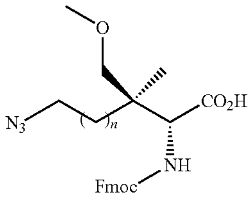
(n = 1-5)

[Chemical Formula 259]
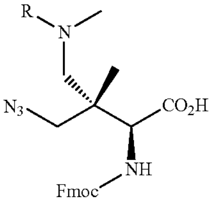
R = Me or Boc
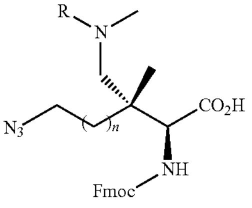
(n = 1-5)
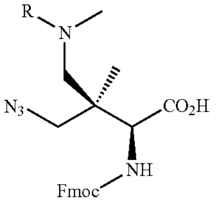
R = Me or Boc
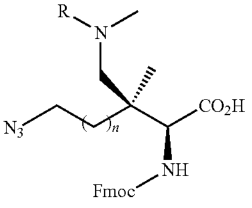
(n = 1-5)
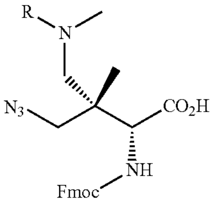
R = Me or Boc
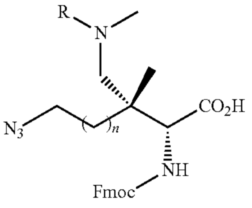
(n = 1-5)
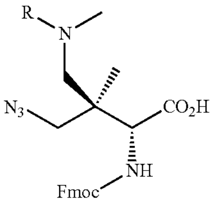
R = Me or Boc
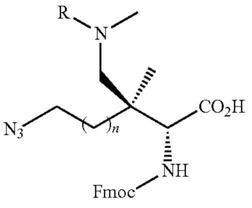
(n = 1-5)
[Chemical Formula 260]
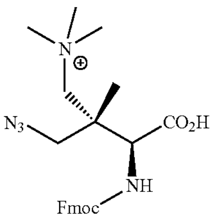
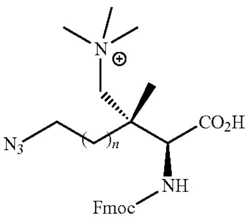
(n = 1-5)
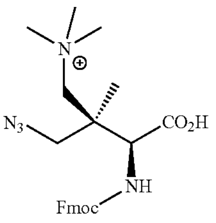
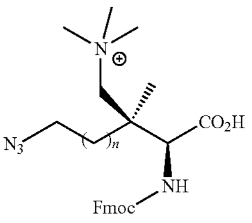
(n = 1-5)
-continued
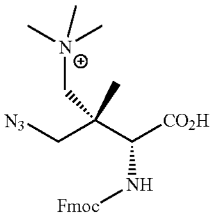
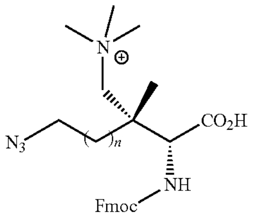
(n = 1-5)
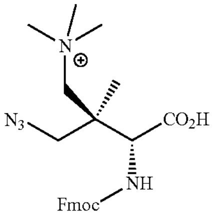
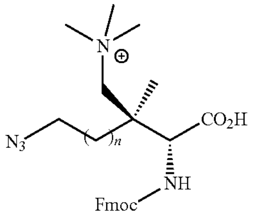
(n = 1-5)
[Chemical Formula 261]
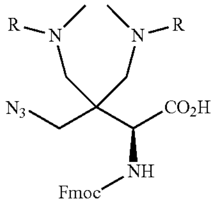
R = Me or Boc
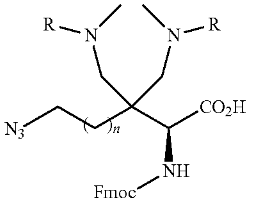
(n = 1-5)
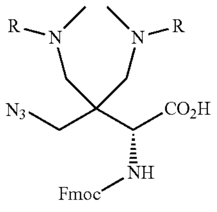
R = Me or Boc
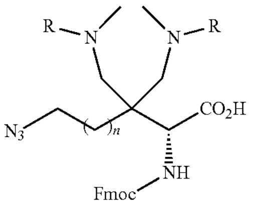
(n = 1-5)
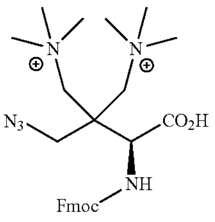
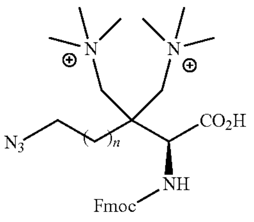
(n = 1-5)
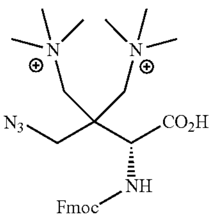
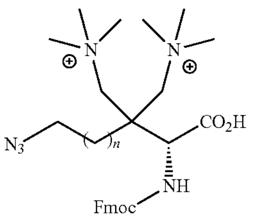
(n = 1-5)

[Chemical Formula 262]
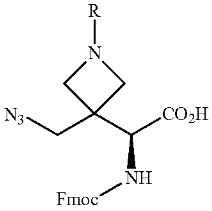
R = Me or Boc
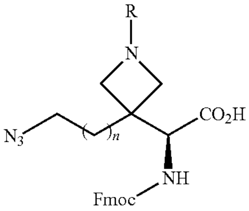
(n = 1-5)
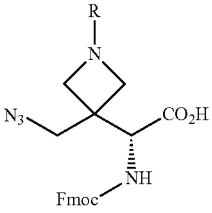
R = Me or Boc
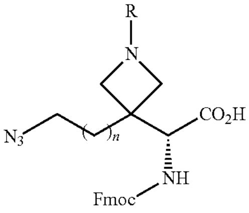
(n = 1-5)
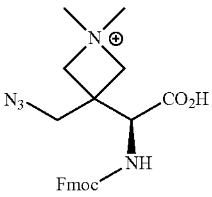
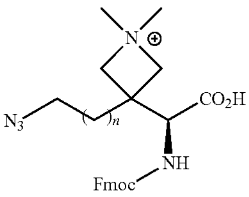
(n = 1-5)
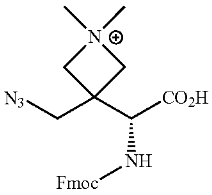
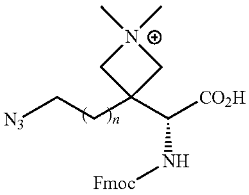
(n = 1-5)
[Chemical Formula 263]
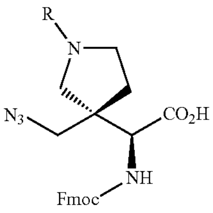
R = Me or Boc
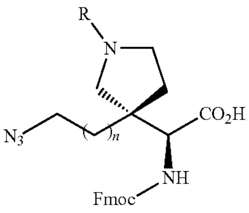
(n = 1-5)
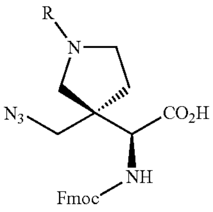
R = Me or Boc
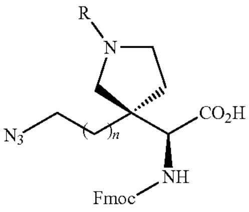
(n = 1-5)
-continued
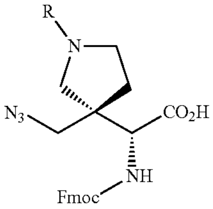
R = Me or Boc
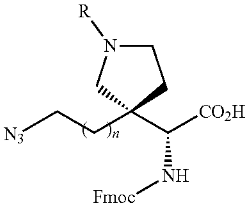
(n = 1-5)
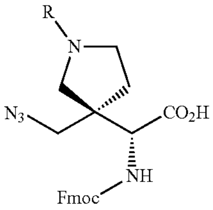
R = Me or Boc
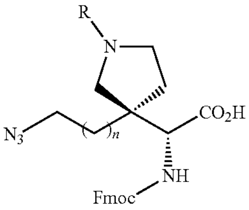
(n = 1-5)
[Chemical Formula 264]
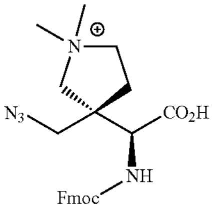
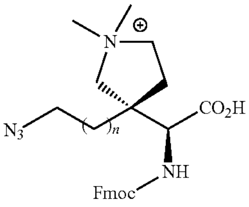
(n = 1-5)
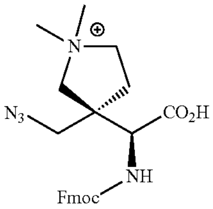
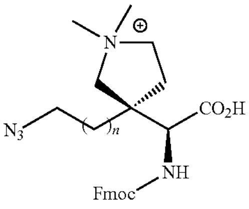
(n = 1-5)
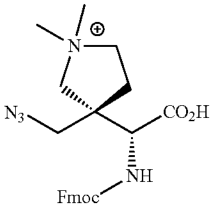
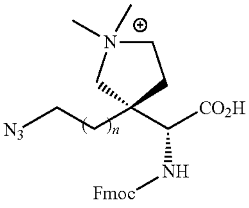
(n = 1-5)
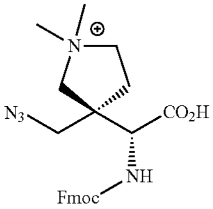
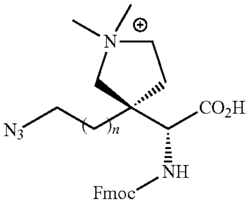
(n = 1-5)

[Chemical Formula 265]
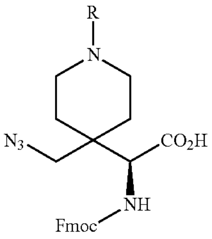
R = Me or Boc
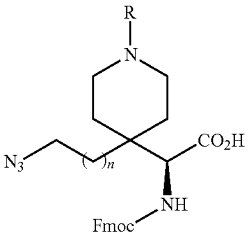
(n = 1 - 5)
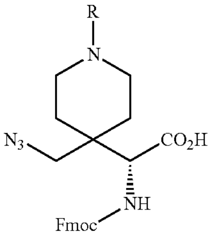
R = Me or Boc
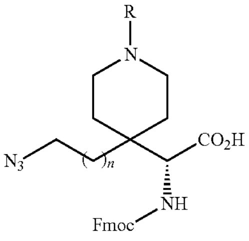
(n = 1 - 5)
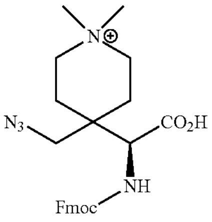
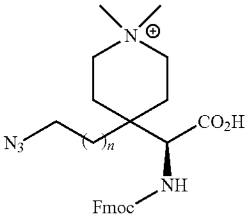
(n = 1 - 5)
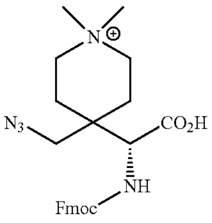
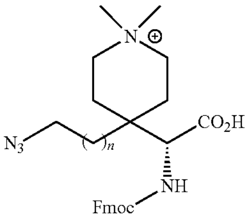
(n = 1 - 5)
[Chemical Formula 266]
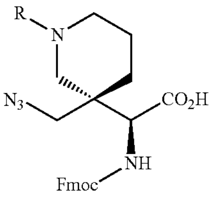
R = Me or Boc
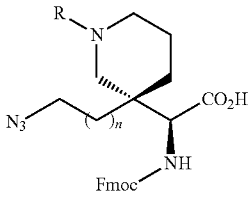
(n = 1-5)
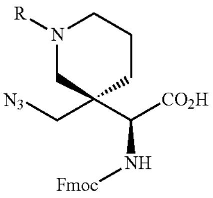
R = Me or Boc
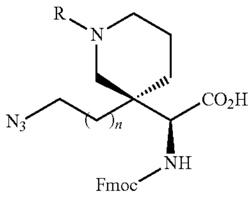
(n = 1-5)
-continued
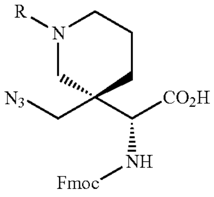
R = Me or Boc
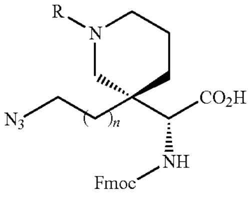
(n = 1-5)
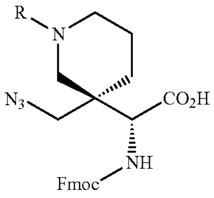
R = Me or Boc
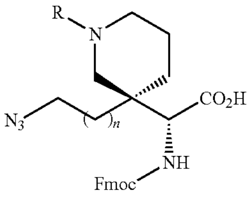
(n = 1-5)
[Chemical Formula 267]
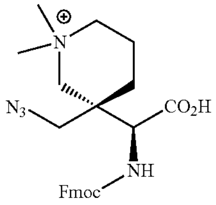
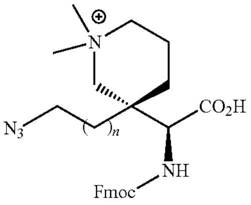
(n = 1-5)
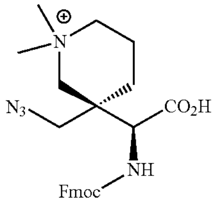
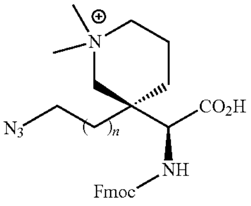
(n = 1-5)
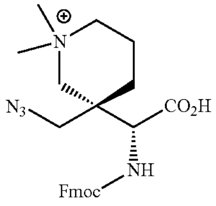
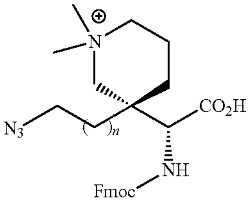
(n = 1-5)
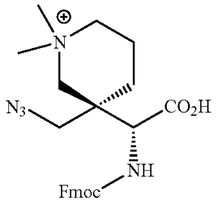
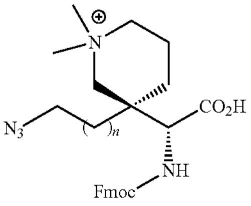
(n = 1-5)

[Chemical Formula 268]
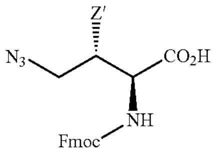
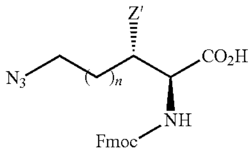
(n = 1-5)
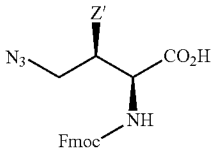
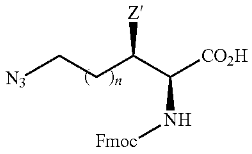
(n = 1-5)
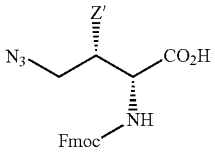
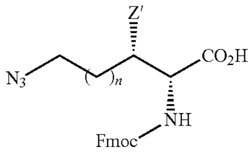
(n = 1-5)
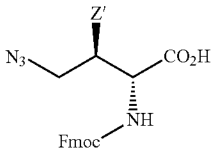
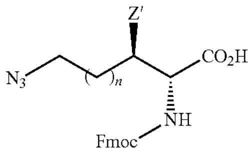
(n = 1-5)
Z' = 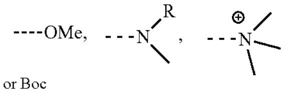
R = Me or Boc
[Chemical Formula 269]
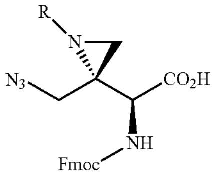
R = Me or Boc
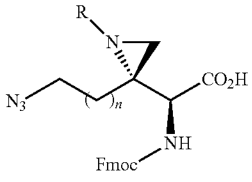
(n = 1-5)
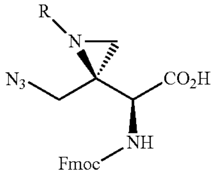
R = Me or Boc
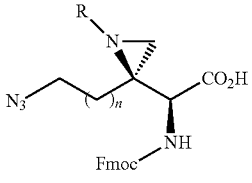
(n = 1-5)
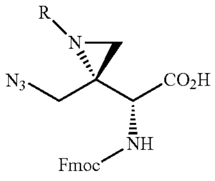
R = Me or Boc
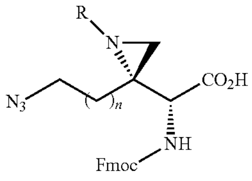
(n = 1-5)
-continued
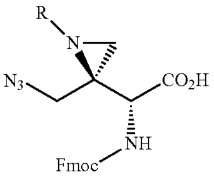
R = Me or Boc
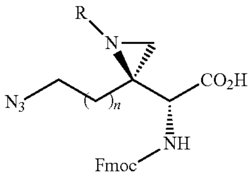
(n = 1-5)
[Chemical Formula 270]
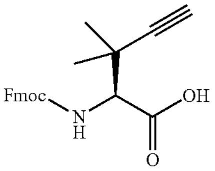
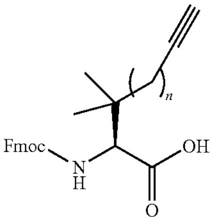
(n = 1-5)
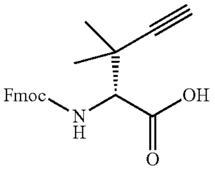
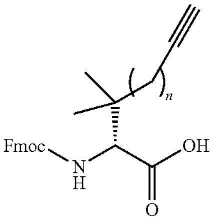
(n = 1-5)
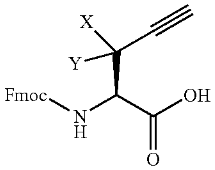
X = $CH_2F$, $CHF_2$, $CF_3$
Y = $CH_2F$, $CHF_2$, $CF_3$
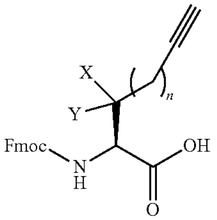
(n = 1-5)
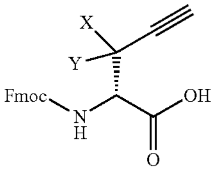
X = $CH_2F$, $CHF_2$, $CF_3$
Y = $CH_2F$, $CHF_2$, $CF_3$
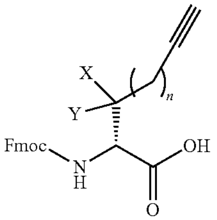
(n = 1-5)

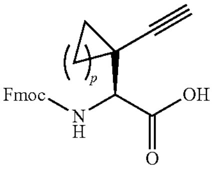
p = 1-10
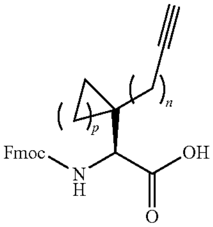
p = 1-10
(n = 1-5)
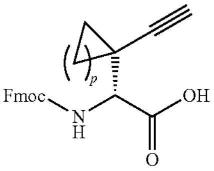
p = 1-10
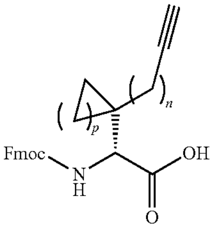
p = 1-10
(n = 1-5)
[Chemical Formula 271]
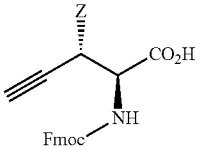
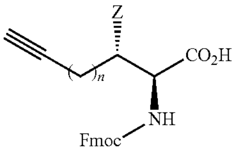
(n = 1-5)
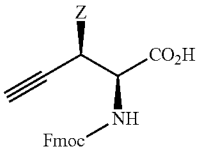
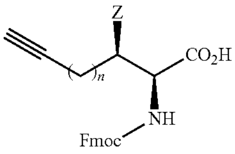
(n = 1-5)
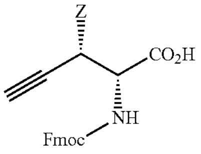
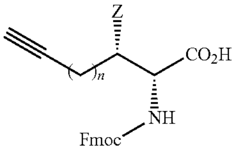
(n = 1-5)
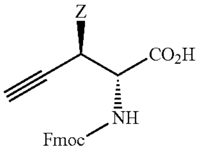
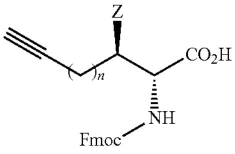
(n = 1-5)
Z = Me, $CH_2F$, $CHF_2$, $CF_3$, $^t$Bu, 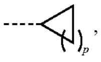 , 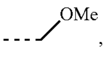 ,
p = 1-10
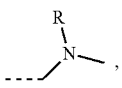 , 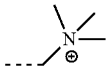
R = Me or Boc
[Chemical Formula 272]
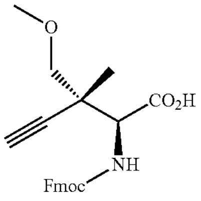
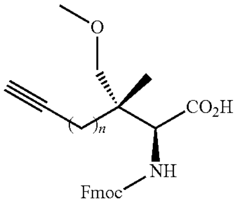
(n = 1-5)
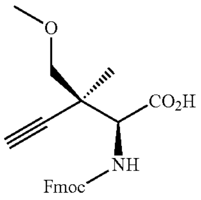
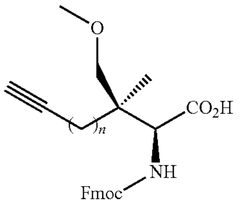
(n = 1-5)
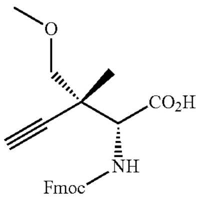
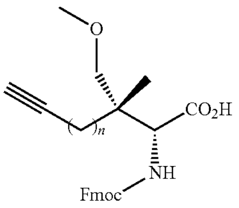
(n = 1-5)
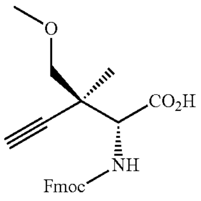
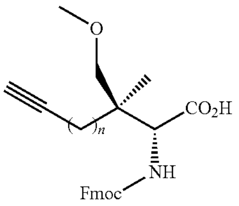
(n = 1-5)
[Chemical Formula 273]
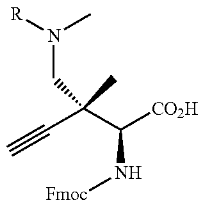
R = Me or Boc
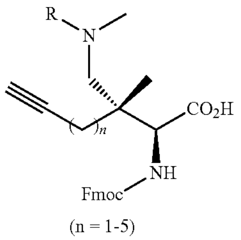
(n = 1-5)
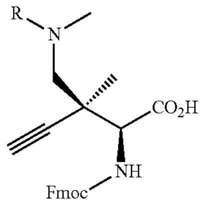
R = Me or Boc
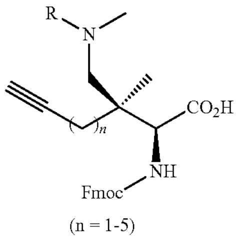
(n = 1-5)

-continued
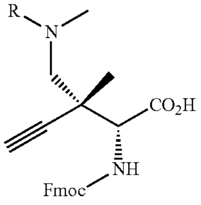
R = Me or Boc
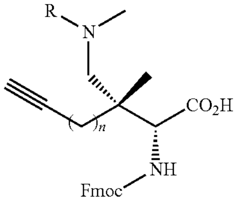
(n = 1-5)
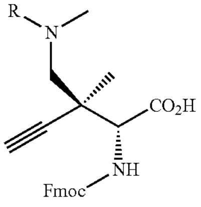
R = Me or Boc
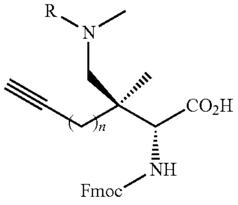
(n = 1-5)
[Chemical Formula 274]
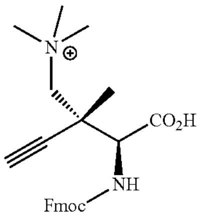
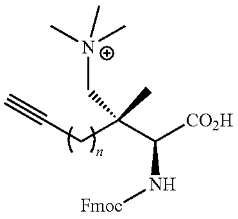
(n = 1-5)
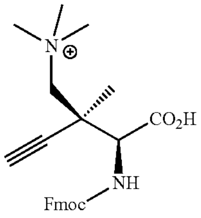
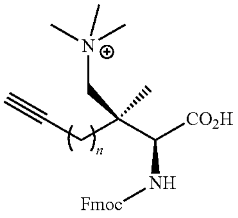
(n = 1-5)
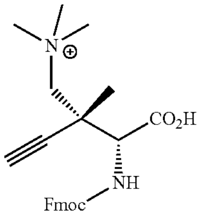
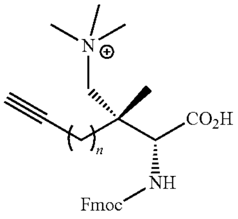
(n = 1-5)
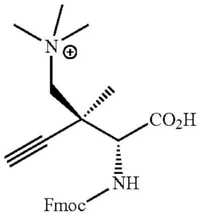
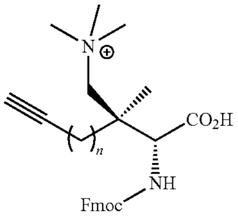
(n = 1-5)
[Chemical Formula 275]
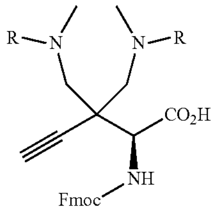
R = Me or Boc
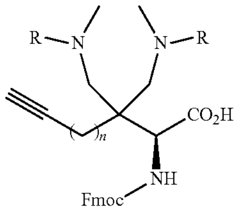
(n = 1-5)
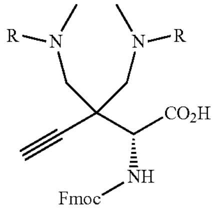
R = Me or Boc
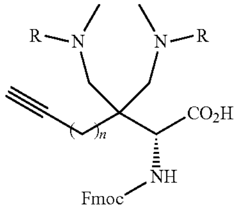
(n = 1-5)
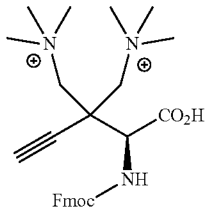
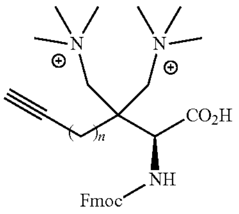
(n = 1-5)
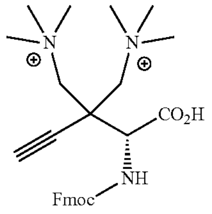
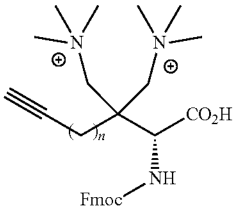
(n = 1-5)
[Chemical Formula 276]
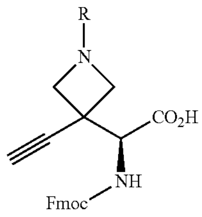
R = Me or Boc
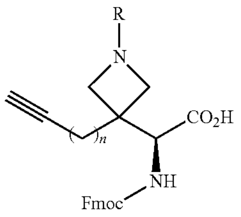
(n = 1-5)
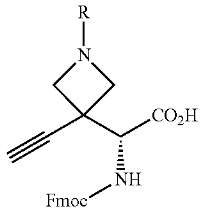
R = Me or Boc
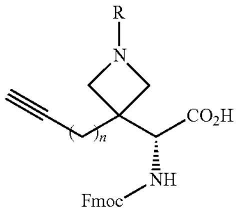
(n = 1-5)

-continued
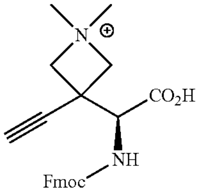
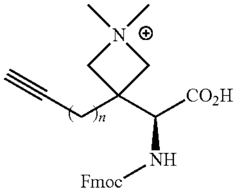
(n = 1-5)
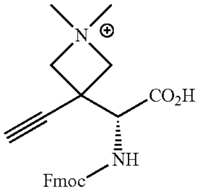
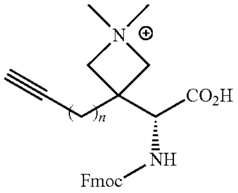
(n = 1-5)
[Chemical Formula 277]
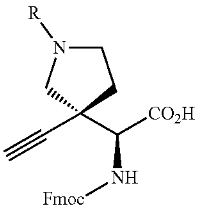
R = Me or Boc
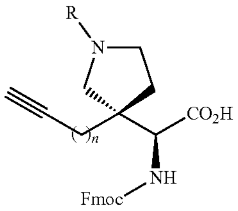
(n = 1-5)
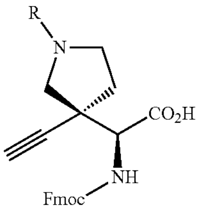
R = Me or Boc
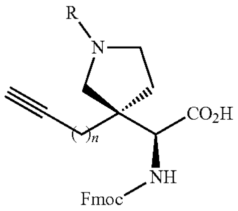
(n = 1-5)
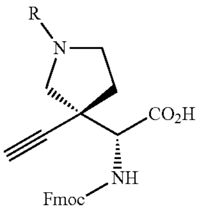
R = Me or Boc
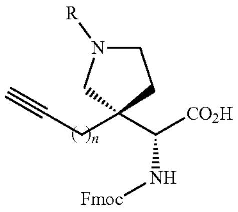
(n = 1-5)
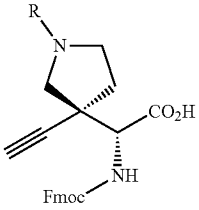
R = Me or Boc
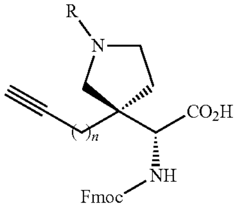
(n = 1-5)
[Chemical Formula 278]
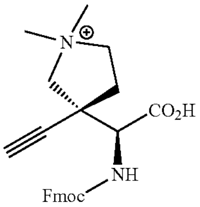
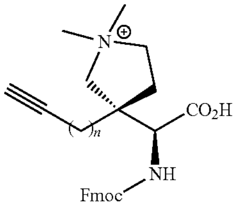
(n = 1 - 5)
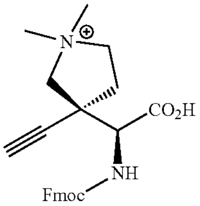
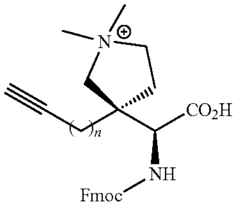
(n = 1 - 5)
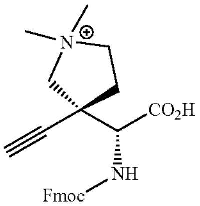
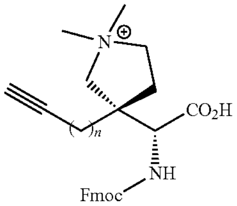
(n = 1 - 5)
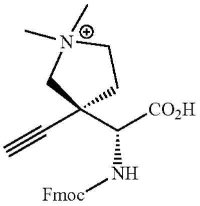
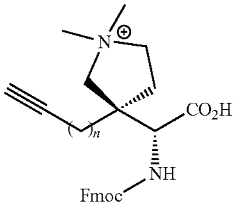
(n = 1 - 5)
[Chemical Formula 279]
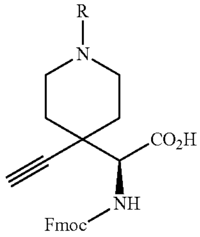
R = Me or Boc
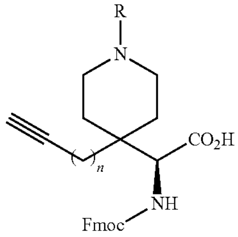
(n = 1-5)
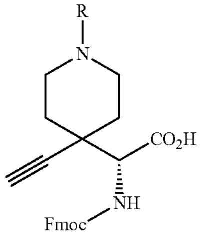
R = Me or Boc
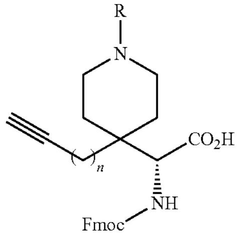
(n = 1-5)

-continued
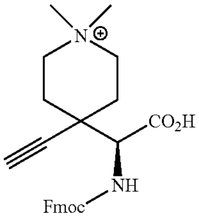
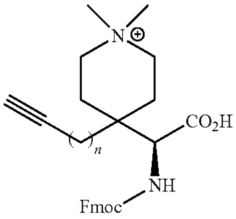
(n = 1-5)
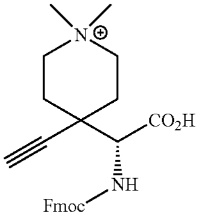
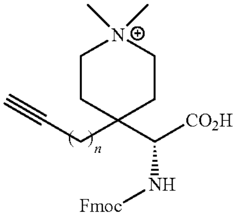
(n = 1-5)
[Chemical Formula 280]
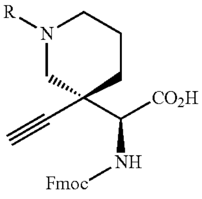
R = Me or Boc
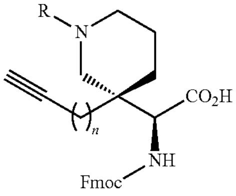
(n = 1 - 5)
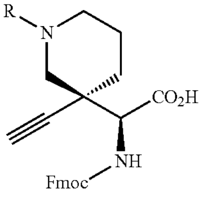
R = Me or Boc
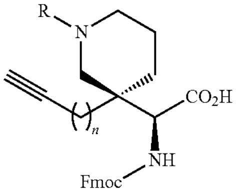
(n = 1 - 5)
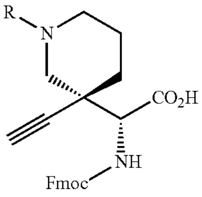
R = Me or Boc
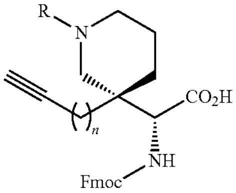
(n = 1 - 5)
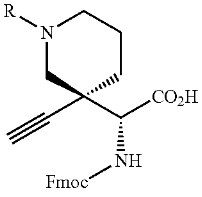
R = Me or Boc
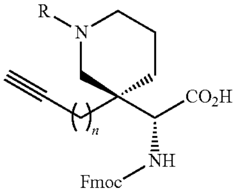
(n = 1 - 5)
[Chemical Formula 281]
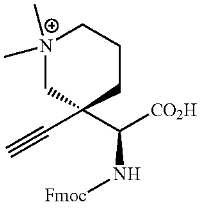
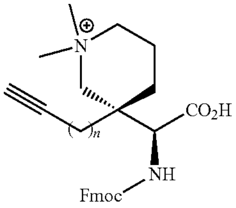
(n = 1-5)
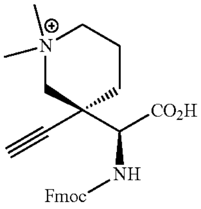
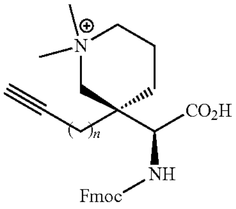
(n = 1-5)
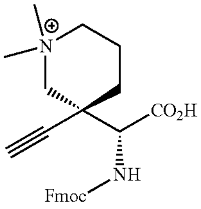
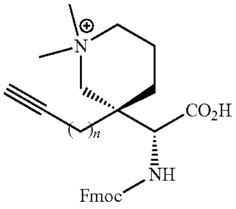
(n = 1-5)
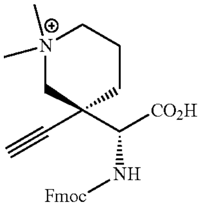
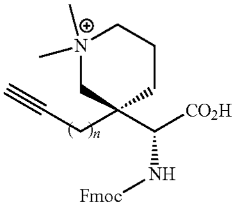
(n = 1-5)
[Chemical Formula 282]
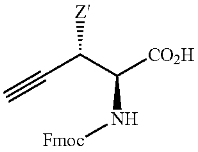
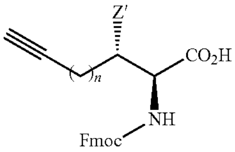
(n = 1-5)
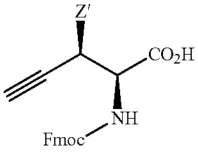
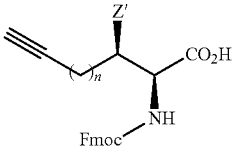
(n = 1-5)
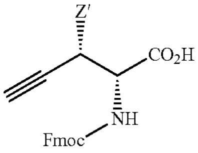
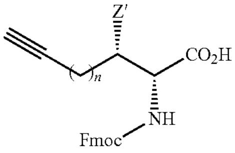
(n = 1-5)

-continued
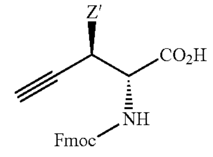
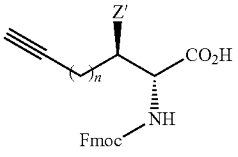
(n = 1-5)
Z' = 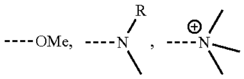
R = Me or Boc
[Chemical Formula 283]
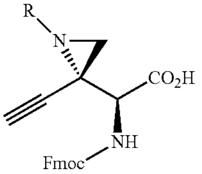
R = Me or Boc
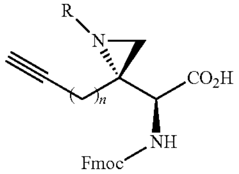
(n = 1-5)
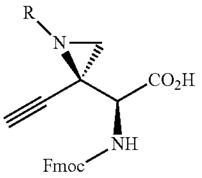
R = Me or Boc
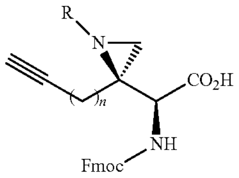
(n = 1-5)
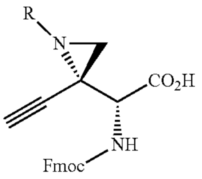
R = Me or Boc
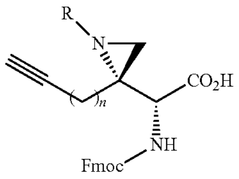
(n = 1-5)
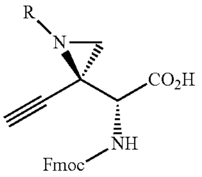
R = Me or Boc
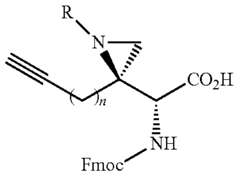
(n = 1-5)
[Chemical Formula 284]
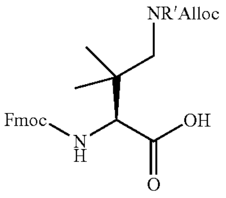
R' = H or Alkyl
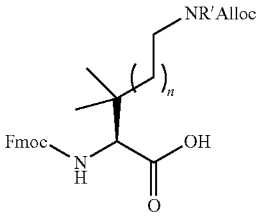
(n = 1-5)
-continued
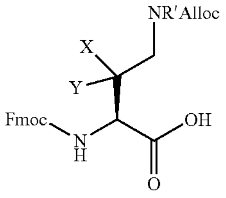
X = $CH_2F$, $CHF_2$, $CF_3$
Y = $CH_2F$, $CHF_2$, $CF_3$
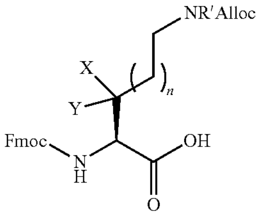
(n = 1-5)
R' = H or Alkyl
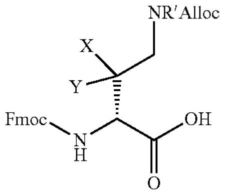
X = $CH_2F$, $CHF_2$, $CF_3$
Y = $CH_2F$, $CHF_2$, $CF_3$
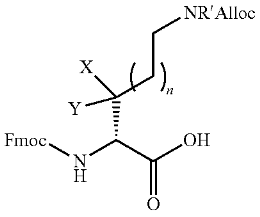
(n = 1-5)
R' = H or Alkyl
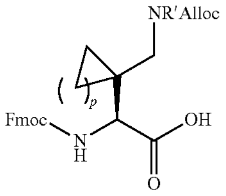
p = 1-10
R' = H or Alkyl
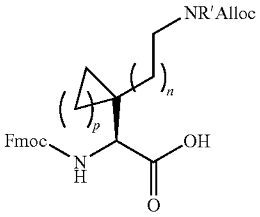
p = 1-10
(n = 1-5)
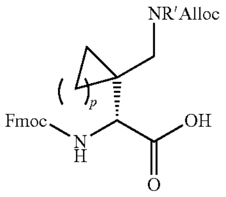
p = 1-10
R' = H or Alkyl
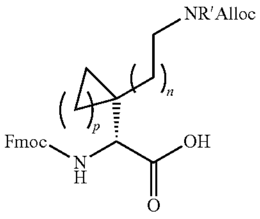
p = 1-10
(n = 1-5)
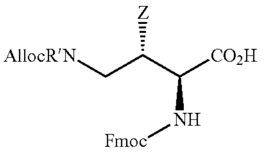
R' = H or Alkyl
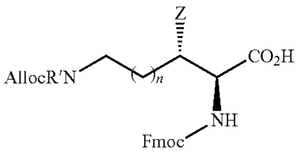
(n = 1-5)
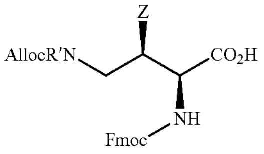
R' = H or Alkyl
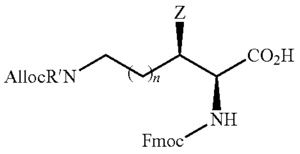
(n = 1-5)

-continued
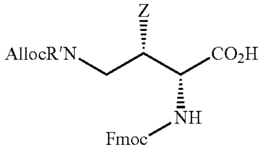
R′ = H or Alkyl
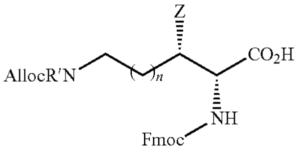
(n = 1-5)
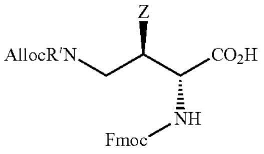
R′ = H or Alkyl
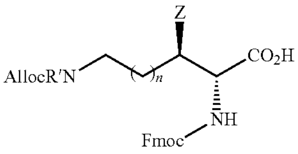
(n = 1-5)
Z = Me, $CH_2F$, $CHF_2$, $CF_3$, ${}^tBu$,
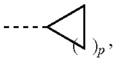
p = 1-10
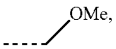
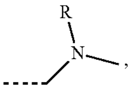
,
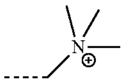
R = Me or Boc
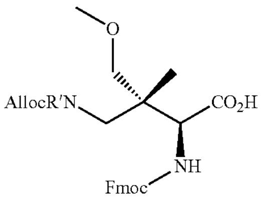
R′ = H or Alkyl
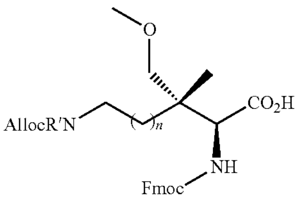
(n = 1-5)
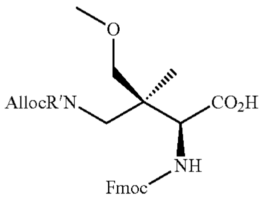
R′ = H or Alkyl
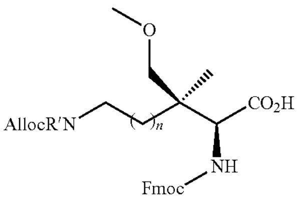
(n = 1-5)
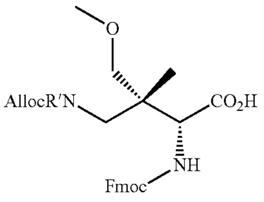
R′ = H or Alkyl
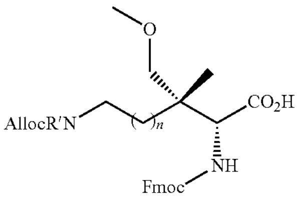
(n = 1-5)
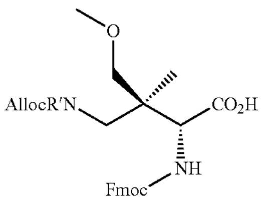
R′ = H or Alkyl
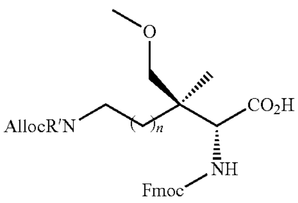
(n = 1-5)
[Chemical Formula 286]
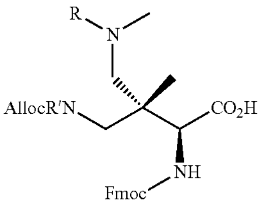
R = Me or Boc
R′ = H or Alkyl
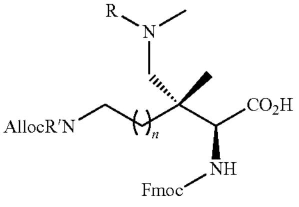
(n = 1 - 5)
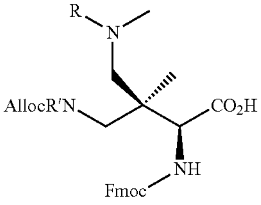
R = Me or Boc
R′ = H or Alkyl
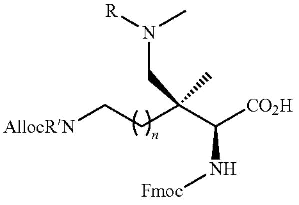
(n = 1 - 5)
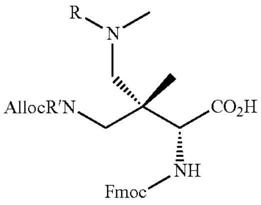
R = Me or Boc
R′ = H or Alkyl
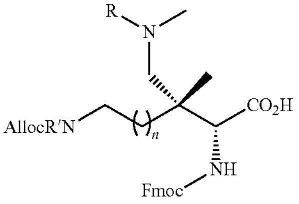
(n = 1 - 5)
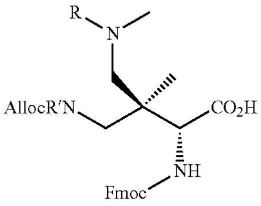
R = Me or Boc
R′ = H or Alkyl
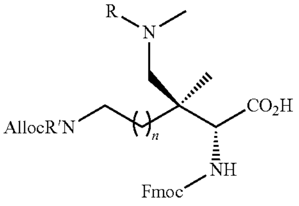
(n = 1 - 5)
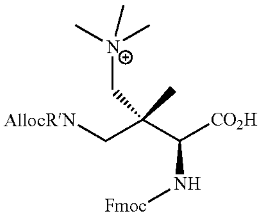
R′ = H or Alkyl
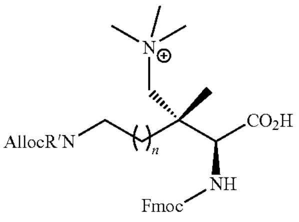
(n = 1 - 5)
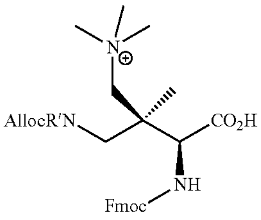
R′ = H or Alkyl
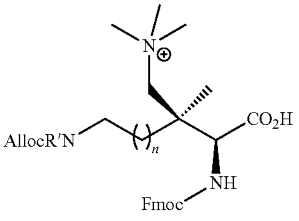
(n = 1 - 5)

-continued
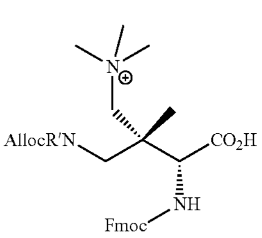
R′ = H or Alkyl
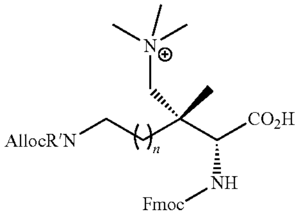
(n = 1 - 5)
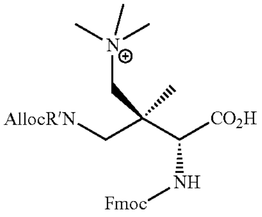
R′ = H or Alkyl
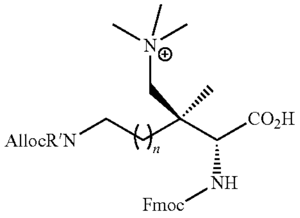
(n = 1 - 5)
[Chemical Formula 287]
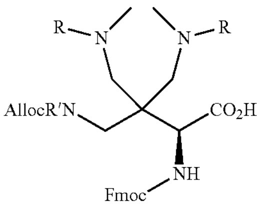
R = Me or Boc
R′ = H or Alkyl
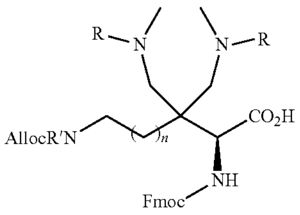
(n = 1-5)
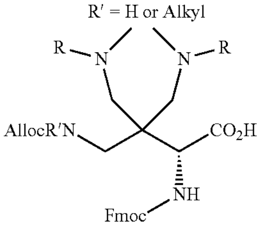
R = Me or Boc
R′ = H or Alkyl
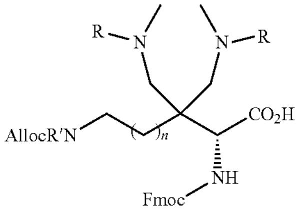
(n = 1-5)
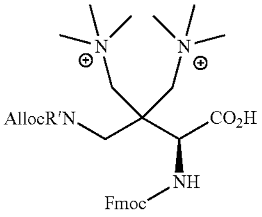
R′ = H or Alkyl
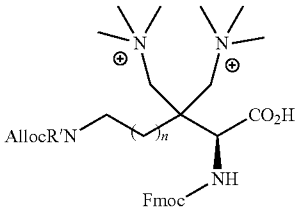
(n = 1-5)
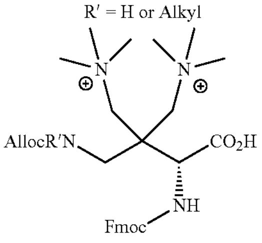
R′ = H or Alkyl
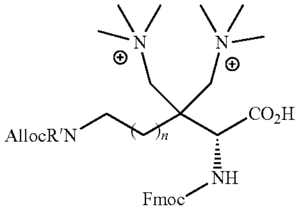
(n = 1-5)
-continued
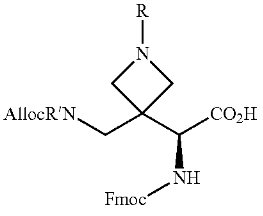
R = Me or Boc
R′ = H or Alkyl
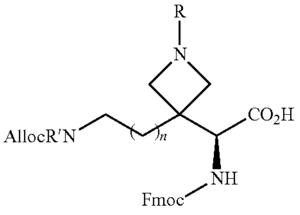
(n = 1-5)
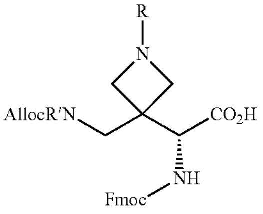
R = Me or Boc
R′ = H or Alkyl
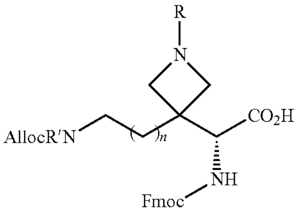
(n = 1-5)
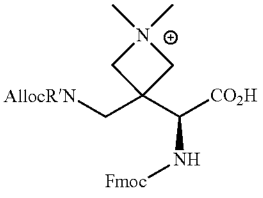
R′ = H or Alkyl
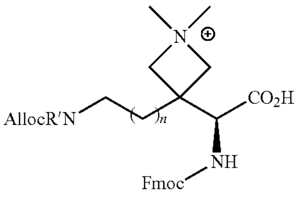
(n = 1-5)
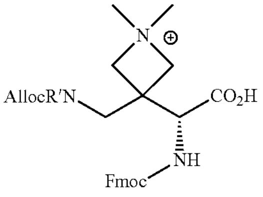
R′ = H or Alkyl
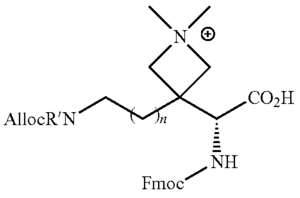
(n = 1-5)
[Chemical Formula 288]
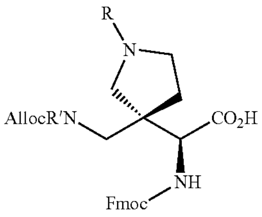
R = Me or Boc
R′ = H or Alkyl
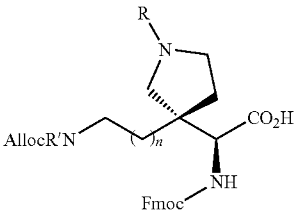
(n = 1-5)
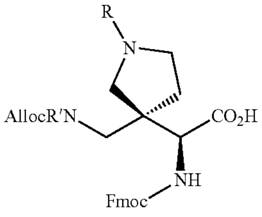
R = Me or Boc
R′ = H or Alkyl
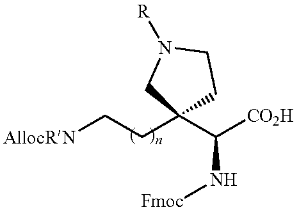
(n = 1-5)

-continued
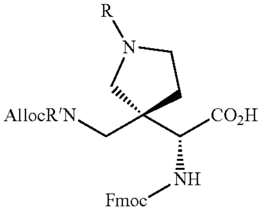
R = Me or Boc
R′ = H or Alkyl
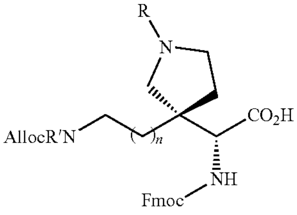
(n = 1-5)
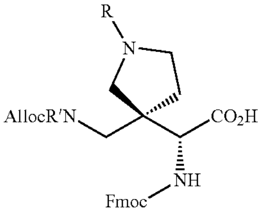
R = Me or Boc
R′ = H or Alkyl
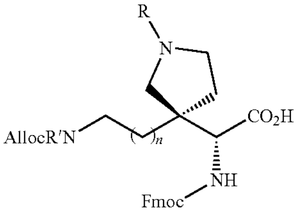
(n = 1-5)
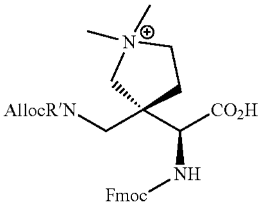
R′ = H or Alkyl
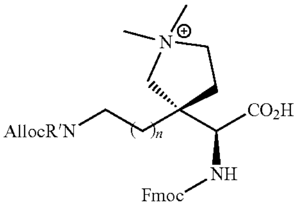
(n = 1-5)
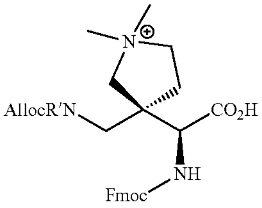
R′ = H or Alkyl
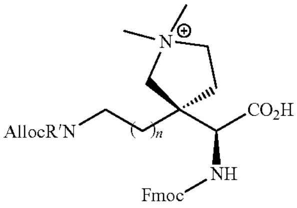
(n = 1-5)
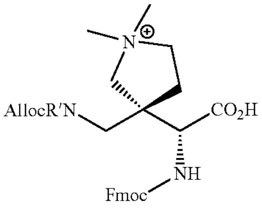
R′ = H or Alkyl
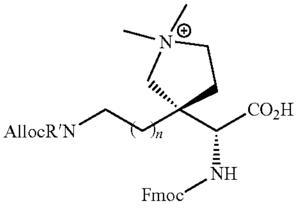
(n = 1-5)
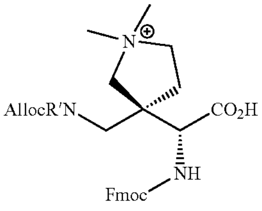
R′ = H or Alkyl
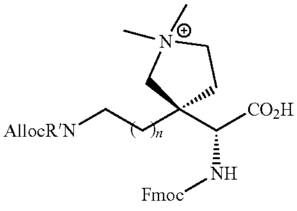
(n = 1-5)
[Chemical Formula 289]
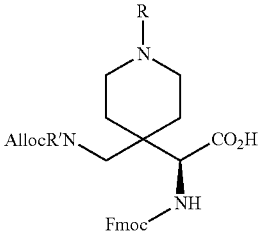
R = Me or Boc
R′ = H or Alkyl
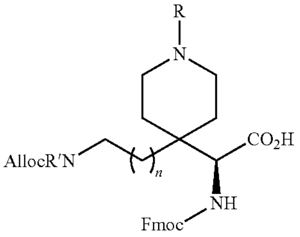
(n = 1-5)
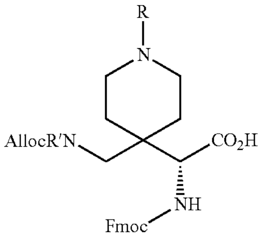
R = Me or Boc
R′ = H or Alkyl
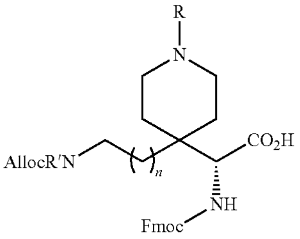
(n = 1-5)
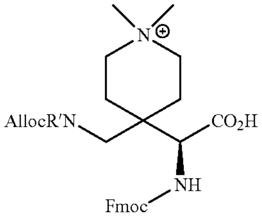
R′ = H or Alkyl
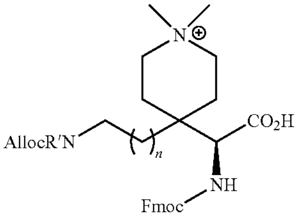
(n = 1-5)
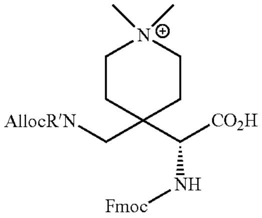
R′ = H or Alkyl
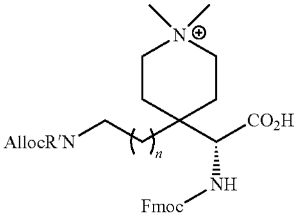
(n = 1-5)
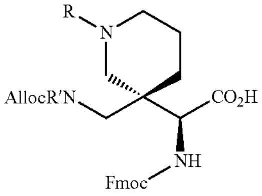
R = Me or Boc
R′ = H or Alkyl
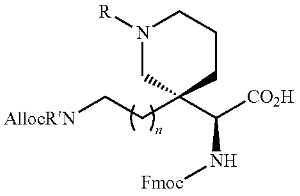
(n = 1-5)
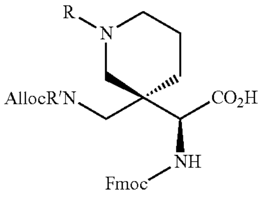
R = Me or Boc
R′ = H or Alkyl
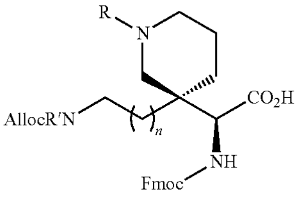
(n = 1-5)

-continued
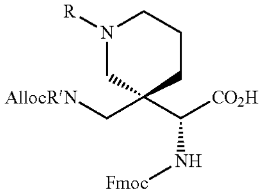
R = Me or Boc
R′ = H or Alkyl
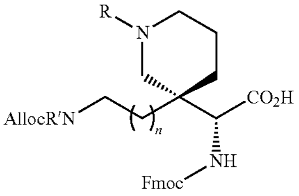
(n = 1-5)
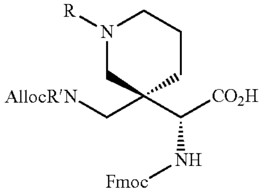
R = Me or Boc
R′ = H or Alkyl
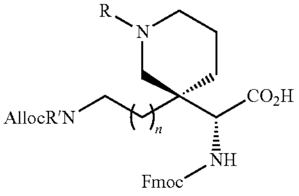
(n = 1-5)
[Chemical Formula 290]
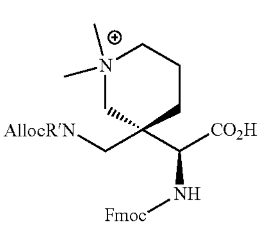
R′ = H or Alkyl
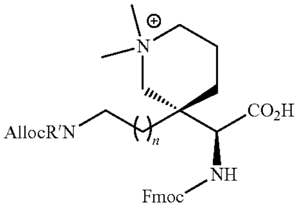
(n = 1-5)
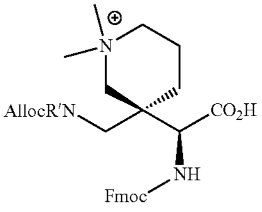
R′ = H or Alkyl
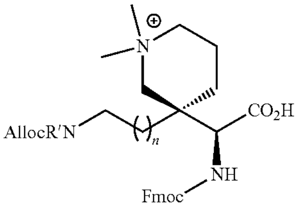
(n = 1-5)
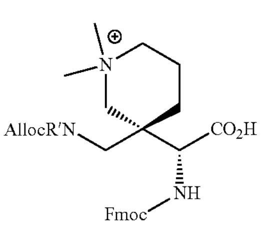
R′ = H or Alkyl
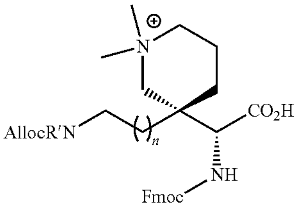
(n = 1-5)
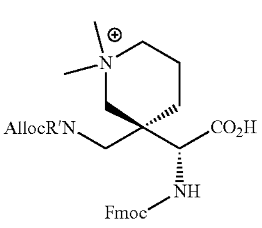
R′ = H or Alkyl
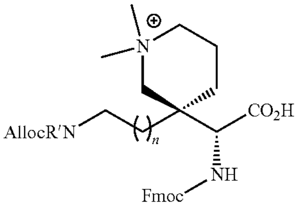
(n = 1-5)
-continued
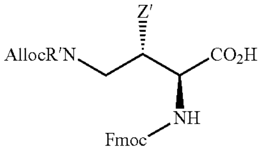
R′ = H or Alkyl
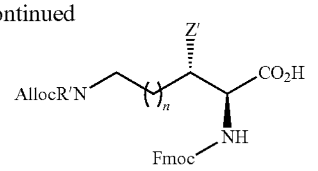
(n = 1-5)
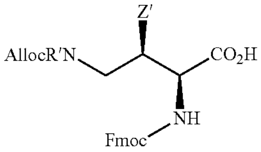
R′ = H or Alkyl
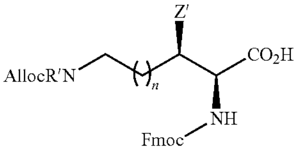
(n = 1-5)
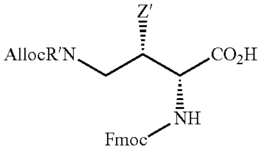
R′ = H or Alkyl
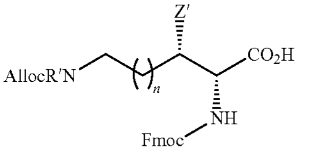
(n = 1-5)
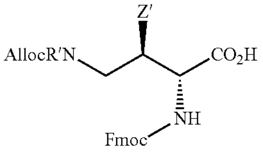
R′ = H or Alkyl
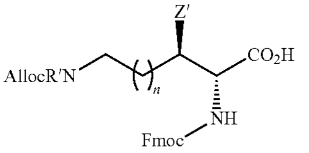
(n = 1-5)
Z′ = 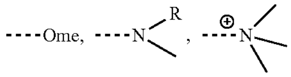
R = Me or Boc
[Chemical Formula 291]
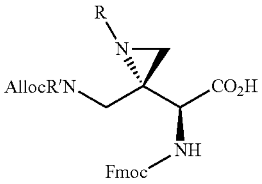
R = Me or Boc
R′ = H or Alkyl
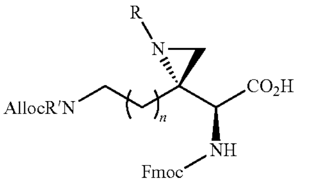
(n = 1-5)
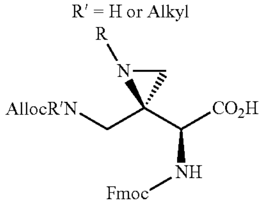
R = Me or Boc
R′ = H or Alkyl
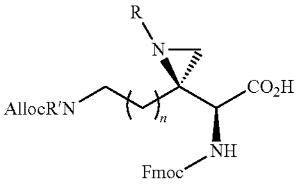
(n = 1-5)
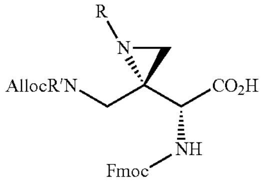
R = Me or Boc
R′ = H or Alkyl
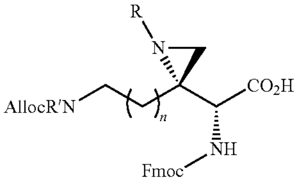
(n = 1-5)

-continued
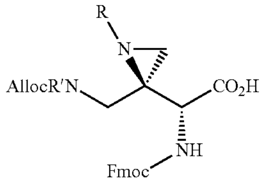
R = Me or Boc
R' = H or Alkyl
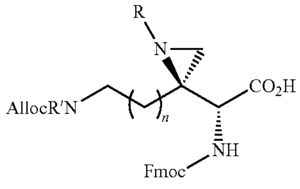
(n = 1-5)
[Chemical Formula 292]
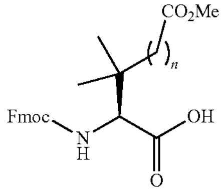
(n = 1-5)
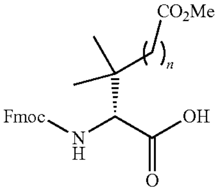
(n = 1-5)
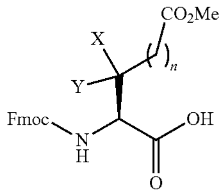
X = $CH_2F$, $CHF_2$, $CF_3$
Y = $CH_2F$, $CHF_2$, $CF_3$
(n = 1-5)
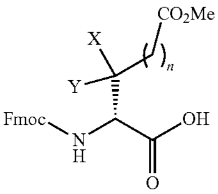
X = $CH_2F$, $CHF_2$, $CF_3$
Y = $CH_2F$, $CHF_2$, $CF_3$
(n = 1-5)
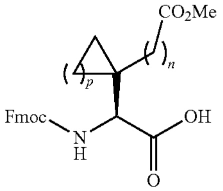
p = 1-10
(n = 1-5)
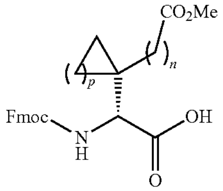
p = 1-10
(n = 1-5)
[Chemical Formula 293]
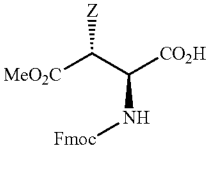
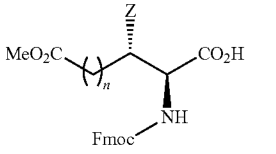
(n = 1-5)
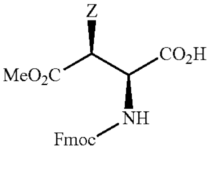
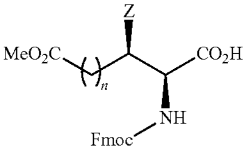
(n = 1-5)
-continued
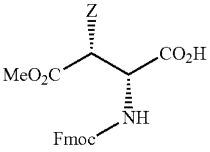
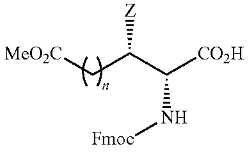
(n = 1-5)
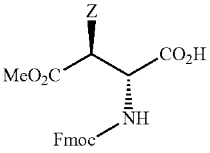
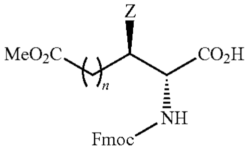
(n = 1-5)
Z = Me, $CH_2F$, $CHF_2$, $CF_3$, $^t$Bu, 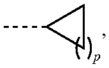, 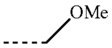,
p = 1-10
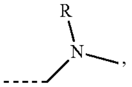, 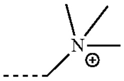
R = Me or Boc
[Chemical Formula 294]
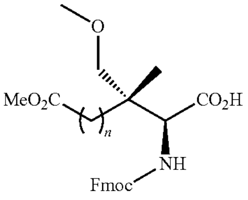
(n = 1-5)
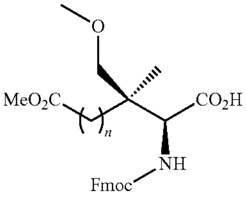
(n = 1-5)
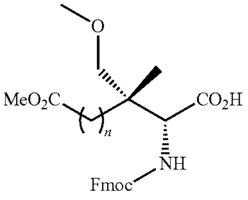
(n = 1-5)
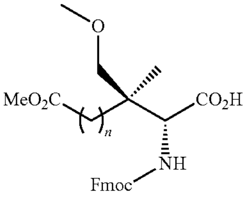
(n = 1-5)
[Chemical Formula 295]
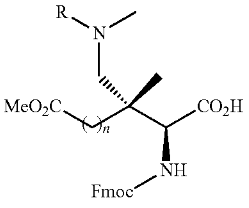
R = Me or Boc
(n = 1-5)
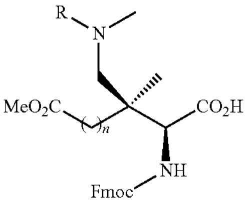
R = Me or Boc
(n = 1-5)

-continued
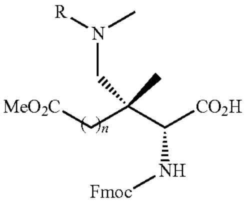
R = Me or Boc
(n = 1-5)
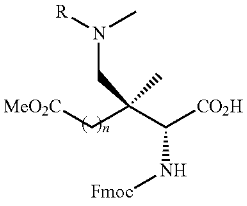
R = Me or Boc
(n = 1-5)
[Chemical Formula 296]
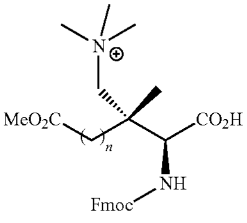
(n=1-5)
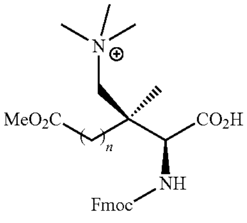
(n=1-5)
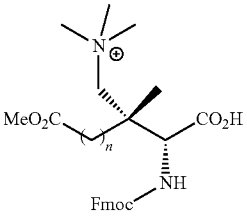
(n=1-5)
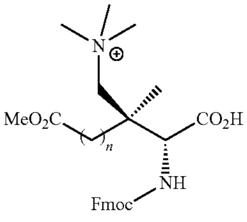
(n=1-5)
[Chemical Formula 297]
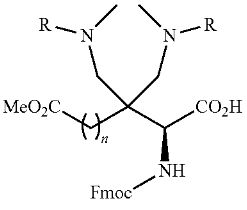
R = Me or Boc
(n = 1-5)
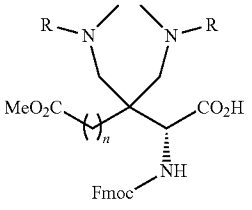
R = Me or Boc
(n = 1-5)
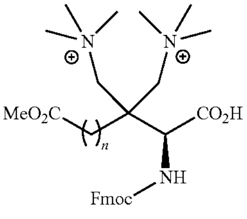
(n = 1-5)
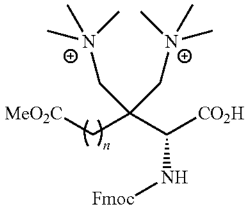
(n = 1-5)
[Chemical Formula 298]
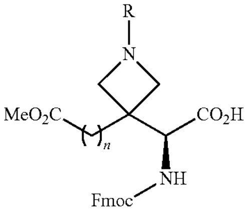
R = Me or Boc
(n = 1-5)
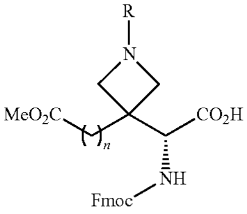
R = Me or Boc
(n = 1-5)
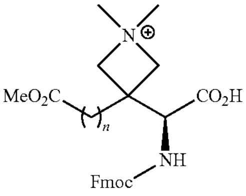
(n = 1-5)
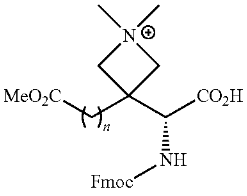
(n = 1-5)
[Chemical Formula 299]
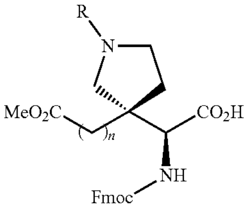
R′ = Me or Boc
(n = 1-5)
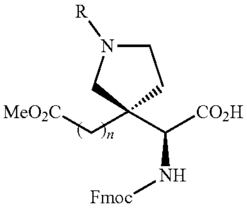
R′ = Me or Boc
(n = 1-5)
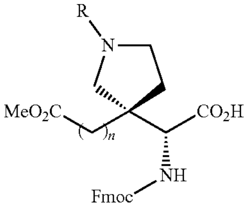
R′ = Me or Boc
(n = 1-5)
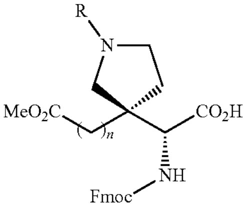
R′ = Me or Boc
(n = 1-5)
[Chemical Formula 300]
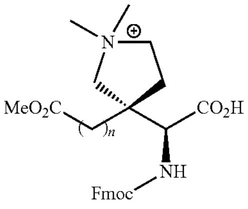
(n = 1-5)
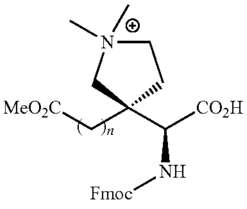
(n = 1-5)

-continued
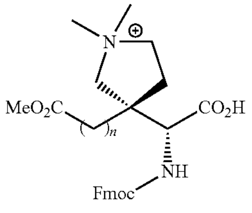
(n = 1-5)
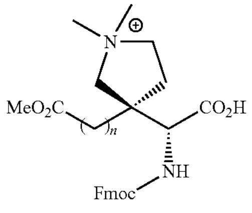
(n = 1-5)
[Chemical Formula 301]
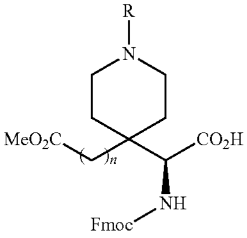
R = Me or Boc
(n = 1-5)
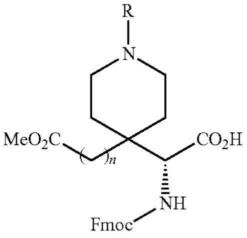
R = Me or Boc
(n = 1-5)
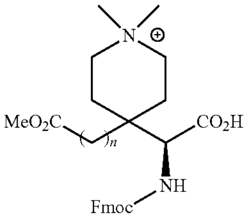
(n = 1-5)
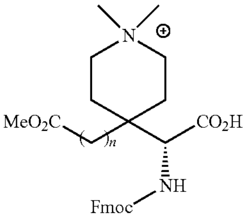
(n = 1-5)
[Chemical Formula 302]
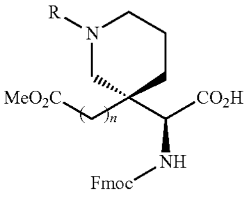
R = Me or Boc
(n = 1-5)
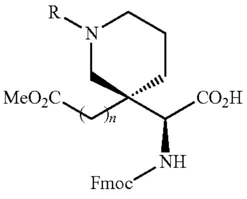
R = Me or Boc
(n = 1-5)
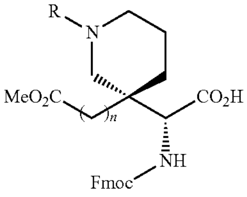
R = Me or Boc
(n = 1-5)
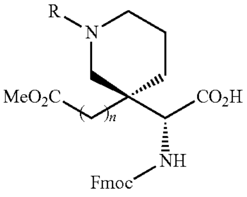
R = Me or Boc
(n = 1-5)
[Chemical Formula 303]
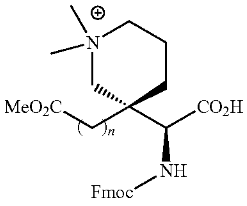
(n = 1-5)
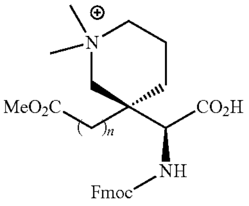
(n = 1-5)
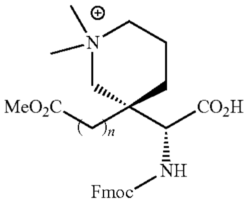
(n = 1-5)
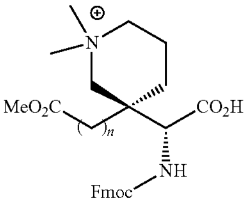
(n = 1-5)
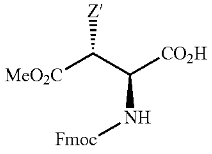
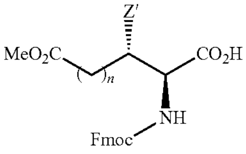
(n = 1-5)
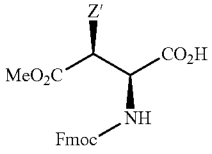
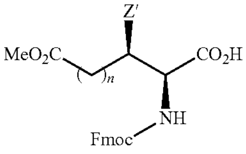
(n = 1-5)
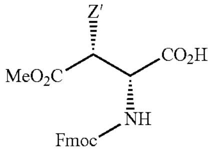
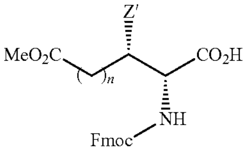
(n = 1-5)
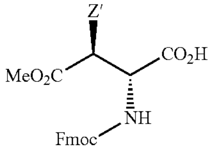
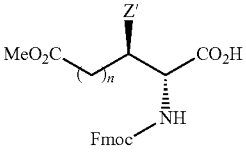
(n = 1-5)
Z = ----OMe, 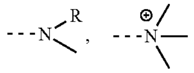
R = Me or Boc

[Chemical Formula 305]

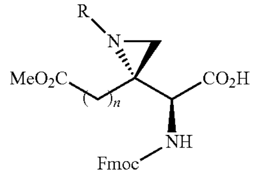

R = Me or Boc
(n = 1-5)

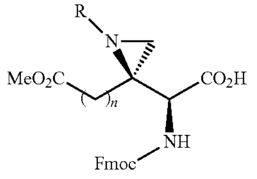

R = Me or Boc
(n = 1-5)

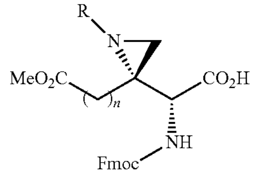

R = Me or Boc
(n = 1-5)

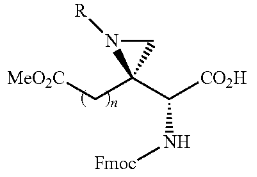

R = Me or Boc
(n = 1-5)

(Example 8) Example of Bridge Construction

In this example, examples of bridge formation are shown in FIGS. 10 to 14.

(1) Olefin Metathesis (FIG. 10)

Olefin geometry: E or Z isomer

Bis(tricyclohexylphosphine)benzylidene ruthenium (IV) dichloride (Grubbs catalyst, 1st generation) (8 mg, 9.7 μmol) dissolved in 1, 2-dichloromethane (DCE) (0.6 mL) was added to the resin and the reaction was stirred for 2 h under nitrogen atmosphere, then washed three times with dichloromethane. This process was repeated until all the starting materials were converted. The bridge formation reaction proceeded successfully with a bridge length greater than or equal to the combination of β-DM4 and β-DM5. In the formula, R1 to R4 represent any substituents in any β-position, n and n' are arbitrary integers, R5 and R6 represent any substituents used in olefin metathesis, and in the specific case of this experiment, R1 to R4 are methyl, R5 and R6 are hydrogen, and n and n' are independently 3 to 6.

In this example, those in which R1-R4 are $CF_3$ will also be implemented. Its production method is the same as above.

(2) Alkyne Metathesis (FIG. 11)

The resin was washed three times with anhydrous ether and anhydrous toluene. Mo catalyst A (1 mg, 0.96 μmol) dissolved in anhydrous toluene (0.5 mL) was added to the resin, and reacted at 40° C. for 1.5 h. The resin was then washed three times with toluene and dichloromethane, respectively.

[Chemical Formula 307-2]

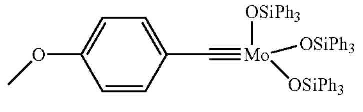

A

In the formula, R1 to R4 indicate any substituents contained in any β-position; and n and n' are arbitrary integers. In the specific case of this experiment, R1 to R4 are methyl, and n and n' each independently represent 3 to 6.

(3) Reductive Amination (FIG. 12)

Dimethylformamide (0.45 mL) and $NaBH_3CN$ (3.8 mg, 0.06 mmol) were added to the resin and the reaction was carried out at r.t. for 6 h. The resin was washed three times with methanol, dimethylformamide, and dichloromethane, respectively. In the formula, R1 to R4 represent any substituents in any β-position, R5 is any group used in reductive amination, and n and n' are arbitrary integers. In the specific case of this experiment, R1 to R4 are methyl, R5 is hydrogen, and n and n' are independently 3 to 6.

(4) Click Chemistry (FIG. 13)

In this example, the click chemistry reaction of a terminal alkyne and azide is shown.

In the formula, R1 to R4 indicate any substituents contained in any β-position, and n and n' are arbitrary integers. In the specific case of this experiment, R1 to R4 are methyl, and n and n' each independently represent 3 to 6.

Reaction by Cu(I) Catalyst

Copper(I) bromide (1.43 mg, 0.011 mmol) dissolved in anhydrous dimethyl sulfoxide (0.6 mL), sodium ascorbate (1.98 mg, 0.011 mmol) dissolved in water (0.1 mL), diisopropylethylamine (0.017 mL), 2, 6-lutidine (0.012 mL, 0.1 mmol) are added to the resin and the mixture is stirred under nitrogen atmosphere for 16 h. The reaction is washed three times with dimethyl sulfoxide, water, methanol and dichloromethane.

Reaction by Ru(II) Catalyst (FIG. 14)

Dimethylformamide (0.5 mL) and Cp*RuCl(COD) (2.3 mg, 6 μmol) are added to the resin, and the mixture is stirred at 60° C. for 5 h, and then washed three times with methanol, sodium dithiocarbamate solution in 0.5% diethyl dimethylformamide, dimethylformamide, and dichloromethane.

In this example, the following Michael addition and carbamate-catalyzed reaction can also be used for bridge formation, and this example provides an example of this production.

(Example 9) Example of Peptide Synthesis

Example of peptide synthesis is shown below.

(1) β-Strand Bridge Peptide

Preparation of Bridge Peptides

Solid-phase peptide synthesis: Peptides are prepared using Fmoc chemistry, for example, using one of the following resins: 2-chlorotrityl chloride resin, Methyl Indole AM resin, (3-formylindolyl) acetamidomethyl polystyrene, Rink-PEG-PS resin (PEG: polyethylene glycol, PS: polystyrene), Rink Amide MBHA, Rink Amide MBHA Low Loading, PAL-NovaSyn TG, NovaPEG Rink Amide resin, or NovaPEG Rink Amide Low Loading resin.

Dry resin is typically swollen before use in dichloromethane and then in N-methyl-2-pyrrolidone (NMP). Fmoc protecting groups are removed using 25% (v/v) piperidine in NMP (4×5 min). Natural amino acids are typically coupled using four equivalents of Fmoc-protected amino acids for 60 minutes, four equivalents of (1-cyano-2-ethoxy-2-oxoethylideneaminooxy)dimethylamino-morpholino-carbenium hexafluorophosphate (COMU) as coupling reagent, and eight equivalent of N, N-diisopropylethylamine (DIPEA) as a base for coupling. Unnatural amino acids (e.g., those described herein) are typically coupled using three equivalents of Fmoc-protected amino for 120 minutes, three acids equivalents of (1-cyano-2-ethoxy-2-oxoethylideneaminooxy)dimethylamino-morpholino Carbenium hexafluorophosphate (COMU) as coupling reagent, and six equivalents of N, N-diisopropylethylamine (DIPEA) as a base. The resin was washed between each coupling and deprotection step using NMP (5×1 min). The side chain protecting groups are removed and the peptide is cleaved from the resin simultaneously using the following procedure: the dried resin is treated with a solution of trifluoroacetic acid: triisopropylsilane: water (95:2.5:2.5) for 3 hours. After completion of the incubation, the volume of the solution is reduced by evaporation under a stream of $N_2$ (gas) and the resulting residue is treated with cold diethyl ether. The precipitated peptides are pelleted by centrifugation, the supernatant is decanted, and the pellet is air-dried. The crude peptides are typically dissolved in a 1:2 solution of acetonitrile:water and then purified by reversed-phase HPLC using acetonitrile containing 0.1% (v/v) trifluoroacetic acid and water containing 0.1% (v/v) trifluoroacetic acid as mobile phase components. The purity of the HPLC fractions is evaluated by LC/MS, and the clean fractions are collected and concentrated by speedvac. The peptides are then lyophilized to a dry state. This procedure yields a β-strand bridge peptide.

Preparation of Bridge Peptides

All the peptides were synthesized by standard Fmoc solid phase synthesis using Rink Amide MBHA resin (100-200 mesh). The condensation reaction of natural amino acids were performed by 1-[bis(dimethylamino)methylene]-1H-1, 2, 3-triazolo[4,5-b]pyridinium 3-oxide hexafluorophosphate (HATU) and the condensation reaction of unnatural amino acids were conducted by 1-[(1-(cyano-2-ethoxy-2-oxoethylideneaminooxy)dimethylaminomorpholino)]uronium hexafluorophosphate (COMU). The condensation reaction conditions are described below.

Condensation Reaction of Natural Amino Acids

Resin (30 μmol)

Natural amino acids (4 eq.)

HATU (34 mg)

N, N-diisopropylethylamine (DIPEA) (42 μL)

N-methyl-2-pyrrolidone (NMP) (0.48 mL)

Reaction time: 2 h

Condensation Reaction of Unnatural Amino Acids

Resin (30 μmol)

Unnatural amino acids (2 eq.)

COMU (19 mg)

N,N-diisopropylethylamine (DIPEA) (21 μL)

N-methyl-2-pyrrolidone (NMP) (0.24 mL)

Reaction time: 6 h

Bridge peptides with the composition and sequence in the following table were prepared by the above procedure.

TABLE B

| PI3K - 4-6 (Ac) | | PI3K - 4-6 (FITC) | |
|---|---|---|---|
| Position | Amino Acid | Position | Amino Acid |
| 0 | R | 0 | R |
| 1 | H | 1 | H |
| 2 | β-DM4 | 2 | β-DM4 |
| 3 | K | 3 | K |
| 4 | β-DM6 | 4 | β-DM6 |
| 5 | F | 5 | F |
| 6 | I | 6 | I |
| 7 | W | 7 | W |
| 8 | Ac | 8 | β-Ala |
| | | 9 | FITC |

Peptide Purification and Mass Spectrometry

Purification was performed by the high-performance liquid chromatograph (Hitachi High-Tech Science, Chromaster) using a 28-min linear gradient (1.0 mL/min, 280 nm) from acetonitrile: 0.1% trifluoroacetic acid in water=30:70 to acetonitrile: 0.1% trifluoroacetic acid in water=54:46.

In the combination of β-DM4 and β-DM6 and β-DM5 and β-5 DM6, the two isomers produced in the olefin metathesis reaction could be separated by a C18 column (hereafter referred to as BP 4-6 1st, BP 4-6 2nd, BP 5-6 1st, and BP 5-6 2nd) (BP stands for Bridge Peptide).

Mass spectrometry analysis was performed by the Bruker Daltonics impact HD ultra-high resolution ESI-UHR-TOF/MS system.

TABLE 5

| Peptide sequence | $[M + H]^+$ found | $[M + 2H]^{2+}$ found | $[M + H]^+$ calculated | $[M + 2H]^{2+}$ calculated |
|---|---|---|---|---|
| Ac-W I F I K I H R - $NH_2$ (WT) | 1153.6923 | 577.4456 | 1153.6999 | 577.3539 |
| Ac-W I F (S)-βDM4 K (S)-βDM5 H R - $NH_2$ (BP 4-5) | 1191.7085 | 596.4425 | 1191.7154 | 596.3616 |
| Ac-W I F (S)-βDM4 K (S)-βDM6 H R - $NH_2$ (BP 4-6 1st) | 1205.7299 | 603.4104 | 1205.7310 | 603.3694 |
| Ac-W I F (S)-βDM4 K (S)-βDM6 H R - $NH_2$ (BP 4-6 2nd) | 1205.7236 | 603.4118 | 1205.7310 | 603.3694 |
| Ac-W I F (S)-βDM5 K (S)-βDM4 H R - $NH_2$ (BP 5-4) | 1191.7101 | 596.4418 | 1191.7154 | 596.3616 |
| Ac-W I F (S)-βDM5 K (S)-βDM5 H R - $NH_2$ (BP 5-5) | 1205.7274 | 603.4289 | 1205.7310 | 603.3694 |
| Ac-W I F (S)-βDM5 K (S)-βDM6 H R - $NH_2$ (BP 5-6 1st) | 1219.7433 | 610.4206 | 1219.7467 | 610.3773 |
| Ac-W I F (S)-βDM5 K (S)-βDM6 H R - $NH_2$ (BP 5-6 2nd) | 1219.7445 | 610.4195 | 1219.7467 | 610.3773 |
| Ac-W I F (S)-βDM6 K (S)-βDM4 H R - $NH_2$ (BP 6-4) | 1205.7301 | 603.4196 | 1205.7310 | 603.3694 |
| Ac-W I F (S)-βDM6 K (S)-βDM5 H R - $NH_2$ (BP 6-5) | 1219.7430 | 610.4250 | 1219.7467 | 610.3773 |
| Ac-W I F (S)-βDM6 K (S)-βDM6 H R - $NH_2$ (BP 6-6) | 1233.7621 | 617.4311 | 1233.7623 | 617.3851 |

(Example 10) Conversion of Methyl Ester to Aldehyde in Solid Phase Peptide Synthesis In this example, the conversion of methyl ester to aldehyde in solid phase peptide synthesis is based on the following scheme.

[Chemical Formula 311]

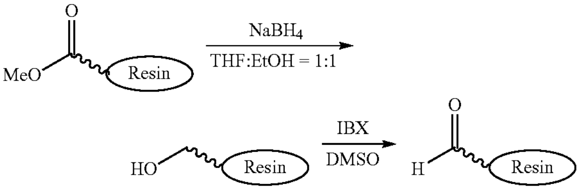

1:1 EtOH: THF (1.5 mL), and $NaBH_4$ (5.7 mg, 0.15 mmol) was added to the resin (30 μmol) and the reaction was carried out at r.t. for 24 h. The resin was washed with methanol and tetrahydrofuran. Dimethyl sulfoxide (1.5 mL)

2- and iodoxybenzoic acid (34 mg, 0.12 mmol) were added sequentially and the reaction was allowed to proceed at r.t. for 18 h. with The resin was washed dimethyl sulfoxide and dichloromethane.

(Example 11) Detection/Confirmation of Adopting β-Strand Structure

In this example, we detected/confirmed that the bridge peptides of the present disclosure adopt a β-strand structure. In this example, it was confirmed that the bridge peptides of the present disclosure adopt the β-strand structure by CD. It can also be shown by NMR and molecular dynamics calculations that the bridge peptide of the present disclosure adopts the β-strand structure.

Analysis by Circular Dichroism (CD)

Circular dichroism (CD) analysis of peptides (concentrations: 40-100 μM) was performed on a JASCO J-820 spectrofluorometer under the following conditions.

The β-strand content is calculated from the CD spectra obtained in the experiment.

Conformational Analysis

Measurement Conditions

Wavelength: 190-260 nm

Temperature: 20° C.

50 mM sodium phosphate buffer solution, pH7.4

Figure 1:
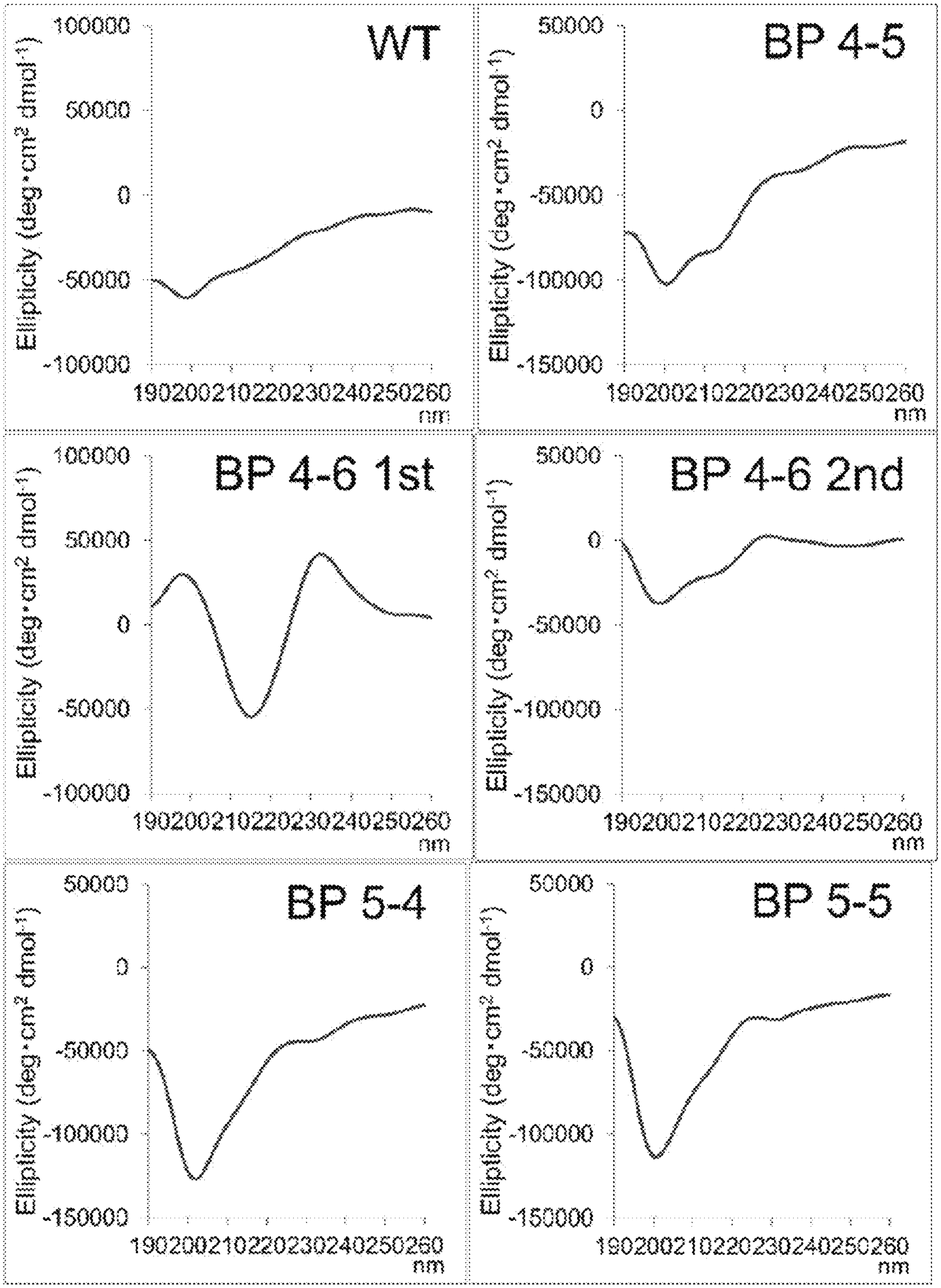
FIG. 1-1 shows the experimental CD spectra of the bridge peptides of the present disclosure. WT stands for wild type and BP stands for bridge peptide. BP4-5 is a bridge peptide composed of β-DM4 (N-terminal side) and β-DM5 (C-terminal side). BP4-6 1st is a bridge peptide composed of β-DM4 (N-terminal side) and β-DM6 (C-terminal side), and was isolated as a first_peak in HPLC purification. BP4-6 2nd is a bridge peptide composed of β-DM4 (N-terminal side) and β-DM6 (C-terminal side), and was isolated as a second_peak in HPLC purification. BP5-4 is a bridge peptide composed of β-DM5 (N-terminal side) and β-DM4 (C-terminal side). BP5-5 is a bridge peptide composed of β-DM5 (N-terminal side) and β-DM5 (C-terminal side).
Figures 1, 2:
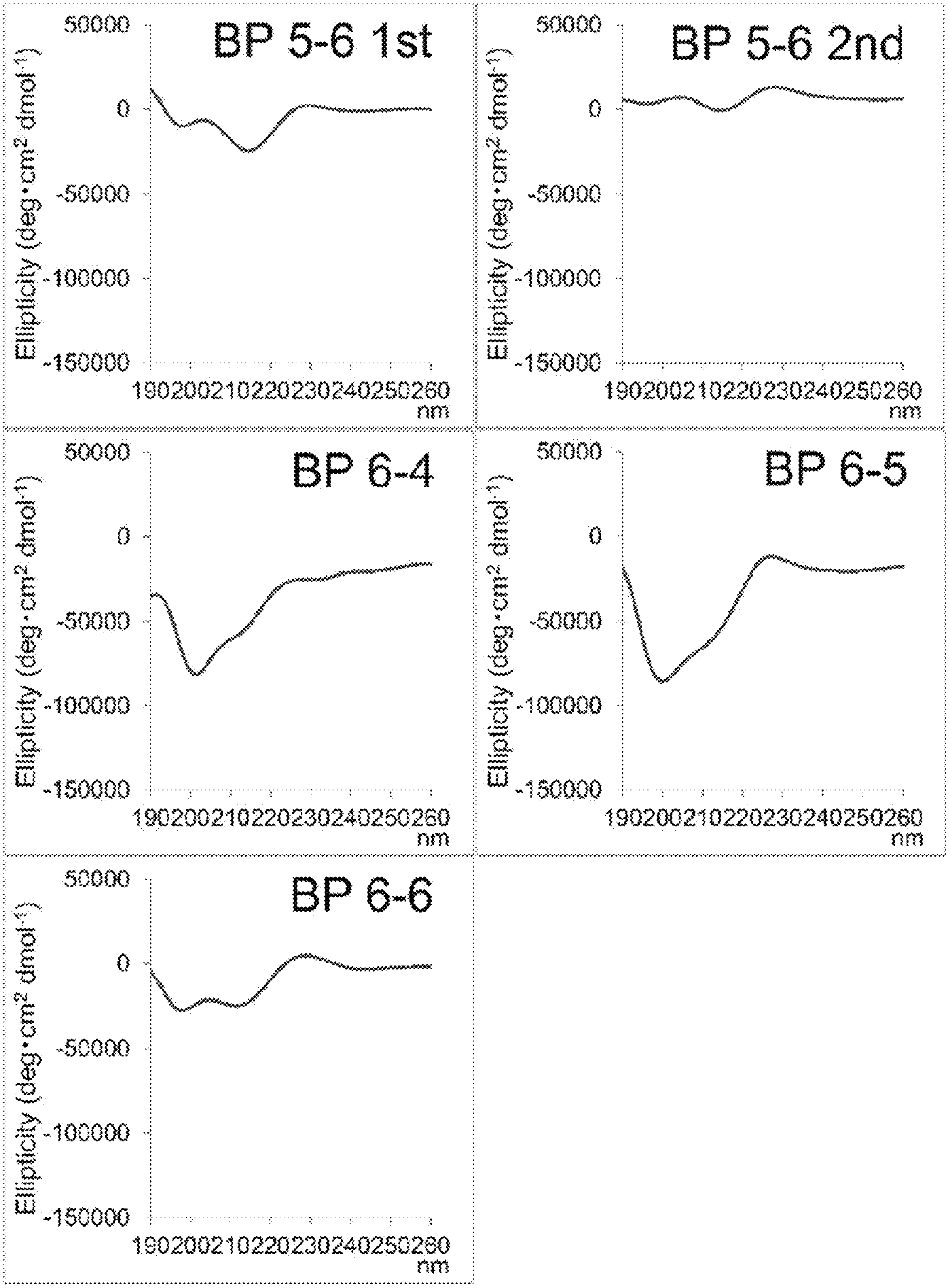
Figure 2:
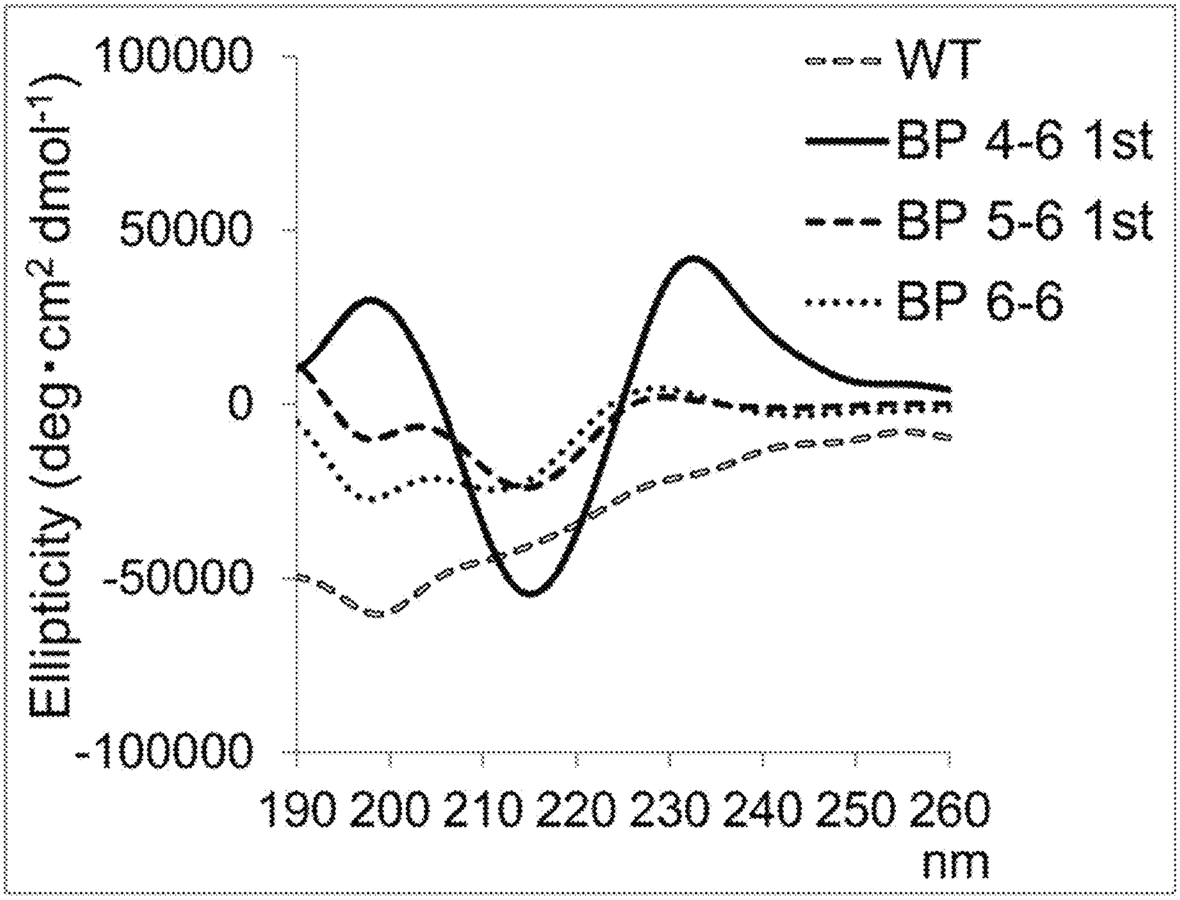

FIG. 1-1 and FIG. 1-2 show the experimental CD spectra of the bridge peptides of the present disclosure.

Effect of Bridge Length on β-Strand

Measurement Conditions

Wavelength: 190-260 nm

Temperature: 20° C.

50 mM sodium phosphate buffer solution, pH7.4

FIG. 2 shows the experimental CD spectra of the bridge peptides of the present disclosure.

(Example 11) Assay

In this example, we investigated the stability to thermal denaturation.

The bridge peptide (BP4-6 1st) synthesized in the above example was tested for stability against thermal denaturation under the following conditions.

Experiment to Evaluate Stability to Thermal Denaturation

Measurement Conditions

Wavelength: 217 nm

Temperature: 0-90° C.

50 mM sodium phosphate buffer solution, pH7.4

FIG. 3 shows the results of experiments to evaluate the stability of the bridge peptides of the present disclosure to thermal denaturation.

(Example 12) NMR Analysis

Peptides are dissolved in $H_2O$: $D_2O$=9:1, and $^1H$-NMR, COSY, HSQC, TOCSY, and NOESY measurements are performed under water suppression conditions.

(Example 13) Stability Against Proteolytic Enzymes

Peptides are dissolved in trypsin digestion buffer (0.1 M ammonium bicarbonate, pH 8.0). Immobilized trypsin on agarose is washed three times with trypsin digestion buffer using a centrifuge, then trypsin digestion buffer is added, and this mixture is added to the peptides dissolved in trypsin digestion buffer.

The stability to degrading enzymes is evaluated by following the reaction over time using a centrifuge and quantitatively analyzing the starting materials and degradation products by HPLC or LC/MS.

(Example 14) Cell Membrane Permeability Assay

HeLa cells are grown in DMEM containing 10% fetal bovine serum and penicillin/streptomycin, treated with trypsin, washed twice with medium using a centrifuge, and seeded into multi-well plates for overnight incubation. FITC-labeled peptides are added to the cells at 37° C. and the cells are incubated at 37° C. The cells are washed twice with medium and twice with PBS, and treated with trypsin at 37° C. HeLa cells are collected and centrifuged, washed twice with medium and twice with PBS, and PBS containing propidium iodide is added to the cell. The cell membrane permeability of the peptides is quantitatively analyzed by FACS.

(Amino Acid Sequence of Peptides and Identification by Mass Spectrometry)

The results are shown in FIG. 15.

(Evaluation of Cell Membrane Permeability by FACS)

The results are shown in FIG. 16.

(Validation of Endocytosis)

(a) Incubation at 4° C.

Hela cells are grown in DMEM containing 10% fetal bovine serum and penicillin/streptomycin, treated with trypsin, washed twice with medium using a centrifuge, and seeded into multi-well plates for overnight incubation. Hela cells are incubated at 4° C. for 30 min, and FITC-labeled peptides are added to the cells at 4° C. HeLa cells are incubated at 4° C., washed twice with medium and twice with PBS, and treated with trypsin at 37° C. Hela cells are collected and centrifuged, washed twice with medium and twice with PBS, and PBS containing propidium iodide is added to the cell. The cell membrane permeability of the peptides is quantitatively analyzed by FACS.

(b) Inhibition of ATP Production by 10 mM Sodium Azide and 50 mM 2-deoxy-D-glucose HeLa cells are grown in DMEM containing 10% fetal bovine serum and penicillin/streptomycin, washed twice with medium using a centrifuge after trypsin treatment, and incubated overnight. HeLa cells are incubated with 10 mM sodium azide and 50 mM 2-deoxy-D-glucose for 60 minutes, FITC-labeled peptides are added to the cells, incubated at 37° C. The HeLa cells are washed twice with medium and twice with PBS, and treated with trypsin at 37° C. Hela cells are collected and centrifuged, washed twice with medium and twice with PBS, and PBS containing propidium iodide is added to the cell. The cell membrane permeability of the peptides is quantitatively analyzed by FACS.

(Example 15) Molecular Dynamics Calculations

Replica exchange molecular dynamics (REMD) simulations implemented in Gromacs were performed to sample the conformation of bridge peptides. The free energy topography is determined from the conformational distribution, and the free energy of β-strand formation and the percentage of β-strand appearance are quantitatively analyzed.

(Peptide Sequence and Ramachandran Plot Analysis)

(a) The results for BP 4-6Z_Ala (a bridge peptide in which the double bond in the cross-link of BP 4-6_Ala is Z) were shown in FIG. 5.

(b) The results for BP 4-6E_Ala (a bridge peptide in which the double bond in the cross-link of BP 4-6_Ala is E) were shown in FIG. 6.

(Example 16) Evaluation of the β-Strand Stabilization Ability by Quantum Chemical Calculations Quantum chemical calculations were performed using Gaussian16 in β-strand structure. The geometry optimization and calculation of the frequencies were performed by the (DFT) at the M06-2X/6-31G(d,p) density functional theory level, and the single point energy calculations were performed with the M06-2X/6-311G(2d,p) functional. All calculations were performed in aqueous medium using the PCM (Polarizable Continuum Model) method (IEFPCM (Integral Equation Formalism variant PCM)).

The stabilizing effect of artificial amino acids and the cross-link on the β-strand structure was evaluated by calculating the energies of the following hypothetical reactions. The stabilizing effect was evaluated by determining the energy difference between the case of alanine and the case of artificial amino acids under β-strand constraint and unconstraint conditions.

[Chemical Formula 314]

$$Ac—(Ala)_9—NH_2 + XY \longrightarrow Ac—AAAXAYAAA—NH_2 + (Ala)_2$$

(a) Evaluation of Strain on β-Strand Structure in Isomers of the olefin moiety of the crosslink The strain in the β-strand structure was evaluated by the N1-N5-N9 angle.

[Chemical Formula 315]

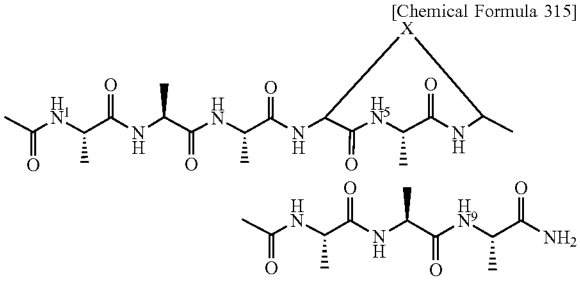

| X | ∠N1-N5-N9 (°) | ΔE (kcal/mol) |
|---|---|---|
| 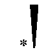 (Same substituent in both positions) | 179.8 | — |
| 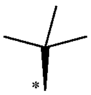 (Same substituent in both positions) | 160.5 | 14.29 |
| 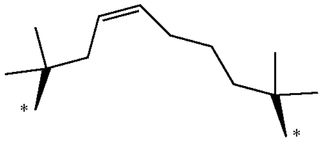 | 165.0 | -2.68 |

-continued

[Chemical Formula 315]

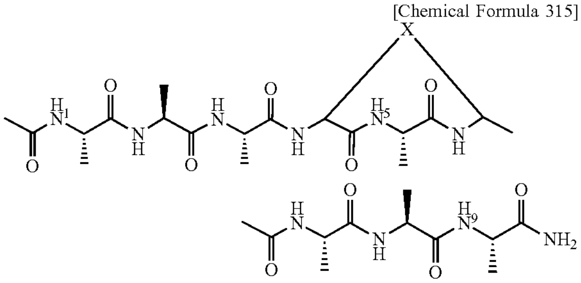

| X | ∠N1-N5-N9 (°) | ΔE (kcal/mol) |
|---|---|---|
| 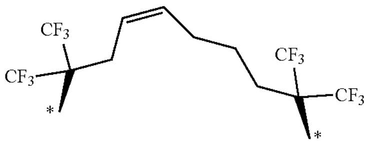 | 164.6 | 2.74 |
| 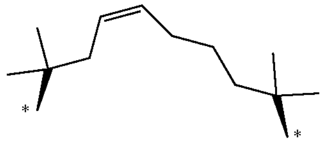 (No constraints) | 170.0 | -6.78 |
| 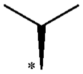 (Same substituent in both positions) | 176.8 | 2.24 |
| 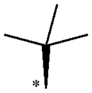 (Same substituent in both positions) (No constraints) | 178.0 | -0.27 |
| 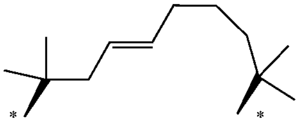 | 153.4 | 0.13 |
| 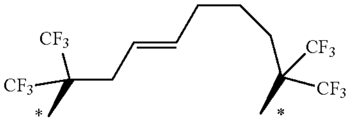 | 150.2 | 6.15 |
| 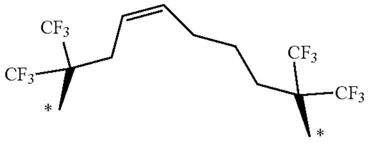 (No constraints) | 171.7 | -0.40 |

* indicates the point of attachment to the peptide chain.

The 3D structure of one of the bridge peptides cross-linked with olefins, resulting from a geometry optimization calculation, is shown in FIG. 7.

(b) Evaluation of Stereoisomers of Artificial Amino Acids

The strain in the β-strand structure was evaluated by the N1-N5-N9 angle.

[Chemical Formula 316]

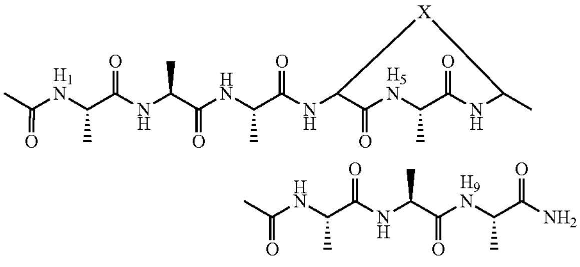

| X | ∠N1-N5-N9 (°) | ΔE (kcal/mol) |
|---|---|---|
| 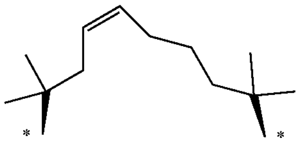 | 165.0 | −2.68 |
| 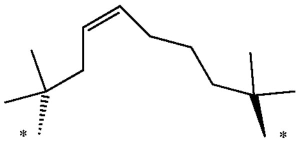 | 141.6 | −5.10 |
| 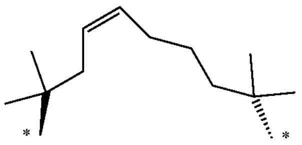 | 168.3 | 14.46 |
| 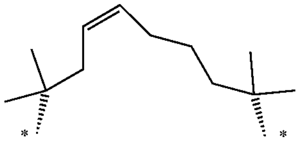 | 131.9 | −7.18 |

* indicates the point of attachment to the peptide chain.

(c) Evaluation of the Bridge Peptides Composed of Structures Other than Olefins

The strain in the β-strand structure was evaluated by the N1-N5-N9 angle.

[Chemical Formula 317]

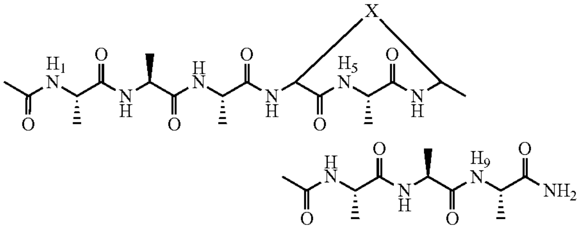

| X | ∠N1-N5-N9 (°) | ΔE (kcal/mol) |
|---|---|---|
| 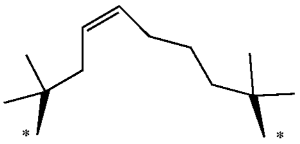 | 165.0 | −2.68 |
| 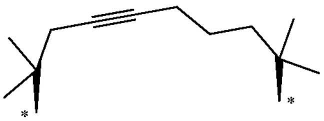 | 155.7 | 0.98 |
| 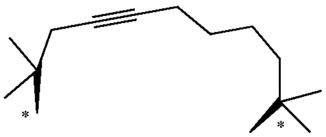 | 160.5 | −3.04 |
| 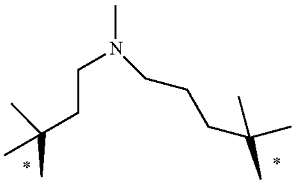 | 159.0 | 0.09 |
| 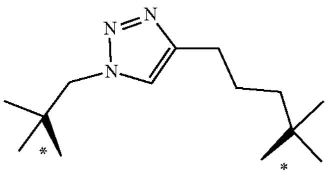 | 161.6 | −0.76 |
| 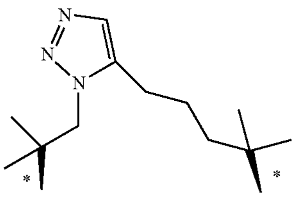 | 167.1 | −2.11 |
| 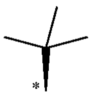 (Same substituent in both positions) | 160.5 | 14.29 |

-continued

[Chemical Formula 317]

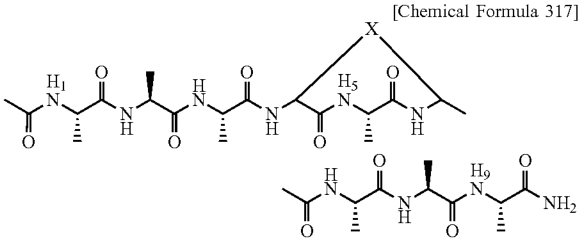

| X | ∠N1-N5-N9 (°) | ΔE (kcal/mol) |
|---|---|---|
| 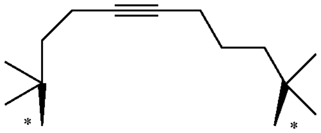 | 162.7 | 1.17 |
| 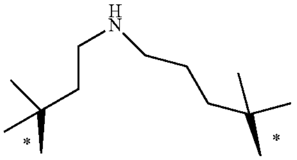 | 159.6 | −0.22 |
| 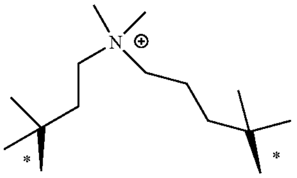 | 161.3 | 1.39 |

-continued

[Chemical Formula 317]

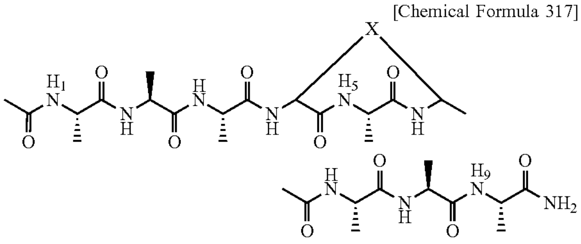

| X | ∠N1-N5-N9 (°) | ΔE (kcal/mol) |
|---|---|---|
| 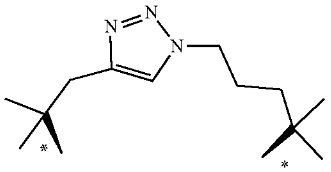 | 161.7 | −1.00 |
| 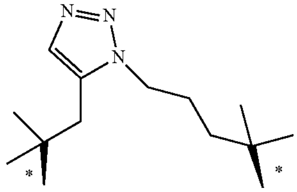 | 167.9 | −2.23 |

* indicates the point of attachment to the peptide chain.

(d) Evaluation of Substituent Effects at the β-Position

The strain in the β-strand structure was evaluated by the N1-N5-N9 angle.

[Chemical Formula 318-1]

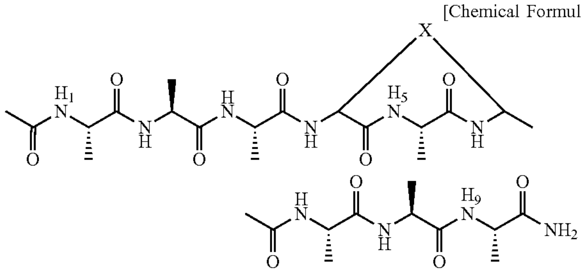

| X | ∠N1-N5-N9 (°) | ΔE (kcal/mol) |
|---|---|---|
| 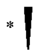 (Same substituent in both positions) | 179.8 | 1 |
| 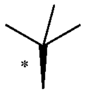 (Same substituent in both positions) | 160.5 | 14.29 |
| 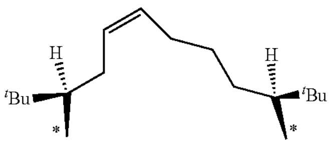 | 162.1 | 0.25 |

-continued
[Chemical Formula 318-1]
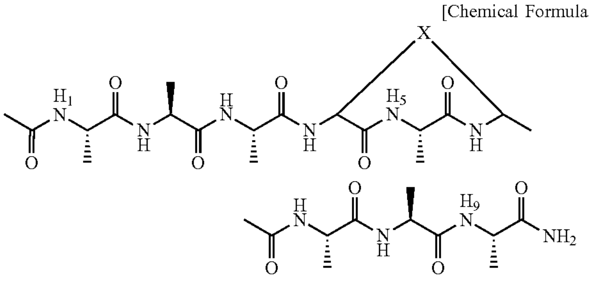
| X | ∠N1-N5-N9 (°) | ΔE (kcal/mol) |
|---|---|---|
| 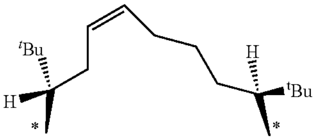 | 160.1 | −2.77 |
| 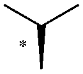 (Same substituent in both positions) | 176.8 | 2.24 |
| 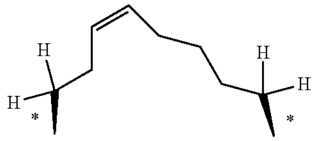 | 163.6 | −5.13 |
| 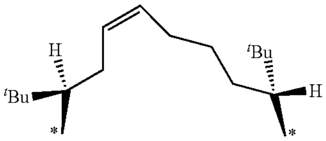 | 163.5 | −2.31 |
| 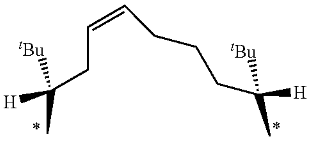 | 165.7 | −5.34 |
| 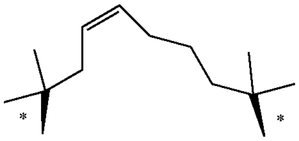 | 165.0 | −2.68 |
| 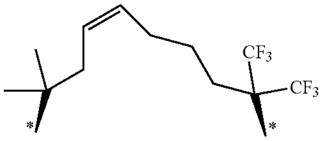 | 167.3 | −0.40 |
| 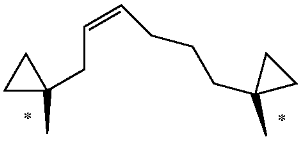 | 163.1 | −4.08 |

-continued
[Chemical Formula 318-1]
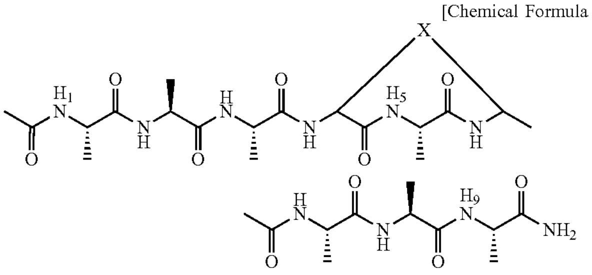
| X | ∠N1-N5-N9 (°) | ΔE (kcal/mol) |
|---|---|---|
| 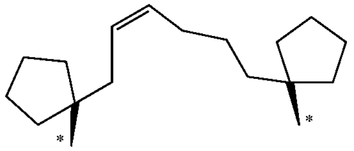 | 164.8 | −3.98 |
| 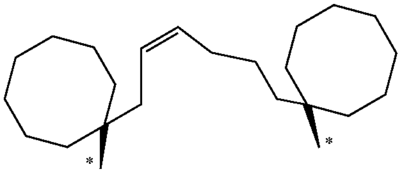 | 162.2 | −0.58 |
| 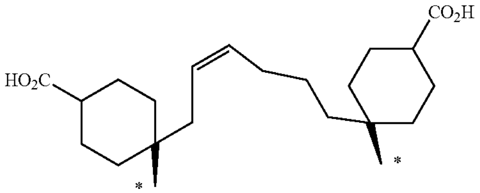 | 162.8 | −0.10 |
| 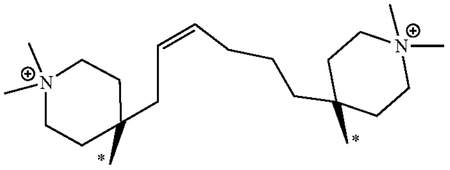 | 165.7 | −0.17 |
| 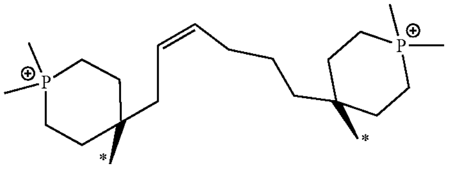 | 165.4 | 0.80 |
| 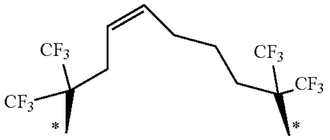 | 164.6 | 2.74 |
| 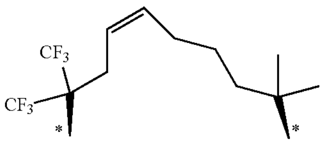 | 162.9 | 0.64 |

-continued
[Chemical Formula 318-1]
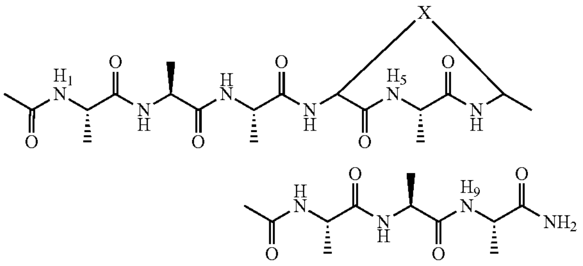
| X | ∠N1-N5-N9 (°) | ΔE (kcal/mol) |
|---|---|---|
| 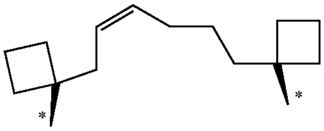 | 168.9 | −5.56 |
| 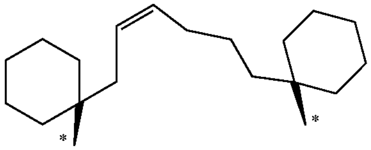 | 162.6 | −0.58 |
| 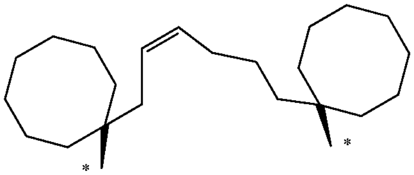 | 164 0 | −2.00 |
| 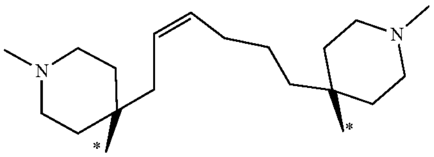 | 162.7 | −0.74 |
| 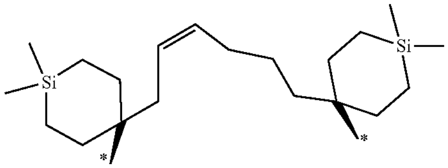 | 163.3 | 0.63 |
| 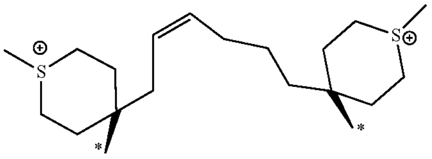 | 164.7 | 0.79 |
* indicates the point of attachment to the peptide chain.

(e) Evaluation of Substituent Effects at the β-Position Under Unconstraint Conditions.

The strain in the β-strand structure was evaluated by the N1-N5-N9 angle.

[Chemical Formula 318-2]

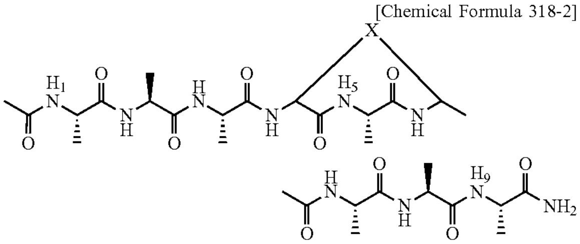

| X | ∠N1-N5-N9 (°) | ΔE (kcal/mol) |
|---|---|---|
| 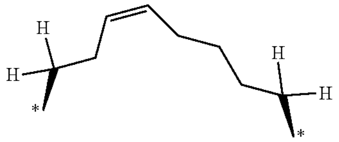 (No constraints) | 150.4 | -6.13 |
| 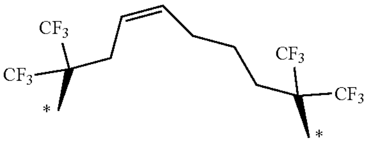 (No constraints) | 171.7 | -0.40 |
| 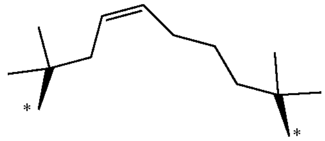 (No constraints) | 170.0 | -6.78 |
| 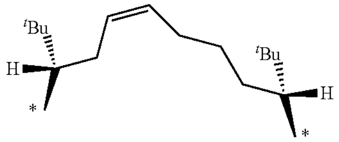 (No constraints) | 164.1 | -6.69 |

* indicates the point of attachment to the peptide chain.

(Example 17) Evaluation of the β-Position's Effect on Selected Secondary Structures by Quantum Chemical Calculations Since the length of the cross-link is not long enough for adopting α-helix structure, the stabilizing effect of the cross-link was evaluated by Gaussian16 in β-strand, $3_{10}$-helix, and polyproline-II helix structures. The geometry optimization calculation of the frequencies were performed by the density functional theory (DFT) at the M06-2X/6-31G (d, p) level, and the single point energy calculations were performed with the M06-2X/6-311G (2d, p) functional. All calculations were performed in aqueous medium using the PCM (Polarizable Continuum Model) method (IEFPCM (Integral Equation Formalism variant PCM)).

The stabilizing effect of artificial amino acids and the cross-link on the secondary structure was evaluated by calculating the energies of the following hypothetical reactions. The stabilizing effect was evaluated by determining the energy difference between the case of alanine and the case of artificial amino acids under β-strand constraint and unconstraint conditions.

1) α-Helix Structure, β-Strand Structure, $3_{10}$-Helix Structure

[Chemical Formula 319]

Ac—(Ala)$_9$—NH$_2$ + XY →

Ac—AAAXAYAAA—NH$_2$ + (Ala)$_2$ 2) (Polyproline-II Helix Structure)

[Chemical Formula 319-2]

Ac—PPPAPAPPP—NH$_2$ + XY →

Ac—PPPXPYPPP—NH$_2$ + (Ala)$_2$ (α-Helix Structure)

[Chemical Formula 319-3]

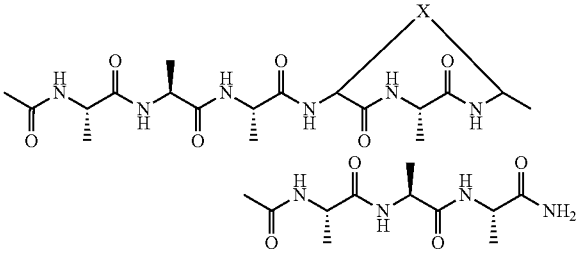

| X | ΔE (kcal/mol) |
|---|---|
|  (Same substituent in both positions) | — |
| 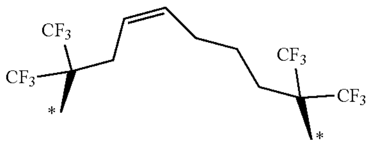 | Impossible to form |
| 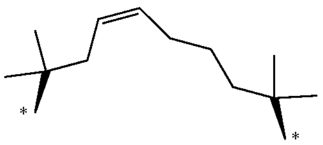 | Impossible to form |
| 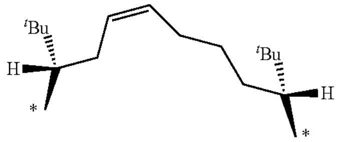 | Impossible to form |

* indicates the point of attachment to the peptide chain.

(β-Strand Structure)

[Chemical Formula 319-4]

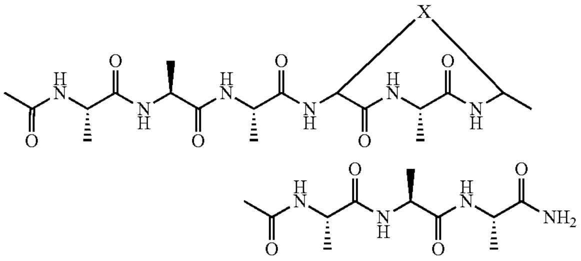

| X | ΔE (kcal/mol) |
| --- | --- |
|  (Same substituent in both positions) | — |
| 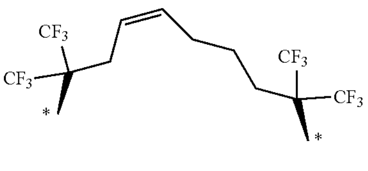 | 2.74 |
| 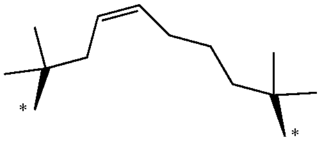 | −2.68 |
| 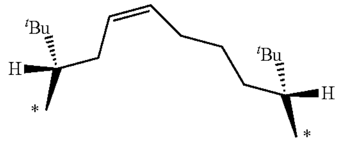 | −5.34 |

* indicates the point of attachment to the peptide chain.

($3_{10}$-Helix Structure)

[Chemical Formula 319-5]

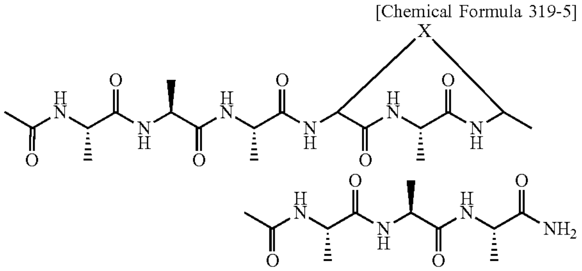

| X | ΔE (kcal/mol) |
| --- | --- |
|  (Same substituent in both positions) | — |

-continued

[Chemical Formula 319-5]

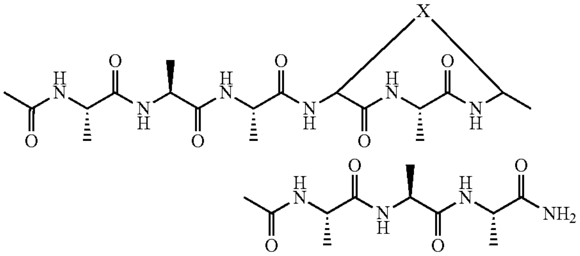

| X | ΔE (kcal/mol) |
| --- | --- |
| 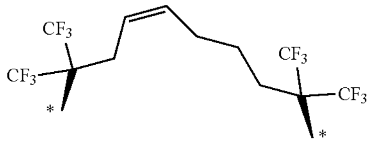 | 7.79 |
| 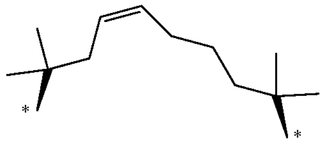 | 2.23 |
| 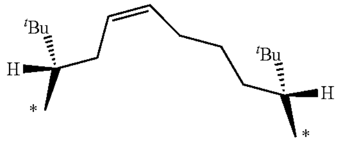 | 0.42 |

* indicates the point of attachment to the peptide chain.

(Polyproline-II Helix Structure)

[Chemical Formula 319-6]

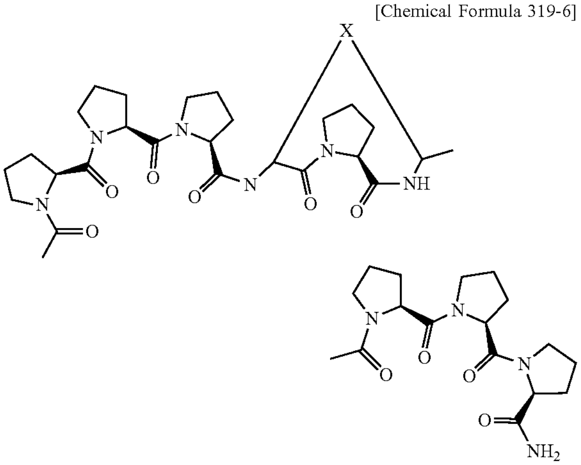

| X | ΔE (kcal/mol) |
| --- | --- |
|  (Same substituent in both positions) | — |

-continued

[Chemical Formula 319-6]

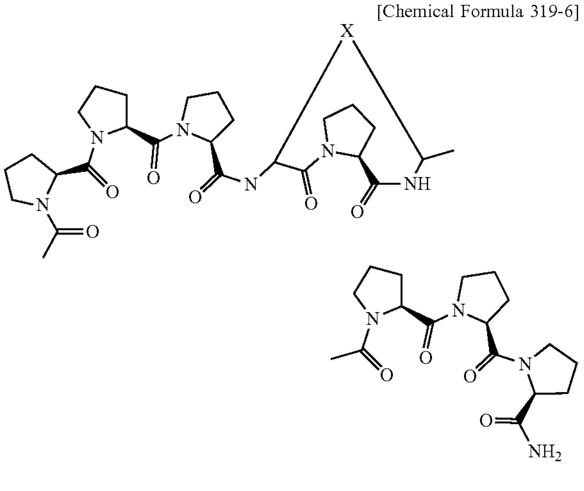

| X | ΔE (kcal/mol) |
|---|---|
| 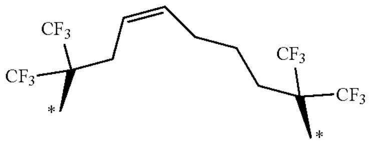 | 6.88 |
| 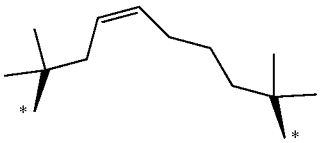 | 2.32 |
| 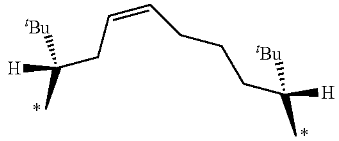 | 3.41 |

* indicates the point of attachment to the peptide chain.

(Note)

As disclosed above, the present disclosure is exemplified by the use of its preferred embodiments. However, it is understood that the scope of the present disclosure should be interpreted based solely on the Claims. It is also understood that any patent, any patent application, and any other references cited herein should be incorporated herein by reference in the same manner as the contents are specifically described herein. The present application claims priority to Japanese Patent Application No. 2020-183344 filed on Oct. 30, 2020 in Japan. The entire content thereof is incorporated herein by reference.

INDUSTRIAL APPLICABILITY

The present disclosure is useful in the field of medicine and other biologically functional products.

The invention claimed is:

1. A bridge peptide, comprising a bridge moiety and a peptide moiety, wherein:

the bridge moiety attaches to position α of the peptide moiety;

a position β of the peptide moiety is tertiary or quaternary; and the bridge peptide has a crosslink formed by a crosslinking method selected from the group consisting of olefin metathesis, alkyne metathesis, click chemistry, reductive amination, Michael addition, and carbamate formation.

2. The bridge peptide of claim 1, wherein the bridge peptide does not have a hydrogen bond to induce or maintain a secondary structure.

3. The bridge peptide of claim 1, wherein the bridge peptide comprises a β-strand structure.

4. The bridge peptide of claim 1, wherein the position β is quaternary.

5. The bridge peptide of claim 1, wherein at least one substituent at the position β comprises a functional group with a size equal to or greater than a methyl group.

6. The bridge peptide of claim 1, wherein two substituents at the position β comprise an independently selected functional group with a size equal to or greater than a methyl group.

7. The bridge peptide of claim 1, wherein a functional group attached to the position β has:

a) a van der Waals volume of 7.24 $Å^3$; or b) a van der Waals radius of 1.2 Å.

8. The bridge peptide of claim 1, wherein at least one functional group attached to the position β has:

a) a van der Waals volume of 21.6 $Å^3$ or greater;

b) a van der Waals radius of 2.00 Å or greater; or c) an A-value of 1.74 (kcal/mol) or greater.

9. The bridge peptide of claim 1, wherein substituents at the position β are each independently hydrogen, optionally substituted alkyl, alkene, alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or two substituents, together with the carbon atom to which they are attached, may form an optionally substituted nonaromatic carbocycle, an optionally substituted nonaromatic heterocycle, optionally substituted aryl, or optionally substituted heteroaryl, provided that two substituents are not both hydrogen.

10. The bridge peptide of claim 1, wherein substituents at the position β are each independently substituted alkyl, substituted alkene, substituted alkyne, optionally substituted heteroalkyl, imine, nitrile, optionally substituted secondary amine, optionally substituted tertiary amine, optionally substituted quaternary ammonium, sulfone ($SO_2$), sulfoxide, or a carbon atom substituent, or two substituents, together with the carbon atom to which they are attached, may form an optionally substituted nonaromatic carbocycle, an optionally substituted nonaromatic heterocycle, optionally substituted aryl, or optionally substituted heteroaryl, provided that two substituents are not both hydrogen.

11. The bridge peptide of claim 1, wherein substituents at the position β are each independently hydrogen, methyl, methoxy, methoxymethyl, secondary amine substituted with methyl or Boc, tertiary amine (substituted with methyl), quaternary ammonium substituted with methyl, or methyl substituted with halogen, or two substituents, together with the carbon atom to which they are attached, may form an unsubstituted saturated $C_{3-12}$ nonaromatic carbocycle or an optionally substituted saturated 3- to 12-membered nonaromatic heterocycle, provided that two substituents are not both hydrogen.

12. The bridge peptide of claim 1, wherein substituents at the position β are each independently methoxy, methoxymethyl, secondary amine substituted with methyl or Boc, tertiary amine (substituted with methyl), quaternary ammonium substituted with methyl, or methyl substituted with halogen, or two substituents, together with the carbon atom to which they are attached, may form an unsubstituted saturated $C_{3-12}$ nonaromatic carbocycle or an optionally substituted saturated 3- to 12-membered nonaromatic heterocycle, provided that two substituents are not both hydrogen.

13. The bridge peptide of claim 1, wherein the bridge peptide has a crosslink formed by a crosslinking method selected from the group consisting of alkyne metathesis, click chemistry, reductive amination, Michael addition, and carbamate formation.

14. The bridge peptide of claim 1, wherein the bridge peptide has a crosslink formed by a crosslinking method selected from the group consisting of olefin metathesis, alkyne metathesis, reductive amination, Michael addition, and carbamate formation.

15. The bridge peptide of claim 1, wherein the position $\alpha$ is attached to a hydrogen or a halogen.

* * * * *